United States Patent [19]
von Deyn et al.

[11] Patent Number: 6,165,944
[45] Date of Patent: Dec. 26, 2000

[54] 4-(3-HETEROCYCLYL-1-BENZOYL) PYRAZOLES AND THEIR USE AS HERBICIDES

[75] Inventors: Wolfgang von Deyn, Neustadt; Regina Luise Hill, Speyer; Ernst Baumann, Dudenhofen; Stefan Engel, Idstein; Guido Mayer, Neustadt; Joachim Rheinheimer; Matthias Witschel, both of Ludwigshafen; Ulf Misslitz, Neustadt; Oliver Wagner; Martina Otten, both of Ludwigshafen; Helmut Walter, Obrigheim; Karl-Otto Westphalen, Speyer, all of Germany

[73] Assignee: BASF Aktiengesellschaft, Ludwigshaften, Germany

[21] Appl. No.: 09/091,292

[22] PCT Filed: Jan. 8, 1997

[86] PCT No.: PCT/EP98/00070

§ 371 Date: Jun. 16, 1998

§ 102(e) Date: Jun. 16, 1998

[87] PCT Pub. No.: WO98/31682

PCT Pub. Date: Jul. 23, 1998

[30] Foreign Application Priority Data

Jan. 17, 1997 [DE] Germany .................. 197 01 446

[51] Int. Cl.[7] .................. A01N 43/56; A01N 43/74; C07D 413/10

[52] U.S. Cl. .................. 504/271; 504/280; 544/316; 544/333; 546/173; 546/241; 546/275.4; 548/123; 548/128; 548/131; 548/143; 548/146; 548/122; 548/187; 548/202; 548/235; 548/236; 548/240; 548/241; 548/237; 548/247; 548/204; 548/263.2; 548/266.2; 548/364.1; 548/364.4; 548/365.1; 548/365.7

[58] Field of Search .................. 504/271, 280; 548/240, 241, 243, 244, 245, 246, 247, 248, 249; 348/240, 247, 364.1

[56] References Cited

U.S. PATENT DOCUMENTS 4,460,597 7/1984 Yanai et al. .................. 424/273

FOREIGN PATENT DOCUMENTS

| 2122188 | 1/1983 | European Pat. Off. . |
|---|---|---|
| 203 428 | 12/1986 | European Pat. Off. . |
| 282944 | 9/1988 | European Pat. Off. . |
| 96/26206 | 8/1996 | WIPO . |
| 97/41105 | 11/1997 | WIPO . |
| 97/46530 | 11/1997 | WIPO . |

*Primary Examiner*—Robert W. Ramsuer
*Attorney, Agent, or Firm*—Keil & Weinkauf

[57] ABSTRACT

4-(3-Heterocyclyl-1-benzoyl)pyrazoles of the formula I

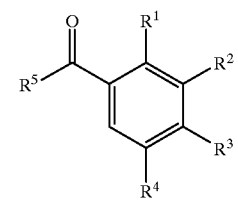

where:

$R^1$ and $R^3$ are each hydrogen, nitro, halogen, cyano, alkyl, haloalkyl, alkoxy, haloalkoxy, alkylthio, haloalkylthio, alkylsulfinyl, haloalkylsulfinyl, alkylsulfonyl, haloalkylsulfonyl, aminosulfonyl, N-alkylaminosulfonyl, N,N-dialkyl)aminosulfonyl, N-alkylsulfonylamino, N-haloalkylsulfonylamino, N-alkyl-N-alkylsulfonylamino or N-alkyl-N-haloalkylsulfonylamino;

$R^2$ is a 5- or 6-membered heterocyclyl radical with or without substitution which comprises 1 to 4 identical or different hetero atoms from the following group: oxygen, sulfur or nitrogen;

$R^4$ is hydrogen, halogen or alkyl;

$R^5$ is substituted pyrazole which is attached in position 4;

and agriculturally useful salts thereof; processes for preparing the 4-(3-heterocyclyl-1-benzoyl)pyrazoles; compositions comprising them; and the use of these derivatives or these compositions comprising them for controlling undesirable plants.

28 Claims, No Drawings

4-(3-HETEROCYCLYL-1-BENZOYL) PYRAZOLES AND THEIR USE AS HERBICIDES

The present invention relates to 4-(3-heterocyclyl-1-benzoyl)pyrazoles of the formula I

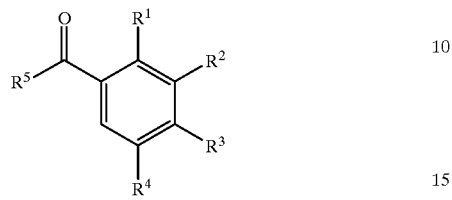

where:
- $R^1$ and $R^3$ are each hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N-($C_1$–$C_6$-alkyl)aminosulfonyl, N,N-di($C_1$–$C_6$-alkyl)aminosulfonyl, N-($C_1$–$C_6$-alkylsulfonyl)amino, N-($C_1$–$C_6$-haloalkylsulfonyl)amino, N-($C_1$–$C_6$-alkyl)-N-($C_1$–$C_6$-alkylsulfonyl)amino or N-($C_1$–$C_6$-alkyl)-N-($C_1$–$C_6$-haloalkylsulfonyl)amino;
- $R^2$ is a 5- or 6-membered heterocyclyl radical with or without substitution which comprises one to four identical or different hetero atoms selected from the following group: oxygen, sulfur or nitrogen;
- $R^4$ is hydrogen, halogen or $C_1$–$C_6$-alkyl;
- $R^5$ is a pyrazole of the formula II

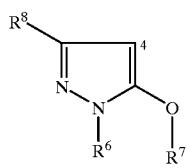

which is attached in position 4
where
- $R^6$ is $C_1$–$C_6$-alkyl;
- $R^7$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylaminocarbonyl, $C_3$–$C_6$-alkenylaminocarbonyl, $C_3$–$C_6$-alkynylaminocarbonyl, di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl, N-($C_3$–$C_6$-alkynyl)-N-($C_1$–$C_6$-alkoxy)aminocarbonyl, di($C_1$–$C_6$-alkyl)aminothiocarbonyl, $C_1$–$C_6$-alkylcarbonyl-$C_1$–$C_6$-alkyl, $C_1$–$C_6$-alkoxyimino-$C_1$–$C_6$-alkyl, N-($C_1$–$C_6$-alkylamino)imino-$C_1$–$C_6$-alkyl or N-(di-$C_1$–$C_6$-alkylamino)imino-$C_1$–$C_6$-alkyl, where the alkyl, cycloalkyl and alkoxy radicals mentioned may be partially or fully halogenated and/or may carry one to three of the following groups: cyano, hydroxyl, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;
- is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, heterocyclyloxycarbonyl, phenylaminocarbonyl, N-($C_1$–$C_6$-alkyl)-N-(phenyl)aminocarbonyl, heterocyclylaminocarbonyl, N-($C_1$–$C_6$-alkyl)-N-(heterocyclyl)aminocarbonyl, phenyl-$C_2$–$C_6$-alkenylcarbonyl or heterocyclyl-$C_2$–$C_6$-alkenylcarbonyl, where the phenyl and the heterocyclyl radical of the last 16 substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;
- $R^8$ is hydrogen, $C_1$–$C_6$-alkyl or $C_1$–$C_6$-haloalkyl;

and agriculturally useful salts thereof.

In addition, the invention relates to processes for preparing compounds of the formula I, to compositions comprising them and to the use of these derivatives or of the compositions comprising them for controlling harmful plants.

Pyrazol-4-ylbenzoyl derivatives are disclosed in the literature, for example in EP-A 282 944, WO 96/26206 and the earlier German patent application DE-A 19 701 446. However, the herbicidal properties of the prior art compounds and their crop plant safety are not entirely satisfactory. It is an object of the present invention to provide novel, in particular herbicidally active, compounds having improved properties.

We have found this object is achieved by the 4-(3-heterocyclyl-1-benzoyl)pyrazoles of the formula I and their herbicidal activity.

Furthermore, we have found herbicidal compositions which comprise the compounds I and have very good herbicidal activity. Moreover, we have found processes for preparing these compositions and methods for controlling undesirable vegetation using the compounds I.

Depending on the substitution pattern, the compounds of the formula I may contain one or more chiral centers and, if this is the case, are present as mixtures of enantiomers or diastereomers. The invention provides both the pure enantiomers or diastereomers and mixtures thereof.

The compounds of the formula I may also be present in the form of their agriculturally useful salts, the kind of salt generally not being important. The salts of those cations or the acid addition salts of those acids whose cations or anions, respectively, do not adversely affect the herbicidal activity of the compounds I are generally suitable.

Suitable cations are in particular ions of the alkali metals, preferably lithium, sodium and potassium, of the alkaline earth metals, preferably calcium and magnesium, and of the transition metals, preferably manganese, copper, zinc and iron, and ammonium, where, if desired, one to four hydrogen atoms may be replaced by $C_1$–$C_4$-alkyl, hydroxyl-$C_1$–$C_4$-alkyl, $C_1$–$C_4$-alkoxy-$C_1$–$C_4$-alkyl, hydroxyl-$C_1$–$C_4$-alkoxy-$C_1$–$C_4$-alkyl, phenyl or benzyl, preferably ammonium, dimethylammonium, di-(2-hydroxyeth-1-yl)ammonium, [2-(2-hydroxyeth-1-oxy)eth-1-yl]ammonium, diisopropylammonium, tetramethylammonium, tetrabutylammonium, trimethylbenzylammonium, and furthermore phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of usable acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, ropionate and butyrate.

Emphasis is given to the compounds of the formula I according to the invention where $R^2$ is a 5- or 6-membered heterocyclyl radical which contains one to four identical or different hetero atoms selected from the following group: oxygen, sulfur or nitrogen; where the heterocyclyl radical is unsubstituted or carries one to three substituents from the following groups:

halogen, cyano, nitro, $C_1$–$C_4$-alkyl, $C_1$–$C_4$-alkoxy-$C_1$–$C_4$-alkyl, di($C_1$–$C_4$-alkoxy)-$C_1$–$C_4$-alkyl, di($C_1$–$C_4$-alkyl)amino-$C_1$–$C_4$-alkyl, [2,2-di(($C_1$–$C_4$-alkyl)hydrazino-1]-$C_1$–$C_4$-alkyl, $C_1$–$C_6$-alkyliminooxy-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, di($C_1$–$C_4$-alkyl)aminocarbonyl-$C_1$–$C_4$-alkyl, $C_1$–$C_4$-haloalkyl, $C_1$–$C_4$-cyanoalkyl, $C_3$–$C_6$-cycloalkyl, $C_1$–$C_4$-alkoxy, $C_1$–$C_4$-alkoxy-$C_1$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $C_1$–$C_4$-alkylcarbonyl, $C_1$–$C_4$-haloalkylcarbonyl, $C_1$–$C_4$-alkoxycarbonyl, $C_1$–$C_4$-alkoxy-$C_1$–$C_4$-alkoxycarbonyl, $C_1$–$C_4$-haloalkoxycarbonyl, $C_3$–$C_6$-alkenyloxycarbonyl, $C_3$–$C_6$-alkynyloxycarbonyl, $C_1$–$C_4$-alkylaminocarbonyl, di($C_1$–$C_4$-alkyl) aminocarbonyl; phenyl or benzyl, where the last two substituents may in turn be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;

hydroxyl, which may alternatively be present in the tautomeric form as oxo group;

$C_3$–$C_6$-spirocycloalkane, where one carbon may be replaced by oxygen or by nitrogen with or without $C_1$–$C_4$-alkyl-substitution; and/or together with a fused phenyl ring, a $C_3$–$C_6$-carbocycle or a 5- or 6-membered heterocycle forms a bicyclic system, where the fused ring system may carry one to three substituents from the following group: halogen, nitro, cyano, $C_1$–$C_4$-alkyl, $C_1$–$C_4$-haloalkyl, $C_1$–$C_4$-alkoxy or $C_1$–$C_4$-haloalkoxy.

The organic moieties mentioned for the substituents $R^1$–$R^8$ or as radicals on phenyl and heterocyclyl radicals are collective terms for individual enumerations of the individual group members. All hydrocarbon chains, i.e. all alkyl, haloalkyl, cyanoalkyl, alkoxy, haloalkoxy, alkylthio, haloalkylthio, alkylsulfinyl, haloalkylsulfinyl, alkylsulfonyl, haloalkylsulfonyl, N-alkylaminosulfonyl, N,N-dialkylaminosulfonyl, dialkylamino, N-alkylsulfonylamino, N-haloalkylsulfonylamino, N-alkyl-N-alkylsulfonylamino, N-alkyl-N-haloalkylsulfonylamino, alkylcarbonyl, haloalkylcarbonyl, alkoxycarbonyl, haloalkoxycarbonyl, alkylcarbonyloxy, alkylaminocarbonyl, dialkylaminocarbonyl, dialkylaminothiocarbonyl, alkoxyalkyl, dialkoxyalkyl, alkylthioalkyl, dialkylaminoalkyl, dialkylhydrazinoalkyl, alkyliminooxyalkyl, alkylcarbonylalkyl, alkoxyiminoalkyl, N-(alkylamino)iminoalkyl, N-(dialkylamino)iminoalkyl, alkoxycarbonylalkyl, dialkylaminocarbonylalkyl, phenylalkenylcarbonyl, heterocyclylalkenylcarbonyl, N-alkoxy-N-alkylaminocarbonyl, N-alkyl-N-phenylaminocarbonyl, N-alkyl-N-heterocyclylaminocarbonyl, phenylalkyl, heterocyclylalkyl, phenylcarbonylalkyl, heterocyclylcarbonylalkyl, dialkylaminoalkoxycarbonyl, alkoxyalkoxycarbonyl, alkenylcarbonyl, alkenyloxycarbonyl, alkenylaminocarbonyl, N-alkenyl-N-alkylaminocarbonyl, N-alkenyl-N-alkoxyaminocarbonyl, alkynylcarbonyl, alkynyloxycarbonyl, alkynylaminocarbonyl, N-alkynyl-N-alkylaminocarbonyl, N-alkynyl-N-alkoxyaminocarbonyl, alkenyl, alkynyl, haloalkenyl, haloalkynyl and alkoxyalkoxy moieties may be straight-chain or branched. Unless stated otherwise, halogenated substituents preferably carry one to five identical or different halogen atoms. In each case, the meaning halogen denotes fluorine, chlorine, bromine or iodine.

Examples of other meanings are:

$C_1$–$C_4$-alkyl: for example methyl, ethyl, propyl, 1-methylethyl, butyl, 1-methylpropyl, 2-methylpropyl or 1,1-dimethylethyl;

$C_1$–$C_6$-alkyl and the alkyl moieties of $C_1$–$C_6$-alkylcarbonyl-$C_1$–$C_6$-alkyl, $C_1$–$C_6$-alkoxyimino-$C_1$–$C_6$-alkyl, N-($C_1$–$C_6$-alkylamino)imino-$C_1$–$C_6$-alkyl, N-(di-$C_1$–$C_6$-alkylamino)imino-$C_1$–$C_6$-alkyl, N-($C_1$–$C_6$-alkoxy)-N-($C_1$–$C_6$-alkyl)aminocarbonyl, N-($C_3$–$C_6$-alkenyl)-N-($C_1$–$C_6$-alkyl)aminocarbonyl, ($C_3$–$C_6$-alkynyl)-N-($C_1$–$C_6$-alkyl)aminocarbonyl, N-($C_1$–$C_6$-alkyl)-N-phenylaminocarbonyl, N-($C_1$–$C_6$-alkyl)-N-heterocyclylaminocarbonyl, phenyl-$C_1$–$C_6$-alkyl, N-($C_1$–$C_6$-alkyl)-N-($C_1$–$C_6$-alkylsulfonyl)amino, N-($C_1$–$C_6$-alkyl)-N-($C_1$–$C_6$-haloalkylsulfonyl)amino, heterocyclyl-$C_1$–$C_6$-alkyl, phenylcarbonyl-$C_1$–$C_6$-alkyl, heterocyclylcarbonyl-$C_1$–$C_6$-alkyl: $C_1$–$C_4$-alkyl as mentioned above and, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl: $C_1$–$C_4$-haloalkyl as mentioned above and, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-cyanoalkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 1-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl or 2-cyanomethylprop-2-yl;

$C_1$–$C_4$-alkoxy, and the alkoxy moieties of di($C_1$–$C_4$-alkoxy)-$C_1$–$C_4$-alkyl: for example methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of $C_1$–$C_6$-alkoxyimino-$C_1$–$C_4$-alkyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl and N-($C_3$–$C_6$-alkynyl)-N-($C_1$–$C_6$-alkoxy)aminocarbonyl: $C_1$–$C_4$-alkoxy as mentioned above and, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethyl- propoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e. for example fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above and, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or decafluorohexoxy;

$C_1$–$C_4$-alkylthio: for example methylthio, ethylthio, propylthio, 1-methylethylthio, butylthio, 1-methylpropylthio, 2-methylpropylthio or 1,1-dimethylethylthio;

$C_1$–$C_6$-alkylthio: $C_1$–$C_4$-alkylthio as mentioned above and, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_4$-haloalkylthio: a $C_1$–$C_4$-alkylthio radical as mentioned above which is partially or fully substituted by fluorine, chlorine, bromine and/or iodine, i.e. for example fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

$C_1$–$C_6$-haloalkylthio: $C_1$–$C_4$-haloalkylthio as mentioned above and, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_6$-alkylsulfinyl ($C_1$–$C_6$-alkyl-S(=O)—) : for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_6$-haloalkylsulfinyl: a $C_1$–$C_6$-alkylsulfinyl radical as mentioned above which is partially or fully substituted by fluorine, chlorine, bromine and/or iodine, i.e. for example fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2- chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_6$-alkylsulfonyl($C_1$–$C_6$-alkyl-S(=O)$_2$—), and the alkylsulfonyl radicals of N-($C_1$–$C_6$-alkylsulfonyl)amino and N-($C_1$–$C_6$-alkyl)-N-($C_1$–$C_6$-alkylsulfonyl)amino: for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_6$-haloalkylsulfonyl, and the haloalkyl radicals of N-($C_1$–$C_6$-haloalkylsulfonyl)amino and N-($C_1$–$C_6$-alkyl)-N-($C_1$–$C_6$-haloalkylsulfonyl)amino: a $C_1$–$C_6$-alkylsulfonyl radical as mentioned above which is partially or fully substituted by fluorine, chlorine, bromine and/or iodine, i.e. for example fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_1$–$C_6$-alkylamino, and the alkylamino radicals of N-($C_1$–$C_6$-alkylamino)imino-$C_1$–$C_6$-alkyl, i.e. for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

($C_1$–$C_4$-alkylamino)sulfonyl: for example methylaminosulfonyl, ethylaminosulfonyl, propylaminosulfonyl, 1-methylethylaminosulfonyl, butylaminosulfonyl, 1-methylpropylaminosulfonyl, 2-methylpropylaminosulfonyl or 1,1-dimethylethylaminosulfonyl;

($C_1$–$C_6$-alkylamino)sulfonyl: ($C_1$–$C_4$-alkylamino)sulfonyl as mentioned above and, for example, pentylaminosulfonyl, 1-methylbutylaminosulfonyl, 2-methylbutylaminosulfonyl, 3-methylbutylaminosulfonyl, 2,2-dimethylpropylaminosulfonyl, 1-ethylpropylaminosulfonyl, hexylaminosulfonyl, 1,1-dimethylpropylaminosulfonyl, 1,2-dimethylpropylaminosulfonyl, 1-methylpentylaminosulfonyl, 2-methylpentylaminosulfonyl, 3-methylpentylaminosulfonyl, 4-methylpentylaminosulfonyl, 1,1-dimethylbutylaminosulfonyl, 1,2-dimethylbutylaminosulfonyl, 1,3-dimethylbutylaminosulfonyl, 2,2-dimethylbutylaminosulfonyl, 2,3-dimethylbutylaminosulfonyl, 3,3-dimethylbutylaminosulfonyl, 1-ethylbutylaminosulfonyl, 2-ethylbutylaminosulfonyl, 1,1,2-trimethylpropylaminosulfonyl, 1,2,2-trimethylpropylaminosulfonyl, 1-ethyl-1-methylpropylaminosulfonyl or 1-ethyl-2-methylpropylaminosulfonyl;

di($C_1$–$C_4$-alkyl)aminosulfonyl: for example N,N-dimethylaminosulfonyl, N,N-diethylaminosulfonyl, N,N-di(1-methylethyl)aminosulfonyl, N,N-dipropylaminosulfonyl, N,N-dibutylaminosulfonyl, N,N-di(1-methylpropyl)aminosulfonyl, N,N-di(2-methylpropyl)aminosulfonyl, N,N-di(1,1-dimethylethyl)aminosulfonyl, N-ethyl-N-methylaminosulfonyl, N-methyl-N-propylaminosulfonyl, N-methyl-N-(1-methylethyl)aminosulfonyl, N-butyl-N-methylaminosulfonyl, N-methyl-N-(1-methylpropyl)aminosulfonyl, N-methyl-N-(2-methylpropyl)aminosulfonyl, N-(1,1-dimethylethyl)-N-methylaminosulfonyl, N-ethyl-N-propylaminosulfonyl, N-ethyl-N-(1-methylethyl)aminosulfonyl, N-butyl-N-ethylaminosulfonyl, N-ethyl-N-(1-methylpropyl)aminosulfonyl, N-ethyl-N-(2-methylpropyl)aminosulfonyl, N-ethyl-N-(1,1-dimethylethyl)aminosulfonyl, N-(1-methylethyl)-N-propylaminosulfonyl, N-butyl-N-propylaminosulfonyl, N-(1-methylpropyl)-N-propylaminosulfonyl, N-(2-methylpropyl)-N-propylaminosulfonyl, N-(1,1-dimethylethyl)-N-propylaminosulfonyl, N-butyl-N-(1-methylethyl)aminosulfonyl, N-(1-methylethyl)-N-(1-methylpropyl)aminosulfonyl, N-(1-methylethyl)-N-(2-methylpropyl)aminosulfonyl, N-(1,1-dimethylethyl)-N-(1-methylethyl)aminosulfonyl, N-butyl-N-(1- methylpropyl)aminosulfonyl, N-butyl-N-(2-methylpropyl)aminosulfonyl, N-butyl-N-(1,1-dimethylethyl)aminosulfonyl, N-(1-methylpropyl)-N-(2-methylpropyl)aminosulfonyl, N-(1,1-dimethylethyl)-N-(1-methylpropyl)aminosulfonyl or N-(1,1-dimethylethyl)-N-(2-methylpropyl)aminosulfonyl;

di($C_1$–$C_6$-alkyl)aminosulfonyl: di($C_1$–$C_4$-alkyl)aminosulfonyl as mentioned above and, for example, N-methyl-N-pentylaminosulfonyl, N-methyl-N-(1-methylbutyl)aminosulfonyl, N-methyl-N-(2-methylbutyl)aminosulfonyl, N-methyl-N-(3-methylbutyl)aminosulfonyl, N-methyl-N-(2,2-dimethylpropyl)aminosulfonyl, N-methyl-N-(1-ethylpropyl)aminosulfonyl, N-methyl-N-hexylaminosulfonyl, N-methyl-N-(1,1-dimethylpropyl)aminoN-methyl-N-N-methyl-N-(1,2-dimethylpropyl)aminosulfonyl, N-methyl-N-(1-methylpentyl)aminosulfonyl, N-methyl-N-(2-methylpentyl)aminosulfonyl, N-methyl-N-(3-methylpentyl)aminosulfonyl, N-methyl-N-(4-methylpentyl)aminosulfonyl, N-methyl-N-(1,1-dimethylbutyl)aminosulfonyl, N-methyl-N-(1,2-dimethylbutyl)aminosulfonyl, N-methyl-N-(1,3-dimethylbutyl)aminosulfonyl, N-methyl-N-(2,2-dimethylbutyl)aminosulfonyl, N-methyl-N-(2,3-dimethylbutyl)aminosulfonyl, N-methyl-N-(3,3-dimethylbutyl)aminosulfonyl, N-methyl-N-(1-ethylbutyl)aminosulfonyl, N-methyl-N-(2-ethylbutyl)aminosulfonyl, N-methyl-N-(1,1,2-trimethylpropyl)aminosulfonyl, N-methyl-N-(1,2,2-trimethylpropyl)aminosulfonyl, N-methyl-N-(1-ethyl-1-methylpropyl)aminosulfonyl, N-methyl-N-(1-ethyl-2-methylpropyl)aminosulfonyl, N-ethyl-N-pentylaminosulfonyl, N-ethyl-N-(1-methylbutyl)aminosulfonyl, N-ethyl-N-(2-methylbutyl)aminosulfonyl, N-ethyl-N-(3-methylbutyl)aminosulfonyl, N-ethyl-N-(2,2-dimethylpropyl)aminosulfonyl, N-ethyl-N-(1-ethylpropyl)aminosulfonyl, N-ethyl-N-hexylaminosulfonyl, N-ethyl-N-(1,1-dimethylpropyl)aminosulfonyl, N-ethyl-N-(1,2-dimethylpropyl)aminosulfonyl, N-ethyl-N-(1-methylpentyl)aminosulfonyl, N-ethyl-N-(2-methylpentyl)aminosulfonyl, N-ethyl-N-(3-methylpentyl)aminosulfonyl, N-ethyl-N-(4-methylpentyl)aminosulfonyl, N-ethyl-N-(1,1-dimethylbutyl)aminosulfonyl, N-ethyl-N-(1,2-dimethylbutyl)aminosulfonyl, N-ethyl-N-(1,3-dimethylbutyl)aminosulfonyl, N-ethyl-N-(2,2-dimethylbutyl)aminosulfonyl, N-ethyl-N-(2,3-dimethylbutyl)aminosulfonyl, N-ethyl-N-(3,3-dimethylbutyl)aminosulfonyl, N-ethyl-N-(1-ethylbutyl)aminosulfonyl, N-ethyl-N-(2-ethylbutyl)aminosulfonyl, N-ethyl-N-(1,1,2-trimethylpropyl)aminosulfonyl, N-ethyl-N-(1,2,2-trimethylpropyl)aminosulfonyl, N-ethyl-N-(1-ethyl-1-methylpropyl)aminosulfonyl, N-ethyl-N-(1-ethyl-2-methylpropyl)aminosulfonyl, N-propyl-N-pentylaminosulfonyl, N-butyl-N-pentylaminosulfonyl, N,N-dipentylaminosulfonyl, N-propyl-N-hexylaminosulfonyl, N-butyl-N-hexylaminosulfonyl, N-pentyl-N-hexylaminosulfonyl or N,N-dihexylaminosulfonyl;

di($C_1$–$C_6$-alkyl)amino, and the dialkylamino radicals of di($C_1$–$C_4$-alkyl)amino-$C_1$–$C_4$-alkoxycarbonyl and N-(di-$C_1$–$C_6$-alkylamino)imino-$C_1$–$C_6$-alkyl: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

$C_1$–$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylcarbonyl, and the alkylcarbonyl radicals of $C_1$–$C_6$-alkylcarbonyl-$C_1$–$C_6$-alkyl: $C_1$–$C_4$-alkylcarbonyl as mentioned above and, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_4$-haloalkylcarbonyl: a $C_1$–$C_4$-alkylcarbonyl radical as mentioned above which is partially or fully substituted by fluorine, chlorine, bromine and/or iodine, i.e. for example chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl or nonafluorobutylcarbonyl;

$C_1$–$C_4$-alkoxycarbonyl, and the alkoxycarbonyl moieties of di($C_1$–$C_4$-alkyl)amino-$C_1$–$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

($C_1$–$C_6$-alkoxy)carbonyl: ($C_1$–$C_4$-alkoxy)carbonyl as mentioned above and, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

$C_1$–$C_4$-haloalkoxycarbonyl: a $C_1$–$C_4$-alkoxycarbonyl radical as mentioned above which is partially or fully substituted by fluorine, chlorine, bromine and/or iodine, i.e. for example fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl or 4-iodobutoxycarbonyl;

($C_1$–$C_4$-alkyl)carbonyloxy: acetyloxy, ethylcarbonyloxy, propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino)carbonyl as mentioned above and, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di($C_1$–$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)aminocarbonyl, N,N-di-(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

di($C_1$–$C_6$-alkyl)aminocarbonyl: di($C_1$–$C_4$-alkyl)aminocarbonyl as mentioned above and, for example, N-methyl-N-pentylaminocarbonyl, N-methyl-N-(1-methylbutyl)aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl-N-hexylaminocarbonyl, N-methyl-N-(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)

aminocarbonyl, N-methyl-N-(2,3-dimethylbutyl) aminocarbonyl, N-methyl-N-(3,3-dimethylbutyl) aminocarbonyl, N-methyl-N-(1-ethylbutyl) aminocarbonyl, N-methyl-N-(2-ethylbutyl) aminocarbonyl, N-methyl-N-(1,1,2-trimethylpropyl) aminocarbonyl, N-methyl-N-(1,2,2-trimethylpropyl) aminocarbonyl, N-methyl-N-(1-ethyl-1-methylpropyl) aminocarbonyl, N-methyl-N-(1-ethyl-2-methylpropyl) aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl) aminocarbonyl, N-ethyl-N-(2,2-dimethylpropyl) aminocarbonyl, N-ethyl-N-(1-ethylpropyl) aminocarbonyl, N-ethyl-N-hexylaminocarbonyl, N-ethyl-N-(1,1-dimethylpropyl)aminocarbonyl, N-ethyl-N-(1,2-dimethylpropyl)aminocarbonyl, N-ethyl-N-(1-methylpentyl)aminocarbonyl, N-ethyl-N-(2-methylpentyl)aminocarbonyl, N-ethyl-N-(3-methylpentyl)aminocarbonyl, N-ethyl-N-(4-methylpentyl)aminocarbonyl, N-ethyl-N-(1,1-dimethylbutyl)aminocarbonyl, N-ethyl-N-(1,2-dimethylbutyl)aminocarbonyl, N-ethyl-N-(1,3-dimethylbutyl)aminocarbonyl, N-ethyl-N-(2,2-dimethylbutyl)aminocarbonyl, N-ethyl-N-(2,3-dimethylbutyl)aminocarbonyl, N-ethyl-N-(3,3-dimethylbutyl)aminocarbonyl, N-ethyl-N-(1-ethylbutyl) aminocarbonyl, N-ethyl-N-(2-ethylbutyl)aminocarbonyl, N-ethyl-N-(1,1,2-trimethylpropyl)aminocarbonyl, N-ethyl-N-(1,2,2-trimethylpropyl)aminocarbonyl, N-ethyl-N-(1-ethyl-1-methylpropyl)aminocarbonyl, N-ethyl-N-(1-ethyl-2-methylpropyl)aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di($C_1$–$C_6$-alkyl)aminothiocarbonyl: for example N,N-dimethylaminothiocarbonyl, N,N-diethylaminothiocarbonyl, N,N-di(1-methylethyl)aminothiocarbonyl, N,N-dipropylaminothiocarbonyl, N,N-dibutylaminothiocarbonyl, N,N-di(1-methylpropyl)aminothiocarbonyl, N,N-di(2-methylpropyl)aminothiocarbonyl, N,N-di(1,1-dimethylethyl)aminothiocarbonyl, N-ethyl-N-methylaminothiocarbonyl, N-methyl-N-propylaminothiocarbonyl, N-methyl-N-(1-methylethyl)aminothiocarbonyl, N-butyl-N-methylaminothiocarbonyl, N-methyl-N-(1-methylpropyl)aminothiocarbonyl, N-methyl-N-(2-methylpropyl)aminothiocarbonyl, N-(1,1-dimethylethyl)-N-methylaminothiocarbonyl, N-ethyl-N-propylaminothiocarbonyl, N-ethyl-N-(1-methylethyl)aminothiocarbonyl, N-butyl-N-ethylaminothiocarbonyl, N-ethyl-N-(1-methylpropyl)aminothiocarbonyl, N-ethyl-N-(2-methylpropyl)aminothiocarbonyl, N-ethyl-N-(1,1-dimethylethyl)aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylaminothiocarbonyl, N-(1,1-dimethylethyl)-N-propylaminothiocarbonyl, N-butyl-N-(1-methylethyl)aminothiocarbonyl, N-(1-methylethyl)-N-(1-methylpropyl)aminothiocarbonyl, N-(1-methylethyl)-N-(2-methylpropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(N-(1-methylpropyl)-N-(N-(1-methylpropyl)-N- (N-(1-methylpropyl)-N-(2-methylpropyl)aminothiocarbonyl, N-(1,1-dimethylethyl)-N-(1-methylpropyl) aminothiocarbonyl, N-(1,1-dimethylethyl)-N-(2-methylpropyl)aminothiocarbonyl, N-methyl-N-pentylaminothiocarbonyl, N-methyl-N-(1-methylbutyl) aminothiocarbonyl, N-methyl-N-(2-methylbutyl) aminothiocarbonyl, N-methyl-N-(3-methylbutyl) aminothiocarbonyl, N-methyl-N-(2,2-dimethylpropyl) aminothiocarbonyl, N-methyl-N-(1-ethylpropyl) aminothiocarbonyl, N-methyl-N-hexylaminothiocarbonyl, N-methyl-N-(1,1-dimethylpropyl)aminothiocarbonyl, N-methyl-N-(1,2-dimethylpropyl)aminothiocarbonyl, N-methyl-N-(1-methylpentyl)aminothiocarbonyl, N-methyl-N-(2-methylpentyl)aminothiocarbonyl, N-methyl-N-(3-methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methylpropyl)aminothiocarbonyl, N-methyl-N-(1-ethyl-2-methylpropyl)aminothiocarbonyl, N-ethyl-N-pentylaminothiocarbonyl, N-ethyl-N-(1-methylbutyl) aminothiocarbonyl, N-ethyl-N-(2-methylbutyl) aminothiocarbonyl, N-ethyl-N-(3-methylbutyl) aminothiocarbonyl, N-ethyl-N-(2,2-dimethylpropyl) aminothiocarbonyl, N-ethyl-N-(1-ethylpropyl) aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl) aminothiocarbonyl, N-ethyl-N-(1,1,2-trimethylpropyl) aminothiocarbonyl, N-ethyl-N-(1,2,2-trimethylpropyl) aminothiocarbonyl, N-ethyl-N-(1-ethyl-1-methylpropyl) aminothiocarbonyl, N-ethyl-N-(1-ethyl-2-methylpropyl) aminothiocarbonyl, N-propyl-N-pentylaminothiocarbonyl, N-butyl-N-pentylaminothiocarbonyl, N,N-dipentylaminothiocarbonyl, N-propyl-N-hexylaminothiocarbonyl, N-butyl-N-hexylaminothiocarbonyl, N-pentyl-N-hexylaminothiocarbonyl or N,N-dihexylaminothiocarbonyl;

$C_1$–$C_4$-alkoxy-$C_1$–$C_4$-alkyl and the alkoxyalkoxy moieties of di($C_1$–$C_4$-alkoxy)-$C_1$–$C_4$-alkyl: $C_1$–$C_4$-alkyl which is substituted by $C_1$–$C_4$-alkoxy as mentioned above, i.e. for example methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy) ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy) propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy) propyl, 3-(butoxy)propyl, 3-(1-methylpropoxy)propyl, 3-(2-methylpropoxy)propyl, 3-(1,1-dimethylethoxy) propyl, 2-(methoxy)butyl, 2-(ethoxy)butyl, 2-(propoxy) butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy) butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl or 4-(1, 1-dimethylethoxy)butyl;

$C_1$–$C_4$-alkylthio-$C_1$–$C_4$-alkyl: $C_1$–$C_4$-alkyl which is substituted by $C_1$–$C_4$-alkylthio as mentioned above, i.e. for example methylthiomethyl, ethylthiomethyl, propylthiomethyl, (1-methylethylthio)methyl, butylthiomethyl, (1-methylpropylthio)methyl, (2-methylpropylthio)methyl, (1,1-dimethylethylthio) methyl, 2-methylthioethyl, 2-ethylthioethyl, 2-(propylthio)ethyl, 2-(1-methylethylthio)ethyl, 2-(butylthio)ethyl, 2-(1-methylpropylthio)ethyl, 2-(2-methylpropylthio)ethyl, 2-(1,1-dimethylethylthio)ethyl, 2-(methylthio)propyl, 3-(methylthio)propyl, 2-(ethylthio) propyl, 3-(ethylthio)propyl, 3-(propylthio)propyl, 3-(butylthio)propyl, 4-(methylthio)butyl, 4-(ethylthio) butyl, 4-(propylthio)butyl or 4-(butylthio)butyl;

di($C_1$–$C_4$-alkyl)amino-$C_1$–$C_4$-alkyl: $C_1$–$C_4$-alkyl which is substituted by di($C_1$–$C_4$-alkyl)amino as mentioned above, i.e. for example N,N-dimethylaminomethyl, N,N-diethylaminomethyl, N,N-dipropylaminomethyl, N,N-di(1-methylethyl)aminomethyl, N,N-dibutylaminomethyl, N,N-di(1-methylpropyl)aminomethyl, N,N-di(2-methylpropyl)aminomethyl, N,N-di(l,l-dimethylethyl) aminomethyl, N-ethyl-N-methylaminomethyl, N-methyl-N-propylaminomethyl, N-methyl-N-(1-methylethyl) aminomethyl, N-butyl-N-methylaminomethyl, N-methyl-N-(1-methylpropyl)aminomethyl, N-methyl-N-(2-methylpropyl)aminomethyl, N-(1,1-dimethylethyl)-N-methylaminomethyl, N-ethyl-N-propylaminomethyl, N-ethyl-N-(1-methylethyl)aminomethyl, N-butyl-N-ethylaminomethyl, N-ethyl-N-(1-methylpropyl) aminomethyl, N-ethyl-N-(2-methylpropyl)aminomethyl, N-ethyl-N-(1,1-dimethylethyl)aminomethyl, N-(1-methylethyl)-N-propylaminomethyl, N-butyl-N-propylaminomethyl, N-(1-methylpropyl)-N-propylaminomethyl, N-(2-methylpropyl)-N-propylaminomethyl, N-(1,1-dimethylethyl)-N-propylaminomethyl, N-butyl-N-(1-methylethyl) aminomethyl, N-(1-methylethyl)-N-(1-methylpropyl) aminomethyl, N-(1-methylethyl)-N-(2-methylpropyl) aminomethyl, N-(1,1-dimethylethyl)-N-(1-methylethyl) aminomethyl, N-butyl-N-(1-methylpropyl)aminomethyl, N-butyl-N-(2-methylpropyl)aminomethyl, N-butyl-N-(1, 1-dimethylethyl)aminomethyl, N-(1-methylpropyl)-N-(2-methylpropyl)aminomethyl, N-(1,1-dimethylethyl)-N-(1-methylpropyl)aminomethyl, N-(1,1-dimethylethyl)-N-(2-methylpropyl)aminomethyl, 2-(N,N-dimethylamino) ethyl, 2-(N,N-diethylamino)ethyl, 2-(N,N-dipropylamino)ethyl, 2-[N,N-di(1-methylethyl)amino] ethyl, 2-[N,N-dibutylamino]ethyl, 2-[N,N-di(1-methylpropyl)amino]ethyl, 2-[N,N-di(2-methylpropyl) amino]ethyl, 2-[N,N-di-(1,1-dimethylethyl)amino]ethyl, 2-[N-ethyl-N-methylamino]ethyl, 2-[N-methyl-N-propylamino]ethyl, 2-[N-methyl-N-(1-methylethyl) amino]ethyl, 2-[N-butyl-N-methylamino]ethyl, 2-[N-methyl-N-(1-methylpropyl)amino]ethyl, 2-[N-methyl-N-(2-methylpropyl)amino]ethyl, 2- [N-(1,1-dimethylethyl)-N-methylamino]ethyl, 2-[N-ethyl-N-propylamino]ethyl, 2-[N-ethyl-N-(1-methylethyl)amino]ethyl, 2-[N-butyl-N-ethylamino]ethyl, 2-[N-ethyl-N-(1-methylpropyl)amino] ethyl, 2-[N-ethyl-N-(2-methylpropyl)amino]ethyl, 2-[N-ethyl-N-(1,1-dimethylethylamino]ethyl, 2-[N-(1-methylethyl)-N-propylamino]ethyl, 2-[N-butyl-N-propylamino]ethyl, 2-[N-(1-methylpropyl)-N-propylamino]thyl, 2-[N-(2-methylpropyl)-N-propylamino]ethyl, 2-[N-(1,1-dimethylethyl)-N-propylamino]ethyl, 2-[N-butyl-N-(1-methylethyl)amino] ethyl, 2-[N-(1-methylethyl)-N-(1-methylpropyl)amino] ethyl, 2-[N-(1-methylethyl)-N-(2-methylpropyl)amino] ethyl, 2-[N-(1,1-dimethylethyl)-N-(1-methylethyl)amino] ethyl, 2-[N-butyl-N-(1-methylpropyl)amino]ethyl, 2-[N-butyl-N-(2-methylpropyl)amino]ethyl, 2-[N-butyl-N-(1, 1-dimethylethyl)amino]ethyl, 2-[N-(1-methylpropyl)-N-(2-methylpropyl)amino]ethyl, 2-[N-(1,1-dimethylethyl)-N-(1-methylpropyl)amino]ethyl, 2-[N-(1,1-dimethylethyl)-N-( 2-methylpropyl)amino]ethyl, 3-(N,N-dimethylamino)propyl, 3-(N,N-diethylamino)propyl, 4-(N,N-dimethylamino)butyl and 4-(N,N-diethylamino) butyl;

[2,2-di($C_1$–$C_4$-alkyl)hydrazino-1]-$C_1$–$C_4$-alkyl: $C_1$–$C_4$-alkyl as mentioned above which is substituted by [2,2-di ($C_1$–$C_4$-alkyl)hydrazino-1], i.e. for example (2,2-dimethylhydrazino-1)methyl, (2,2-diethylhydrazino-1) methyl, (2,2-dipropylhydrazino-1)methyl, [2,2-di(1-methylethyl)hydrazino-1)methyl, (2,2-dibutylhydrazino-1)methyl, [2,2-di(1-methylpropyl)hydrazino-1)methyl, [2,2-di(2-methylpropyl)hydrazino-1]methyl, [2,2-di(1,1-dimethylethyl)hydrazino-1)methyl, (2-ethyl-2-methylhydrazino-1)methyl, (2-methyl-2-propylhydrazino-1)methyl, [2-methyl-2-(1-methylethyl) hydrazino-1]methyl, (2-butyl-2-methylhydrazino-1) methyl, [2-methyl-2-(1-methylpropyl)hydrazino-1] methyl, [2-methyl-2-(2-methylpropyl)hydrazino-1] methyl, [2-(1,1-dimethylethyl)-2-methylhydrazino-1] methyl, (2-ethyl-2-propylhydrazino-1)methyl, [2-ethyl-2-(1-methylethyl)hydrazino-1]methyl, (2-butyl-2-ethylhydrazino-1)methyl, [2-ethyl-2-(1-methylpropyl) hydrazino-1]methyl, [2-ethyl-2-(2-methylpropyl) hydrazino-1]methyl, [2-ethyl-2-(1,1-dimethylethyl) hydrazino-1]methyl, [2-(1-methylethyl)-2-propylhydrazino-1]methyl, (2-butyl-2-propylhydrazino-1)methyl, [2-(1-methylpropyl)-2-propylhydrazino-1] methyl, [2-(2-methylpropyl)-2-propylhydrazino-1] methyl, [2-(1,1-dimethylethyl)-2-propylhydrazino-1] methyl, [2-butyl-2-(1-methylethyl)hydrazino-1]methyl, [2-(1-methylethyl)-2-(1-methylpropyl)hydrazino-1] methyl, [2-(1-methylethyl)-2-(2-methylpropyl) hydrazino-1]methyl, [2-(1,1-dimethylethyl)-2-(1-methylethyl)hydrazino-1]methyl, [2-butyl-2-(1-methylpropyl)hydrazino-1]methyl, [2-butyl-2-(2-methylpropyl)hydrazino-1]methyl, [2-butyl-2-(1,1-dimethylethyl)hydrazino-1]methyl, [2-(1-methylpropyl)-2-(2-methylpropyl)hydrazino-1]methyl, [2-(1,1- dimethylethyl)-2-(1-methylpropyl)hydrazino-1]methyl, [2-(1,1-dimethylethyl)-2-(2-methylpropyl)hydrazino-1] methyl, 2-(2,2-dimethylhydrazino-1)ethyl, 2-(2,2-diethylhydrazino-1)ethyl, 2-(2,2-dipropylhydrazino-1) ethyl, 2-[2,2-di(1-methylethyl)hydrazino-1]ethyl, 2-(2,2-dibutylhydrazino-1)ethyl, 2-[2,2-di(1-methylpropyl) hydrazino-1]ethyl, 2-[2,2-di(2-methylpropyl)hydrazino-1]ethyl, 2-[2,2-di(1,1-dimethylethyl)hydrazino-1]ethyl, 2-(2-ethyl-2-methylhydrazino-1)ethyl, 2-(2-methyl-2-propylhydrazino-1)ethyl, 2-[2-methyl-2-(1-methylethyl) hydrazino-1]ethyl, 2-(2-butyl-2-methylhydrazino-1) ethyl, 2-[2-methyl-2-(1-methylpropyl)hydrazino-1]ethyl, 2-[2-methyl-2-(2-methylpropyl)hydrazino-1]ethyl, 2-[2-(1,1-dimethylethyl)-2-methylhydrazino-1]ethyl, 2-(2-ethyl-2-propylhydrazino-1)ethyl, 2-[2-ethyl-2-(1-methylethyl)hydrazino-1]ethyl, 2-(2-butyl-2-ethylhydrazino-1)ethyl, 2-[2-ethyl-2-(1-methylpropyl) hydrazino-1]ethyl, 2-[2-ethyl-2-(1-methylpropyl) hydrazino-1]ethyl, 2-[2-ethyl-2-(2-methylpropyl) hydrazino-1]ethyl, 2-[2-ethyl-2-(1,1-dimethylethyl) hydrazino-1]ethyl, 2-[2-(1-methylethyl)-2-propylhydrazino-1]ethyl, 2-(2-butyl-2-propylhydrazino-1)ethyl, 2-[2-(1-methylpropyl)-2-propylhydrazino-1] ethyl, 2-[2-(2-methylpropyl)-2-propylhydrazino-1]ethyl, 2-[2-(1,1-dimethylethyl)-2-propylhydrazino-1]ethyl, 2-[2-butyl-2-(1-methylethyl)hydrazino-1]ethyl, 2-[2-(1-methylethyl)-2-(1-methylpropyl)hydrazino-1]ethyl, 2-[2-(1-methylethyl)-2-(2-methylpropyl)hydrazino-1]ethyl, 2-[2-(1,1-dimethylethyl)-2-(1-methylethyl)hydrazino-1] ethyl, 2-[2-butyl-2-(1-methylpropyl)hydrazino-1]ethyl, 2-[2-butyl-2-(2-methylpropyl)hydrazino-1]ethyl, 2-[2-butyl-2-(1,1-dimethylethyl)hydrazino-1]ethyl, 2-[2-(1-methylpropyl)-2-(2-methylpropyl)hydrazino-1]ethyl, 2-[2-(1,1-dimethylethyl)-2-(1-methylpropyl)hydrazino-1]ethyl, 2-[2-(1,1-dimethylethyl)-2-(2-methylpropyl) hydrazino-1]ethyl, 3-(2,2-dimethylhydrazino-1)propyl, 3-(2,2-diethylhydrazino-1)propyl, 4-(2,2-dimethylhydrazino-1)butyl or 4-(2,2-diethylhydrazino-1) butyl;

$C_1$–$C_6$-alkyliminooxy-$C_1$–$C_4$-alkyl: $C_1$–$C_4$-alkyl as mentioned above which is substituted by $C_1$–$C_6$-alkyliminooxy, i.e. for example methyliminooxymethyl, ethyliminooxymethyl, 1-propyliminooxymethyl, 2-propyliminooxymethyl, 1-butyliminooxymethyl, 2-butyliminooxymethyl, 2-methylprop-1-yliminooxymethyl, 1-pentyliminooxymethyl, 2-pentyliminooxymethyl, 3-pentyliminooxymethyl, 3-methylbut-2-yliminooxymethyl, 2-methylbut-1-yliminooxymethyl, 3-methylbut-1-yliminooxymethyl, 1-hexyliminooxymethyl, 2-hexyliminooxymethyl, 3-hexyliminooxymethyl, 2-methylpent-1-yliminooxymethyl, 3-methylpent-1-yliminooxymethyl, 4-methylpent-1-yliminooxymethyl, 2-ethylbut-1-yliminooxymethyl, 3-ethylbut-1-yliminooxymethyl, 2,3-dimethylbut-1-yliminooxymethyl, 3-methylpent-2-yliminooxymethyl, 4-methylpent-2-yliminooxymethyl, 3,3-dimethylbut-2-yliminooxymethyl, 2-(methyliminooxy)ethyl, 2-(ethyliminooxy)ethyl, 2-(1-propyliminooxy)ethyl, 2-(2-propyliminooxy)ethyl, 2-(1-butyliminooxy)ethyl, 2-(2-butyliminooxy)ethyl, 2-(2-methylprop-1-yliminooxy)ethyl, 2-(1-pentyliminooxy) ethyl, 2-(2-pentyliminooxy)ethyl, 2-(3-pentyliminooxy) ethyl, 2-(3-methylbut-2-yliminooxy)ethyl, 2-(2-methylbut-2-yliminooxy)ethyl, 2-(3-methylbut-1-yliminooxy)ethyl, 2-(1-hexyliminooxy)ethyl, 2-(2-hexyliminooxy)ethyl, 2-(3-hexyliminooxy)ethyl, 2-(2-methylpent-1-yliminooxy)ethyl, 2-(3-methylpent-1-yliminooxy)ethyl, 2-(4-methylpent-1-yliminooxy)ethyl, 2-(2-ethylbut-1-yliminooxy)ethyl, 2-(3-ethylbut-1-yliminooxy)ethyl, 2-(2,3-dimethylbut-1-yliminooxy) ethyl, 2-(3-methylpent-2-yliminooxy)ethyl, 2-(4-methylpent-2-yliminooxy)ethyl, 2-(3,3-dimethylbut-2-yliminooxy)ethyl, 3-(methyl iminooxy)propyl, 3-(ethyl iminooxy)propyl, 3-(1-propyliminooxy)propyl, 3-(2-propyliminooxy)propyl, 4-(methyliminooxy)butyl, 4-(ethyliminooxy)butyl, 4-(1-propyliminooxy)butyl or 4-(2-propyliminooxy)butyl;

$C_1$–$C_4$-alkoxycarbonyl-$C_1$–$C_4$-alkyl: $C_1$–$C_4$-alkyl which is substituted by $C_1$–$C_4$-alkoxycarbonyl as mentioned above, i.e. for example methoxycarbonylmethyl, ethoxycarbonylmethyl, propoxycarbonylmethyl, (1-methylethoxycarbonyl)methyl, butoxycarbonylmethyl, (1-methylpropoxycarbonyl) methyl, (2-methylpropoxycarbonyl)methyl, (1,1-dimethylethoxycarbonyl)methyl, 1-(methoxycarbonyl) ethyl, 1-(ethoxycarbonyl)ethyl, 1-(propyloxycarbonyl) ethyl, 1-(1-methylethoxycarbonyl)ethyl, 1-(butoxycarbonyl)ethyl, 1-(1-methylpropoxycarbonyl) ethyl, 1-(2-methylpropoxycarbonyl)ethyl, 1-(1,1-dimethylethoxycarbonyl)ethyl, 2-(methoxycarbonyl) ethyl, 2-(ethoxycarbonyl)ethyl, 2-(propoxycarbonyl) ethyl, 2-(1-methylethoxycarbonyl)ethyl, 2-(butoxycarbonyl)ethyl, 2-(1-methylpropoxycarbonyl) ethyl, 2-(2-methylpropoxycarbonyl)ethyl, 2-(1,1-dimethylethoxycarbonyl)ethyl, 1-(methoxycarbonyl) propyl, 1-(ethoxycarbonyl)propyl, 1-(propoxycarbonyl) propyl, 1-(1-methylethoxycarbonyl)propyl, 1-(butoxycarbonyl)propyl, 1-(1-methylpropoxycarbonyl) propyl, 1-(2-methylpropoxycarbonyl)propyl, 1-(1,1-dimethylethoxycarbonyl)propyl, 2-(methoxycarbonyl) propyl, 2-(ethoxycarbonyl)propyl, 2-(propoxycarbonyl) propyl, 2-(1-methylethoxycarbonyl)propyl, 2-(butoxycarbonyl)propyl, 2-(1-methylpropoxycarbonyl) propyl, 2-(2-methylpropoxycarbonyl)propyl, 2-(1,1-dimethylethoxycarbonyl)propyl, 3-(methoxycarbonyl) propyl, 3-(ethoxycarbonyl)propyl, 3-(propoxycarbonyl) propyl, 3-(1-methylethoxycarbonyl)propyl, 3-(butoxycarbonyl)propyl, 3-(1-methylpropoxycarbonyl) propyl, 3-(2-methylpropoxycarbonyl)propyl, 3-(1,1-dimethylethoxycarbonyl)propyl, 1-(methoxycarbonyl) butyl, 1-(ethoxycarbonyl)butyl, 1-(propyloxycarbonyl) butyl, 1-(1-methylethoxycarbonyl)butyl, 1-(butoxycarbonyl)butyl, 1-(1-methylpropoxycarbonyl) butyl, 1-(2-methylpropoxycarbonyl)butyl, 1-(1,1-dimethylethoxycarbonyl)butyl, 2-(methoxycarbonyl) butyl, 2-(ethoxycarbonyl)butyl, 2-(propoxycarbonyl) butyl, 2-(1-methyl ethoxycarbonyl)butyl, 2-(butoxycarbonyl)butyl, 2-(1-methylpropoxycarbonyl) butyl, 2-(2-methylpropoxycarbonyl)butyl, 2-(1,1-dimethylethoxycarbonyl)butyl, 3-(methoxycarbonyl) butyl, 3-(ethoxycarbonyl)butyl, 3-(propoxycarbonyl) butyl, 3-(1-methylethoxycarbonyl)butyl, 3-(butoxycarbonyl)butyl, 3-(1-methylpropoxycarbonyl) butyl, 3-(2-methylpropoxycarbonyl)butyl, 3-(1,1-dimethylethoxycarbonyl)butyl, 4-(methoxycarbonyl) butyl, 4-(ethoxycarbonyl)butyl, 4-(propoxycarbonyl) butyl, 4-(1-methylethoxycarbonyl)butyl, 4-(butoxycarbonyl)butyl, 4-(1-methylpropoxy)butoxy, 4-(2-methylpropoxy)butoxy or 4-(1,1-dimethylethoxycarbonyl)butyl;

di($C_1$–$C_4$-alkyl)aminocarbonyl-$C_1$–$C_4$-alkyl: CL-$C_4$-alkyl which is substituted by di($C_1$–$C_4$-alkyl)amino as mentioned above, i.e. for example N,N-dimethylaminocarbonylmethyl, N,N- diethylaminocarbonylmethyl, N,N-dipropylaminocarbonylmethyl, N,N-di(1-methylethyl)aminocarbonylmethyl, N,N-dibutylaminocarbonylmethyl, N,N-di(1-methylpropyl)aminocarbonylmethyl, N,N-di(2-methylpropyl)aminocarbonylmethyl, N,N-di(1,1-dimethylethyl)aminocarbonylmethyl, N-ethyl-N-methylaminocarbonylmethyl, N-methyl-N-propylaminocarbonylmethyl, N-methyl-N-(1-methylethyl)aminocarbonylmethyl, N-butyl-N-methylaminocarbonylmethyl, N-methyl-N-(1-methylpropyl)aminocarbonylmethyl, N-methyl-N-(2-methylpropyl)aminocarbonylmethyl, N-(1,1-dimethylethyl)-N-methylaminocarbonylmethyl, N-ethyl-N-propylaminocarbonylmethyl, N-ethyl-N-(1-methylethyl)aminocarbonylmethyl, N-butyl-N-ethylaminocarbonylmethyl, N-ethyl-N-(1-methylpropyl)aminocarbonylmethyl, N-ethyl-N-(2-methylpropyl)aminocarbonylmethyl, N-ethyl-N-(1,1-dimethylethyl)aminocarbonylmethyl, N-(1-methylethyl)-N-propylaminocarbonylmethyl, N-butyl-N-propylaminocarbonylmethyl, N-(1-methylpropyl)-N-propylaminocarbonylmethyl, N-(2-methylpropyl)-N-propylaminocarbonylmethyl, N-(1,1-dimethylethyl)-N-propylaminocarbonylmethyl, N-butyl-N-(1-methylethyl)aminocarbonylmethyl, N-(1-methylethyl)-N-(1-methylpropyl)aminocarbonylmethyl, N-(1-methylethyl)-N-(2-methylpropyl)aminocarbonylmethyl, N-(1,1-dimethylethyl)-N-(1-methylethyl)aminocarbonylmethyl, N-butyl-N-(1-methylpropyl)aminocarbonylmethyl, N-butyl-N-(2-methylpropyl)aminocarbonylmethyl, N-butyl-N-(1,1-dimethylethyl)aminocarbonylmethyl, N-(1-methylpropyl)-N-(2-methylpropyl)aminocarbonylmethyl, N-(1,1-dimethylethyl)-N-(1-methylpropyl)aminocarbonylmethyl, N-(1,1-dimethylethyl)-N-(2-methylpropyl)aminocarbonylmethyl, N,N-dimethylaminocarbonylethyl, N,N-diethylaminocarbonylethyl, N,N-dipropylaminocarbonylethyl, N,N-di(1-methylethyl)aminocarbonylethyl, N,N-dibutylaminocarbonylethyl, N,N-di(1-methylpropyl)aminocarbonylethyl, N,N-di(2-methylpropyl)aminocarbonylethyl, N,N-di(1,1-dimethylethyl)aminocarbonylethyl, N-ethyl-N-methylaminocarbonylethyl, N-methyl-N-propylaminocarbonylethyl, N-methyl-N-(1-methylethyl)aminocarbonylethyl, N-butyl-N-methylaminocarbonylethyl, N-methyl-N-(1-methylpropyl)aminocarbonylethyl, N-methyl-N-(2-methylpropyl)aminocarbonylethyl, N-(1,1-dimethylethyl)-N-methylaminocarbonylethyl, N-ethyl-N-propylaminocarbonylethyl, N-ethyl-N-(1-methylethyl)aminocarbonylethyl, N-butyl-N-ethylaminocarbonylethyl, N-ethyl-N-(1-methylpropyl)aminocarbonylethyl, N-ethyl-N-(2-methylpropyl)aminocarbonylethyl, N-ethyl-N-(1,1-dimethylethyl)aminocarbonylethyl, N-(1-methylethyl)-N-propylaminocarbonylethyl, N-butyl-N-propylaminocarbonylethyl, N-(1-methylpropyl)-N-propylaminocarbonylethyl, N-(2-methylpropyl)-N-propylaminocarbonylethyl, N-(1,1-dimethylethyl)-N-propylaminocarbonylethyl, N-butyl-N-(1-methylethyl)aminocarbonylethyl, N-(1-methylethyl)-N-(1-methylpropyl)aminocarbonylethyl, -(1-methylethyl)-N-(2-methylpropyl)aminocarbonylethyl, N-(1,1-dimethylethyl)-N-(1-methylethyl)aminocarbonylethyl, N-butyl-N-(1-methylpropyl)aminocarbonylethyl, N-butyl-N-(2-methylpropyl)aminocarbonylethyl, N-butyl-N-(1,1-dimethylethyl)aminocarbonylethyl, N-(1-methylpropyl)-N-(2-methylpropyl)aminocarbonylethyl, N-(1,1-dimethylethyl)-N-(1-methylpropyl)aminocarbonylethyl, N-(1,1-dimethylethyl)-N-(2-methylpropyl)aminocarbonylethyl, N,N-dimethylaminocarbonylpropyl, N,N-diethylaminocarbonylpropyl, N,N-dipropylaminocarbonylpropyl, N,N-di(1-methylethyl)aminocarbonylpropyl, N,N-dibutylaminocarbonylpropyl, N,N-di(1-methylpropyl)aminocarbonylpropyl, N,N-di(2-methylpropyl)aminocarbonylpropyl, N,N-di(1,1-dimethylethyl)aminocarbonylpropyl, N-ethyl-N-methylaminocarbonylpropyl, N-methyl-N-propylaminocarbonylpropyl, N-methyl-N-(1-methylethyl)aminocarbonylpropyl, N-butyl-N-methylaminocarbonylpropyl, N-methyl-N-(1-methylpropyl)aminocarbonylpropyl, N-methyl-N-(2-methylpropyl)aminocarbonylpropyl, N-(1,1-dimethylethyl)-N-methylaminocarbonylpropyl, N-ethyl-N-propylaminocarbonylpropyl, N-ethyl-N-(1-methylethyl)aminocarbonylpropyl, N-butyl-N-ethylaminocarbonylpropyl, N-ethyl-N-(1-methylpropyl)aminocarbonylpropyl, N-ethyl-N-(2-methylpropyl)aminocarbonylpropyl, N-ethyl-N-(1,1-dimethylethyl)aminocarbonylpropyl, N-(1-methylethyl)-N-propylaminocarbonylpropyl, N-butyl-N-propylaminocarbonylpropyl, N-(1-methylpropyl)-N-propylaminocarbonylpropyl, N-(2-methylpropyl)-N-propylaminocarbonylpropyl, N-(1,1-dimethylethyl)-N-propylaminocarbonylpropyl, N-butyl-N-(1-methylethyl)aminocarbonylpropyl, N-(1-methylethyl)-N-(1-methylpropyl)aminocarbonylpropyl, N-(1-methylethyl)-N-(2-methylpropyl)aminocarbonylpropyl, N-(1,1-dimethylethyl)-N-(1-methylethyl)aminocarbonylpropyl, N-butyl-N-(1-methylpropyl)aminocarbonylpropyl, N-butyl-N-(2-methylpropyl)aminocarbonylpropyl, N-butyl-N-(1,1-dimethylethyl)aminocarbonylpropyl, N-(1-methylpropyl)-N-(2-methylpropyl)aminocarbonylpropyl, N-(1,1-dimethylethyl)-N-(1-methylpropyl)aminocarbonylpropyl, N-(1,1-dimethylethyl)-N-(2-methylpropyl)aminocarbonylpropyl, N,N-dimethylaminocarbonylbutyl, N,N-diethylaminocarbonylpropyl, N,N-dipropylaminocarbonylbutyl, N,N-di(1-methylethyl)aminocarbonylbutyl, N,N-dibutylaminocarbonylbutyl, N,N-di(1-methylpropyl)aminocarbonylbutyl, N,N-di(2-methylpropyl)aminocarbonylbutyl, N,N-di(1,1-dimethylethyl)aminocarbonylbutyl, N-ethyl-N-methylaminocarbonylbutyl, N-methyl-N-propylaminocarbonylbutyl, N-methyl-N-(1-methylethyl)aminocarbonylbutyl, N-butyl-N-methylaminocarbonylbutyl, N-methyl-N-(1-methylpropyl)aminocarbonylbutyl, N-methyl-N-(2-methylpropyl)aminocarbonylbutyl, N-(1,1-dimethylethyl)-N-methylaminocarbonylbutyl, N-ethyl-N-propylaminocarbonylbutyl, N-ethyl-N-(1-methylethyl)aminocarbonylbutyl, N-butyl-N-ethylaminocarbonylbutyl, N-ethyl-N-(1-methylpropyl)aminocarbonylbutyl, N-ethyl-N-(2-methylpropyl)aminocarbonylbutyl, N-ethyl-N-(1,1-dimethylethyl)aminocarbonylbutyl, N-(1-methylethyl)-N-propylaminocarbonylbutyl, N-butyl-N-propylaminocarbonylbutyl, N-(1-methylpropyl)-N-propylaminocarbonylbutyl, N-(2-methylpropyl)-N-propylaminocarbonylbutyl, N-(1,1-dimethylethyl)-N-propylaminocarbonylbutyl, N-butyl-N-(1-methylethyl)

aminocarbonylbutyl, N-(1-methylethyl)-N-(1-methylpropyl)aminocarbonylbutyl, N-(1-methylethyl)-N-(2-methylpropyl)aminocarbonylbutyl, N-(1,1-dimethylethyl)-N-(1-methylethyl)aminocarbonylbutyl, N-butyl-N-(1-methylpropyl)aminocarbonylbutyl, N-butyl-N-(2-methylpropyl)aminocarbonylbutyl, N-butyl-N-(1,1-dimethylethyl)aminocarbonylbutyl, N-(1-methylpropyl)-N-(2-methylpropyl)aminocarbonylbutyl, N-(1,1-dimethylethyl)-N-(1-methylpropyl)aminocarbonylbutyl or N-(1,1-dimethylethyl)-N-(2-methylpropyl)aminocarbonylbutyl;

$C_1$–$C_4$-alkoxy-$C_1$–$C_4$-alkoxy, and the alkoxyalkoxy moieties of $C_1$–$C_4$-alkoxy-$C_1$–$C_4$-alkoxycarbonyl: $C_1$–$C_4$-alkoxy which is substituted by $C_1$–$C_4$-alkoxy as mentioned above, i.e. for example methoxymethoxy, ethoxymethoxy, propoxymethoxy, (1-methylethoxy)methoxy, butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_3$–$C_6$-alkenyl and the alkenyl moieties of $C_3$–$C_6$-alkenylcarbonyl, $C_3$–$C_6$-alkenyloxycarbonyl, $C_3$–$C_6$-alkenylaminocarbonyl, N-($C_3$–$C_6$-alkenyl)-N-($C_1$–$C_6$-alkyl)aminocarbonyl, N-($C_3$–$C_6$-alkenyl)-N-($C_1$–$C_6$-alkoxy)aminocarbonyl: for example prop-2-en-1-yl, but-1-en-4-yl, 1-methylprop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkenyl and the alkenyl moieties of $C_2$–$C_6$-alkenylcarbonyl, phenyl-$C_2$–$C_6$-alkenylcarbonyl and heterocyclyl-$C_2$–$C_6$-alkenylcarbonyl: $C_3$–$C_6$-alkenyl as mentioned above, and ethenyl;

$C_3$–$C_6$-haloalkenyl: a $C_3$–$C_6$-alkenyl radical as mentioned above which is partially or fully substituted by fluorine, chlorine, bromine and/or iodine, ie. for example 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-3-enyl;

$C_3$–$C_6$-alkynyl, and the alkynyl moieties of $C_3$–$C_6$-alkynylcarbonyl, $C_3$–$C_6$-alkynyloxycarbonyl, $C_3$–$C_6$-alkynylaminocarbonyl, N-($C_3$–$C_6$-alkynyl)-N-($C_1$–$C_6$-alkyl)aminocarbonyl, N-($C_3$–$C_6$-alkynyl)-N-($C_1$–$C_6$-alkoxy)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl, and the alkynyl moieties of $C_2$–$C_6$-alkynylcarbonyl: $C_3$–$C_6$-alkynyl as mentioned above, and ethynyl;

$C_3$–$C_6$-haloalkynyl: a $C_3$–$C_6$-alkynyl radical as mentioned above which is partially or fully substituted by fluorine, chlorine, bromine and/or iodine, i.e. for example 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_3$–$C_6$-cycloalkyl, and the cycloalkyl moieties of $C_3$–$C_6$-cycloalkylcarbonyl: for example cyclopropyl, cyclobutyl, cyclopentyl or cyclohexyl;

$C_3$–$C_6$-spirocycloalkane (a $C_3$–$C_6$-cycloalkyl radical where one ring member—the so-called spiro atom—belongs both to the $C_3$–$C_6$-cycloalkyl radical and to the radical to which the cyclic radical is attached): for example spirocyclopropyl, spirocyclobutyl, spirocyclopentyl or spirocyclohexyl;

heterocyclyl, and heterocyclyl moieties of heterocyclylcarbonyl, heterocyclyl-$C_1$–$C_6$-alkyl, heterocyclyloxycarbonyl, heterocyclylcarbonyl-$C_1$–$C_6$-alkyl, N-($C_1$–$C_6$-alkyl)-N-(heterocyclyl)aminocarbonyl, heterocyclylaminocarbonyl: a saturated, partially saturated or unsaturated 5- or 6-membered heterocyclic ring which contains one to four identical or different hetero atoms selected from the following group: oxygen, sulfur or nitrogen, and can be bonded via C or N, i.e. for example C-bonded 5-membered saturated rings such as:

tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bonded 5-membered partially saturated rings such as:
2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl;

C-bonded 5-membered unsaturated rings such as:
2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bonded 6-membered saturated rings such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

C-bonded 6-membered partially saturated rings such as:
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5- dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-thiazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

C-bonded 6-membered unsaturated rings such as:

pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bonded 5-membered saturated rings such as:

tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bonded 5-membered partially saturated rings such as:

2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydro-isoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl;

N-bonded 5-membered unsaturated rings such as:

pyrrol-1-yl, pyrazol-1-yl, imidazol-1-yl, 1,2,3-triazol-1-yl, 1,2,4-triazol-1-yl, tetrazol-1-yl;

N-bonded 6-membered saturated rings such as:

piperidin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl; and N-bonded 6-membered partially saturated rings such as:

1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

where, if appropriate, the sulfur of the heterocycles mentioned may be oxidized to S=O or S(=O)$_2$
and where a bicyclic ring system may be formed together with a fused phenyl ring or a C$_3$–C$_6$-carbocycle or a further 5- to 6-membered heterocycle.

All phenyl rings or heterocyclyl radicals (except for the radicals mentioned under R$^2$) and all phenyl components in phenyl-C$_1$–C$_6$-alkyl, phenylcarbonyl-C$_1$–C$_6$-alkyl, phenylcarbonyl, phenylalkenylcarbonyl, phenoxycarbonyl, phenylaminocarbonyl and N-(C$_1$–C$_6$-alkyl)-N-phenylaminocarbonyl or heterocyclyl components in heterocyclyl-C$_1$–C$_6$-alkyl, heterocyclylcarbonyl-C$_1$–C$_6$-alkyl, heterocyclylcarbonyl, heterocyclylalkenylcarbonyl, heterocyclyloxycarbonyl, heterocyclylaminocarbonyl and N-(C$_1$–C$_6$-alkyl)-N-heterocyclylaminocarbonyl are, unless stated otherwise, preferably unsubstituted or carry one to three halogen atoms and/or one nitro group, one cyano radical and/or one or two methyl, trifluoromethyl, methoxy or trifluoromethoxy substituents.

With respect to the use of the compounds of the formula I according to the invention as herbicides, the variables preferably have the following meanings, in each case either on their own or in combination:

R$^1$ is nitro, halogen, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl or C$_1$–C$_6$-haloalkylsulfonyl; particularly preferably nitro, halogen, such as chlorine or bromine, C$_1$–C$_6$-alkyl such as methyl or ethyl, C$_1$–C$_6$-alkoxy such as methoxy or ethoxy, C$_1$–C$_6$-haloalkyl such as trifluoromethyl, C$_1$–C$_6$-alkylsulfonyl such as methylsulfonyl or ethylsulfonyl, or C$_1$–C$_6$-haloalkylsulfonyl such as trifluoromethylsulfonyl;

R$^2$ is a 5- or 6-membered C-bonded heterocyclyl radical with or without substitution which contains one to four identical or different hetero atoms selected from the following group: oxygen, sulfur or nitrogen;

is particularly preferably a 5-membered C-bonded heterocyclyl radical with or without substitution which contains one to three identical or different hetero atoms selected from the following group: oxygen, sulfur or nitrogen; very particularly preferably a 5-membered C-bonded saturated or partially saturated heterocyclyl radical with or without substitution which contains one to three identical or different hetero atoms selected from the following group: oxygen, sulfur or nitrogen; most particularly preferably a 5-membered C-bonded saturated or partially unsaturated heterocyclyl radical which contains two identical or different hetero atoms selected from the following group: oxygen, sulfur or nitrogen, where the heterocyclyl radical is unsubstituted or carries one or two substituents from the following group:

halogen such as chlorine or bromine, cyano, C$_1$–C$_4$-alkyl such as methyl, ethyl, propyl, 1-methylethyl or 2-methylpropyl, C$_1$–C$_4$-alkoxy-C$_1$–C$_4$-alkyl such as 2-methoxyethyl or 2-ethoxyethyl, C$_1$–C$_4$-haloalkyl such as, for example, chloromethyl, bromomethyl, fluoromethyl, difluoromethyl or trifluoromethyl, C$_3$–C$_6$-cycloalkyl such as cyclopropyl, cyclopentyl or cyclohexyl, C$_1$–C$_4$-alkoxy such as methoxy or ethoxy, C$_1$–C$_4$-haloalkoxy such as, for example, difluoromethoxy or 2,2,2-trifluoroethoxy, C$_1$–C$_4$-alkylthio such as methylthio or ethylthio, di(C$_1$–C$_4$-alkyl)amino such as dimethylamino or diethylamino, C$_1$–C$_4$-alkoxycarbonyl such as methoxycarbonyl, ethoxycarbonyl, propoxycarbonyl or 1-methylethoxycarbonyl, C$_1$–C$_4$-alkylaminocarbonyl such as methylaminocarbonyl or ethylaminocarbonyl, di(C$_1$–C$_4$-alkyl)aminocarbonyl such as dimethylaminocarbonyl or diethylaminocarbonyl, phenyl which may be partially or fully halogenated and/or may carry one to three of the following groups: nitro, cyano, C$_1$–C$_4$-alkyl, C$_1$–C$_4$-haloalkyl, C$_1$–C$_4$-alkoxy or C$_1$–C$_4$-haloalkoxy;

hydroxyl

C$_3$–C$_6$-spirocycloalkane where one carbon may be replaced by oxygen, such as spirocyclopentane, spirocyclohexane or 4-spirotetrahydropyrane and/or forms a bicyclic system with a fused phenyl ring, a C$_3$–C$_6$-carbocycle. From among these substituents, particular preference is given to the following: C$_1$–C$_4$-alkyl, C$_3$–C$_6$-cycloalkyl, C$_1$–C$_4$-haloalkyl, C$_1$–C$_4$-alkoxy-C$_1$–C$_4$-alkyl, C$_1$–C$_4$-alkoxy and C$_1$–C$_4$-alkoxycarbonyl;

likewise, very particular preference is given to a 5-membered C-bonded heterocyclyl radical with or without substitution which contains two identical or different hetero atoms selected from the following group: oxygen, sulfur or nitrogen; most particular preference is given to a 5-membered C-bonded heterocyclyl radical which contains two identical or different hetero atoms selected from the following group: oxygen, sulfur or nitrogen, where the heterocyclyl radical is unsubstituted or carries one or two substituents from the following group:

halogen such as chlorine or bromine, cyano, C$_1$–C$_4$-alkyl such as methyl, ethyl, propyl, 1-methylethyl or 2-methylpropyl, C$_1$–C$_4$-alkoxy-C$_1$–C$_4$-alkyl such as 2-methoxyethyl or 2-ethoxyethyl, C$_1$–C$_4$-haloalkyl such as, for example, chloromethyl, bromomethyl, fluoromethyl, difluoromethyl or trifluoromethyl, C$_3$–C$_6$-cycloalkyl such as cyclopropyl, cyclopentyl or cyclohexyl, C$_1$–C$_4$-alkoxy such as methoxy or ethoxy, C$_1$–C$_4$-haloalkoxy such as, for example, difluoromethoxy or 2,2,2-trifluoroethoxy, C$_1$–C$_4$-alkylthio such as methylthio or ethylthio, di(C$_1$–C$_4$-alkyl)amino such as dimethylamino or diethylamino, C$_1$–C$_4$-alkoxycarbonyl such as methoxycarbonyl, ethoxycarbonyl, propoxycarbonyl or 1-methylethoxycarbonyl, C$_1$–C$_4$-alkylaminocarbonyl such as methylaminocarbonyl or ethylaminocarbonyl, di(C$_1$–C$_4$-alkyl)aminocarbonyl such as dimethylaminocarbonyl or diethylaminocarbonyl, phenyl which may be partially or fully halogenated and/or may carry one to three of the following groups: nitro, cyano, C$_1$–C$_4$-alkyl, C$_1$–C$_4$-haloalkyl, C$_1$–C$_4$-alkoxy or C$_1$–C$_4$-haloalkoxy;

hydroxyl

C$_3$–C$_6$-spirocycloalkane where one carbon may be replaced by oxygen, such as spirocyclopentane, spirocyclohexane or 4-spirotetrahydropyrane and/or forms a bicyclic system with a fused phenyl ring, a C$_3$–C$_6$-carbocycle. From among these substituents, particular preference is given to the following: C$_1$–C$_4$-alkyl, C$_3$–C$_6$-cycloalkyl, C$_1$–C$_4$-haloalkyl, C$_1$–C$_4$-alkoxy-C$_1$–C$_4$-alkyl, C$_1$–C$_4$-alkoxy and C$_1$–C$_4$-alkoxycarbonyl;

likewise, particular preference is given to a 6-membered C-bonded saturated, partially saturated or unsaturated heterocyclyl radical with or without substitution which contains one to three identical or different hetero atoms selected from the following group: oxygen, sulfur and nitrogen;

very particular preference is given to a 6-membered C-bonded saturated, partially saturated or unsaturated heterocyclyl radical with or without substitution which contains two identical or different hetero atoms selected from the following group: oxygen, sulfur or nitrogen;

likewise, particular preference is given to a 5- or 6-membered N-bonded saturated, partially saturated or unsaturated heterocyclyl radical with or without substitution which contains one to three identical or different hetero atoms selected from the following group: oxygen, sulfur or nitrogen;

$R^3$ is nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl; particularly preferably nitro, halogen, such as chlorine or bromine, $C_1$–$C_6$-haloalkyl such as trifluoromethyl, $C_1$–$C_6$-alkylsulfonyl such as methylsulfonyl, ethylsulfonyl or propylsulfonyl, or $C_1$–$C_6$-haloalkylsulfonyl such as trifluoromethylsulfonyl;

$R^4$ is hydrogen;

$R^6$ is $C_1$–$C_6$-alkyl; particularly preferably $C_1$–$C_4$-alkyl; very particularly preferably methyl, ethyl, propyl, 2-methylprop-1-yl or butyl;

$R^7$ is $C_1$–$C_6$-alkyl, $C_3$–$C_6$-alkenyl, $C_3$–$C_6$-alkynyl, $C_1$–$C_6$-alkylcarbonyl, $C_2$–$C_6$-alkenylcarbonyl, $C_3$–$C_6$-cycloalkylcarbonyl, $C_1$–$C_6$-alkoxycarbonyl, $C_1$–$C_6$-alkylaminocarbonyl, di($C_1$–$C_6$-alkyl)aminocarbonyl, N-($C_1$–$C_6$-alkoxy)-N-($C_1$–$C_6$-alkyl)aminocarbonyl, di($C_1$–$C_6$-alkyl)aminothiocarbonyl, $C_1$–$C_6$-alkoxyimino-$C_1$–$C_6$-alkyl, where the alkyl, cycloalkyl and alkoxy radicals mentioned may be partially or fully halogenated and/or may carry one to three of the following groups: cyano, hydroxyl, $C_1$–$C_4$-alkoxy, $C_1$–$C_4$-alkylthio, $C_1$–$C_4$-alkylcarbonyl, di($C_1$–$C_4$-alkyl)amino, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl; phenyl, phenyl-$C_1$–$C_6$-alkyl, phenylcarbonyl-$C_1$–$C_6$-alkyl, phenyl-$C_2$–$C_6$-alkenylcarbonyl or phenylcarbonyl where the phenyl radical of the last 5 substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

particularly preferably $C_1$–$C_6$-alkyl, $C_3$–$C_6$-alkenyl, $C_3$–$C_6$-alkynyl, $C_1$–$C_6$-alkylcarbonyl, $C_2$–$C_6$-alkenylcarbonyl, $C_1$–$C_6$-alkoxycarbonyl, di($C_1$–$C_6$-alkyl)aminocarbonyl, N-($C_1$–$C_6$-alkoxy)-N-($C_1$–$C_6$-alkyl)aminocarbonyl or di($C_1$–$C_6$-alkyl)aminothiocarbonyl, where the alkyl or alkoxy radicals mentioned may be partially or fully halogenated and/or may carry one to three of the following groups: cyano, $C_1$–$C_4$-alkoxy, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, $C_1$–$C_4$-alkylaminocarbonyl, di-($C_1$–$C_4$-alkyl)aminocarbonyl or $C_1$–$C_4$-alkylcarbonyloxy;

phenyl-$C_1$–$C_6$-alkyl, phenylcarbonyl-$C_1$–$C_6$-alkyl, phenyl-$C_2$–$C_6$-alkenylcarbonyl or phenylcarbonyl, where the phenyl ring of the last 4 substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

very particularly preferably $C_1$–$C_6$-alkyl, $C_1$–$C_6$-cyanoalkyl, $C_1$–$C_4$-alkoxy-$C_1$–$C_6$-alkyl, $C_1$–$C_4$-alkylcarbonyloxy-$C_1$–$C_6$-alkyl, $C_1$–$C_4$-alkoxycarbonyl-$C_1$–$C_6$-alkyl, $C_1$–$C_4$-alkoxy-$C_1$–$C_4$-alkoxycarbonyl-$C_1$–$C_6$-alkyl, di($C_1$–$C_4$-alkyl)amino-$C_1$–$C_4$-alkoxycarbonyl-$C_1$–$C_6$-alkyl, $C_1$–$C_4$-alkylaminocarbonyl-$C_1$–$C_6$-alkyl, di($C_1$–$C_4$-alkyl)aminocarbonyl-$C_1$–$C_6$-alkyl, $C_3$–$C_6$-alkenyl, $C_3$–$C_6$-alkynyl, $C_1$–$C_6$-alkylcarbonyl, $C_2$–$C_6$-alkenylcarbonyl, $C_1$–$C_6$-alkoxycarbonyl, di($C_1$–$C_6$-alkyl)aminocarbonyl, N-($C_1$–$C_6$-alkoxy)-N-($C_1$–$C_6$-alkyl)aminocarbonyl, di($C_1$–$C_6$-alkyl)aminothiocarbonyl, phenyl-$C_1$–$C_6$-alkyl, phenylcarbonyl-$C_1$–$C_6$-alkyl, phenyl-$C_2$–$C_6$-alkenylcarbonyl or phenylcarbonyl, where the phenyl ring of the last 4 substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^8$ is hydrogen or $C_1$–$C_6$-alkyl; in particular hydrogen or methyl.

Very particular preference is given to compounds of the formula I where $R^2$ is 2-furyl, 3-furyl, 2-thienyl, 3-thienyl, pyrrol-1-yl, pyrrol-2-yl, tetrahydrooxazol-2-yl, tetrahydrothiazol-2-yl, 1,3-dioxolan-2-yl, 1,3-oxathiolan-2-yl, 1,3-dithiolan-2-yl, 4,5-dihydroisoxazol-3-yl, 4,5-dihydro-1H-imidazol-2-yl, 4,5-dihydrooxazol-2-yl, 4,5-dihydrothiazol-2-yl, pyrazol-3-yl, pyrazol-4-yl, isoxazol-3-yl, isoxazol-5-yl, isothiazol-3-yl, oxazol-2-yl, oxazol-5-yl, thiazol-2-yl, thiazol-4-yl, thiazol-5-yl, 1,2,4-oxadiazol-3-yl, 1,3,4-oxadiazol-2-yl, 1,2,4-thiadiazol-5-yl, 1,3,4-thiadiazol-2-yl, 1,2,4-triazol-1-yl, 1,2,4-triazol-3-yl, pyridin-2-yl, pyridin-3-yl, pyridin-4-yl, 1,3-dioxan-2-yl, 1,3-dithian-2-yl, 1,3-oxathian-2-yl, tetrahydro-1,3-oxazin-2-yl, tetrahydro-1,3-thiazin-2-yl, 4H-5,6-dihydro-1,3-thiazin-2-yl, 3H-1,2,4-dithiazol-5-yl, 2H-1,3,4-dithiazol-5-yl or 2H-1,3,4-oxathiazol-5-yl;

with or without substitution.

Most particular preference is given to compounds of the formula I where $R^2$ is 1,3-dioxolan-2-yl, 1,3-dithiolan-2-yl, 4,5-dihydrothiazol-2-yl, isoxazol-3-yl, oxazol-2-yl, thiazol-2-yl, 4,5-dihydroisoxazol-3-yl, 4,5-dihydrooxazol-2-yl, 1,3-dioxan-2-yl, 1,3-dithian-2-yl or 4H-5,6-dihydro-1,3-thiazin-2-yl with or without substitution; particularly preferably thiazol-2-yl, 1,3-dithiolan-2-yl, 1,3-dioxan-2-yl, 4,5-dihydrothiazol-2-yl, 4,5-dihydroisoxazol-3-yl or isoxazol-3-yl with or without substitution.

Likewise, very particular preference is given to the compounds of the formula I where $R^2$ is tetrahydrooxazol-2-yl, tetrahydrothiazol-2-yl, 1,3-dioxolan-2-yl, 1,3-oxathiolan-2-yl, 1,3-dithiolan-2-yl, 4,5-dihydroisoxazol-3-yl, 4,5-dihydro-1H-imidazol-2-yl, 4,5-dihydrooxazol-2-yl, 4,5-dihydrothiazol-2-yl, 3H-1,2,4-dithiazol-5-yl, 2H-1,3,4-dithiazol-5-yl or 2H-1,3,4-oxathiazol-5-yl with or without substitution.

Most particular preference is given to the compounds of the formula I where $R^2$ is 1,3-dioxolan-2-yl, 1,3-dithiolan-2-yl, 4,5-dihydrothiazol-2-yl, 4,5-dihydroisoxazol-3-yl or 4,5-dihydrooxazol-2-yl with or without substitution; very particularly preferably 1,3-dithiolan-2-yl, 4,5-dihydrothiazol-2-yl or 4,5-dihydroisoxazol-3-yl with or without substitution; most particularly preferably 4,5-dihydroisoxazol-3-yl with or without substitution.

Likewise, very particular preference is given to the compounds of the formula I where $R^2$ is pyridin-2-yl, pyridin-3-yl, pyridin-4-yl, 1,3-dioxan-2-yl, 1,3-dithian-2-yl, 1,3-oxathian-2-yl, tetrahydro-1,3-oxazin-2-yl, tetrahydro-1,3-thiazin-2-yl or 4H-5,6-dihydro-1,3-thiazin-2-yl with or without substitution.

Most particular preference is given to the compounds of the formula I where $R^2$ is 1,3-dioxan-2-yl, 1,3-dithian-2-yl or 4H-4,5-dihydrothiazin-2-yl with or without substitution; very particularly preferably 1,3-dioxan-2-yl with or without substitution.

Likewise, very particular preference is given to the compounds of the formula I where $R^2$ is 2-furyl, 3-furyl, 2-thienyl, 3-thienyl, pyrrol-1-yl, pyrrol-2-yl, pyrazol-3-yl, pyrazol-4-yl, isoxazol-3-yl, isoxazol-4-yl, isothiazol-3-yl, oxazol-2-yl, oxazol-5-yl, thiazol-2-yl, thiazol-4-yl, thiazol-5-yl, 1,2,4-oxadiazol-3-yl, 1,2,4-oxadiazol-5-yl, 1,3,4-oxadiazol-2-yl, 1,2,4-thiadiazol-5-yl, 1,3,4-thiadiazol-2-yl, 1,2,4-triazol-1-yl or 1,2,4-triazol-3-yl with or without substitution;

$R^7$ is $C_1$–$C_6$-alkyl, $C_3$–$C_6$-alkenyl, $C_3$–$C_6$-alkynyl, $C_1$–$C_6$-alkylcarbonyl, $C_2$–$C_6$-alkenylcarbonyl, $C_3$–$C_6$-cycloalkylcarbonyl, $C_1$–$C_6$-alkoxycarbonyl, $C_1$–$C_6$-alkylaminocarbonyl, di($C_1$–$C_6$-alkyl)aminocarbonyl, N-($C_1$–$C_6$-alkoxy)-N-($C_1$–$C_6$-alkyl)aminocarbonyl, di($C_1$–$C_6$-alkyl)aminothiocarbonyl, $C_1$–$C_6$-alkoxyimino-$C_1$–$C_6$-alkyl, where the alkyl, cycloalkyl or alkoxy radicals mentioned may be partially or fully halogenated and/or may carry one to three of the following groups: cyano, hydroxyl, $C_1$–$C_4$-alkoxy, $C_1$–$C_4$-alkylthio, $C_1$–$C_4$-alkylcarbonyl, di($C_1$–$C_4$-alkyl)amino, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl.

Most particular preference is given to the compounds of the formula I where $R^2$ is isoxazol-3-yl, oxazol-2-yl or thiazol-2-yl with or without substitution; very particularly preferably isoxazol-3-yl or thiazol-2-yl with or without substitution.

Most particular preference is given to the compounds Ia1 (=I where $R^1$=Cl, $R^3$=$SO_2CH_3$, $R^6$, $R^7$=$CH_3$ and $R^8$=H), in particular the compounds of Table 1.

TABLE 1

| No. | $R^2$ | $R^4$ |
|---|---|---|
| Ia.1 | 2-thienyl | H |
| Ia.2 | 3-thienyl | H |
| Ia.3 | 2-furyl | H |

TABLE 1-continued

| No. | $R^2$ | $R^4$ |
|---|---|---|
| Ia.4 | 3-furyl | H |
| Ia.5 | 3-methylisoxazol-5-yl | H |
| Ia.6 | 5-thiazolyl | H |
| Ia.7 | 4-thiazolyl | H |
| Ia.8 | 2-thiazolyl | H |
| Ia.9 | 3-methylisothiazol-5-yl | H |
| Ia.10 | 3-isoxazolyl | H |
| Ia.11 | 5-phenylthiazol-2-yl | H |
| Ia.12 | 2-pyridyl | H |
| Ia.13 | 3-pyridyl | H |
| Ia.14 | 4-pyridyl | H |
| Ia.15 | 1-methyl-2-pyrrolyl | H |
| Ia.16 | 1-methyl-1,2,4-triazol-5-yl | H |
| Ia.17 | 2-benzothiazolyl | H |
| Ia.18 | 2-quinolinyl | H |
| Ia.19 | 1-methylbenzimidazol-2-yl | H |
| Ia.20 | 2-oxazolyl | H |
| Ia.21 | 1-phenylpyrazol-5-yl | H |
| Ia.22 | 1-methylpyrazol-3-yl | H |
| Ia.23 | 1-methylpyrazol-5-yl | H |
| Ia.24 | 1,5-dimethylpyrazol-3-yl | H |
| Ia.25 | 1-phenylpyrazol-3-yl | H |
| Ia.26 | 1,4-dimethylpyrazol-5-yl | H |
| Ia.27 | 1,3-dimethylpyrazol-4-yl | H |
| Ia.28 | 1,5-dimethylpyrazol-4-yl | H |
| Ia.29 | 1-methylpyrazol-4-yl | H |
| Ia.30 | 1,3-dimethylpyrazol-5-yl | H |
| Ia.31 | 4-methyloxazol-2-yl | H |
| Ia.32 | 5-methylthiothiazol-2-yl | H |
| Ia.33 | 4-methoxy-1-methylpyrazol-5-yl | H |
| Ia.34 | 3-cyclopropylisoxazol-5-yl | H |
| Ia.35 | 5-methylisoxazol-3-yl | H |
| Ia.36 | 4-methyl-5-phenylthiazol-2-yl | H |
| Ia.37 | 5-methylthiazol-2-yl | H |
| Ia.38 | 44-bromo-2-thienyl | H |
| Ia.39 | 5-methyl-2-thienyl | H |
| Ia.40 | 4-methyl-2-thienyl | H |
| Ia.41 | 4-methylthiazol-2-yl | H |
| Ia.42 | 4-chlorothiazol-2-yl | H |
| Ia.43 | 4,5-dimethylthiazol-2-yl | H |
| Ia.44 | 4-phenylthiazol-2-yl | H |
| Ia.45 | 2-methoxythiazol-5-yl | H |
| Ia.46 | 4-methyl-2-pyridyl | H |
| Ia.47 | 6-(2-methoxyethyl)-2-pyridyl | H |
| Ia.48 | 6-methylthio-2-pyridyl | H |
| Ia.49 | 6-methoxy-3-pyridyl | H |
| Ia.50 | 6-methoxy-2-pyridyl | H |
| Ia.51 | 6-methyl-2-pyridyl | H |
| Ia.52 | 6-(2,2,2-trifluoroethoxy)-2-pyridyl | H |
| Ia.53 | 6-(2,2,2-trifluoroethoxy)-3-pyridyl | H |
| Ia.54 | 5-pyrimidinyl | H |
| Ia.55 | 6-dimethylamino-3-pyridyl | H |
| Ia.56 | 1,2,4-thiadiazol-5-yl | H |
| Ia.57 | 3-ethoxycarbonyl-1-methylpyrazol-5-yl | H |
| Ia.58 | 2-methylthiopyrimidin-5-yl | H |
| Ia.59 | 2-pyrimidinyl | H |
| Ia.60 | 2-methylthiopyrimidin-4-yl | H |
| Ia.61 | 5-methylthio-1,3,4-thiadiazol-2-yl | H |
| Ia.62 | 5-methoxy-1,3,4-thiadiazol-2-yl | H |
| Ia.63 | 4,5-dihydrothiazol-2-yl | H |
| Ia.64 | 5-methyloxazol-2-yl | H |
| Ia.65 | 5-phenyloxazol-2-yl | H |
| Ia.66 | 2-methyloxazol-5-yl | H |
| Ia.67 | 2-phenyloxazol-5-yl | H |
| Ia.68 | 2-methyl-1,3,4-oxadiazol-5-yl | H |
| Ia.69 | 2-phenyl-1,3,4-oxadiazol-5-yl | H |

TABLE 1-continued

| No. | R² | R⁴ |
|---|---|---|
| Ia.70 | 5-trifluoromethyl-1,2,4-oxadiazol-3-yl | H |
| Ia.71 | 5-methyl-1,2,4-oxadiazol-3-yl | H |
| Ia.72 | 5-phenyl-1,2,4-oxadiazol-3-yl | H |
| Ia.73 | 5-phenylisoxazol-3-yl | H |
| Ia.74 | 1-(4-chlorophenyl)-1,2,4-triazol-3-yl | H |
| Ia.75 | 5-cyano-4,5-dihydroisoxazol-3-yl | H |
| Ia.76 | 5,6-dihydro-4H-1,3-thiazin-2-yl | H |
| Ia.77 | 1,3-dithiolan-2-yl | H |
| Ia.78 | 1,3-dioxolan-2-yl | H |
| Ia.79 | 5,5-dimethyl-1,3-dioxan-2-yl | H |
| Ia.80 | 1,3-dithian-2-yl | H |
| Ia.81 | 5,5-dimethyl-1,3-dithian-2-yl | H |
| Ia.82 | 1,3-dioxan-2-yl | H |
| Ia.83 | 1,3-oxathiolan-2-yl | H |
| Ia.84 | 1,2,4-triazol-1-yl | H |
| Ia.85 | 3-methyl-1,2,4-thiadiazol-5-yl | H |
| Ia.86 | 1,2,4-thiadiazol-5-yl | H |
| Ia.87 | thiazolin-4,5-dion-2-yl | H |
| Ia.88 | 3-oxo-3-H-1,2,4-dithiazol-5-yl | H |
| Ia.89 | 2-oxo-2-H-1,3,4-dithiazol-5-yl | H |
| Ia.90 | 1-pyrrolyl | H |
| Ia.91 | 5,5-dimethy-4,5-diihydroisoxazol-3-yl | H |
| Ia.92 | 4,5-dihydroisoxazol-3-yl | H |
| Ia.93 | 5-ethyl-4,5-diihydroisoxazol-3-yl | H |
| Ia.94 | 5,5-diethyl-4,5-dihydroisoxazol-3-yl | H |
| Ia.95 | (4,5-dihydroisoxazol-spirocyclopentan)-3-yl | H |
| Ia.96 | 4,5-dihydrooxazol-2-yl | H |
| Ia.97 | 5-methyl-4,5-dihydrooxazol-2-yl | H |
| Ia.98 | 4,4-dimethyl-4,5-dihydrooxazol-2-yl | H |
| Ia.99 | 5-ethyl-4,5-dihydrooxazol-2-yl | H |
| Ia.100 | 5,5-dimethyl-4,5-dihydrooxazol-2-yl | H |
| Ia.101 | 4,5-dimethyl-4,5-dihydrooxazol-2-yl | H |
| Ia.102 | 4,5-diethyl-4,5-dihydrooxazol-2-yl | H |
| Ia.103 | 5,5-dimethyl-4-oxooxazolin-2-yl | H |
| Ia.104 | 5,5-diethyl-4-oxooxazolin-2-yl | H |
| Ia.105 | 5-methyl-4-oxo-2-oxazolin-2-yl | H |
| Ia.106 | 4-ethyl-4-oxo-2-oxazolin-2-yl | H |
| Ia.107 | 4-oxo-2-oxazolin-2-yl | H |
| Ia.108 | 5-methyl-4,5-dihydrothiazol-2-yl | H |
| Ia.109 | 5-ethyl-4,5-dihydrothiazol-2-yl | H |
| Ia.110 | 4,4-dimethyl-4,5-dihydrothiazol-2-yl | H |
| Ia.111 | 5,5-dimethyl-4,5-dihydrothiazol-2-yl | H |
| Ia.112 | 4,5-dimethyl-4,5-dihydrothiazol-2-yl | H |
| Ia.113 | 5-methyl-4,5-dihydroimidazol-2-yl | H |
| Ia.114 | 5-ethyl-4,5-diihydroimidazol-2-yl | H |
| Ia.115 | 4,5-dihydroimidazol-2-yl | H |
| Ia.116 | 5,5-dimethyl-4,5-dihydroimidazol-2-yl | H |
| Ia.117 | 4,4-dimethyl-4,5-dihydroimidazol-2-yl | H |
| Ia.118 | 4,5-dimethyl-4,5-dihydroimidazol-2-yl | H |
| Ia.119 | 1,5-dimethyl-4,5-dihydroimidazol-2-yl | H |
| Ia.120 | 1-methyl-5-ethyl-4,5-dihydroimidazol-2-yl | H |
| Ia.121 | 1-methyl-4,5-dihydroimidazol-2-yl | H |
| Ia.122 | 1,5,5-trimethyl-4,5-dihydroimidazol-2-yl | H |
| Ia.123 | 1,4,4-trimethyl-4,5-dihydroimidazol-2-yl | H |
| Ia.124 | 1,4,5-trimethyl-4,5-dihydroimidazol-2-yl | H |
| Ia.125 | 5-oxo-2-thiazolin-2-yl | H |
| Ia.126 | 4-methyl-5-oxo-2-thiazolin-2-yl | H |
| Ia.127 | 4-ethyl-5-oxo-2-thiazolin-2-yl | H |
| Ia.128 | 4,4-dimethyl-5-oxo-2-thiazolin-2-yl | H |
| Ia.129 | 4,5-dihydro-5-oxo-1H-imidazol-2-yl | H |
| Ia.130 | 4-methyl-4,5-dihydro-5-oxo-1H-imidazol-2-yl | H |
| Ia.131 | 4-ethyl-4,5-dihydro-5-oxo-1H-imidazol-2-yl | H |
| Ia.132 | 4-isopropyl-4,5-dihydro-5-oxo-1H-imidazol-2-yl | H |
| Ia.133 | 4,4-dimethyl-4,5-dihydro-5-oxo-1H-imidazol-2-yl | H |
| Ia.134 | 4-isopropyl-4-methyl-4,5-dihydro-5-oxo-1H-imidazol-2-yl | H |
| Ia.135 | 1-methyl-4,5-dihydro-5-oxoimidazol-2-yl | H |
| Ia.136 | 1,4-dimethyl-4,5-dihydro-5-oxoimidazol-2-yl | H |
| Ia.137 | 1,4,4-trimethyl-4,5-dihydro-5-oxoimidazol-2-yl | H |
| Ia.138 | 5-methoxycarbonyl-4,5-dihydroisoxazol-3-yl | H |
| Ia.139 | 5-ethoxycarbonyl-4,5-dihydroisoxazol-3-yl | H |
| Ia.140 | 5-methylaminocarbonyl-4,5-dihydroisoxazol-3-yl | H |
| Ia.141 | 5-ethylaminocarbonyl-4,5-dihydroisoxazol-3-yl | H |
| Ia.142 | 5-dimethylaminocarbonyl-4,5-dihydroisoxazol-3-yl | H |
| Ia.143 | 5-methyl-4,5-dihydroisoxazol-3-yl | H |
| Ia.144 | 5-isopropyl-4,5-dihydroisoxazol-3-yl | H |
| Ia.145 | 5,5-dimethyl-4,5-dihydroisoxazol-3-yl | H |
| Ia.146 | (4,5-dihydroisoxazol-5-spiro-4-cyclopentan)-3-yl | H |
| Ia.147 | 4,5-dimethyl-4,5-dihydroisoxazol-3-yl | H |
| Ia.148 | 2-oxo-1,3,4-oxathiazol-5-yl | H |
| Ia.149 | 3a,5,6,6a-tetrahydro-4H-cyclopent[d]isoxazol-3-yl a) | H |
| Ia.150 | 3a,4,5,6,7,7a-hexahydro-1,2-benzoisoxazol-3-yl b) | H |
| Ia.151 | 1,3-thiazol-5(4H)-thion-2-yl | H |
| Ia.152 | 4-methyl-1,3-thiazol-5(4H)-thion-2-yl | H |
| Ia.153 | 4,4-dimethyl-1,3-thiazol-5(4H)-thion-2-yl | H |
| Ia.154 | 4,5-dihydro-5-oxo-1,2,4-oxadiazol-3-yl | H |
| Ia.155 | 4,5-dihydro-4-methyl-5-oxo-1,2,4-oxadiazol-3-yl | H |
| Ia.156 | 4,5-dihydro-5-methyl-1,2,4-oxadiazol-3-yl | H |
| Ia.157 | 4,5-dihydro-5-ethyl-1,2,4-oxadiazol-3-yl | H |
| Ia.158 | 4,5-dihydro-5,5-dimethyl-1,2,4-oxadiazol-3-yl | H |
| Ia.159 | 4,5-dihydro-4,5-dimethyl-1,2,4-oxadiazol-3-yl | H |
| Ia.160 | 4,5-dihydro-4,5,5-trimethyl-1,2,4-oxadiazol-3-yl | H |
| Ia.161 | 2,4-dihydro-1,2,4-triazol-3-on-5-yl | H |
| Ia.162 | 2,4-dihydro-methyl-1,2,4-triazol-3-on-5-yl | H |
| Ia.163 | 2,4-dihydro-1-methyl-1,2,4-triazol-3-on-5-yl | H |
| Ia.164 | 2,4-dihydro-1,4-dimethyl-1,2,4-triazol-3-on-5-yl | H | a) 3a,5,6,6a-tetrahydro-4H-cyclopent[d]isoxazol-3-yl is b) 3a,4,5,6,7,7a-hexahydro-1,2-benzoisoxazol-3-yl is Likewise, most particular preference is given to the compounds Ia2; in particular to the compounds Ia2.1–Ia2.164, which differ from the compounds Ia1.1–Ia1.164 in that $R^6$ is ethyl:

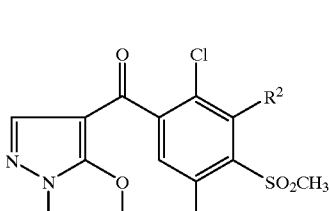

Ia2

Likewise, most particular preference is given to the compounds Ia3; in particular to the compounds Ia3.1–Ia3.164, which differ from the compounds Ia1.1–Ia1.164 in that $R^6$ is n-propyl:

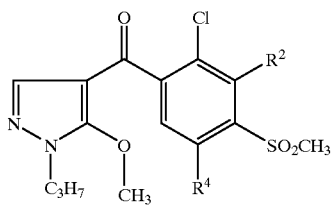
Ia3

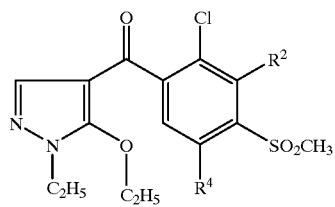
Ia7

Likewise, most particular preference is given to the compounds Ia4; in particular to the compounds Ia4.1–Ia4.164, which differ from the compounds Ia1.1–Ia1.164 in that $R^6$ is isobutyl:

Likewise, most particular preference is given to the compounds Ia8; in particular to the compounds Ia8.1–Ia8.164, which differ from the compounds Ia1.1–Ia1.164 in that $R^6$ is n-propyl and $R^7$ is ethyl:

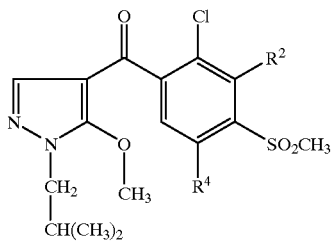
Ia4

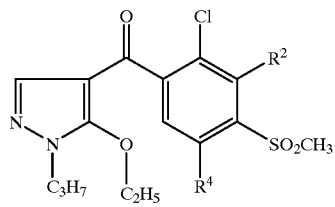
Ia8

Likewise, most particular preference is given to the compounds Ia5; in particular to the compounds Ia5.1–Ia5.164, which differ from the compounds Ia1.1–Ia1.164 in that $R^8$ is methyl:

Likewise, most particular preference is given to the compounds Ia9; in particular to the compounds Ia9.1–Ia9.164, which differ from the compounds Ia1.1–Ia1.164 in that $R^6$ is isobutyl and $R^7$ is ethyl:

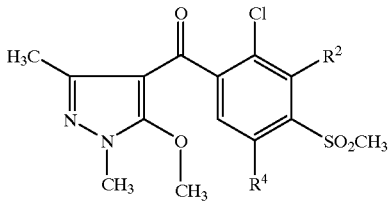
Ia5

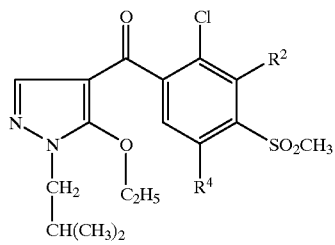
Ia9

Likewise, most particular preference is given to the compounds Ia.6; in particular to the compounds Ia6.1–Ia6.164, which differ from the compounds Ia1.1–Ia1.164 in that $R^7$ is ethyl:

Likewise, most particular preference is given to the compounds Ia10; in particular to the compounds Ia10.1–Ia10.164, which differ from the compounds Ia1.1–Ia1.164 in that $R^7$ is ethyl and $R^8$ is methyl:

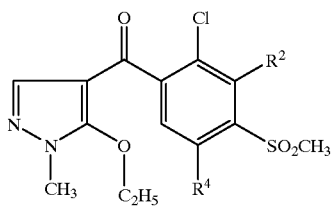
Ia6

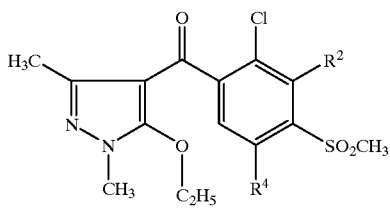
Ia10

Likewise, most particular preference is given to the compounds Ia7; in particular to the compounds Ia7.1–Ia7.164, which differ from the compounds Ia1.1–Ia1.164 in that $R^6$ and $R^7$ are each ethyl:

Likewise, most particular preference is given to the compounds Ia11; in particular to the compounds Ia11.1–Ia11.164, which differ from the compounds Ia1.1–Ia1.164 in that $R^7$ is cyanomethyl:

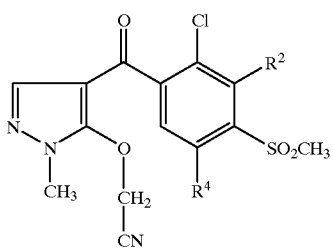
Ia11

Likewise, most particular preference is given to the compounds Ia12; in particular to the compounds Ia12.1–Ia12.164, which differ from the compounds Ia1.1–Ia1.164 in that $R^6$ is ethyl and $R^7$ is cyanomethyl:

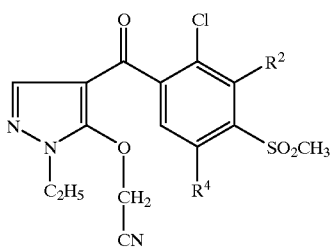
Ia12

Likewise, most particular preference is given to the compounds Ia13; in particular to the compounds Ia13.1–Ia13.164, which differ from the compounds Ia1.1–Ia1.164 in that $R^7$ is cyanomethyl and $R^8$ is methyl:

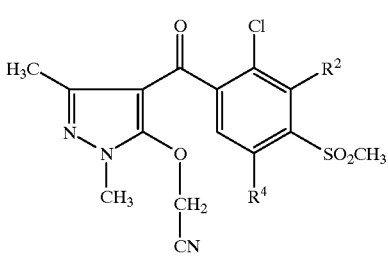
Ia13

Likewise, most particular preference is given to the compounds Ia14; in particular to the compounds Ia14.1–Ia14.164, which differ from the compounds Ia1.1–Ia1.164 in that $R^7$ is methoxymethyl:

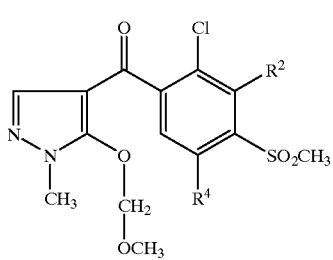
Ia14

Likewise, most particular preference is given to the compounds Ia15; in particular to the compounds Ia15.1–Ia15.164, which differ from the compounds Ia1.1–Ia1.164 in that $R^6$ is ethyl and $R^7$ is methoxymethyl:

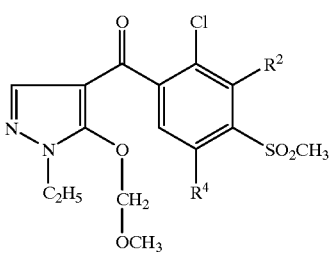
Ia15

Likewise, most particular preference is given to the compounds Ia16; in particular to the compounds Ia16.1–Ia16.164, which differ from the compounds Ia1.1–Ia1.164 in that $R^7$ is methoxymethyl and $R^8$ is methyl:

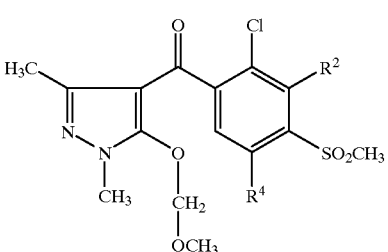
Ia16

Likewise, most particular preference is given to the compounds Ia17; in particular to the compounds Ia17.1–Ia17.164, which differ from the compounds Ia1.1–Ia1.164 in that $R^7$ is methylcarbonyloxymethyl:

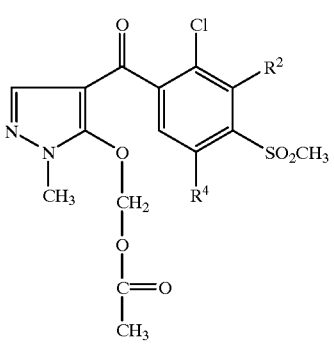
Ia17

Likewise, most particular preference is given to the compounds Ia18; in particular to the compounds Ia18.1–Ia18.164, which differ from the compounds Ia1.1–Ia1.164 in that $R^6$ is ethyl and $R^7$ is methylcarbonyloxymethyl:

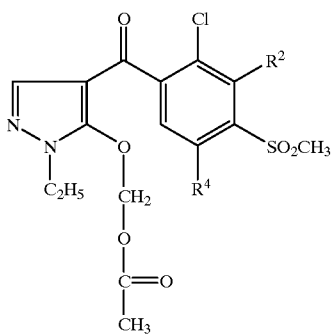

Ia18

Likewise, most particular preference is given to the compounds Ia19; in particular to the compounds Ia19.1–Ia19.164, which differ from the compounds Ia1.1–Ia1.164 in that $R^7$ is methylcarbonyloxymethyl and $R^8$ is methyl:

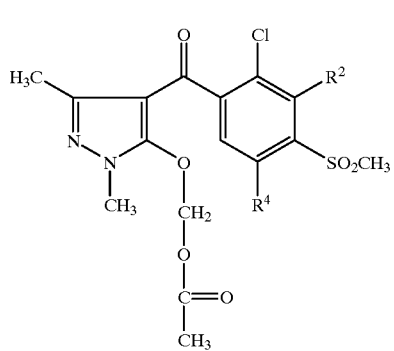

Ia19

Likewise, most particular preference is given to the compounds Ia20; in particular to the compounds Ia20.1–Ia20.164, which differ from the compounds Ia1.1–Ia1.164 in that $R^7$ is tert-butylcarbonyloxymethyl:

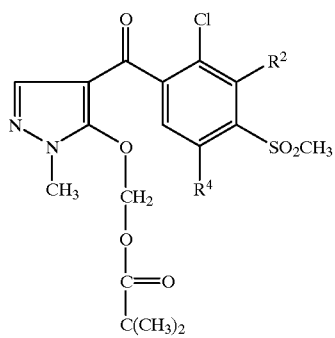

Ia20

Likewise, most particular preference is given to the compounds Ia21; in particular to the compounds Ia21.1–Ia21.164, which differ from the compounds Ia1.1–Ia1.164 in that $R^6$ is ethyl and $R^7$ is tert-butylcarbonyloxymethyl:

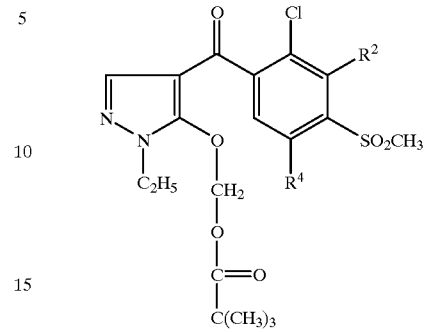

Ia21

Likewise, most particular preference is given to the compounds Ia22; in particular to the compounds Ia22.1–Ia22.164, which differ from the compounds Ia1.1–Ia1.164 in that $R^7$ is tert-butylcarbonyloxymethyl and $R^8$ is methyl:

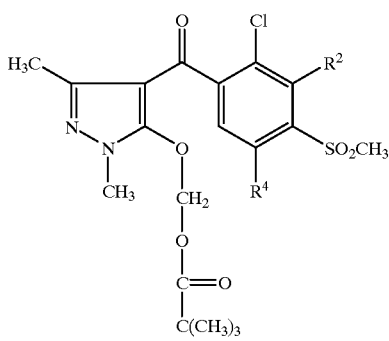

Ia22

Likewise, most particular preference is given to the compounds Ia23; in particular to the compounds Ia23.1–Ia23.164, which differ from the compounds Ia1.1–Ia1.164 in that $R^7$ is methoxycarbonylmethyl:

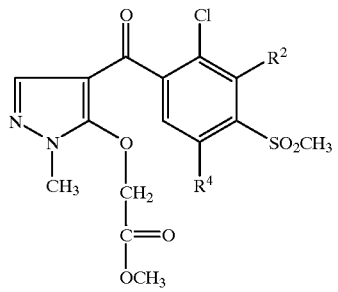

Ia23

Likewise, most particular preference is given to the compounds Ia24; in particular to the compounds Ia24.1–Ia24.164, which differ from the compounds Ia1.1–Ia1.164 in that $R^6$ is ethyl and $R^7$ is methoxycarbonylmethyl:

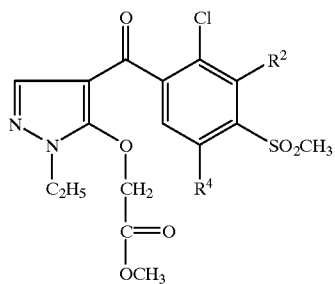
Ia24

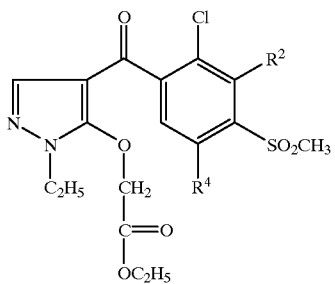
Ia27

Likewise, most particular preference is given to the compounds Ia25; in particular to the compounds Ia25.1–Ia25.164, which differ from the compounds Ia1.1–Ia1.164 in that $R^7$ is methoxycarbonylmethyl and $R^8$ is methyl:

Likewise, most particular preference is given to the compounds Ia28; in particular to the compounds Ia28.1–Ia28.164, which differ from the compounds Ia1.1–Ia1.164 in that $R^7$ is ethoxycarbonylmethyl and $R^8$ is methyl:

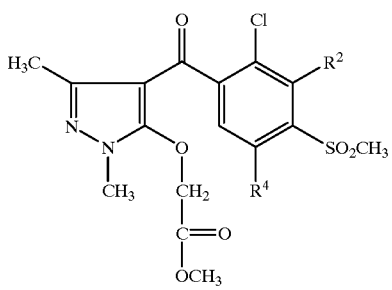
Ia25

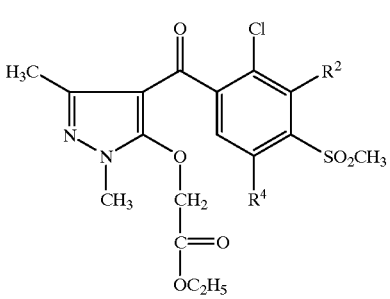
Ia28

Likewise, most particular preference is given to the compounds Ia26; in particular to the compounds Ia26.1–Ia26.164, which differ from the compounds Ia1.1–Ia1.164 in that $R^7$ is ethoxycarbonylmethyl:

Likewise, most particular preference is given to the compounds Ia29; in particular to the compounds Ia29.1–Ia29.164, which differ from the compounds Ia1.1–Ia1.164 in that $R^7$ is 1-methoxycarbonyleth-1-yl:

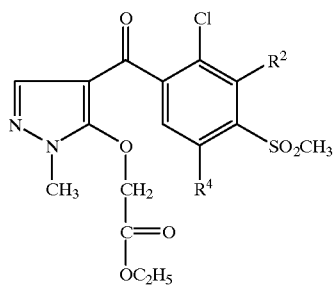
Ia26

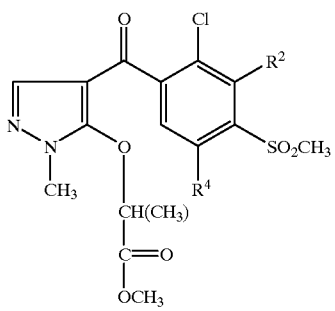
Ia29

Likewise, most particular preference is given to the compounds Ia27; in particular to the compounds Ia27.1–Ia27.164, which differ from the compounds Ia1.1–Ia1.164 in that $R^6$ is ethyl and $R^7$ is ethoxycarbonylmethyl:

Likewise, most particular preference is given to the compounds Ia30; in particular to the compounds Ia30.1–Ia30.164, which differ from the compounds Ia1.1–Ia1.164 in that $R^6$ is ethyl and $R^7$ is 1-methoxycarbonyleth-1-yl:

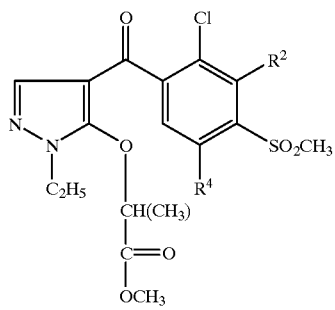

Ia30

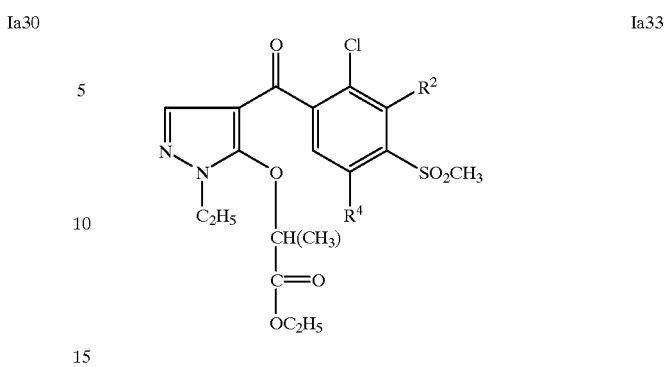

Ia33

Likewise, most particular preference is given to the compounds Ia31; in particular to the compounds Ia31.1–Ia31.164, which differ from the compounds Ia1.1–Ia1.164 in that $R^7$ is 1-methoxycarbonyleth-1-yl and $R^8$ is methyl:

Likewise, most particular preference is given to the compounds Ia34; in particular to the compounds Ia34.1–Ia34.164, which differ from the compounds Ia1.1–Ia1.164 in that $R^7$ is 1-ethoxycarbonyleth-1-yl and $R^8$ is methyl:

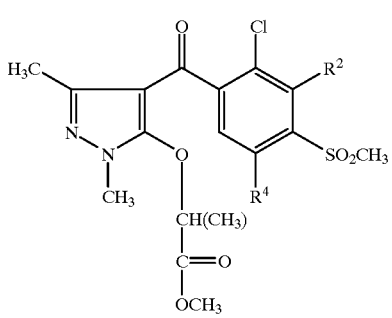

Ia31

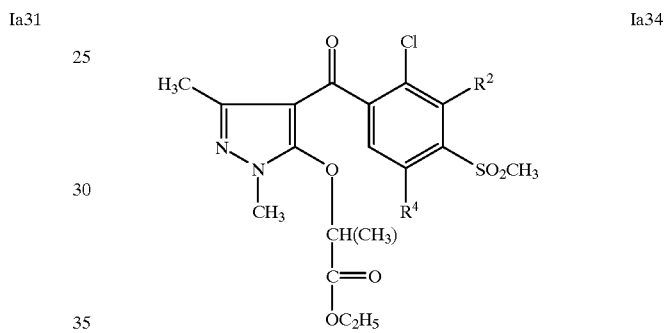

Ia34

Likewise, most particular preference is given to the compounds Ia32; in particular to the compounds Ia32.1–Ia32.164, which differ from the compounds Ia1.1–Ia1.164 in that $R^7$ is 1-ethoxycarbonyleth-1-yl:

Likewise, most particular preference is given to the compounds Ia35; in particular to the compounds Ia35.1–Ia35.164, which differ from the compounds Ia1.1–Ia1.164 in that $R^7$ is 2-methoxyeth-1-oxycarbonylmethyl:

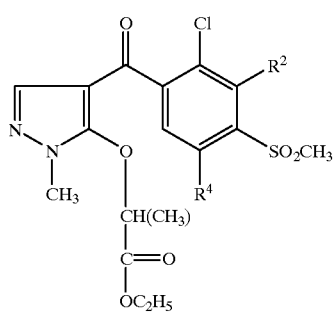

Ia32

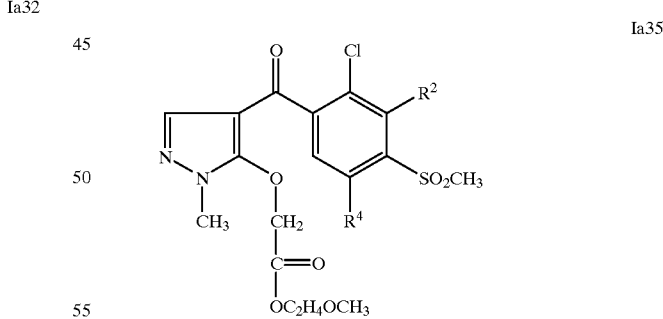

Ia35

Likewise, most particular preference is given to the compounds Ia33; in particular to the compounds Ia33.1–Ia33.164, which differ from the compounds Ia1.1–Ia1.164 in that $R^6$ is ethyl and $R^7$ is 1-ethoxycarbonyleth-1-yl:

Likewise, most particular preference is given to the compounds Ia36; in particular to the compounds Ia36.1–Ia36.164, which differ from the compounds Ia1.1–Ia1.164 in that $R^6$ is ethyl and $R^7$ is 2-methoxyeth-1-oxycarbonylmethyl:

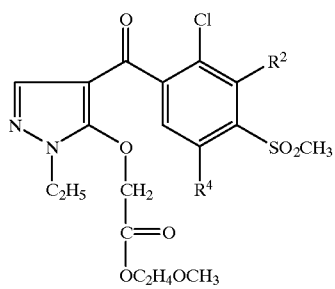

Ia36

Likewise, most particular preference is given to the compounds Ia37; in particular to the compounds Ia37.1–Ia37.164, which differ from the compounds Ia1.1–Ia1.164 in that $R^7$ is 2-methoxyeth-1-oxycarbonylmethyl and $R^8$ is methyl:

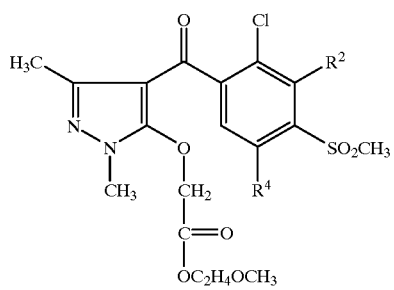

Ia37

Likewise, most particular preference is given to the compounds Ia38; in particular to the compounds Ia38.1–Ia38.164, which differ from the compounds Ia1.1–Ia1.164 in that $R^7$ is 2-dimethylaminoeth-1-oxycarbonylmethyl:

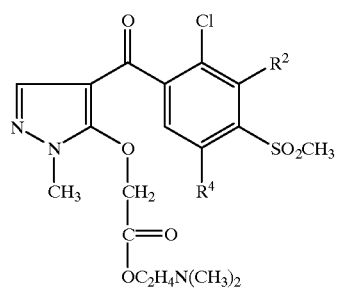

Ia38

Likewise, most particular preference is given to the compounds Ia39; in particular to the compounds Ia39.1–Ia39.164, which differ from the compounds Ia1.1–Ia1.164 in that $R^6$ is ethyl and $R^7$ is 2-dimethylaminoeth-1-oxycarbonylmethyl:

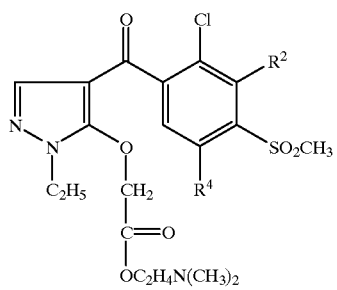

Ia39

Likewise, most particular preference is given to the compounds Ia40; in particular to the compounds Ia40.1–Ia40.164, which differ from the compounds Ia1.1–Ia1.164 in that $R^7$ is 2-dimethylaminoeth-1-oxycarbonylmethyl and $R^8$ is methyl:

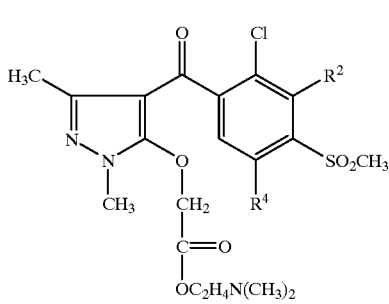

Ia40

Likewise, most particular preference is given to the compounds Ia41; in particular to the compounds Ia41.1–Ia41.164, which differ from the compounds Ia1.1–Ia1.164 in that $R^7$ is methylaminocarbonylmethyl:

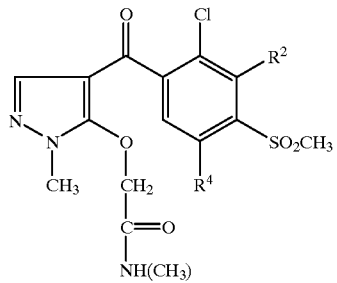

Ia41

Likewise, most particular preference is given to the compounds Ia42; in particular to the compounds Ia42.1–Ia42.164, which differ from the compounds Ia1.1–Ia1.164 in that R6 is ethyl and $R^7$ is methylaminocarbonylmethyl:

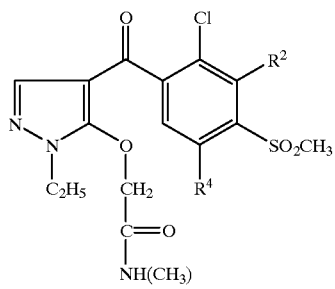

Ia42

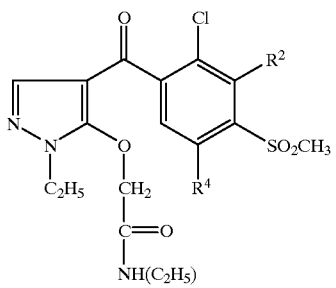

Ia45

Likewise, most particular preference is given to the compounds Ia43; in particular to the compounds Ia43.1–Ia43.164, which differ from the compounds Ia1.1–Ia1.164 in that $R^7$ is methylaminocarbonylmethyl and $R^8$ is methyl:

Likewise, most particular preference is given to the compounds Ia46; in particular to the compounds Ia46.1–Ia46.164, which differ from the compounds Ia1.1–Ia1.164 in that $R^7$ is ethylaminocarbonylmethyl and $R^8$ is methyl:

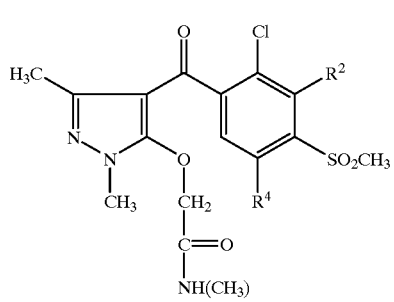

Ia43

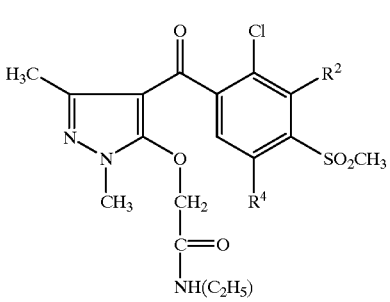

Ia46

Likewise, most particular preference is given to the compounds Ia44; in particular to the compounds Ia44.1–Ia44.164, which differ from the compounds Ia1.1–Ia1.164 in that $R^7$ is ethylaminocarbonylmethyl:

Likewise, most particular preference is given to the compounds Ia47; in particular to the compounds Ia47.1–Ia47.164, which differ from the compounds Ia1.1–Ia1.164 in that $R^7$ is dimethylaminocarbonylmethyl:

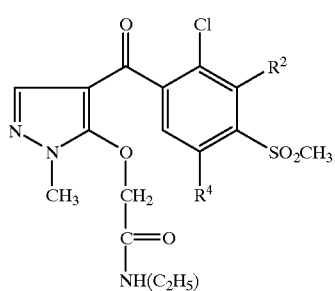

Ia44

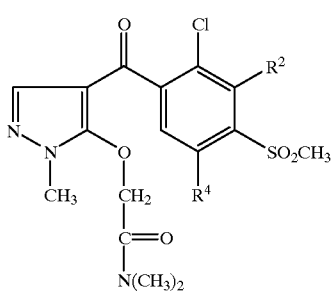

Ia47

Likewise, most particular preference is given to the compounds Ia45; in particular to the compounds Ia45.1–Ia45.164, which differ from the compounds Ia1.1–Ia1.164 in that $R^6$ is ethyl and $R^7$ is ethylaminocarbonylmethyl:

Likewise, most particular preference is given to the compounds Ia48; in particular to the compounds Ia48.1–Ia48.164, which differ from the compounds Ia1.1–Ia1.164 in that $R^6$ is ethyl and $R^7$ is dimethylaminocarbonylmethyl:

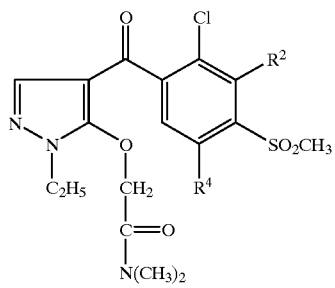

Ia48

Likewise, most particular preference is given to the compounds Ia49; in particular to the compounds Ia49.1–Ia49.164, which differ from the compounds Ia1.1–Ia1.164 in that $R^7$ is dimethylaminocarbonylmethyl and $R^8$ is methyl:

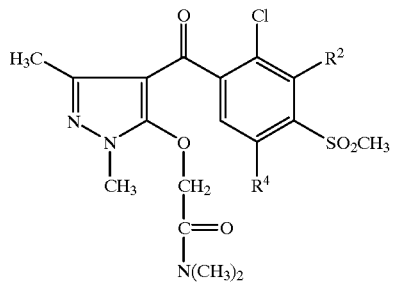

Ia49

Likewise, most particular preference is given to the compounds Ia50; in particular to the compounds Ia50.1–Ia50.164, which differ from the compounds Ia1.1–Ia1.164 in that $R^7$ is diethylaminocarbonylmethyl:

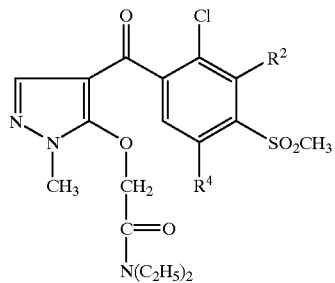

Ia50

Likewise, most particular preference is given to the compounds Ia51; in particular to the compounds Ia51.1–Ia51.164, which differ from the compounds Ia1.1–Ia1.164 in that $R^6$ is ethyl and $R^7$ is diethylaminocarbonylmethyl:

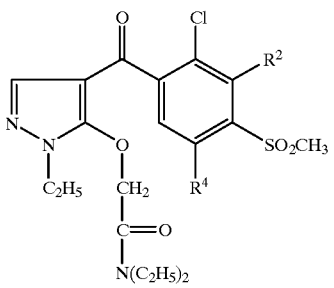

Ia51

Likewise, most particular preference is given to the compounds Ia52; in particular to the compounds Ia52.1–Ia52.164, which differ from the compounds Ia1.1–Ia1.164 in that $R^7$ is diethylaminocarbonylmethyl and $R^8$ is methyl:

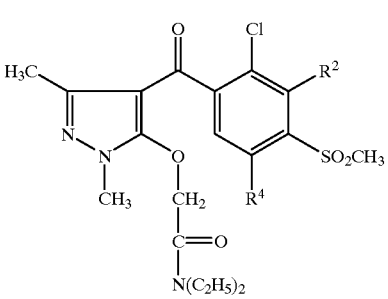

Ia52

Likewise, most particular preference is given to the compounds Ia53; in particular to the compounds Ia53.1–Ia53.164, which differ from the compounds Ia1.1–Ia1.164 in that $R^7$ is allyl:

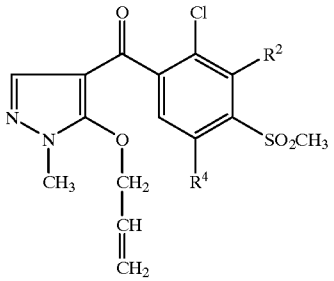

Ia53

Likewise, most particular preference is given to the compounds Ia54; in particular to the compounds Ia54.1–Ia54.164, which differ from the compounds Ia1.1–Ia1.164 in that $R^6$ is ethyl and $R^7$ is allyl:

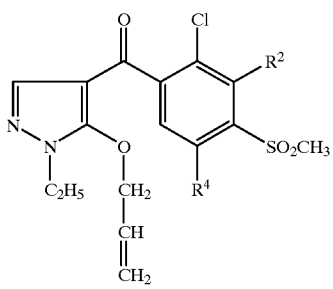

Ia54

Likewise, most particular preference is given to the compounds Ia55; in particular to the compounds Ia55.1–Ia55.164, which differ from the compounds Ia1.1–Ia1.164 in that $R^7$ is allyl and $R^8$ is methyl:

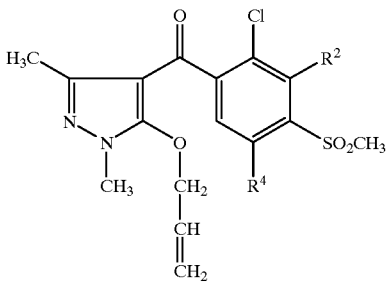

Ia55

Likewise, most particular preference is given to the compounds Ia56; in particular to the compounds Ia56.1–Ia56.164, which differ from the compounds Ia1.1–Ia1.164 in that $R^7$ is propargyl:

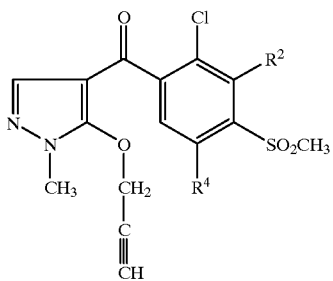

Ia56

Likewise, most particular preference is given to the compounds Ia57; in particular to the compounds Ia57.1–Ia57.164, which differ from the compounds Ia1.1–Ia1.164 in that $R^6$ is ethyl and $R^7$ is propargyl:

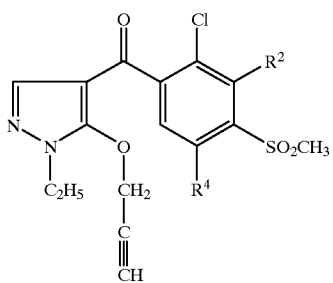

Ia57

Likewise, most particular preference is given to the compounds Ia58; in particular to the compounds Ia58.1–Ia58.164, which differ from the compounds Ia1.1–Ia1.164 in that $R^7$ is propargyl and $R^8$ is methyl:

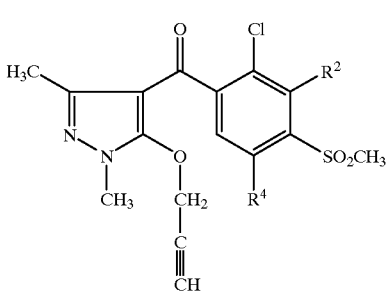

Ia58

Likewise, most particular preference is given to the compounds Ia59; in particular to the compounds Ia59.1–Ia59.164, which differ from the compounds Ia1.1–Ia1.164 in that $R^7$ is methylcarbonyl:

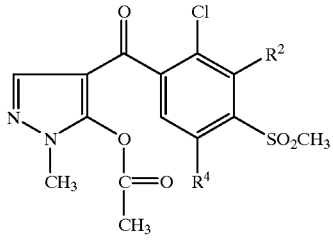

Ia59

Likewise, most particular preference is given to the compounds Ia60; in particular to the compounds Ia60.1–Ia60.164, which differ from the compounds Ia1.1–Ia1.164 in that $R^6$ is ethyl and $R^7$ is methylcarbonyl:

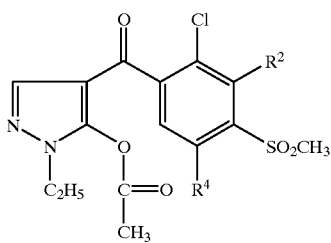

Ia60

Likewise, most particular preference is given to the compounds Ia61; in particular to the compounds Ia61.1–Ia61.164, which differ from the compounds Ia1.1–Ia1.164 in that $R^6$ is n-propyl and $R^7$ is methylcarbonyl:

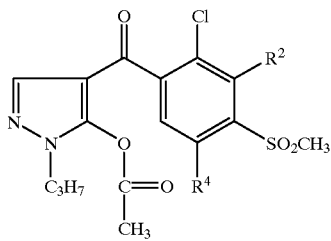

Ia61

Likewise, most particular preference is given to the compounds Ia62; in particular to the compounds Ia62.1–Ia62.164, which differ from the compounds Ia1.1–Ia1.164 in that $R^6$ is isobutyl and $R^7$ is methylcarbonyl:

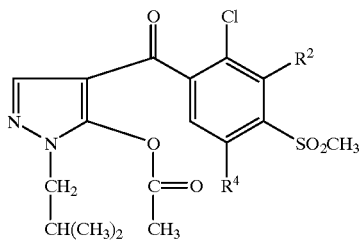

Ia62

Likewise, most particular preference is given to the compounds Ia63; in particular to the compounds Ia63.1–Ia63.164, which differ from the compounds Ia1.1–Ia1.164 in that $R^7$ is methylcarbonyl and $R^8$ is methyl:

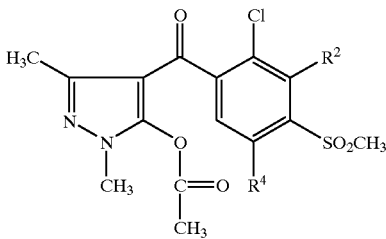

Ia63

Likewise, most particular preference is given to the compounds Ia64; in particular to the compounds Ia64.1–Ia64.164, which differ from the compounds Ia1.1–Ia1.164 in that $R^7$ is ethylcarbonyl:

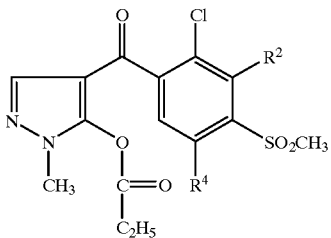

Ia64

Likewise, most particular preference is given to the compounds Ia65; in particular to the compounds Ia65.1–Ia65.164, which differ from the compounds Ia1.1–Ia1.164 in that $R^6$ is ethyl and $R^7$ is ethylcarbonyl:

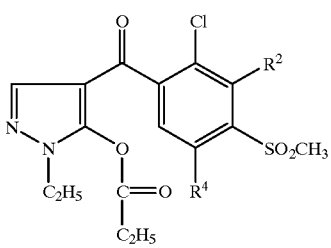

Ia65

Likewise, most particular preference is given to the compounds Ia66; in particular to the compounds Ia66.1–Ia66.164, which differ from the compounds Ia1.1–Ia1.164 in that $R^6$ is n-propyl and $R^7$ is ethylcarbonyl:

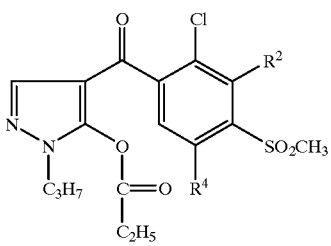

Ia66

Likewise, most particular preference is given to the compounds Ia67; in particular to the compounds Ia67.1–Ia67.164, which differ from the compounds Ia1.1–Ia1.164 in that $R^6$ is isobutyl and $R^7$ is ethylcarbonyl:

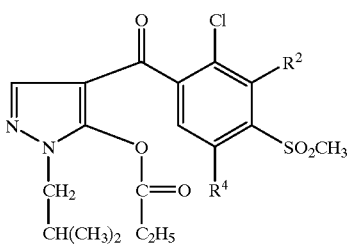

Ia67

Likewise, most particular preference is given to the compounds Ia68; in particular to the compounds Ia68.1–Ia68.164, which differ from the compounds Ia1.1–Ia1.164 in that $R^7$ is ethylcarbonyl and $R^8$ is methyl:

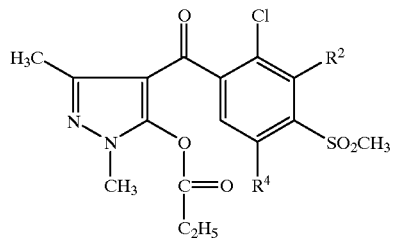

Ia68

Likewise, most particular preference is given to the compounds Ia69; in particular to the compounds Ia69.1–Ia69.164, which differ from the compounds Ia1.1–Ia1.164 in that R⁷ is methoxycarbonyl:

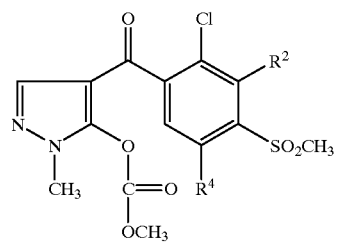

Ia69

Likewise, most particular preference is given to the compounds Ia70; in particular to the compounds Ia70.1–Ia70.164, which differ from the compounds Ia1.1–Ia1.164 in that $R^6$ is ethyl and $R^7$ is methoxycarbonyl:

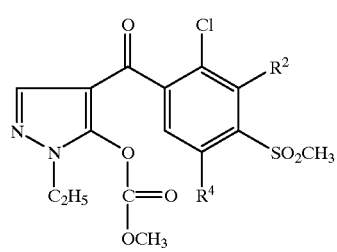

Ia70

Likewise, most particular preference is given to the compounds Ia71; in particular to the compounds Ia71.1–Ia71.164, which differ from the compounds Ia1.1–Ia1.164 in that $R^7$ is methoxycarbonyl and $R^8$ is methyl:

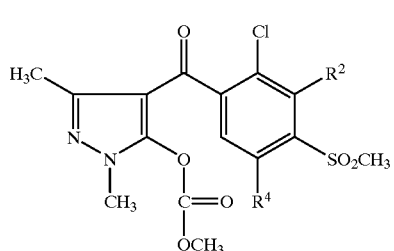

Ia71

Likewise, most particular preference is given to the compounds Ia72; in particular to the compounds Ia72.1–Ia72.164, which differ from the compounds Ia1.1–Ia1.164 in that $R^7$ is ethoxycarbonyl:

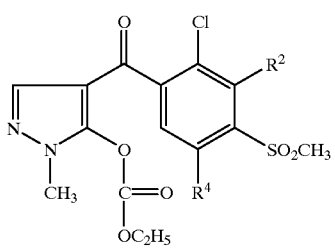

Ia72

Likewise, most particular preference is given to the compounds Ia73; in particular to the compounds Ia73.1–Ia73.164, which differ from the compounds Ia1.1–Ia1.164 in that $R^6$ is ethyl and $R^7$ is ethoxycarbonyl:

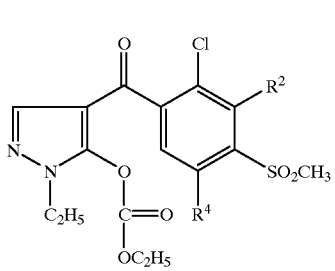

Ia73

Likewise, most particular preference is given to the compounds Ia74; in particular to the compounds Ia74.1–Ia74.164, which differ from the compounds Ia1.1–Ia1.164 in that $R^7$ is ethoxycarbonyl and $R^8$ is methyl:

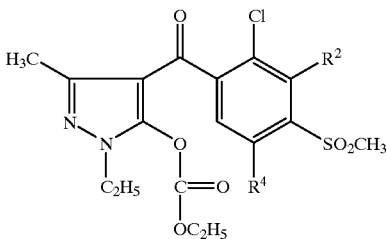

Ia74

Likewise, most particular preference is given to the compounds Ia75; in particular to the compounds Ia75.1–Ia75.164, which differ from the compounds Ia1.1–Ia1.164 in that $R^7$ is dimethylaminocarbonyl:

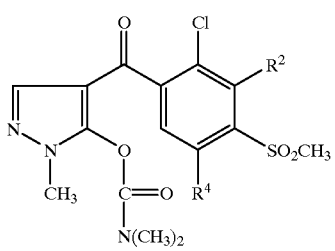

Ia75

Likewise, most particular preference is given to the compounds Ia76; in particular to the compounds Ia76.1–Ia76.164, which differ from the compounds- Ia1.1–Ia1.164 in that $R^6$ is ethyl and $R^7$ is dimethylaminocarbonyl:

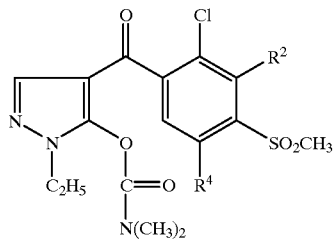

Ia76

Likewise, most particular preference is given to the compounds Ia77; in particular to the compounds Ia77.1–Ia77.164, which differ from the compounds Ia1.1–Ia1.164 in that $R^7$ is dimethylaminocarbonyl and $R^8$ is methyl:

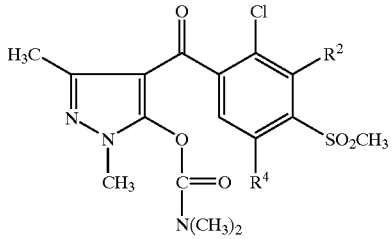

Ia77

Likewise, most particular preference is given to the compounds Ia78; in particular to the compounds Ia78.1–Ia78.164, which differ from the compounds Ia1.1–Ia1.164 in that $R^7$ is diethylaminocarbonyl:

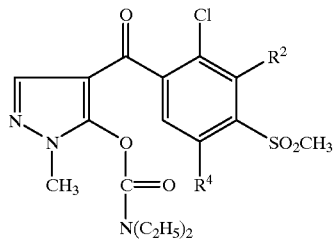

Ia78

Likewise, most particular preference is given to the compounds Ia79; in particular to the compounds Ia79.1–Ia79.164, which differ from the compounds Ia1.1–Ia1.164 in that $R^6$ is ethyl and $R^7$ is diethylaminocarbonyl:

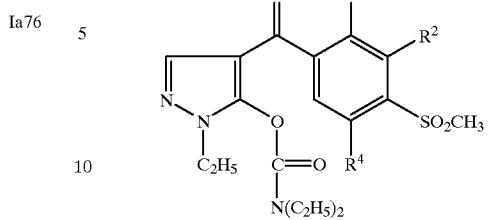

Ia79

Likewise, most particular preference is given to the compounds Ia80; in particular to the compounds Ia80.1–Ia80.164, which differ from the compounds Ia1.1–Ia1.164 in that $R^7$ is diethylaminocarbonyl and $R^8$ is methyl:

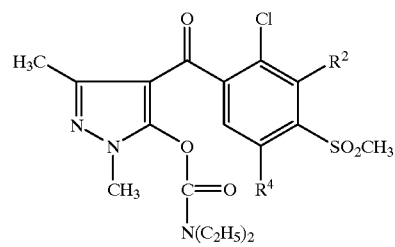

Ia80

Likewise, most particular preference is given to the compounds Ia81; in particular to the compounds Ia81.1–Ia81.164, which differ from the compounds Ia1.1–Ia1.164 in that $R^7$ is N-methoxy-N-methylaminocarbonyl:

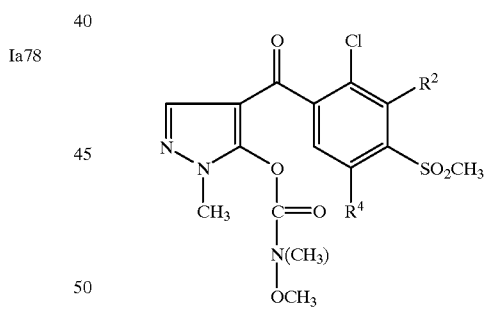

Ia81

Likewise, most particular preference is given to the compounds Ia82; in particular to the compounds Ia82.1–Ia82.164, which differ from the compounds Ia1.1–Ia1.164 in that $R^6$ is ethyl and $R^7$ is N-methoxy-N-methylaminocarbonyl:

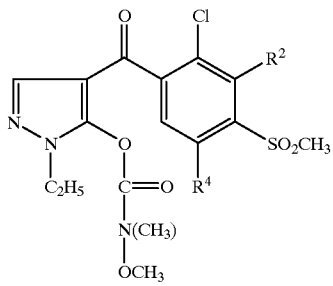

Ia82

Likewise, most particular preference is given to the compounds Ia83; in particular to the compounds Ia83.1–Ia83.164, which differ from the compounds Ia1.1–Ia1.164 in that $R^7$ is N-methoxy-N-methylaminocarbonyl and $R^8$ is methyl:

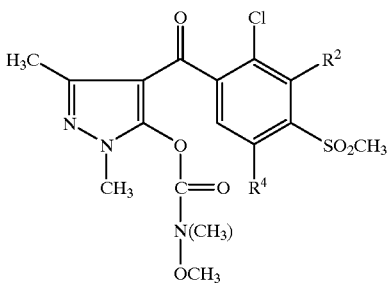

Ia83

Likewise, most particular preference is given to the compounds Ia84; in particular to the compounds Ia84.1–Ia84.164, which differ from the compounds Ia1.1–Ia1.164 in that $R^7$ is benzyl:

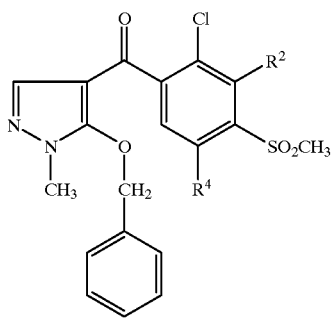

Ia84

Likewise, most particular preference is given to the compounds Ia85; in particular to the compounds Ia85.1–Ia85.164, which differ from the compounds Ia1.1–Ia1.164 in that $R^6$ is ethyl and $R^7$ is benzyl:

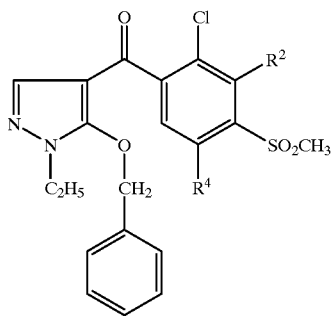

Ia85

Likewise, most particular preference is given to the compounds Ia86; in particular to the compounds Ia86.1–Ia86.164, which differ from the compounds Ia1.1–Ia1.164 in that $R^6$ is n-propyl and $R^7$ is benzyl:

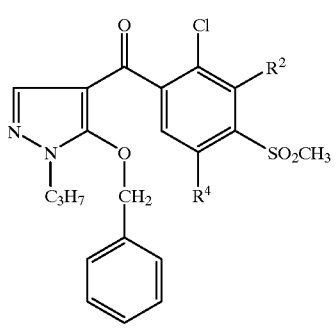

Ia86

Likewise, most particular preference is given to the compounds Ia87; in particular to the compounds Ia87.1–Ia87.164, which differ from the compounds Ia1.1–Ia1.164 in that $R^6$ is isobutyl and $R^7$ is benzyl:

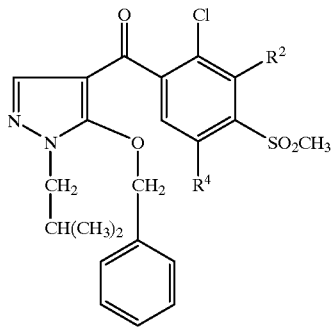

Ia87

Likewise, most particular preference is given to the compounds Ia88; in particular to the compounds Ia88.1–Ia88.164, which differ from the compounds Ia1.1–Ia1.164 in that $R^7$ is benzyl and $R^8$ is methyl:

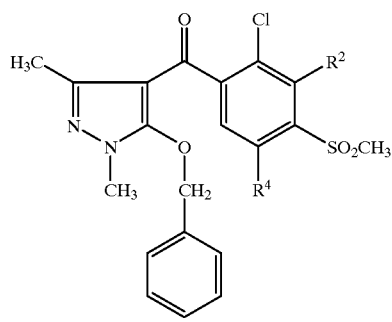
Ia88

Likewise, most particular preference is given to the compounds Ia89; in particular to the compounds Ia89.1–Ia89.164, which differ from the compounds Ia1.1–Ia1.164 in that $R^7$ is 4-methylphenylmethyl:

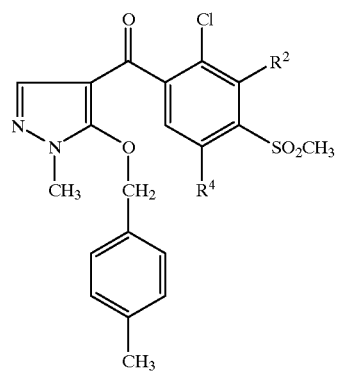
Ia89

Likewise, most particular preference is given to the compounds Ia90; in particular to the compounds Ia90.1–Ia90.164, which differ from the compounds Ia1.1–Ia1.164 in that $R^6$ is ethyl and $R^7$ is 4-methylphenylmethyl:

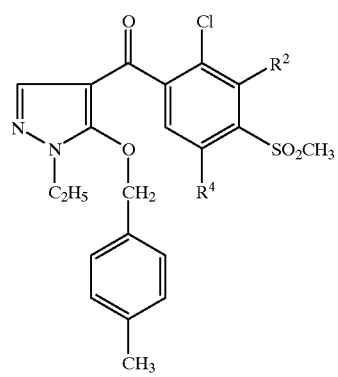
Ia90

Likewise, most particular preference is given to the compounds Ia91; in particular to the compounds Ia91.1–Ia91.164, which differ from the compounds Ia1.1–Ia1.164 in that $R^6$ is n-propyl and $R^7$ is 4-methylphenylmethyl:

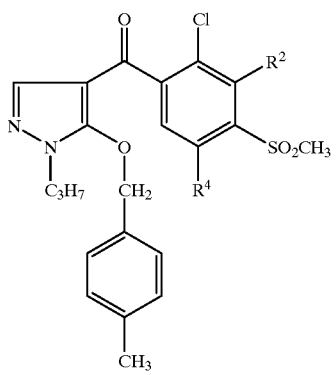
Ia91

Likewise, most particular preference is given to the compounds Ia92; in particular to the compounds Ia92.1–Ia92.164, which differ from the compounds Ia1.1–Ia1.164 in that $R^6$ is isobutyl and $R^7$ is 4-methylphenylmethyl:

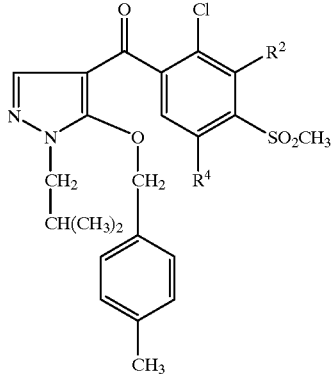
Ia92

Likewise, most particular preference is given to the compounds Ia93; in particular to the compounds Ia93.1–Ia93.164, which differ from the compounds Ia1.1–Ia1.164 in that $R^7$ is 4-methylphenylmethyl and $R^8$ is methyl:

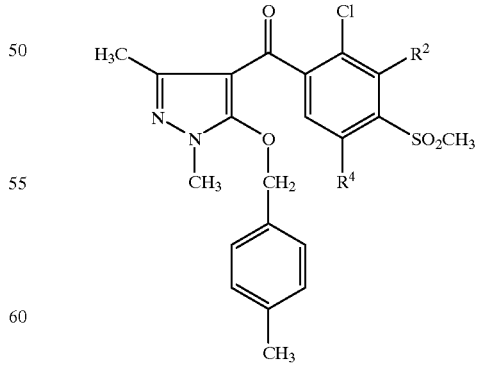
Ia93

Likewise, most particular preference is given to the compounds Ia94; in particular to the compounds Ia94.1–Ia94.164, which differ from the compounds Ia1.1–Ia1.164 in that $R^7$ is 4-chlorophenylmethyl:

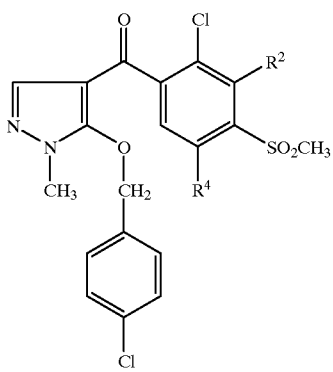

Ia94

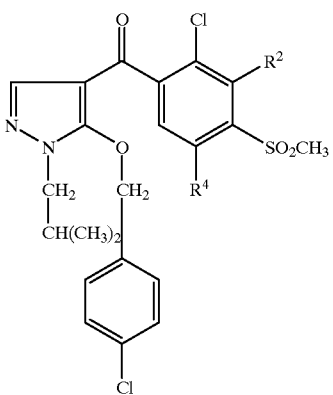

Ia97

Likewise, most particular preference is given to the compounds Ia95; in particular to the compounds Ia95.1–Ia95.164, which differ from the compounds Ia1.1–Ia1.164 in that $R^6$ is ethyl and $R^7$ is 4-chlorophenylmethyl:

Likewise, most particular preference is given to the compounds Ia98; in particular to the compounds Ia98.1–Ia98.164, which differ from the compounds Ia1.1–Ia1.164 in that $R^7$ is 4-chlorophenylmethyl and $R^8$ is methyl:

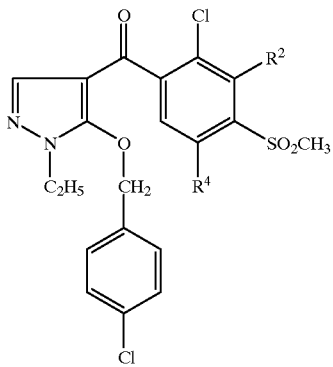

Ia95

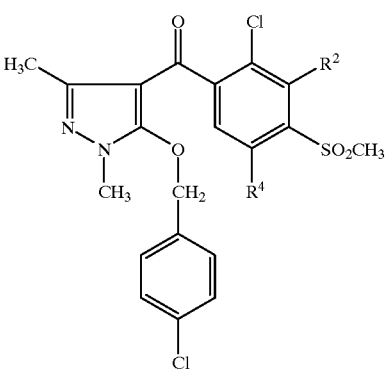

Ia98

Likewise, most particular preference is given to the compounds Ia96; in particular to the compounds Ia96.1–Ia96.164, which differ from the compounds Ia1.1–Ia1.164 in that $R^6$ is n-propyl and $R^7$ is 4-chlorophenylmethyl:

Likewise, most particular preference is given to the compounds Ia99; in particular to the compounds Ia99.1–Ia99.164, which differ from the compounds Ia1.1–Ia1.164 in that $R^7$ is 4-methoxyphenylmethyl:

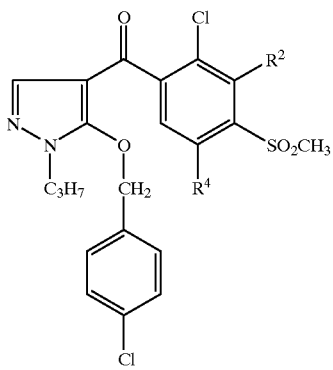

Ia96

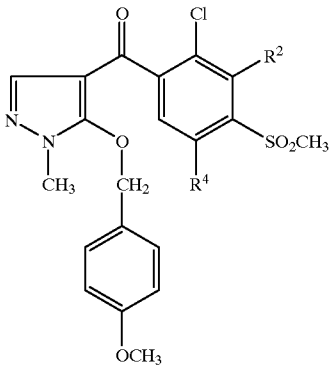

Ia99

Likewise, most particular preference is given to the compounds Ia97; in particular to the compounds Ia97.1–Ia97.164, which differ from the compounds Ia1.1–Ia1.164 in that $R^6$ is isobutyl and $R^7$ is 4-chlorophenylmethyl:

Likewise, most particular preference is given to the compounds Ia100; in particular to the compounds Ia100.1–Ia100.164, which differ from the compounds Ia1.1–Ia1.164 in that $R^6$ is ethyl and $R^7$ is 4-methoxyphenylmethyl:

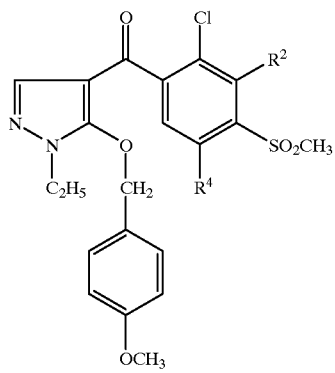

Ia100

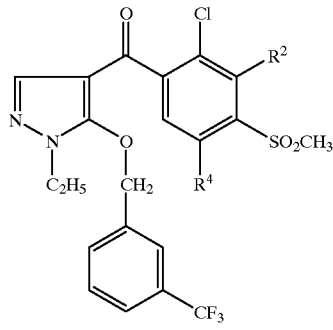

Ia103

Likewise, most particular preference is given to the compounds Ia104; in particular to the compounds Ia104.1–Ia104.164, which differ from the compounds Ia1.1–Ia1.164 in that $R^7$ is 3-trifluoromethylphenylmethyl and $R^8$ is methyl:

Likewise, most particular preference is given to the compounds Ia101; in particular to the compounds Ia101.1–Ia101.164, which differ from the compounds Ia1.1–Ia1.164 in that $R^7$ is 4-methoxyphenylmethyl and $R^8$ is methyl:

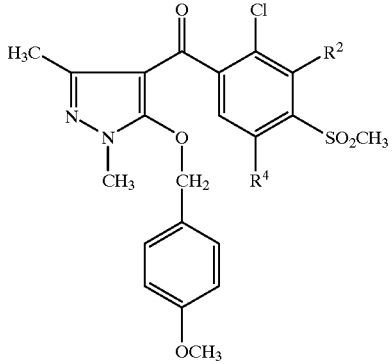

Ia101

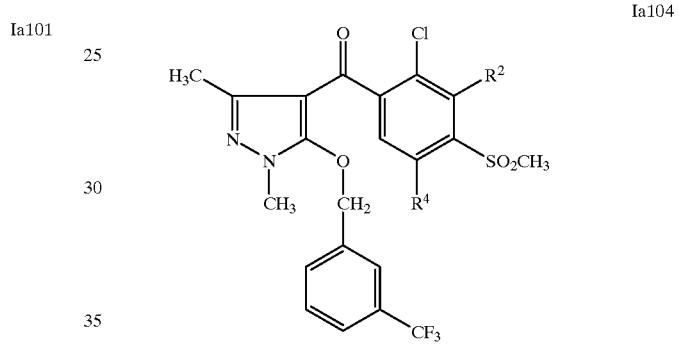

Ia104

Likewise, most particular preference is given to the compounds Ia105; in particular to the compounds Ia105.1–Ia105.164, which differ from the compounds Ia1.1–Ia1.164 in that $R^7$ is 2,4-dichlorophenylmethyl:

Likewise, most particular preference is given to the compounds Ia102; in particular to the compounds Ia102.1–Ia102.164, which differ from the compounds Ia1.1–Ia1.164 in that $R^7$ is 3-trifluoromethylphenylmethyl:

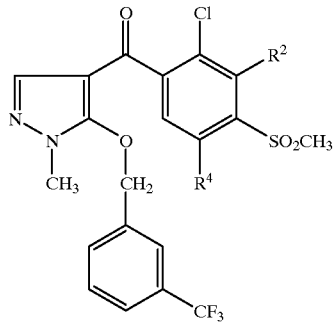

Ia102

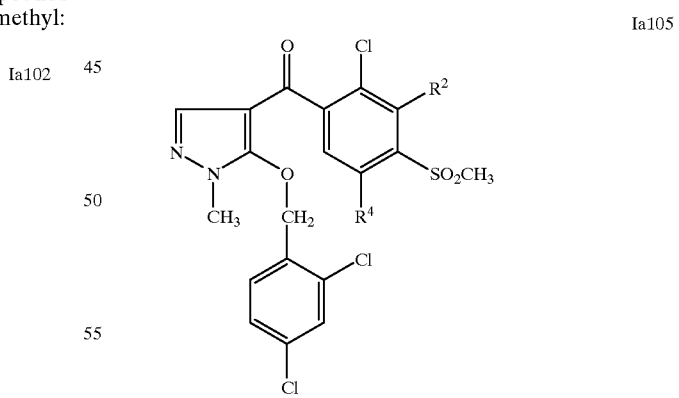

Ia105

Likewise, most particular preference is given to the compounds Ia103; in particular to the compounds Ia103.1–Ia103.164, which differ from the compounds Ia1.1–Ia1.164 in that $R^6$ is ethyl and $R^7$ is 3-trifluoromethylphenylmethyl:

Likewise, most particular preference is given to the compounds Ia106; in particular to the compounds Ia106.1–Ia106.164, which differ from the compounds Ia1.1–Ia1.164 in that $R^6$ is ethyl and $R^7$ is 2,4-dichlorophenylmethyl:

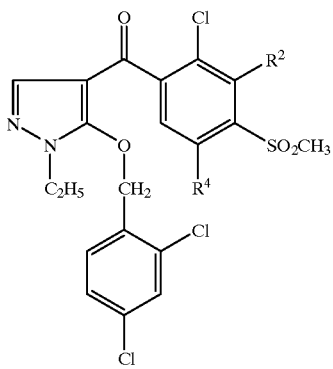

Ia106

Likewise, most particular preference is given to the compounds Ia107; in particular to the compounds Ia107.1–Ia107.164, which differ from the compounds Ia1.1–Ia1.164 in that $R^7$ is 2,4-dichlorophenylmethyl and $R^8$ is methyl:

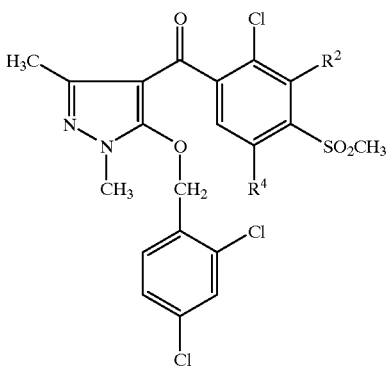

Ia107

Likewise, most particular preference is given to the compounds Ia108; in particular to the compounds Ia108.1–Ia108.164, which differ from the compounds Ia1.1–Ia1.164 in that $R^7$ is phenylcarbonylmethyl:

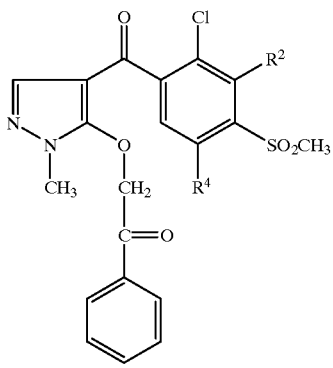

Ia108

Likewise, most particular preference is given to the compounds Ia109; in particular to the compounds Ia109.1–Ia109.164, which differ from the compounds Ia1.1–Ia1.164 in that $R^6$ is ethyl and $R^7$ is phenylcarbonylmethyl:

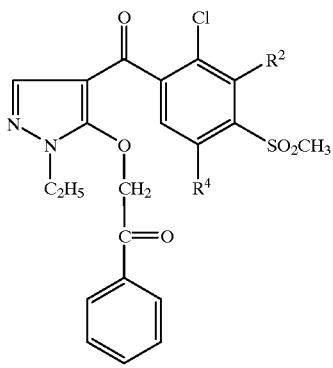

Ia109

Likewise, most particular preference is given to the compounds Ia110; in particular to the compounds Ia110.1–Ia110.164, which differ from the compounds Ia1.1–Ia1.164 in that $R^6$ is n-propyl and $R^7$ is phenylcarbonylmethyl:

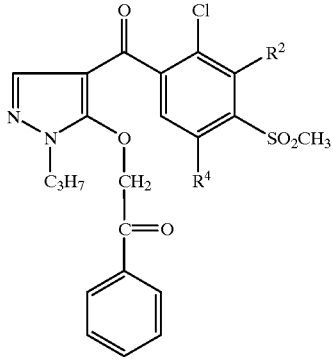

Ia110

Likewise, most particular preference is given to the compounds Ia111; in particular to the compounds Ia111.1–Ia111.164, which differ from the compounds Ia1.1–Ia1.164 in that $R^6$ is isobutyl and $R^7$ is phenylcarbonylmethyl:

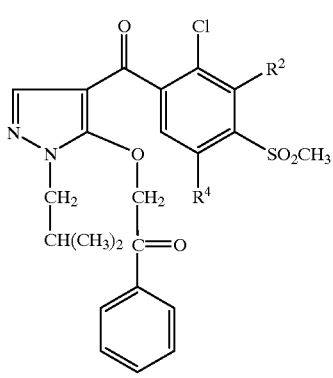

Ia111

Likewise, most particular preference is given to the compounds Ia112; in particular to the compounds Ia112.1–Ia112.164, which differ from the compounds Ia1.1–Ia1.164 in that $R^7$ is phenylcarbonylmethyl and $R^8$ is methyl:

Ia112

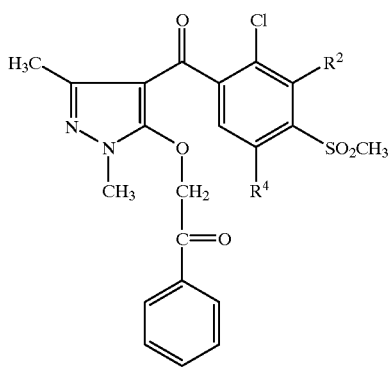

Likewise, most particular preference is given to the compounds Ia113; in particular to the compounds Ia113.1–Ia113.164, which differ from the compounds Ia1.1–Ia1.164 in that $R^7$ is 4-methylphenylcarbonylmethyl:

Ia113

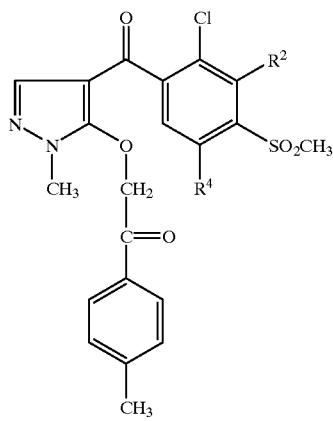

Likewise, most particular preference is given to the compounds Ia114; in particular to the compounds Ia114.1–Ia114.164, which differ from the compounds Ia1.1–Ia1.164 in that $R^6$ is ethyl and $R^7$ is 4-methylphenylcarbonylmethyl:

Ia114

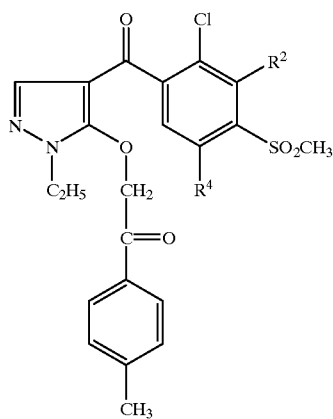

Likewise, most particular preference is given to the compounds Ia115; in particular to the compounds Ia115.1–Ia115.164, which differ from the compounds Ia1.1–Ia1.164 in that $R^7$ is 4-methylphenylcarbonylmethyl and $R^8$ is methyl:

Ia115

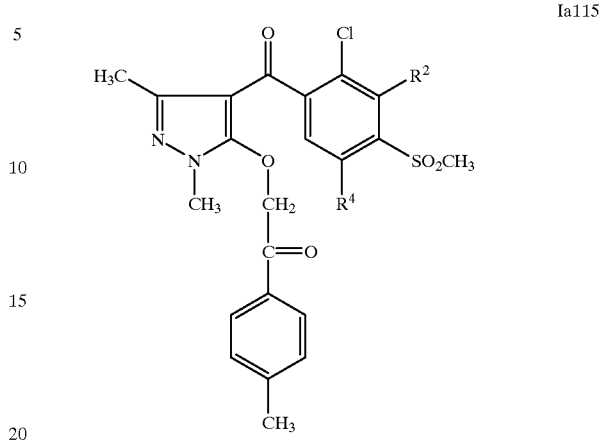

Likewise, most particular preference is given to the compounds Ia116; in particular to the compounds Ia116.1–Ia116.164, which differ from the compounds Ia1.1–Ia1.164 in that $R^7$ is 1-(phenylcarbonyl)eth-1-yl:

Ia116

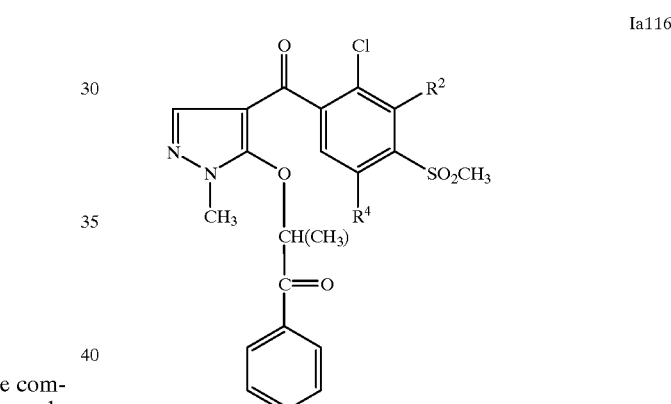

Likewise, most particular preference is given to the compounds Ia117; in particular to the compounds Ia117.1–Ia117.164, which differ from the compounds Ia1.1–Ia1.164 in that $R^6$ is ethyl and $R^7$ is 1-(phenylcarbonyl)eth-1-yl:

Ia117

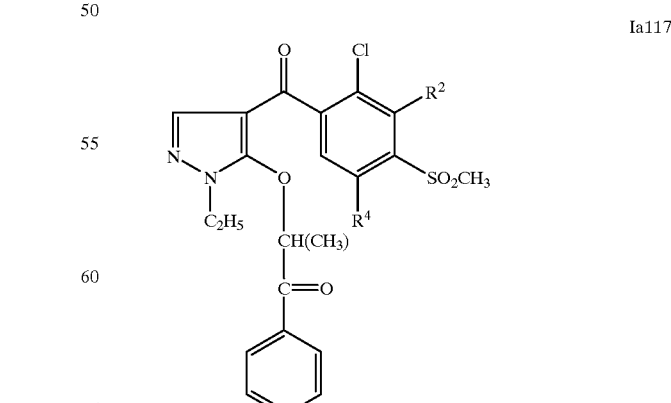

Likewise, most particular preference is given to the compounds Ia118; in particular to the compounds Ia118.1–Ia118.164, which differ from the compounds Ia1.1–Ia1.164 in that $R^7$ is 1-(phenylcarbonyl)eth-1-yl and $R^8$ is methyl:

Ia118

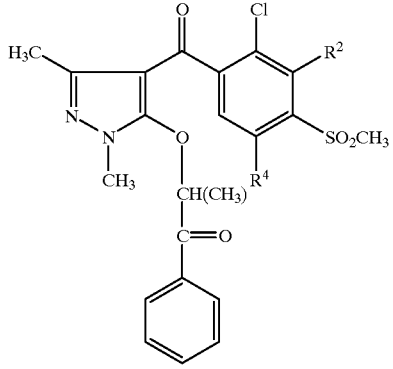

Likewise, most particular preference is given to the compounds Ia119; in particular to the compounds Ia119.1–Ia119.164, which differ from the compounds Ia1.1–Ia1.164 in that $R^7$ is phenylcarbonyl:

Ia119

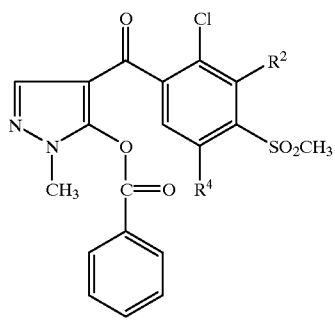

Likewise, most particular preference is given to the compounds Ia120; in particular to the compounds Ia120.1–Ia120.164, which differ from the compounds Ia1.1–Ia1.164 in that $R^6$ is ethyl and $R^7$ is phenylcarbonyl:

Ia120

Likewise, most particular preference is given to the compounds Ia121; in particular to the compounds Ia121.1–Ia121.164, which differ from the compounds Ia1.1–Ia1.164 in that $R^7$ is phenylcarbonyl and $R^8$ is methyl:

Ia121

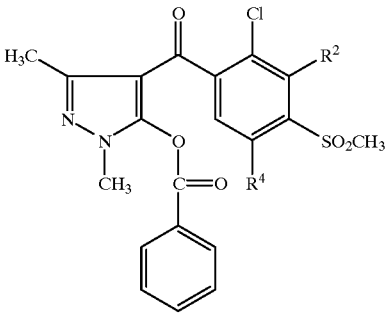

Likewise, most particular preference is given to the compounds Ia122; in particular to the compounds Ia122.1–Ia122.164, which differ from the compounds Ia1.1–Ia1.164 in that $R^7$ is 4-methylphenylcarbonyl:

Ia122

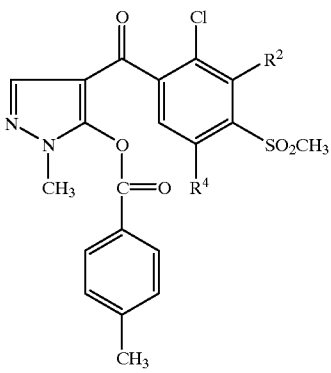

Likewise, most particular preference is given to the compounds Ia123; in particular to the compounds Ia123.1–Ia123.164, which differ from the compounds Ia1.1–Ia1.164 in that $R^6$ is ethyl and $R^7$ is 4-methylphenylcarbonyl:

Ia123

Likewise, most particular preference is given to the compounds Ia124; in particular to the compounds Ia124.1–Ia124.164, which differ from the compounds Ia1.1–Ia1.164 in that $R^7$ is 4-methylphenylcarbonyl and $R^8$ is methyl:

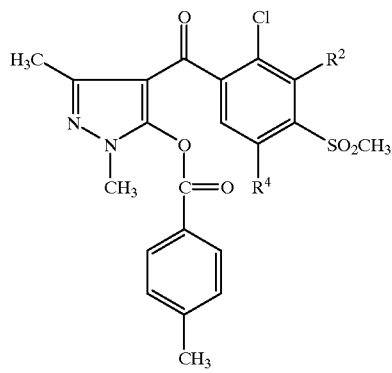

Ia124

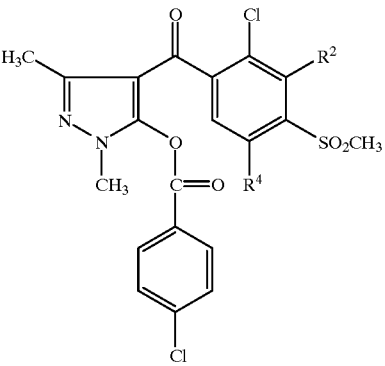

Ia127

Likewise, most particular preference is given to the compounds Ia125; in particular to the compounds Ia125.1–Ia125.164, which differ from the compounds Ia1.1–Ia1.164 in that $R^7$ is 4-chlorophenylcarbonyl:

Likewise, most particular preference is given to the compounds Ia128; in particular to the compounds Ia128.1–Ia128.164, which differ from the compounds Ia1.1–Ia1.164 in that $R^7$ is 4-methoxyphenylcarbonyl:

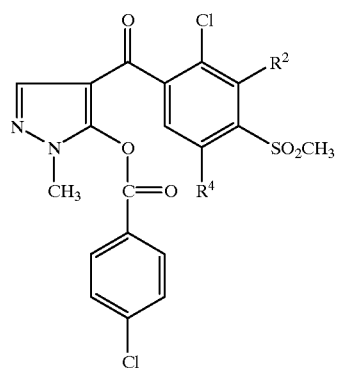

Ia125

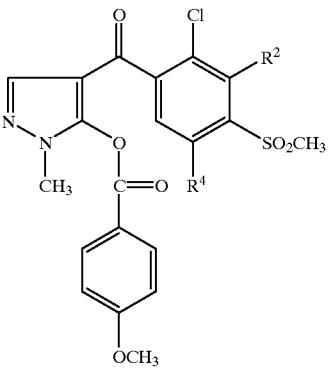

Ia128

Likewise, most particular preference is given to the compounds Ia126; in particular to the compounds Ia126.1–Ia126.164, which differ from the compounds Ia1.1–Ia1.164 in that $R^6$ is ethyl and $R^7$ is 4-chlorophenylcarbonyl:

Likewise, most particular preference is given to the compounds Ia129; in particular to the compounds Ia129.1–Ia129.164, which differ from the compounds Ia1.1–Ia1.164 in that $R^6$ is ethyl and $R^7$ is 4-methoxyphenylcarbonyl:

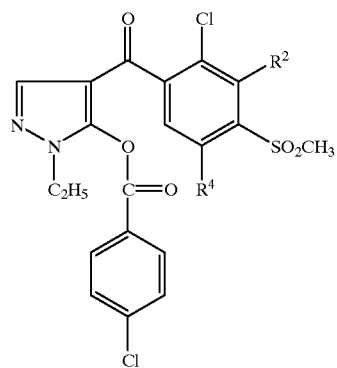

Ia126

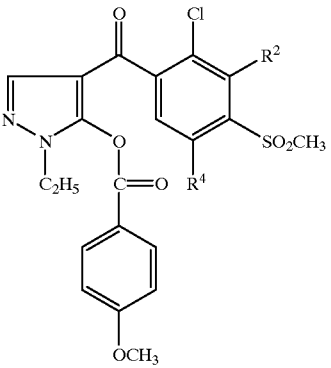

Ia129

Likewise, most particular preference is given to the compounds Ia127; in particular to the compounds Ia127.1–Ia127.164, which differ from the compounds Ia1.1–Ia1.164 in that $R^7$ is 4-chlorophenylcarbonyl and $R^8$ is methyl:

Likewise, most particular preference is given to the compounds Ia130; in particular to the compounds Ia130.1–Ia130.164, which differ from the compounds Ia1.1–Ia1.164 in that $R^7$ is 4-methoxyphenylcarbonyl and $R^8$ is methyl:

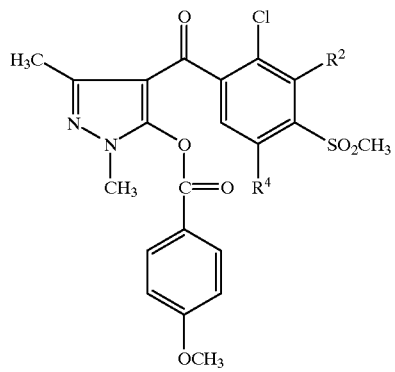

Ia130

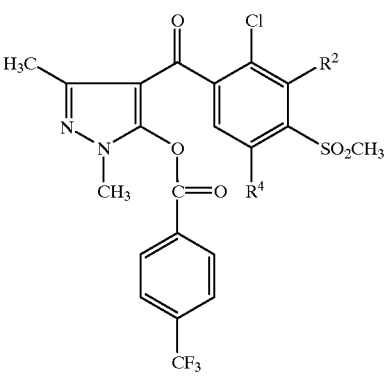

Ia133

Likewise, most particular preference is given to the compounds Ia131; in particular to the compounds Ia131.1–Ia131.164, which differ from the compounds Ia1.1–Ia1.164 in that $R^7$ is 4-trifluoromethylphenylcarbonyl:

Likewise, most particular preference is given to the compounds Ia134; in particular to the compounds Ia134.1–Ia134.164, which differ from the compounds Ia1.1–Ia1.164 in that $R^7$ is 2,4-dichlorophenylcarbonyl:

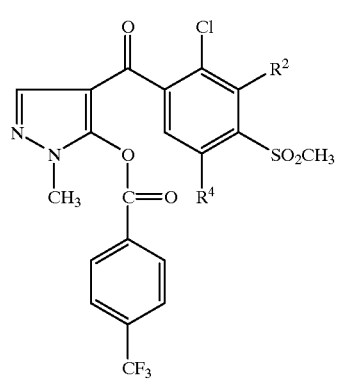

Ia131

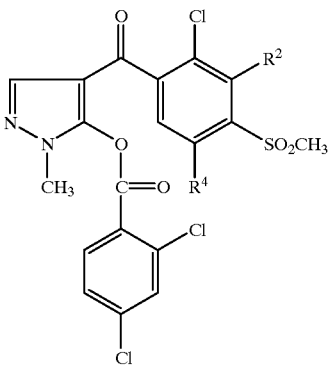

Ia134

Likewise, most particular preference is given to the compounds Ia132; in particular to the compounds Ia132.1–Ia132.164, which differ from the compounds Ia1.1–Ia1.164 in that $R^6$ is ethyl and $R^7$ is 4-trifluoromethylphenylcarbonyl:

Likewise, most particular preference is given to the compounds Ia135; in particular to the compounds Ia135.1–Ia135.164, which differ from the compounds Ia1.1–Ia1.164 in that $R^6$ is ethyl and $R^7$ is 2,4-dichlorophenylcarbonyl:

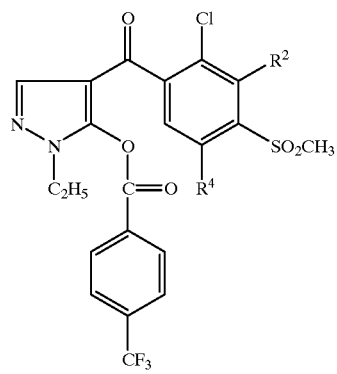

Ia132

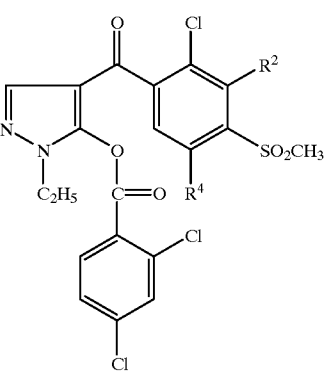

Ia135

Likewise, most particular preference is given to the compounds Ia133; in particular to the compounds Ia133.1–Ia133.164, which differ from the compounds Ia1.1–Ia1.164 in that $R^7$ is 4-trifluoromethylphenylcarbonyl and $R^8$ is methyl:

Likewise, most particular preference is given to the compounds Ia136; in particular to the compounds Ia136.1–Ia136.164, which differ from the compounds Ia1.1–Ia1.164 in that $R^7$ is 2,4-dichlorophenylcarbonyl and $R^8$ is methyl:

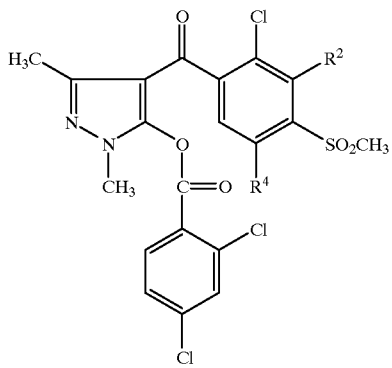

Ia136

Likewise, most particular preference is given to the compounds Ia137; in particular to the compounds Ia137.1–Ia137.164, which differ from the compounds Ia1.1–Ia1.164 in that $R^3$ is chlorine:

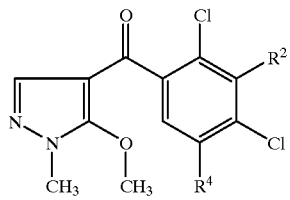

Ia137

Likewise, most particular preference is given to the compounds Ia138; in particular to the compounds Ia138.1–Ia138.164, which differ from the compounds Ia1.1–Ia1.164 in that $R^3$ is chlorine and $R^6$ is ethyl:

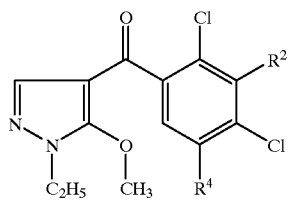

Ia138

Likewise, most particular preference is given to the compounds Ia139; in particular to the compounds Ia139.1–Ia139.164, which differ from the compounds Ia1.1–Ia1.164 in that $R^3$ is chlorine and $R^6$ is n-propyl:

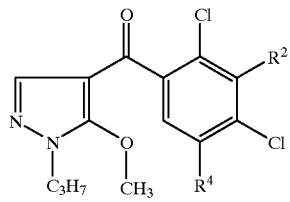

Ia139

Likewise, most particular preference is given to the compounds Ia140; in particular to the compounds Ia140.1–Ia140.164, which differ from the compounds Ia1.1–Ia1.164 in that $R^3$ is chlorine and $R^6$ is isobutyl:

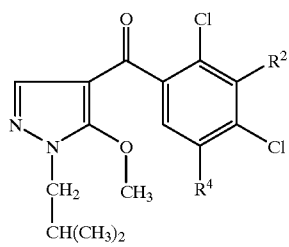

Ia140

Likewise, most particular preference is given to the compounds Ia141; in particular to the compounds Ia141.1–Ia141.164, which differ from the compounds Ia1.1–Ia1.164 in that $R^3$ is chlorine and $R^8$ is methyl:

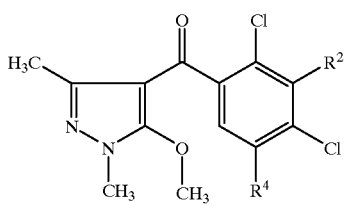

Ia141

Likewise, most particular preference is given to the compounds Ia142; in particular to the compounds Ia142.1–Ia142.164, which differ from the compounds Ia1.1–Ia1.164 in that $R^3$ is chlorine and $R^7$ is ethyl:

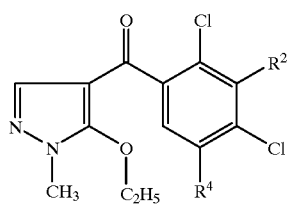

Ia142

Likewise, most particular preference is given to the compounds Ia143; in particular to the compounds Ia143.1–Ia143.164, which differ from the compounds Ia1.1–Ia1.164 in that $R^3$ is chlorine and $R^6$ and $R^7$ are each ethyl:

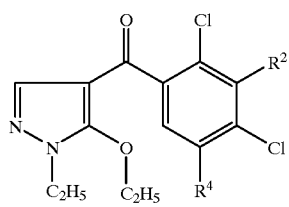

Ia143

Likewise, most particular preference is given to the compounds Ia144; in particular to the compounds Ia144.1–Ia144.164, which differ from the compounds Ia1.1–Ia1.164 in that $R^3$ is chlorine, $R^6$ is n-propyl and $R^7$ is ethyl:

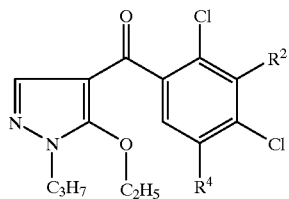
Ia144

Likewise, most particular preference is given to the compounds Ia145; in particular to the compounds Ia145.1–Ia145.164, which differ from the compounds Ia1.1–Ia1.164 in that $R^3$ is chlorine, $R^6$ is isobutyl and $R^7$ is ethyl:

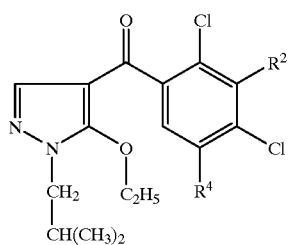
Ia145

Likewise, most particular preference is given to the compounds Ia146; in particular to the compounds Ia146.1–Ia146.164, which differ from the compounds Ia1.1–Ia1.164 in that $R^3$ is chlorine, $R^7$ is ethyl and $R^8$ is methyl:

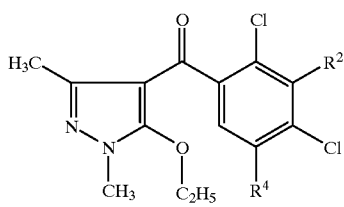
Ia146

Likewise, most particular preference is given to the compounds Ia147; in particular to the compounds Ia147.1–Ia147.164, which differ from the compounds Ia1.1–Ia1.164 in that $R^3$ is chlorine and $R^7$ is cyanomethyl:

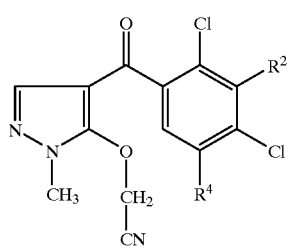
Ia147

Likewise, most particular preference is given to the compounds Ia148; in particular to the compounds Ia148.1–Ia148.164, which differ from the compounds Ia1.1–Ia1.164 in that $R^3$ is chlorine, $R^6$ is ethyl and $R^7$ is cyanomethyl:

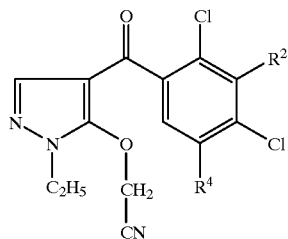
Ia148

Likewise, most particular preference is given to the compounds Ia149; in particular to the compounds Ia149.1–Ia149.164, which differ from the compounds Ia1.1–Ia1.164 in that $R^3$ is chlorine, $R^7$ is cyanomethyl and $R^8$ is methyl:

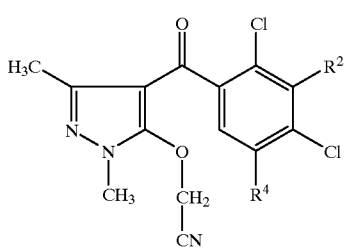
Ia149

Likewise, most particular preference is given to the compounds Ia150; in particular to the compounds Ia150.1–Ia150.164, which differ from the compounds Ia1.1–Ia1.164 in that $R^3$ is chlorine and $R^7$ is methoxymethyl:

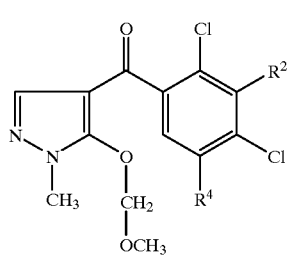
Ia150

Likewise, most particular preference is given to the compounds Ia151; in particular to the compounds Ia151.1–Ia151.164, which differ from the compounds Ia1.1–Ia1.164 in that $R^3$ is chlorine, $R^6$ is ethyl and $R^7$ is methoxymethyl:

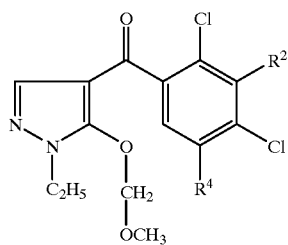
Ia151

Likewise, most particular preference is given to the compounds Ia152; in particular to the compounds Ia152.1–Ia152.164, which differ from the compounds Ia1.1–Ia1.164 in that $R^3$ is chlorine, $R^7$ is methoxymethyl and $R^8$ is methyl:

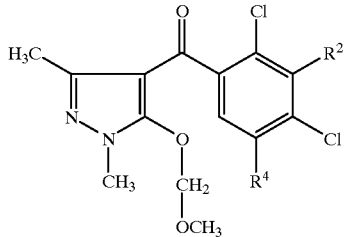

Ia152

Likewise, most particular preference is given to the compounds Ia153; in particular to the compounds Ia153.1–Ia153.164, which differ from the compounds Ia1.1–Ia1.164 in that $R^3$ is chlorine and $R^7$ is methylcarbonyloxymethyl:

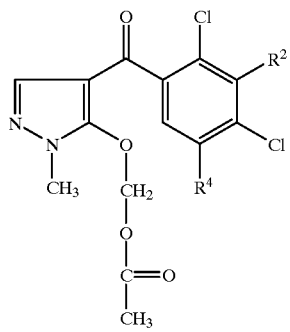

Ia153

Likewise, most particular preference is given to the compounds Ia154; in particular to the compounds Ia154.1–Ia154.164, which differ from the compounds Ia1.1–Ia1.164 in that $R^3$ is chlorine, $R^6$ is ethyl and $R^7$ is methylcarbonyloxymethyl:

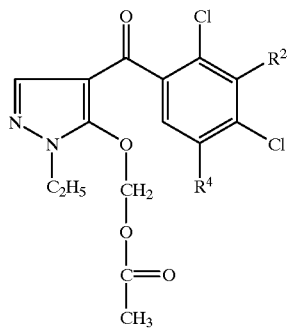

Ia154

Likewise, most particular preference is given to the compounds Ia155; in particular to the compounds Ia155.1–Ia155.164, which differ from the compounds Ia1.1–Ia1.164 in that $R^3$ is chlorine, $R^7$ is methylcarbonyloxymethyl and $R^8$ is methyl:

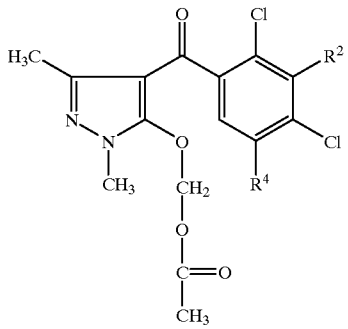

Ia155

Likewise, most particular preference is given to the compounds Ia156; in particular to the compounds Ia156.1–Ia156.164, which differ from the compounds Ia1.1–Ia1.164 in that $R^3$ is chlorine and $R^7$ is tert-butylcarbonyloxymethyl:

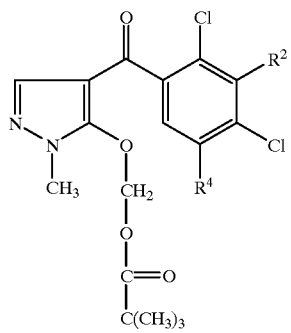

Ia156

Likewise, most particular preference is given to the compounds Ia157; in particular to the compounds Ia157.1–Ia157.164, which differ from the compounds Ia1.1–Ia1.164 in that $R^3$ is chlorine, $R^6$ is ethyl and $R^7$ is tert-butylcarbonyloxymethyl:

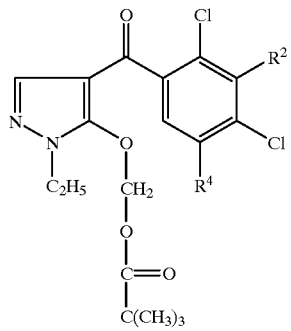

Ia157

Likewise, most particular preference is given to the compounds Ia158; in particular to the compounds Ia158.1–Ia158.164, which differ from the compounds Ia1.1–Ia1.164 in that $R^3$ is chlorine, $R^7$ is tert-butylcarbonyloxymethyl and $R^8$ is methyl:

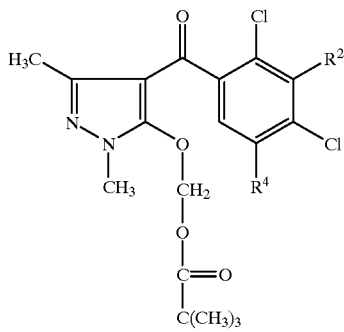

Ia158

Likewise, most particular preference is given to the compounds Ia159; in particular to the compounds Ia159.1–Ia159.164, which differ from the compounds Ia1.1–Ia1.164 in that $R^3$ is chlorine and $R^7$ is methoxycarbonylmethyl:

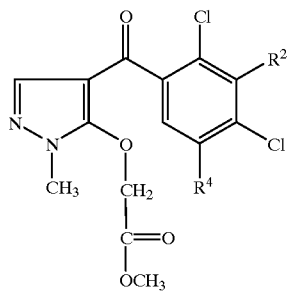

Ia159

Likewise, most particular preference is given to the compounds Ia160; in particular to the compounds Ia160.1–Ia160.164, which differ from the compounds Ia1.1–Ia1.164 in that $R^3$ is chlorine, $R^6$ is ethyl and $R^7$ is methoxycarbonylmethyl:

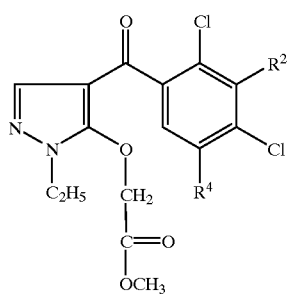

Ia160

Likewise, most particular preference is given to the compounds Ia161; in particular to the compounds Ia161.1–Ia161.164, which differ from the compounds Ia1.1–Ia1.164 in that $R^3$ is chlorine, $R^7$ is methoxycarbonylmethyl and $R^8$ is methyl:

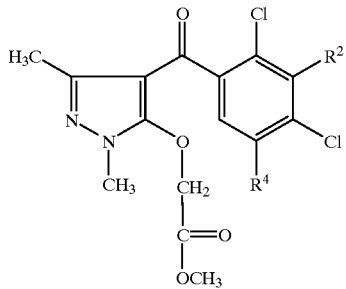

Ia161

Likewise, most particular preference is given to the compounds Ia162; in particular to the compounds Ia162.1–Ia162.164, which differ from the compounds Ia1.1–Ia1.164 in that $R^3$ is chlorine and $R^7$ is ethoxycarbonylmethyl:

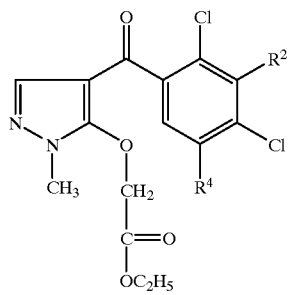

Ia162

Likewise, most particular preference is given to the compounds Ia163; in particular to the compounds Ia163.1–Ia163.164, which differ from the compounds Ia1.1–Ia1.164 in that $R^3$ is chlorine, $R^6$ is ethyl and $R^7$ is ethoxycarbonylmethyl:

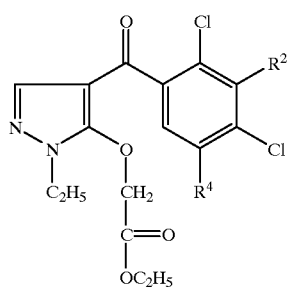

Ia163

Likewise, most particular preference is given to the compounds Ia164; in particular to the compounds Ia164.1–Ia164.164, which differ from the compounds Ia1.1–Ia1.164 in that $R^3$ is chlorine, $R^7$ is ethoxycarbonylmethyl and $R^8$ is methyl:

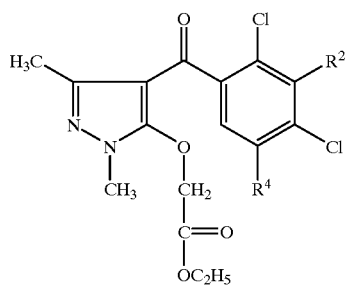

Ia164

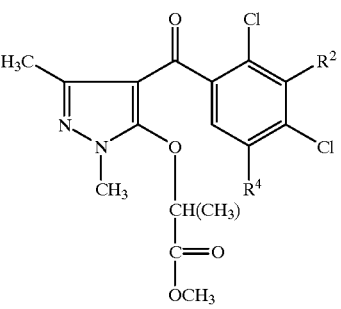

Ia167

Likewise, most particular preference is given to the compounds Ia165; in particular to the compounds Ia165.1–Ia165.164, which differ from the compounds Ia1.1–Ia1.164 in that $R^3$ is chlorine and $R^7$ is 1-methoxycarbonyleth-1-yl:

Likewise, most particular preference is given to the compounds Ia168; in particular to the compounds Ia168.1–Ia168.164, which differ from the compounds Ia1.1–Ia1.164 in that $R^3$ is chlorine and $R^7$ is 1-ethoxycarbonyleth-1-yl:

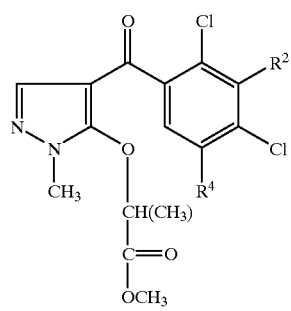

Ia165

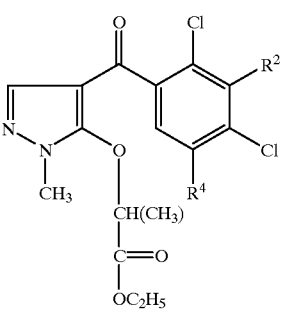

Ia168

Likewise, most particular preference is given to the compounds Ia166; in particular to the compounds Ia166.1–Ia166.164, which differ from the compounds Ia1.1–Ia1.164 in that $R^3$ is chlorine, $R^6$ is ethyl and $R^7$ is 1-methoxycarbonyleth-1-yl:

Likewise, most particular preference is given to the compounds Ia169; in particular to the compounds Ia169.1–Ia169.164, which differ from the compounds Ia1.1–Ia1.164 in that $R^3$ is chlorine, $R^6$ is ethyl and $R^7$ is 1-ethoxycarbonyleth-1-yl:

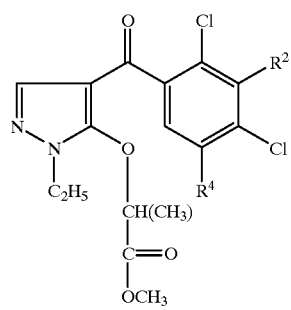

Ia166

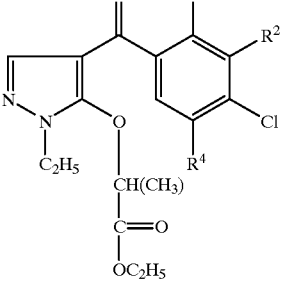

Ia169

Likewise, most particular preference is given to the compounds Ia167; in particular to the compounds Ia167.1–Ia167.164, which differ from the compounds Ia1.1–Ia1.164 in that $R^3$ is chlorine, $R^7$ is 1-methoxycarbonyleth-1-yl and $R^8$ is methyl:

Likewise, most particular preference is given to the compounds Ia170; in particular to the compounds Ia170.1–Ia170.164, which differ from the compounds Ia1.1–Ia1.164 in that $R^3$ is chlorine, $R^7$ is 1-ethoxycarbonyleth-1-yl and $R^8$ is methyl:

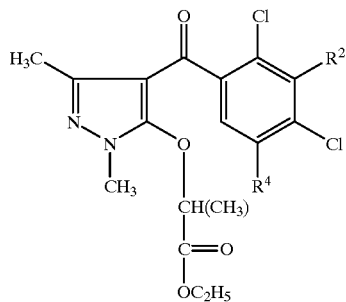

Ia170

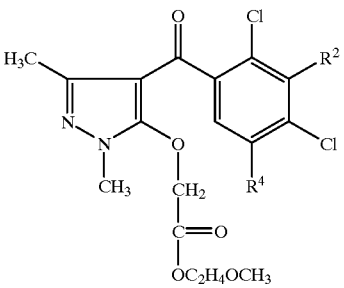

Ia173

Likewise, most particular preference is given to the compounds Ia171; in particular to the compounds Ia171.1–Ia171.164, which differ from the compounds Ia1.1–Ia1.164 in that $R^3$ is chlorine and $R^7$ is 2-methoxyeth-1-oxycarbonylmethyl:

Likewise, most particular preference is given to the compounds Ia174; in particular to the compounds Ia174.1–Ia174.164, which differ from the compounds Ia1.1–Ia1.164 in that $R^3$ is chlorine and $R^7$ is 2-dimethylaminoeth-1-oxycarbonylmethyl:

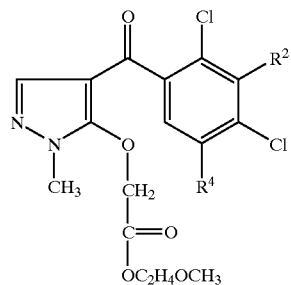

Ia171

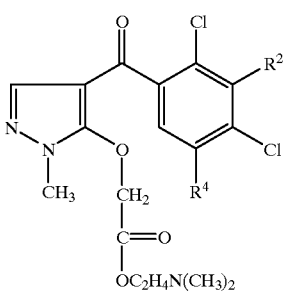

Ia174

Likewise, most particular preference is given to the compounds Ia172; in particular to the compounds Ia172.1–Ia172.164, which differ from the compounds Ia1.1–Ia1.164 in that $R^3$ is chlorine, $R^6$ is ethyl and $R^7$ is 2-methoxyeth-1-oxycarbonylmethyl:

Likewise, most particular preference is given to the compounds Ia175; in particular to the compounds Ia175.1–Ia175.164, which differ from the compounds Ia1.1–Ia1.164 in that $R^3$ is chlorine, $R^6$ is ethyl and $R^7$ is 2-dimethylaminoeth-1-oxycarbonylmethyl:

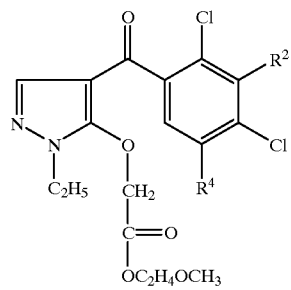

Ia172

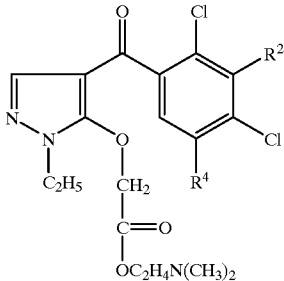

Ia175

Likewise, most particular preference is given to the compounds Ia173; in particular to the compounds Ia173.1–Ia173.164, which differ from the compounds Ia1.1–Ia1.164 in that $R^3$ is chlorine, $R^7$ is 2-methoxyeth-1-oxycarbonylmethyl and $R^8$ is methyl:

Likewise, most particular preference is given to the compounds Ia176; in particular to the compounds Ia176.1–Ia176.164, which differ from the compounds Ia1.1–Ia1.164 in that $R^3$ is chlorine, $R^7$ is 2-dimethylaminoeth-1-oxycarbonylmethyl and $R^8$ is methyl:

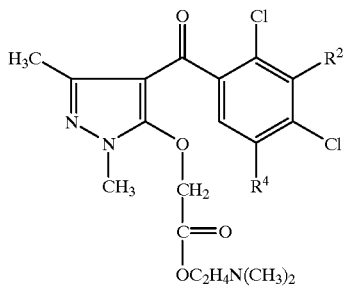
Ia176

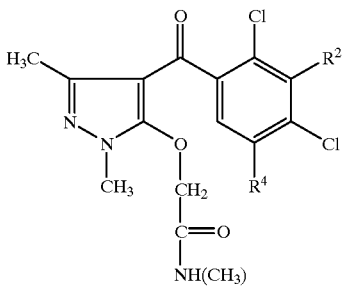
Ia179

Likewise, most particular preference is given to the compounds Ia177; in particular to the compounds Ia177.1–Ia177.164, which differ from the compounds Ia1.1–Ia1.164 in that $R^3$ is chlorine and $R^7$ is methylaminocarbonylmethyl:

Likewise, most particular preference is given to the compounds Ia180; in particular to the compounds Ia180.1–Ia180.164, which differ from the compounds Ia1.1–Ia1.164 in that $R^3$ is chlorine and $R^7$ is ethylaminocarbonylmethyl:

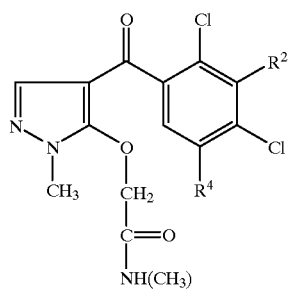
Ia177

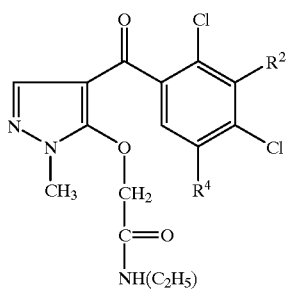
Ia180

Likewise, most particular preference is given to the compounds Ia178; in particular to the compounds Ia178.1–Ia178.164, which differ from the compounds Ia1.1–Ia1.164 in that $R^3$ is chlorine, $R^6$ is ethyl and $R^7$ is methylaminocarbonylmethyl:

Likewise, most particular preference is given to the compounds Ia181; in particular to the compounds Ia181.1–Ia181.164, which differ from the compounds Ia1.1–Ia1.164 in that $R^3$ is chlorine, $R^6$ is ethyl and $R^7$ is ethylaminocarbonylmethyl:

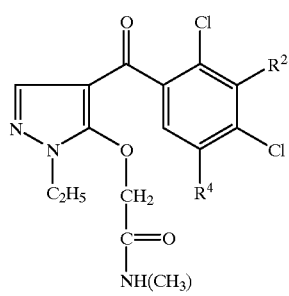
Ia178

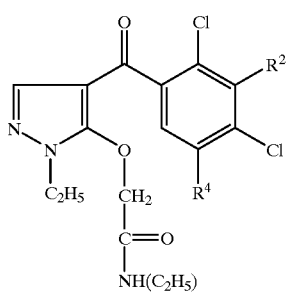
Ia181

Likewise, most particular preference is given to the compounds Ia179; in particular to the compounds Ia179.1–Ia179.164, which differ from the compounds Ia1.1–Ia1.164 in that $R^3$ is chlorine, $R^7$ is methylaminocarbonylmethyl and $R^8$ is methyl:

Likewise, most particular preference is given to the compounds Ia182; in particular to the compounds Ia182.1–Ia182.164, which differ from the compounds Ia1.1–Ia1.164 in that $R^3$ is chlorine, $R^7$ is ethylaminocarbonylmethyl and $R^8$ is methyl:

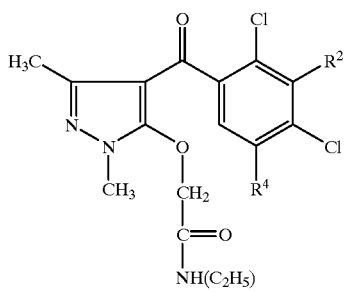

Ia182

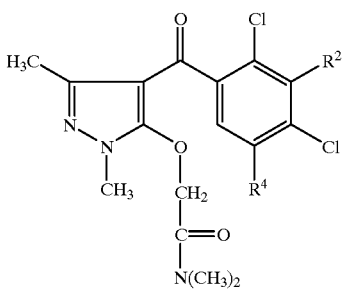

Ia185

Likewise, most particular preference is given to the compounds Ia183; in particular to the compounds Ia183.1–Ia183.164, which differ from the compounds Ia1.1–Ia1.164 in that $R^3$ is chlorine and $R^7$ is dimethylaminocarbonylmethyl:

Likewise, most particular preference is given to the compounds Ia186; in particular to the compounds Ia186.1–Ia186.164, which differ from the compounds Ia1.1–Ia1.164 in that $R^3$ is chlorine and $R^7$ is diethylaminocarbonylmethyl:

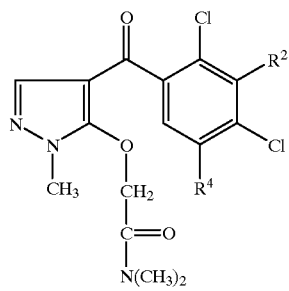

Ia183

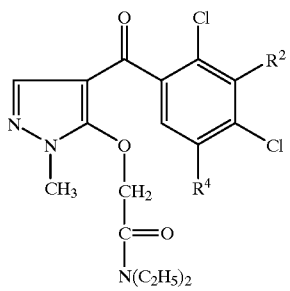

Ia186

Likewise, most particular preference is given to the compounds Ia184; in particular to the compounds Ia184.1–Ia184.164, which differ from the compounds Ia1.1–Ia1.164 in that $R^3$ is chlorine, $R^6$ is ethyl and $R^7$ is dimethylaminocarbonylmethyl:

Likewise, most particular preference is given to the compounds Ia187; in particular to the compounds Ia187.1–Ia187.164, which differ from the compounds Ia1.1–Ia1.164 in that $R^3$ is chlorine, $R^6$ is ethyl and $R^7$ is diethylaminocarbonylmethyl:

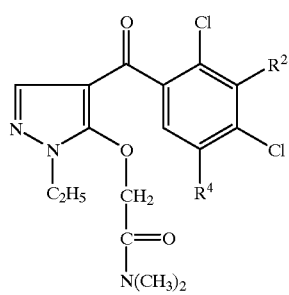

Ia184

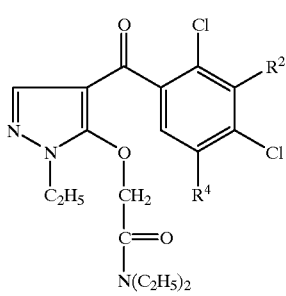

Ia187

Likewise, most particular preference is given to the compounds Ia185; in particular to the compounds Ia185.1–Ia185.164, which differ from the compounds Ia1.1–Ia1.164 in that $R^3$ is chlorine, $R^7$ is dimethylaminocarbonylmethyl and $R^8$ is methyl:

Likewise, most particular preference is given to the compounds Ia188; in particular to the compounds Ia188.1–Ia188.164, which differ from the compounds Ia1.1–Ia1.164 in that $R^3$ is chlorine, $R^7$ is diethylaminocarbonylmethyl and $R^8$ is methyl:

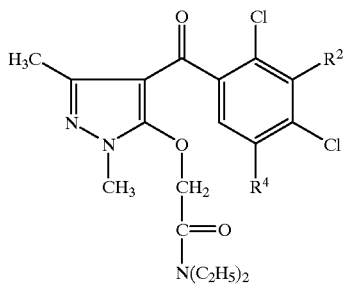

Ia188

Likewise, most particular preference is given to the compounds Ia189; in particular to the compounds Ia189.1–Ia189.164, which differ from the compounds Ia1.1–Ia1.164 in that $R^3$ is chlorine and $R^7$ is allyl:

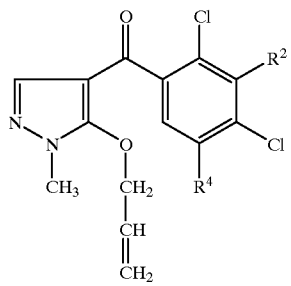

Ia189

Likewise, most particular preference is given to the compounds Ia190; in particular to the compounds Ia190.1–Ia190.164, which differ from the compounds Ia1.1–Ia1.164 in that $R^3$ is chlorine, $R^6$ is ethyl and $R^7$ is allyl:

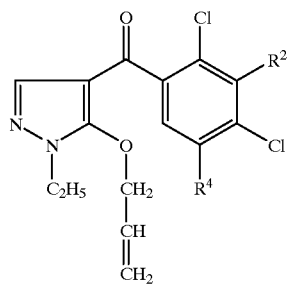

Ia190

Likewise, most particular preference is given to the compounds Ia191; in particular to the compounds Ia191.1–Ia191.164, which differ from the compounds Ia1.1–Ia1.164 in that $R^3$ is chlorine, $R^7$ is allyl and $R^8$ is methyl:

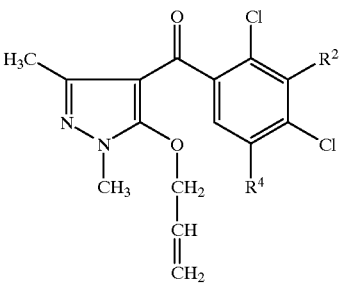

Ia191

Likewise, most particular preference is given to the compounds Ia192; in particular to the compounds Ia192.1–Ia192.164, which differ from the compounds Ia1.1–Ia1.164 in that $R^3$ is chlorine and $R^7$ is propargyl:

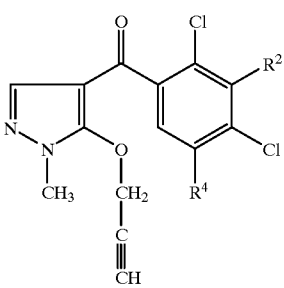

Ia192

Likewise, most particular preference is given to the compounds Ia193; in particular to the compounds Ia193.1–Ia193.164, which differ from the compounds Ia1.1–Ia1.164 in that $R^3$ is chlorine, $R^6$ is ethyl and $R^7$ is propargyl:

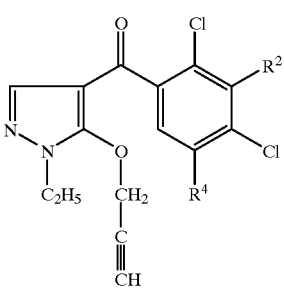

Ia193

Likewise, most particular preference is given to the compounds Ia194; in particular to the compounds Ia194.1–Ia194.164, which differ from the compounds Ia1.1–Ia1.164 in that $R^3$ is chlorine, $R^7$ is propargyl and $R^8$ is methyl:

Ia194

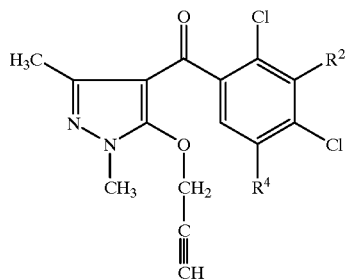

Likewise, most particular preference is given to the compounds Ia195; in particular to the compounds Ia195.1–Ia195.164, which differ from the compounds Ia1.1–Ia1.164 in that $R^3$ is chlorine and $R^7$ is methylcarbonyl:

Ia195

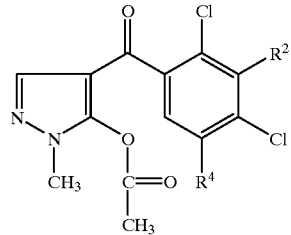

Likewise, most particular preference is given to the compounds Ia196; in particular to the compounds Ia196.1–Ia196.164, which differ from the compounds Ia1.1–Ia1.164 in that $R^3$ is chlorine, $R^6$ is ethyl and $R^7$ is methylcarbonyl:

Ia196

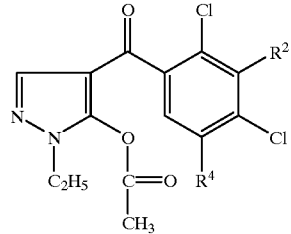

Likewise, most particular preference is given to the compounds Ia197; in particular to the compounds Ia197.1–Ia197.164, which differ from the compounds Ia1.1–Ia1.164 in that $R^3$ is chlorine, $R^6$ is n-propyl und $R^7$ is methylcarbonyl:

Ia197

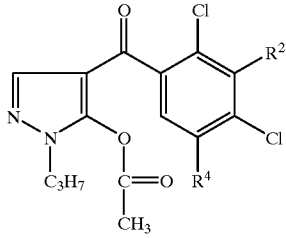

Likewise, most particular preference is given to the compounds Ia198; in particular to the compounds Ia198.1–Ia198.164, which differ from the compounds Ia1.1–Ia1.164 in that $R^3$ is chlorine, $R^6$ is isobutyl und $R^7$ is methylcarbonyl:

Ia198

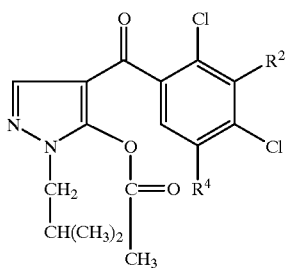

Likewise, most particular preference is given to the compounds Ia199; in particular to the compounds Ia199.1–Ia199.164, which differ from the compounds Ia1.1–Ia1.164 in that $R^3$ is chlorine, $R^7$ is methylcarbonyl and $R^8$ is methyl:

Ia199

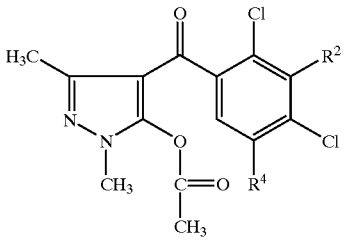

Likewise, most particular preference is given to the compounds Ia200; in particular to the compounds Ia200.1–Ia200.164, which differ from the compounds Ia1.1–Ia1.164 in that $R^3$ is chlorine and $R^7$ is ethylcarbonyl:

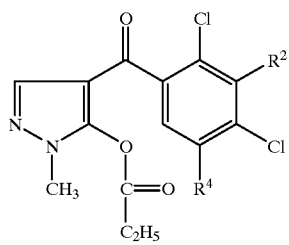

Ia200

Likewise, most particular preference is given to the compounds Ia201; in particular to the compounds Ia201.1–Ia201.164, which differ from the compounds Ia1.1–Ia1.164 in that $R^3$ is chlorine, $R^6$ is ethyl and $R^7$ is ethylcarbonyl:

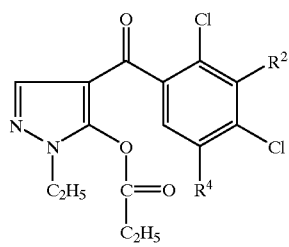

Ia201

Likewise, most particular preference is given to the compounds Ia202; in particular to the compounds Ia202.1–Ia202.164, which differ from the compounds Ia1.1–Ia1.164 in that $R^3$ is chlorine, $R^6$ is n-propyl und $R^7$ is ethylcarbonyl:

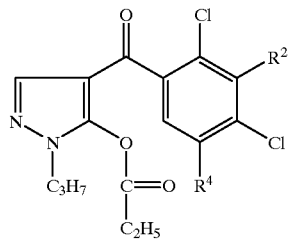

Ia202

Likewise, most particular preference is given to the compounds Ia203; in particular to the compounds Ia203.1–Ia203.164, which differ from the compounds Ia1.1–Ia1.164 in that $R^3$ is chlorine, $R^6$ is isobutyl und $R^7$ is ethylcarbonyl:

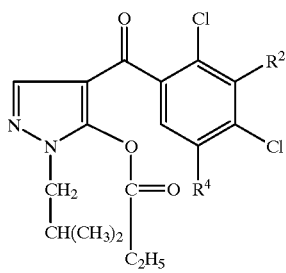

Ia203

Likewise, most particular preference is given to the compounds Ia204; in particular to the compounds Ia204.1–Ia204.164, which differ from the compounds Ia1.1–Ia1.164 in that $R^3$ is chlorine, $R^7$ is ethylcarbonyl and $R^8$ is methyl:

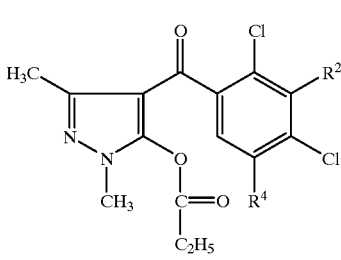

Ia204

Likewise, most particular preference is given to the compounds Ia205; in particular to the compounds Ia205.1–Ia205.164, which differ from the compounds Ia1.1–Ia1.164 in that $R^3$ is chlorine and $R^7$ is methoxycarbonyl:

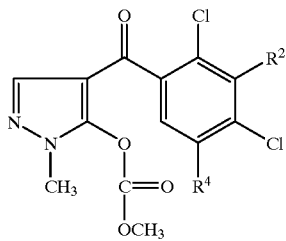

Ia205

Likewise, most particular preference is given to the compounds Ia206; in particular to the compounds Ia206.1–Ia206.164, which differ from the compounds Ia1.1–Ia1.164 in that $R^3$ is chlorine, $R^6$ is ethyl and $R^7$ is methoxycarbonyl:

Ia206

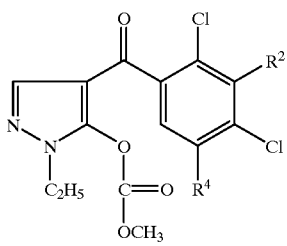

Likewise, most particular preference is given to the compounds Ia207; in particular to the compounds Ia207.1–Ia207.164, which differ from the compounds Ia1.1–Ia1.164 in that $R^3$ is chlorine, $R^7$ is methoxycarbonyl and $R^8$ is methyl:

Ia207

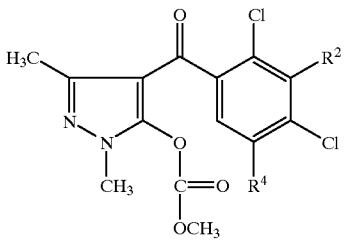

Likewise, most particular preference is given to the compounds Ia208; in particular to the compounds Ia208.1–Ia208.164, which differ from the compounds Ia1.1–Ia1.164 in that $R^3$ is chlorine and $R^7$ is ethoxycarbonyl:

Ia208

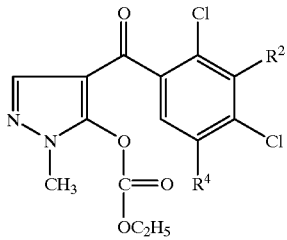

Likewise, most particular preference is given to the compounds Ia209; in particular to the compounds Ia209.1–Ia209.164, which differ from the compounds Ia1.1–Ia1.164 in that $R^3$ is chlorine, $R^6$ is ethyl and $R^7$ is ethoxycarbonyl:

Ia209

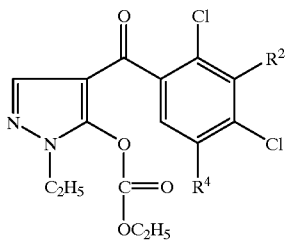

Likewise, most particular preference is given to the compounds Ia210; in particular to the compounds Ia210.1–Ia210.164, which differ from the compounds Ia1.1–Ia1.164 in that $R^3$ is chlorine, $R^7$ is ethoxycarbonyl and $R^8$ is methyl:

Ia210

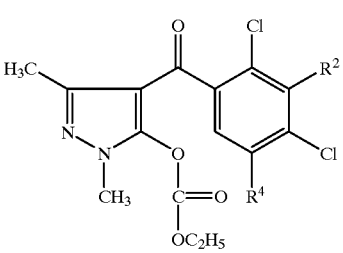

Likewise, most particular preference is given to the compounds Ia211; in particular to the compounds Ia211.1–Ia211.164, which differ from the compounds Ia1.1–Ia1.164 in that $R^3$ is chlorine and $R^7$ is dimethylaminocarbonyl:

Ia211

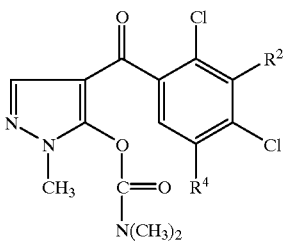

Likewise, most particular preference is given to the compounds Ia212; in particular to the compounds Ia212.1–Ia212.164, which differ from the compounds Ia1.1–Ia1.164 in that $R^3$ is chlorine, $R^6$ is ethyl and $R^7$ is dimethylaminocarbonyl:

Ia212

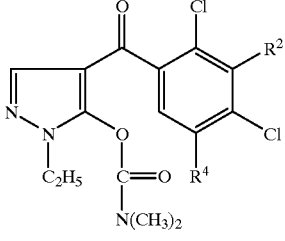

Likewise, most particular preference is given to the compounds Ia213; in particular to the compounds Ia213.1–Ia213.164, which differ from the compounds Ia1.1–Ia1.164 in that $R^3$ is chlorine, $R^7$ is dimethylaminocarbonyl and $R^8$ is methyl:

Ia213

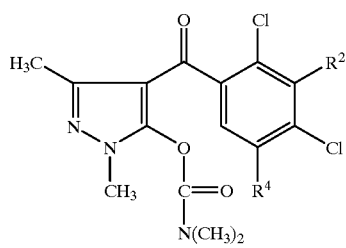

Likewise, most particular preference is given to the compounds Ia214; in particular to the compounds Ia214.1–Ia214.164, which differ from the compounds Ia1.1–Ia1.164 in that $R^3$ is chlorine and $R^7$ is diethylaminocarbonyl:

Ia214

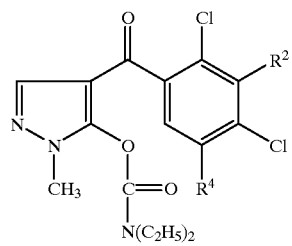

Likewise, most particular preference is given to the compounds Ia215; in particular to the compounds Ia215.1–Ia215.164, which differ from the compounds Ia1.1–Ia1.164 in that $R^3$ is chlorine, $R^6$ is ethyl and $R^7$ is diethylaminocarbonyl:

Ia215

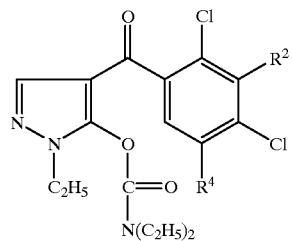

Likewise, most particular preference is given to the compounds Ia216; in particular to the compounds Ia216.1–Ia216.164, which differ from the compounds Ia1.1–Ia1.164 in that $R^3$ is chlorine, $R^7$ is diethylaminocarbonyl and $R^8$ is methyl:

Ia216

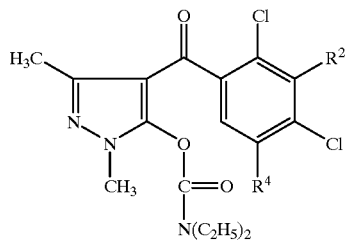

Likewise, most particular preference is given to the compounds Ia217; in particular to the compounds Ia217.1–Ia217.164, which differ from the compounds Ia1.1–Ia1.164 in that $R^3$ is chlorine and $R^7$ is N-methoxy-N-methylaminocarbonyl:

Ia217

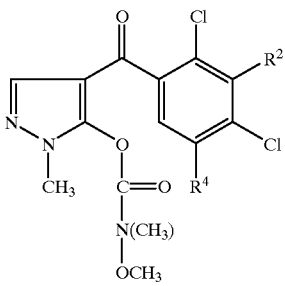

Likewise, most particular preference is given to the compounds Ia218; in particular to the compounds Ia218.1–Ia218.164, which differ from the compounds Ia1.1–Ia1.164 in that $R^3$ is chlorine, $R^6$ is ethyl and $R^7$ is N-methoxy-N-methylaminocarbonyl:

Ia218

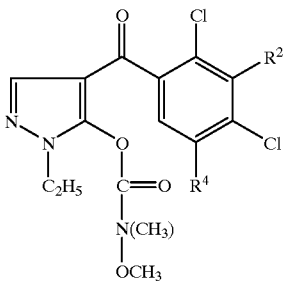

Likewise, most particular preference is given to the compounds Ia219; in particular to the compounds Ia219.1–Ia219.164, which differ from the compounds Ia1.1–Ia1.164 in that $R^3$ is chlorine, $R^7$ is N-methoxy-N-methylaminocarbonyl and $R^8$ is methyl:

Ia219

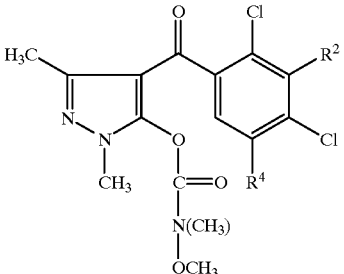

Likewise, most particular preference is given to the compounds Ia220; in particular to the compounds Ia220.1–Ia220.164, which differ from the compounds Ia1.1–Ia1.164 in that $R^3$ is chlorine and $R^7$ is benzyl:

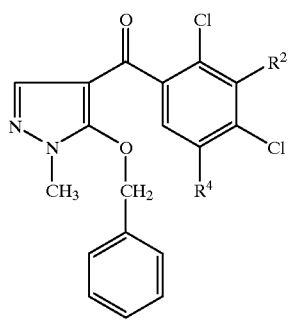

Ia220

Likewise, most particular preference is given to the compounds Ia221; in particular to the compounds Ia221.1–Ia221.164, which differ from the compounds Ia1.1–Ia1.164 in that $R^3$ is chlorine, $R^6$ is ethyl and $R^7$ is benzyl:

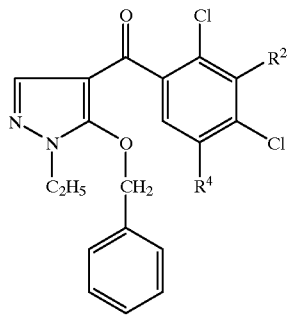

Ia221

Likewise, most particular preference is given to the compounds Ia222; in particular to the compounds Ia222.1–Ia222.164, which differ from the compounds Ia1.1–Ia1.164 in that $R^3$ is chlorine, $R^6$ is n-propyl and $R^7$ is benzyl:

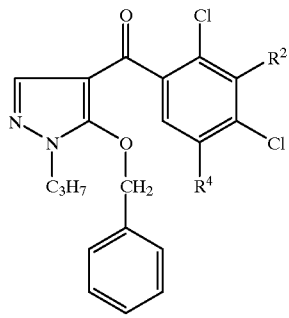

Ia222

Likewise, most particular preference is given to the compounds Ia223; in particular to the compounds Ia223.1–Ia223.164, which differ from the compounds Ia1.1–Ia1.164 in that $R^3$ is chlorine, $R^6$ is isobutyl und $R^7$ is benzyl:

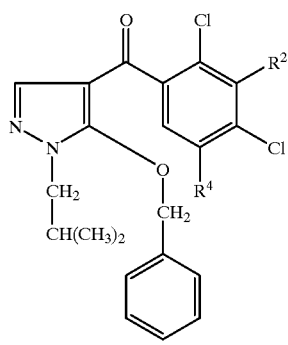

Ia223

Likewise, most particular preference is given to the compounds Ia224; in particular to the compounds Ia224.1–Ia224.164, which differ from the compounds Ia1.1–Ia1.164 in that $R^3$ is chlorine, $R^7$ is benzyl and $R^8$ is methyl:

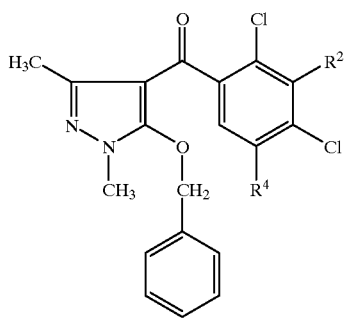

Ia224

Likewise, most particular preference is given to the compounds Ia225; in particular to the compounds Ia225.1–Ia225.164, which differ from the compounds Ia1.1–Ia1.164 in that $R^3$ is chlorine and $R^7$ is 4-methylphenylmethyl:

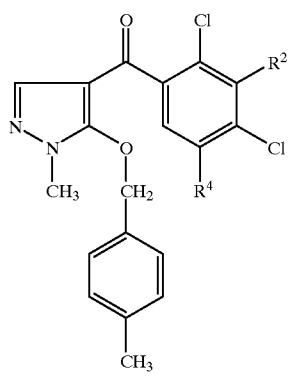

Ia225

Likewise, most particular preference is given to the compounds Ia226; in particular to the compounds Ia226.1–Ia226.164, which differ from the compounds Ia1.1–Ia1.164 in that $R^3$ is chlorine, $R^6$ is ethyl and $R^7$ is 4-methylphenylmethyl:

Ia1.1–Ia1.164 in that $R^3$ is chlorine, $R^7$ is 4-methylphenylmethyl and $R^8$ is methyl:

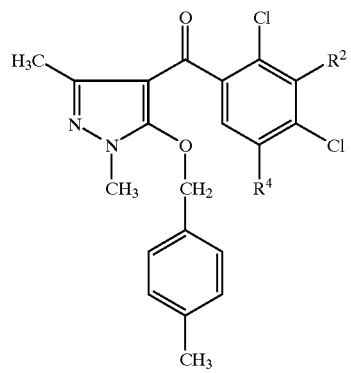

Ia229

Likewise, most particular preference is given to the compounds Ia230; in particular to the compounds Ia230.1–Ia230.164, which differ from the compounds Ia1.1–Ia1.164 in that $R^3$ is chlorine and $R^7$ is 4-chlorophenylmethyl:

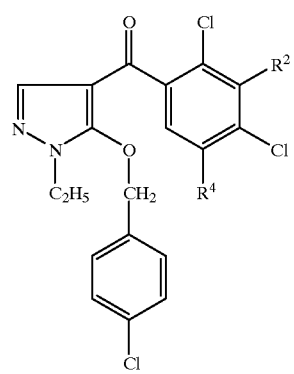

Ia230

Likewise, most particular preference is given to the compounds Ia231; in particular to the compounds Ia231.1–Ia231.164, which differ from the compounds Ia1.1–Ia1.164 in that $R^3$ is chlorine, $R^6$ is ethyl and $R^7$ is 4-chlorophenylmethyl:

Ia231

Likewise, most particular preference is given to the compounds Ia232; in particular to the compounds Ia232.1–Ia232.164, which differ from the compounds

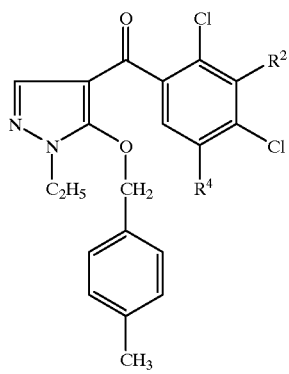

Ia226

Likewise, most particular preference is given to the compounds Ia227; in particular to the compounds Ia227.1–Ia227.164, which differ from the compounds Ia1.1–Ia1.164 in that $R^3$ is chlorine, $R^6$ is n-propyl and $R^7$ is 4-methylphenylmethyl:

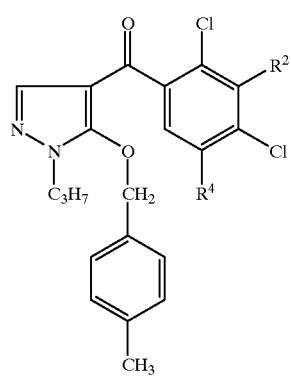

Ia227

Likewise, most particular preference is given to the compounds Ia228; in particular to the compounds Ia228.1–Ia228.164, which differ from the compounds Ia1.1–Ia1.164 in that $R^3$ is chlorine, $R^6$ is isobutyl und $R^7$ is 4-methylphenylmethyl:

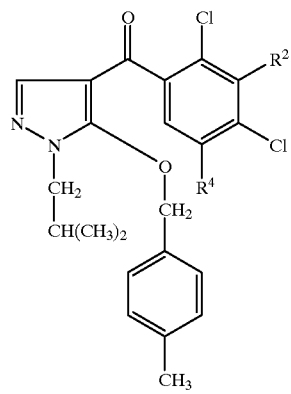

Ia228

Likewise, most particular preference is given to the compounds Ia229; in particular to the compounds Ia229.1–Ia229.164, which differ from the compounds Ia1.1–Ia1.164 in that R³ is chlorine, R⁶ is n-propyl and R⁷ is 4-chlorophenylmethyl:

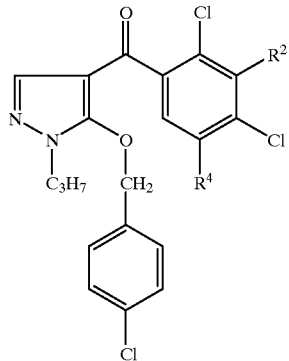

Ia232

Likewise, most particular preference is given to the compounds Ia233; in particular to the compounds Ia233.1–Ia233.164, which differ from the compounds Ia1.1–Ia1.164 in that R³ is chlorine, R⁶ is isobutyl und R⁷ is 4-chlorophenylmethyl:

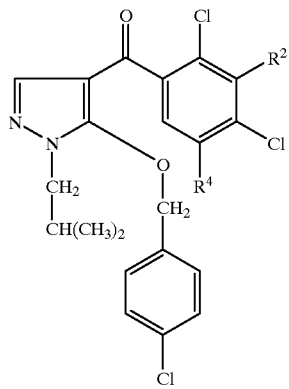

Ia233

Likewise, most particular preference is given to the compounds Ia234; in particular to the compounds Ia234.1–Ia234.164, which differ from the compounds Ia1.1–Ia1.164 in that R³ is chlorine, R⁷ is 4-chlorophenylmethyl and R⁸ is methyl:

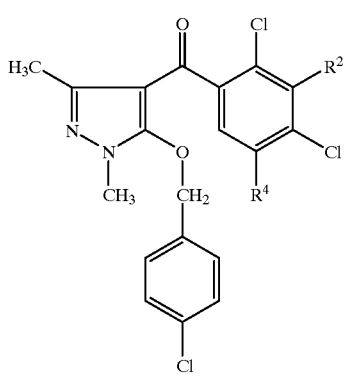

Ia234

Likewise, most particular preference is given to the compounds Ia235; in particular to the compounds Ia235.1–Ia235.164, which differ from the compounds Ia1.1–Ia1.164 in that R³ is chlorine and R⁷ is 4-methoxyphenylmethyl:

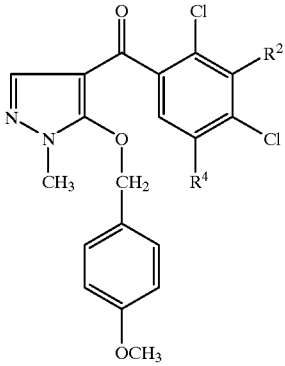

Ia235

Likewise, most particular preference is given to the compounds Ia236; in particular to the compounds Ia236.1–Ia236.164, which differ from the compounds Ia1.1–Ia1.164 in that R³ is chlorine, R⁶ is ethyl and R⁷ is 4-methoxyphenylmethyl:

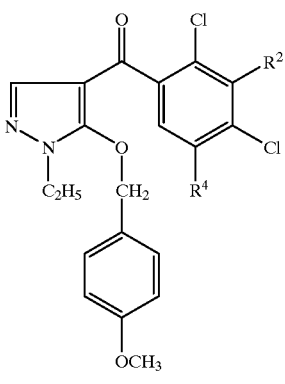

Ia236

Likewise, most particular preference is given to the compounds Ia237; in particular to the compounds Ia237.1–Ia237.164, which differ from the compounds Ia1.1–Ia1.164 in that R³ is chlorine, R⁷ is 4-methoxyphenylmethyl and R⁸ is methyl:

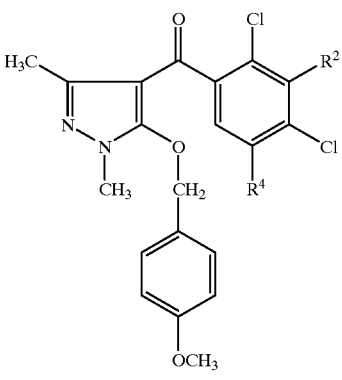

Ia237

Likewise, most particular preference is given to the compounds Ia238; in particular to the compounds Ia238.1–Ia238.164, which differ from the compounds Ia1.1–Ia1.164 in that $R^3$ is chlorine and $R^7$ is 3-trifluoromethylphenylmethyl:

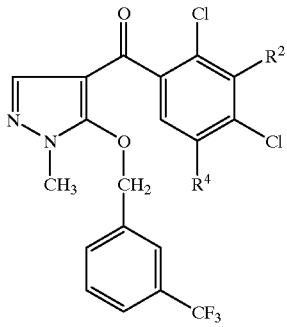

Ia238

Likewise, most particular preference is given to the compounds Ia239; in particular to the compounds Ia239.1–Ia239.164, which differ from the compounds Ia1.1–Ia1.164 in that $R^3$ is chlorine, $R^6$ is ethyl and $R^7$ is 3-trifluoromethylphenylmethyl:

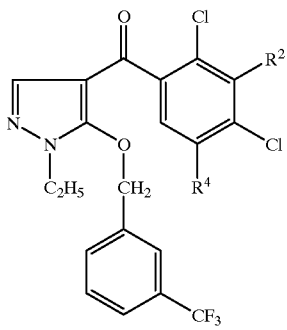

Ia239

Likewise, most particular preference is given to the compounds Ia237; in particular to the compounds Ia237.1–Ia237.164, which differ from the compounds Ia1.1–Ia1.164 in that $R^3$ is chlorine, $R^7$ is 3-trifluoromethylphenylmethyl and $R^8$ is methyl:

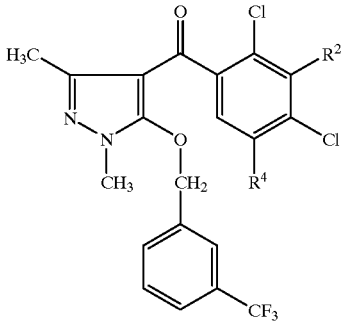

Ia240

Likewise, most particular preference is given to the compounds Ia241; in particular to the compounds Ia241.1–Ia241.164, which differ from the compounds Ia1.1–Ia1.164 in that $R^3$ is chlorine and $R^7$ is 2,4-dichlorophenylmethyl:

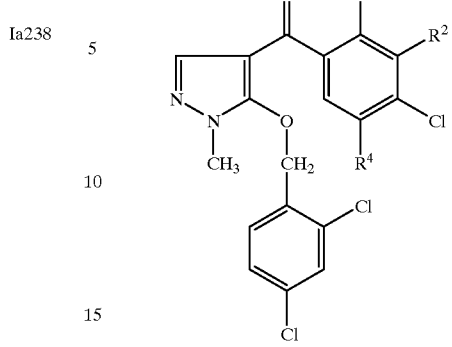

Ia241

Likewise, most particular preference is given to the compounds Ia242; in particular to the compounds Ia242.1–Ia242.164, which differ from the compounds Ia1.1–Ia1.164 in that $R^3$ is chlorine, $R^6$ is ethyl and $R^7$ is 2,4-dichlorophenylmethyl:

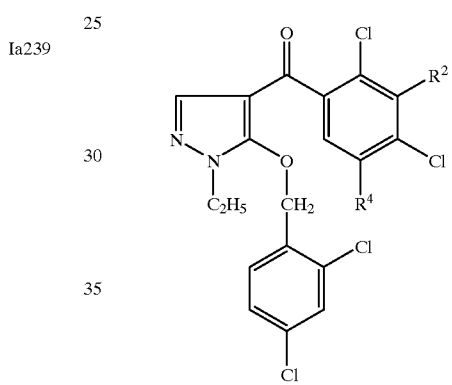

Ia242

Likewise, most particular preference is given to the compounds Ia243; in particular to the compounds Ia243.1–Ia243.164, which differ from the compounds Ia1.1–Ia1.164 in that $R^3$ is chlorine, $R^7$ is 2,4-dichlorophenylmethyl and $R^8$ is methyl:

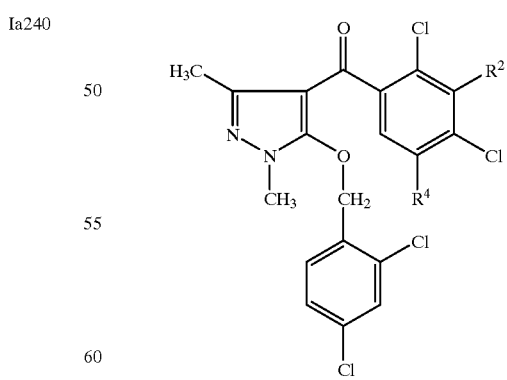

Ia243

Likewise, most particular preference is given to the compounds Ia244; in particular to the compounds Ia244.1–Ia244.164, which differ from the compounds Ia1.1–Ia1.164 in that $R^3$ is chlorine and $R^7$ is phenylcarbonylmethyl:

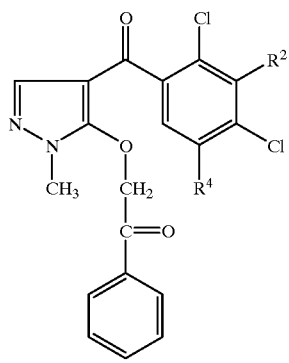
Ia244

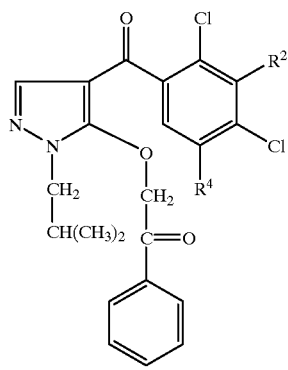
Ia247

Likewise, most particular preference is given to the compounds Ia245; in particular to the compounds Ia245.1–Ia245.164, which differ from the compounds Ia1.1–Ia1.164 in that $R^3$ is chlorine, $R^6$ is ethyl and $R^7$ is phenylcarbonylmethyl:

Likewise, most particular preference is given to the compounds Ia248; in particular to the compounds Ia248.1–Ia248.164, which differ from the compounds Ia1.1–Ia1.164 in that $R^3$ is chlorine, $R^7$ is phenylcarbonylmethyl and $R^8$ is methyl:

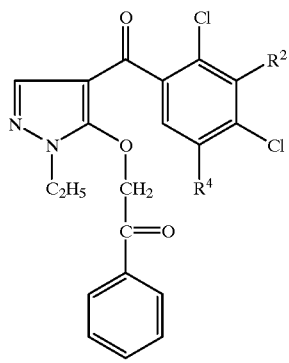
Ia245

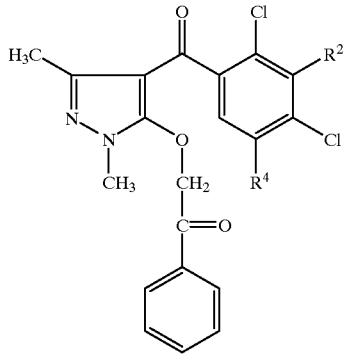
Ia248

Likewise, most particular preference is given to the compounds Ia246; in particular to the compounds Ia246.1–Ia246.164, which differ from the compounds Ia1.1–Ia1.164 in that $R^3$ is chlorine, $R^6$ is n-propyl and $R^7$ is phenylcarbonylmethyl:

Likewise, most particular preference is given to the compounds Ia249; in particular to the compounds Ia249.1–Ia249.164, which differ from the compounds Ia1.1–Ia1.164 in that $R^3$ is chlorine and $R^7$ is 4-methylphenylcarbonylmethyl:

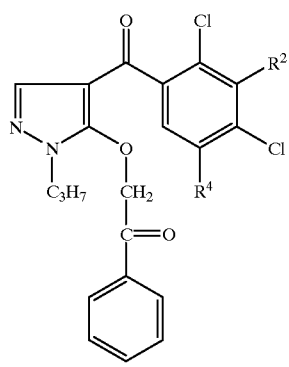
Ia246

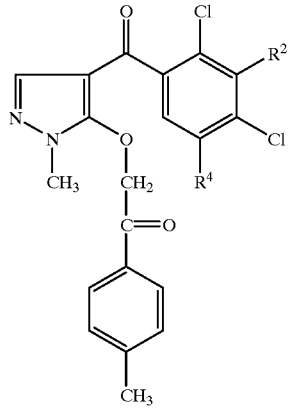
Ia249

Likewise, most particular preference is given to the compounds Ia247; in particular to the compounds Ia247.1–Ia247.164, which differ from the compounds Ia1.1–Ia1.164 in that $R^3$ is chlorine, $R^6$ is isobutyl and $R^7$ is phenylcarbonylmethyl:

Likewise, most particular preference is given to the compounds Ia250; in particular to the compounds Ia250.1–Ia250.164, which differ from the compounds Ia1.1–Ia1.164 in that $R^3$ is chlorine, $R^6$ is ethyl and $R^7$ is 4-methylphenylcarbonylmethyl:

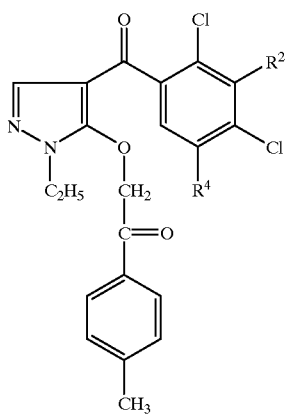

Ia250

Likewise, most particular preference is given to the compounds Ia251; in particular to the compounds Ia251.1–Ia251.164, which differ from the compounds Ia1.1–Ia1.164 in that $R^3$ is chlorine, $R^7$ is 4-methylphenylcarbonylmethyl and $R^8$ is methyl:

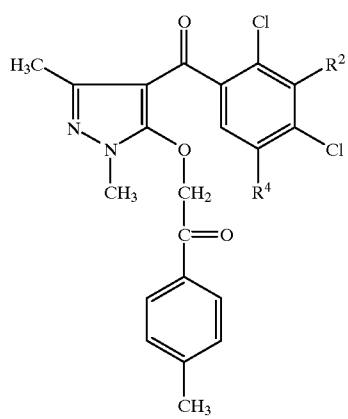

Ia251

Likewise, most particular preference is given to the compounds Ia252; in particular to the compounds Ia252.1–Ia252.164, which differ from the compounds Ia1.1–Ia1.164 in that $R^3$ is chlorine and $R^7$ is 1-(phenylcarbonyl)eth-1-yl:

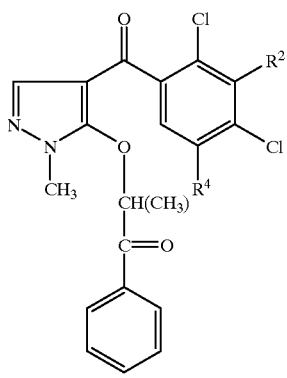

Ia252

Likewise, most particular preference is given to the compounds Ia253; in particular to the compounds Ia253.1–Ia253.164, which differ from the compounds Ia1.1–Ia1.164 in that $R^3$ is chlorine, $R^6$ is ethyl and $R^7$ is 1-(phenylcarbonyl)eth-1-yl:

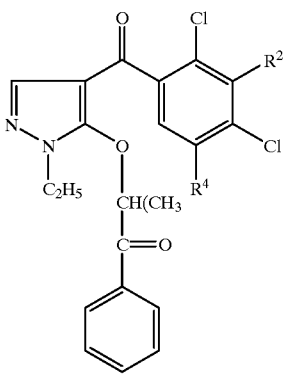

Ia253

Likewise, most particular preference is given to the compounds Ia254; in particular to the compounds Ia254.1–Ia254.164, which differ from the compounds Ia1.1–Ia1.164 in that $R^3$ is chlorine, $R^7$ is 1-(phenylcarbonyl)eth-1-yl and $R^8$ is methyl:

Ia254

Likewise, most particular preference is given to the compounds Ia255; in particular to the compounds Ia255.1–Ia255.164, which differ from the compounds Ia1.1–Ia1.164 in that $R^3$ is chlorine and $R^7$ is phenylcarbonyl:

Ia255

Likewise, most particular preference is given to the compounds Ia256; in particular to the compounds Ia256.1–Ia256.164, which differ from the compounds Ia1.1–Ia1.164 in that $R^3$ is chlorine, $R^6$ is ethyl and $R^7$ is phenylcarbonyl:

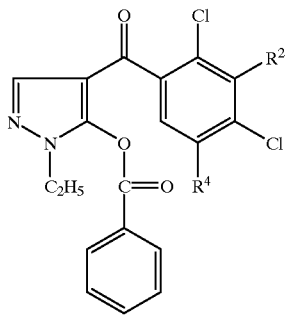
Ia256

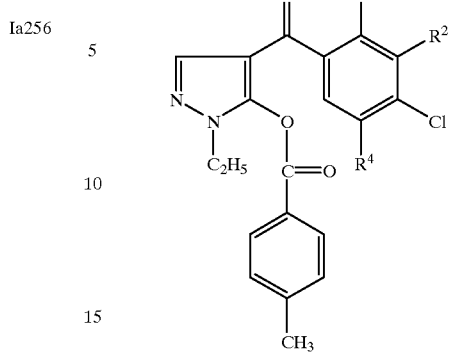
Ia259

Likewise, most particular preference is given to the compounds Ia257; in particular to the compounds Ia257.1–Ia257.164, which differ from the compounds Ia1.1–Ia1.164 in that $R^3$ is chlorine, $R^7$ is phenylcarbonyl and $R^8$ is methyl:

Likewise, most particular preference is given to the compounds Ia260; in particular to the compounds Ia260.1–Ia260.164, which differ from the compounds Ia1.1–Ia1.164 in that $R^3$ is chlorine, $R^7$ is 4-methylphenylcarbonyl and $R^8$ is methyl:

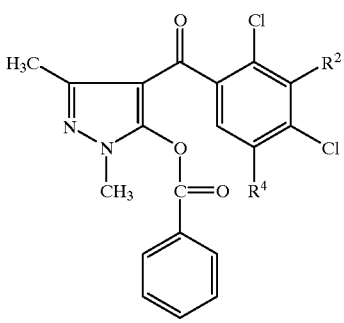
Ia257

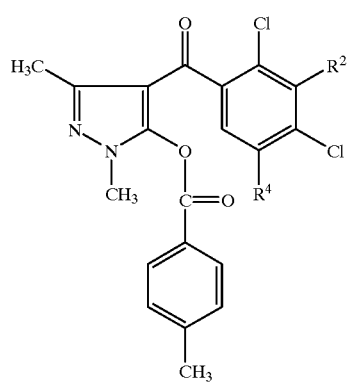
Ia260

Likewise, most particular preference is given to the compounds Ia258; in particular to the compounds Ia258.1–Ia258.164, which differ from the compounds Ia1.1–Ia1.164 in that $R^3$ is chlorine and $R^7$ is 4-methylphenylcarbonyl:

Likewise, most particular preference is given to the compounds Ia261; in particular to the compounds Ia261.1–Ia261.164, which differ from the compounds Ia1.1–Ia1.164 in that $R^3$ is chlorine and $R^7$ is 4-chlorophenylcarbonyl:

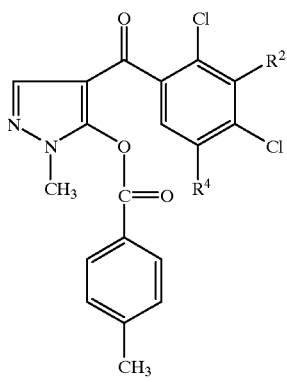
Ia258

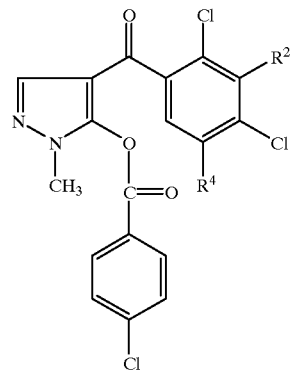
Ia261

Likewise, most particular preference is given to the compounds Ia259; in particular to the compounds Ia259.1–Ia259.164, which differ from the compounds Ia1.1–Ia1.164 in that $R^3$ is chlorine, $R^6$ is ethyl and $R^7$ is 4-methylphenylcarbonyl:

Likewise, most particular preference is given to the compounds Ia262; in particular to the compounds Ia262.1–Ia262.164, which differ from the compounds Ia1.1–Ia1.164 in that $R^3$ is chlorine, $R^6$ is ethyl and $R^7$ is 4-chlorophenylcarbonyl:

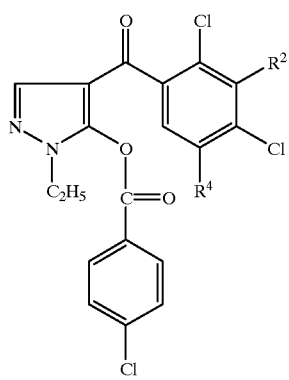

Ia262

Likewise, most particular preference is given to the compounds Ia263; in particular to the compounds Ia263.1–Ia263.164, which differ from the compounds Ia1.1–Ia1.164 in that $R^3$ is chlorine, $R^7$ is 4-chlorophenylcarbonyl and $R^8$ is methyl:

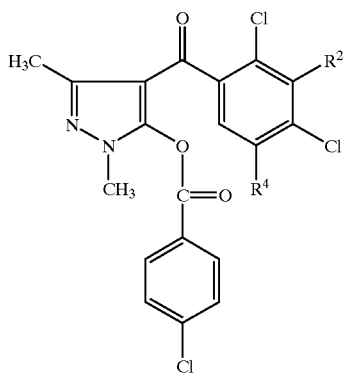

Ia263

Likewise, most particular preference is given to the compounds Ia264; in particular to the compounds Ia264.1–Ia264.164, which differ from the compounds Ia1.1–Ia1.164 in that $R^3$ is chlorine and $R^7$ is 4-methoxyphenylcarbonyl:

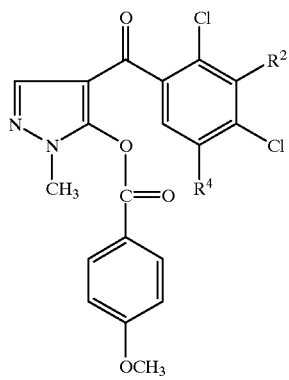

Ia264

Likewise, most particular preference is given to the compounds Ia265; in particular to the compounds Ia265.1–Ia265.164, which differ from the compounds Ia1.1–Ia1.164 in that $R^3$ is chlorine, $R^6$ is ethyl and $R^7$ is 4-methoxyphenylcarbonyl:

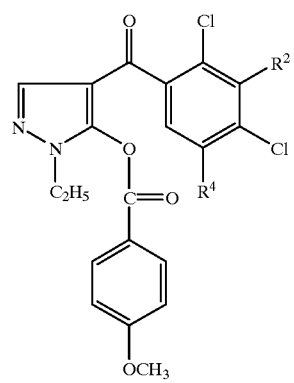

Ia265

Likewise, most particular preference is given to the compounds Ia266; in particular to the compounds Ia266.1–Ia266.164, which differ from the compounds Ia1.1–Ia1.164 in that $R^3$ is chlorine, $R^7$ is 4-methoxyphenylcarbonyl and $R^8$ is methyl:

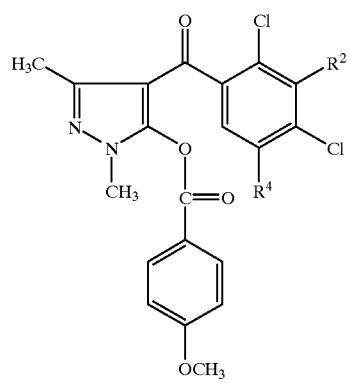

Ia266

Likewise, most particular preference is given to the compounds Ia267; in particular to the compounds Ia267.1–Ia267.164, which differ from the compounds Ia1.1–Ia1.164 in that $R^3$ is chlorine and $R^7$ is 4-trifluoromethylphenylcarbonyl:

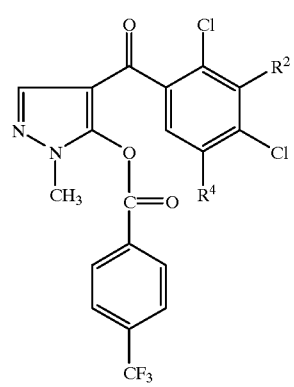

Ia267

Likewise, most particular preference is given to the compounds Ia268; in particular to the compounds Ia268.1–Ia268.164, which differ from the compounds Ia1.1–Ia1.164 in that $R^3$ is chlorine, $R^6$ is ethyl and $R^7$ is 4-trifluoromethylphenylcarbonyl:

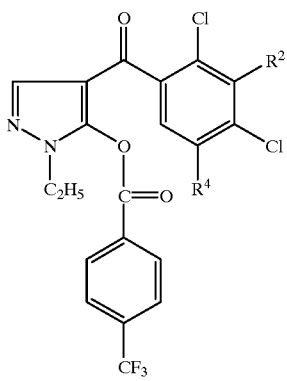

Likewise, most particular preference is given to the compounds Ia269; in particular to the compounds Ia269.1–Ia269.164, which differ from the compounds Ia1.1–Ia1.164 in that $R^3$ is chlorine, $R^7$ is 4-trifluoromethylphenylcarbonyl and $R^8$ is methyl:

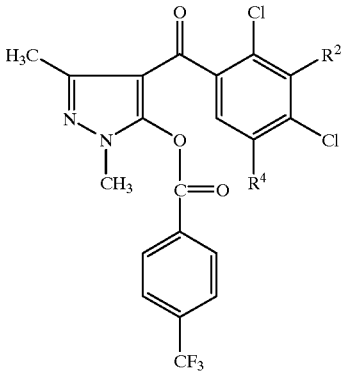

Likewise, most particular preference is given to the compounds Ia270; in particular to the compounds Ia270.1–Ia270.164, which differ from the compounds Ia1.1–Ia1.164 in that $R^3$ is chlorine and $R^7$ is 2,4-dichlorophenylcarbonyl:

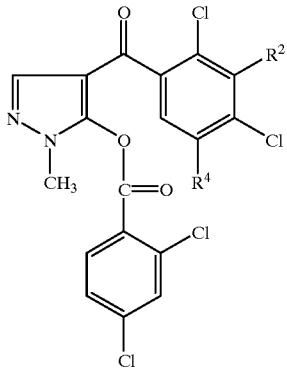

Likewise, most particular preference is given to the compounds Ia271; in particular to the compounds Ia271.1–Ia271.164, which differ from the compounds Ia1.1–Ia1.164 in that $R^3$ is chlorine, $R^6$ is ethyl and $R^7$ is 2,4-dichlorophenylcarbonyl:

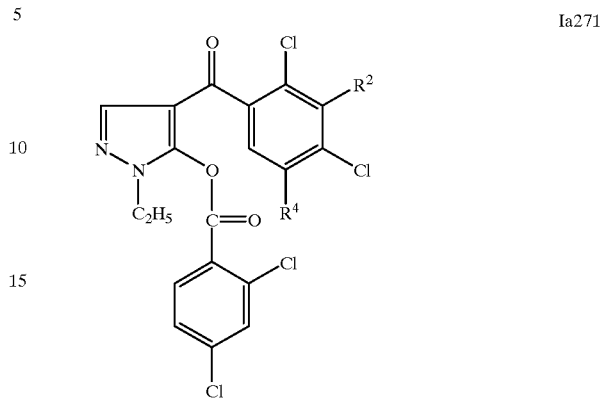

Likewise, most particular preference is given to the compounds Ia272; in particular to the compounds Ia272.1–Ia272.164, which differ from the compounds Ia1.1–Ia1.164 in that $R^3$ is chlorine, $R^7$ is 2,4-dichlorophenylcarbonyl and $R^8$ is methyl:

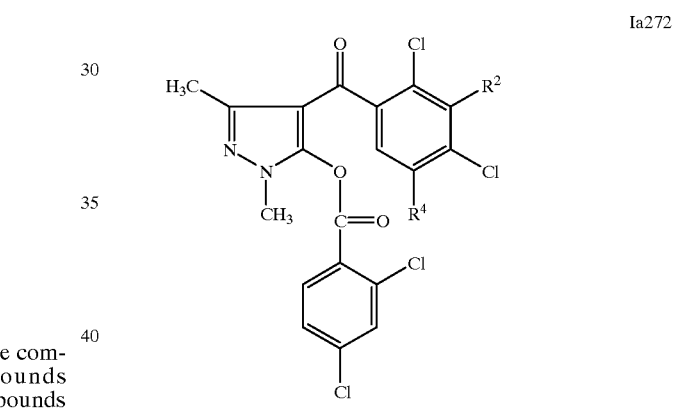

Likewise, most particular preference is given to the compounds Ia273; in particular to the compounds Ia273.1–Ia273.164, which differ from the compounds Ia1.1–Ia1.164 in that $R^1$ is methyl:

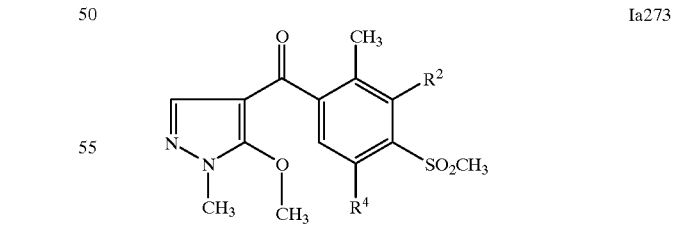

Likewise, most particular preference is given to the compounds Ia274; in particular to the compounds Ia274.1–Ia274.164, which differ from the compounds Ia1.1–Ia1.164 in that $R^1$ is methyl and $R^6$ is ethyl:

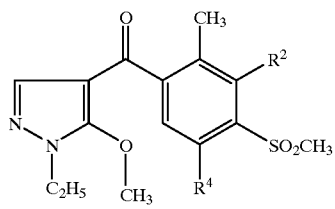

Ia274

Likewise, most particular preference is given to the compounds Ia275; in particular to the compounds Ia275.1–Ia275.164, which differ from the compounds Ia1.1–Ia1.164 in that $R^1$ is methyl and $R^6$ is n-propyl:

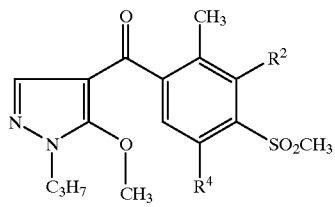

Ia275

Likewise, most particular preference is given to the compounds Ia276; in particular to the compounds Ia276.1–Ia276.164, which differ from the compounds Ia1.1–Ia1.164 in that $R^1$ is methyl and $R^6$ is isobutyl:

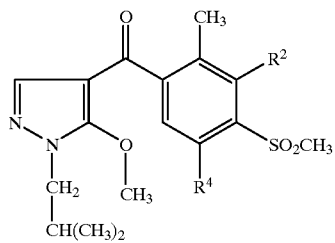

Ia276

Likewise, most particular preference is given to the compounds Ia277; in particular to the compounds Ia277.1–Ia277.164, which differ from the compounds Ia1.1–Ia1.164 in that $R^1$ and $R^8$ are each methyl:

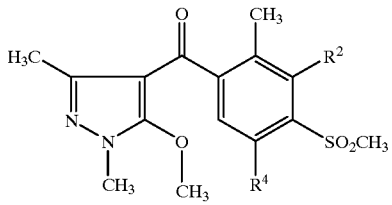

Ia277

Likewise, most particular preference is given to the compounds Ia278; in particular to the compounds Ia278.1–Ia278.164, which differ from the compounds Ia1.1–Ia1.164 in that $R^1$ is methyl and $R^7$ is ethyl:

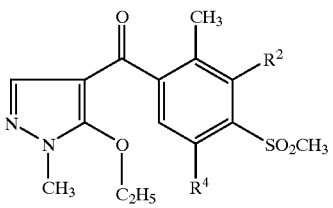

Ia278

Likewise, most particular preference is given to the compounds Ia279; in particular to the compounds Ia279.1–Ia279.164, which differ from the compounds Ia1.1–Ia1.164 in that $R^1$ is methyl and $R^6$ and $R^7$ are each ethyl:

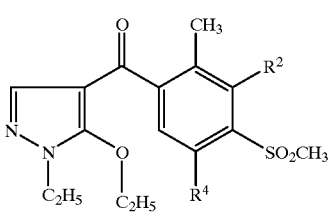

Ia279

Likewise, most particular preference is given to the compounds Ia280; in particular to the compounds Ia280.1–Ia280.164, which differ from the compounds Ia1.1–Ia1.164 in that $R^1$ is methyl, $R^6$ is n-propyl and $R^7$ is ethyl:

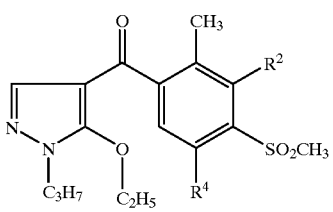

Ia280

Likewise, most particular preference is given to the compounds Ia281; in particular to the compounds Ia281.1–Ia281.164, which differ from the compounds Ia1.1–Ia1.164 in that $R^1$ is methyl, $R^6$ is isobutyl and $R^7$ is ethyl:

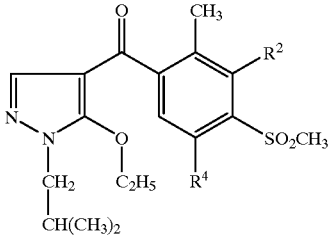

Ia281

Likewise, most particular preference is given to the compounds Ia282; in particular to the compounds Ia282.1–Ia282.164, which differ from the compounds Ia1.1–Ia1.164 in that $R^1$ is methyl, $R^7$ is ethyl and $R^8$ is methyl:

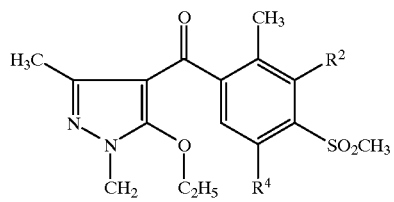
Ia282

Likewise, most particular preference is given to the compounds Ia283; in particular to the compounds Ia283.1–Ia283.164, which differ from the compounds Ia1.1–Ia1.164 in that $R^1$ is methyl and $R^7$ is cyanomethyl:

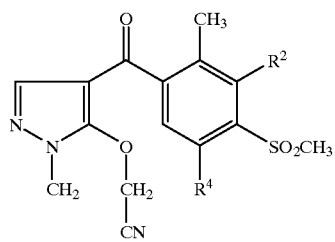
Ia283

Likewise, most particular preference is given to the compounds Ia284; in particular to the compounds Ia284.1–Ia284.164, which differ from the compounds Ia1.1–Ia1.164 in that $R^1$ is methyl, $R^6$ is ethyl and $R^7$ is cyanomethyl:

Ia284

Likewise, most particular preference is given to the compounds Ia285; in particular to the compounds Ia285.1–Ia285.164, which differ from the compounds Ia1.1–Ia1.164 in that $R^1$ is methyl, $R^7$ is cyanomethyl and $R^8$ is methyl:

Ia285

Likewise, most particular preference is given to the compounds Ia286; in particular to the compounds Ia286.1–Ia286.164, which differ from the compounds Ia1.1–Ia1.164 in that $R^1$ is methyl and $R^7$ is methoxymethyl:

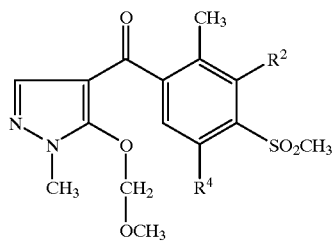
Ia286

Likewise, most particular preference is given to the compounds Ia287; in particular to the compounds Ia287.1–Ia287.164, which differ from the compounds Ia1.1–Ia1.164 in that $R^1$ is methyl, $R^6$ is ethyl and $R^7$ is methoxymethyl:

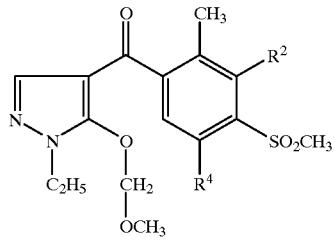
Ia287

Likewise, most particular preference is given to the compounds Ia288; in particular to the compounds Ia288.1–Ia288.164, which differ from the compounds Ia1.1–Ia1.164 in that $R^1$ is methyl, $R^7$ is methoxymethyl and $R^8$ is methyl:

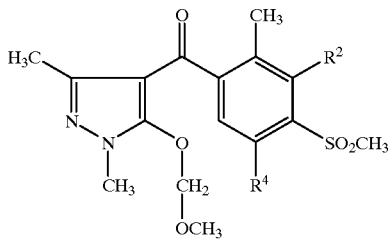
Ia288

Likewise, most particular preference is given to the compounds Ia289; in particular to the compounds Ia289.1–Ia289.164, which differ from the compounds Ia1.1–Ia1.164 in that $R^1$ is methyl and $R^7$ is methylcarbonyloxymethyl:

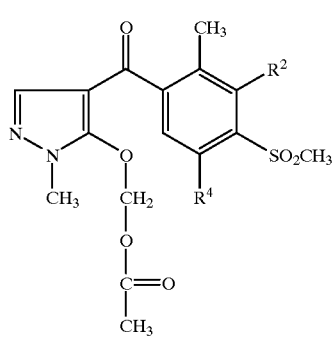
Ia289

Likewise, most particular preference is given to the compounds Ia290; in particular to the compounds Ia290.1–Ia290.164, which differ from the compounds Ia1.1–Ia1.164 in that R¹ is methyl, R⁶ is ethyl and R⁷ is methylcarbonyloxymethyl:

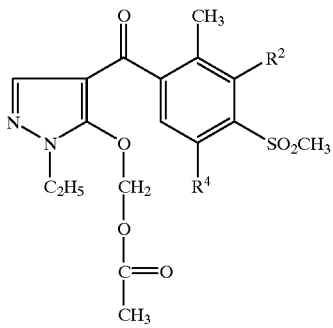

Ia290

Likewise, most particular preference is given to the compounds Ia291; in particular to the compounds Ia291.1–Ia291.164, which differ from the compounds Ia1.1–Ia1.164 in that R¹ is methyl, R⁷ is methylcarbonyloxymethyl and R⁸ is methyl:

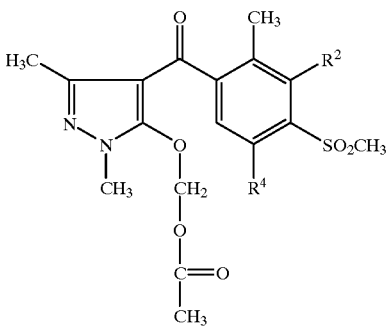

Ia291

Likewise, most particular preference is given to the compounds Ia292; in particular to the compounds Ia292.1–Ia292.164, which differ from the compounds Ia1.1–Ia1.164 in that R¹ is methyl and R⁷ is tert-butylcarbonyloxymethyl:

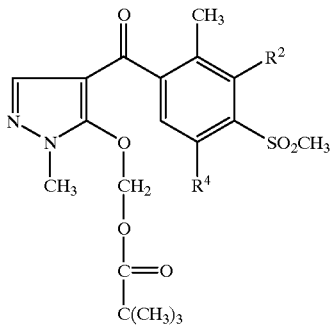

Ia292

Likewise, most particular preference is given to the compounds Ia293; in particular to the compounds Ia293.1–Ia293.164, which differ from the compounds Ia1.1–Ia1.164 in that R¹ is methyl, R⁶ is ethyl and R⁷ is tert-butylcarbonyloxymethyl:

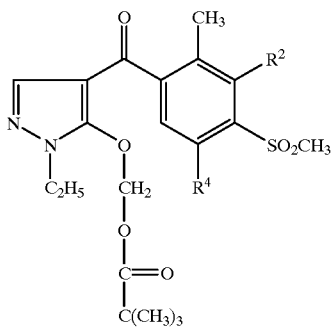

Ia293

Likewise, most particular preference is given to the compounds Ia294; in particular to the compounds Ia294.1–Ia294.164, which differ from the compounds Ia1.1–Ia1.164 in that R¹ is methyl, R⁷ is tert-butylcarbonyloxymethyl and R⁸ is methyl:

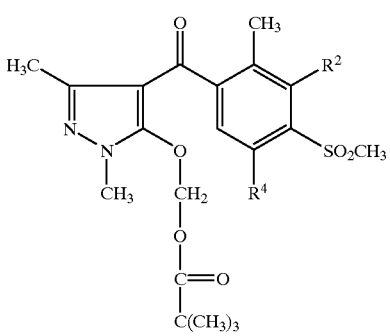

Ia294

Likewise, most particular preference is given to the compounds Ia295; in particular to the compounds Ia295.1–Ia295.164, which differ from the compounds Ia1.1–Ia1.164 in that R¹ is methyl and R⁷ is methoxycarbonylmethyl:

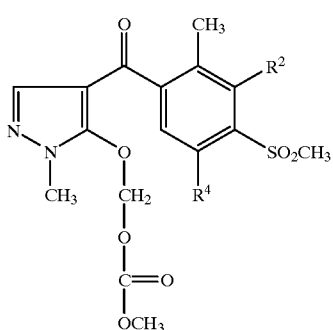

Ia295

Likewise, most particular preference is given to the compounds Ia296; in particular to the compounds Ia296.1–Ia296.164, which differ from the compounds Ia1.1–Ia1.164 in that R¹ is methyl, R⁶ is ethyl and R⁷ is methoxycarbonylmethyl:

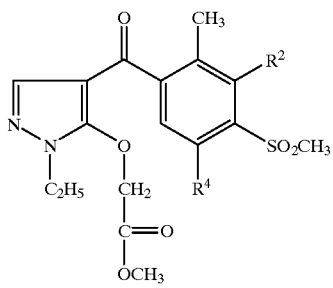

Ia296

Likewise, most particular preference is given to the compounds Ia297; in particular to the compounds Ia297.1–Ia297.164, which differ from the compounds Ia1.1–Ia1.164 in that $R^1$ is methyl, $R^7$ is methoxycarbonylmethyl and $R^8$ is methyl:

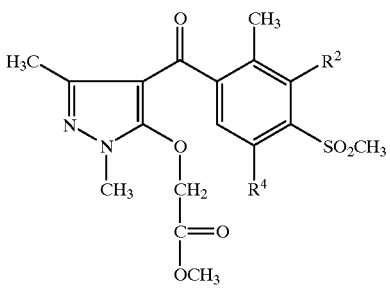

Ia297

Likewise, most particular preference is given to the compounds Ia298; in particular to the compounds Ia298.1–Ia298.164, which differ from the compounds Ia1.1–Ia1.164 in that $R^1$ is methyl and $R^7$ is ethoxycarbonylmethyl:

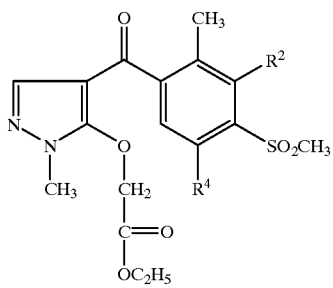

Ia298

Likewise, most particular preference is given to the compounds Ia299; in particular to the compounds Ia299.1–Ia299.164, which differ from the compounds Ia1.1–Ia1.164 in that $R^1$ is methyl, $R^6$ is ethyl and $R^7$ is ethoxycarbonylmethyl:

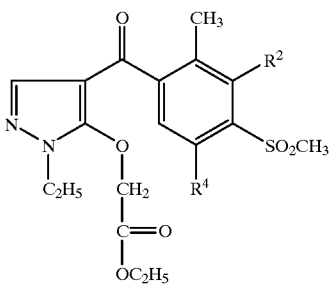

Ia299

Likewise, most particular preference is given to the compounds Ia300; in particular to the compounds Ia300.1–Ia300.164, which differ from the compounds Ia1.1–Ia1.164 in that $R^1$ is methyl, $R^7$ is ethoxycarbonylmethyl and $R^8$ is methyl:

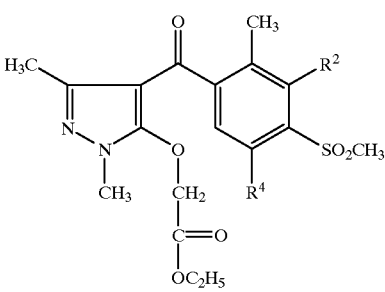

Ia300

Likewise, most particular preference is given to the compounds Ia301; in particular to the compounds Ia301.1–Ia301.164, which differ from the compounds Ia1.1–Ia1.164 in that $R^1$ is methyl and $R^7$ is 1-methoxycarbonyleth-1-yl:

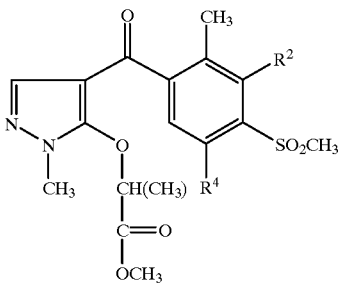

Ia301

Likewise, most particular preference is given to the compounds Ia302; in particular to the compounds Ia302.1–Ia302.164, which differ from the compounds Ia1.1–Ia1.164 in that $R^1$ is methyl, $R^6$ is ethyl and $R^7$ is 1-methoxycarbonyleth-1-yl:

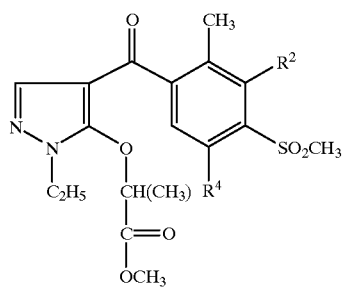
Ia302

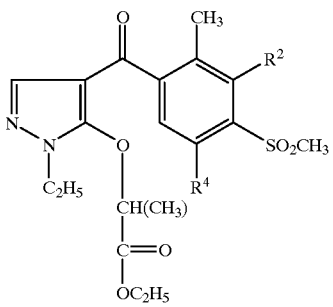
Ia305

Likewise, most particular preference is given to the compounds Ia303; in particular to the compounds Ia303.1–Ia303.164, which differ from the compounds Ia1.1–Ia1.164 in that $R^1$ is methyl, $R^7$ is 1-methoxycarbonyleth-1-yl and $R^8$ is methyl:

Likewise, most particular preference is given to the compounds Ia306; in particular to the compounds Ia306.1–Ia306.164, which differ from the compounds Ia1.1–Ia1.164 in that $R^1$ is methyl, $R^7$ is 1-ethoxycarbonyleth-1-yl and $R^8$ is methyl:

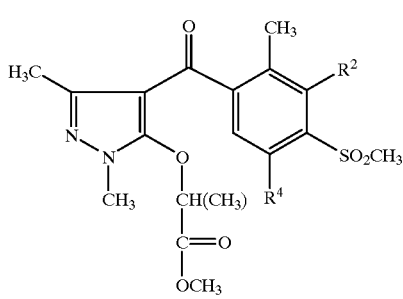
Ia303

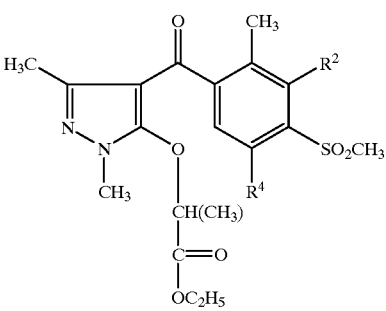
Ia306

Likewise, most particular preference is given to the compounds Ia304; in particular to the compounds Ia304.1–Ia304.164, which differ from the compounds Ia1.1–Ia1.164 in that $R^1$ is methyl and $R^7$ is 1-ethoxycarbonyleth-1-yl:

Likewise, most particular preference is given to the compounds Ia307; in particular to the compounds Ia307.1–Ia307.164, which differ from the compounds Ia1.1–Ia1.164 in that $R^1$ is methyl and $R^7$ is 2-methoxyeth-1-oxycarbonylmethyl:

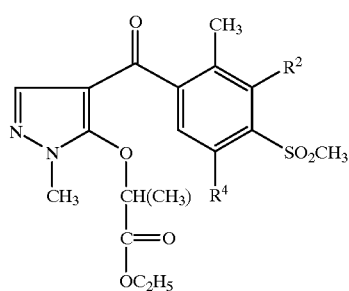
Ia304

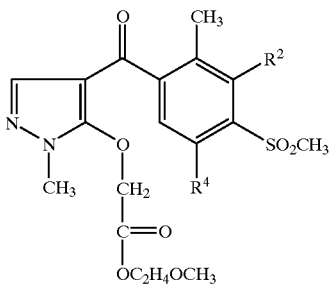
Ia307

Likewise, most particular preference is given to the compounds Ia305; in particular to the compounds Ia305.1–Ia305.164, which differ from the compounds Ia1.1–Ia1.164 in that $R^1$ is methyl, $R^6$ is ethyl and $R^7$ is 1-ethoxycarbonyleth-1-yl:

Likewise, most particular preference is given to the compounds Ia308; in particular to the compounds Ia308.1–Ia308.164, which differ from the compounds Ia1.1–Ia1.164 in that $R^1$ is methyl, $R^6$ is ethyl and $R^7$ is 2-methoxyeth-1-oxycarbonylmethyl:

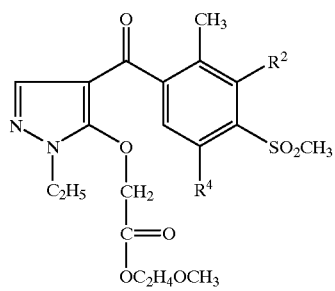

Ia308

Likewise, most particular preference is given to the compounds Ia309; in particular to the compounds Ia309.1–Ia309.164, which differ from the compounds Ia1.1–Ia1.164 in that $R^1$ is methyl, $R^7$ is 2-methoxyeth-1-oxycarbonylmethyl and $R^8$ is methyl:

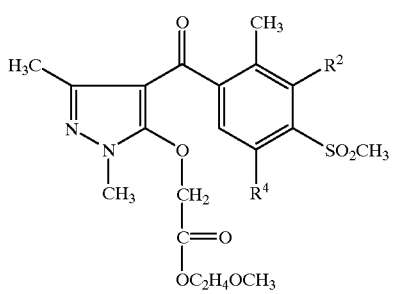

Ia309

Likewise, most particular preference is given to the compounds Ia310; in particular to the compounds Ia310.1–Ia310.164, which differ from the compounds Ia1.1–Ia1.164 in that $R^1$ is methyl and $R^7$ is 2-dimethylaminoeth-1-oxycarbonylmethyl:

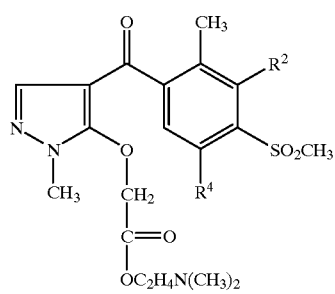

Ia310

Likewise, most particular preference is given to the compounds Ia311; in particular to the compounds Ia311.1–Ia311.164, which differ from the compounds Ia1.1–Ia1.164 in that $R^1$ is methyl, $R^6$ is ethyl and $R^7$ is 2-dimethylaminoeth-1-oxycarbonylmethyl:

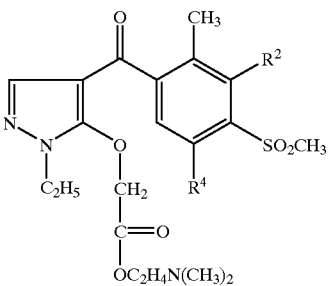

Ia311

Likewise, most particular preference is given to the compounds Ia312; in particular to the compounds Ia312.1–Ia312.164, which differ from the compounds Ia1.1–Ia1.164 in that $R^1$ is methyl, $R^7$ is 2-dimethylaminoeth-1-oxycarbonylmethyl and $R^8$ is methyl:

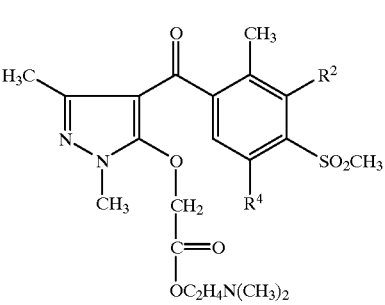

Ia312

Likewise, most particular preference is given to the compounds Ia313; in particular to the compounds Ia313.1–Ia313.164, which differ from the compounds Ia1.1–Ia1.164 in that $R^1$ is methyl and $R^7$ is methylaminocarbonylmethyl:

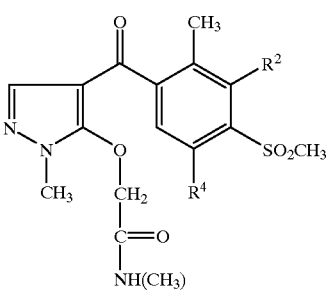

Ia313

Likewise, most particular preference is given to the compounds Ia314; in particular to the compounds Ia314.1–Ia314.164, which differ from the compounds Ia1.1–Ia1.164 in that $R^1$ is methyl, $R^6$ is ethyl and $R^7$ is methylaminocarbonylmethyl:

Ia314

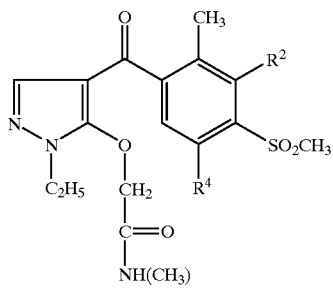

Ia317

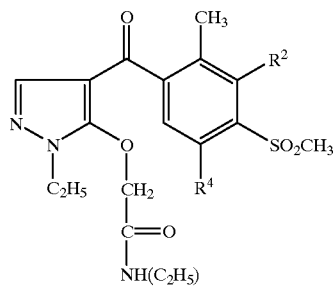

Likewise, most particular preference is given to the compounds Ia315; in particular to the compounds Ia315.1–Ia315.164, which differ from the compounds Ia1.1–Ia1.164 in that $R^1$ is methyl, $R^7$ is methylaminocarbonylmethyl and $R^8$ is methyl:

Likewise, most particular preference is given to the compounds Ia318; in particular to the compounds Ia318.1–Ia318.164, which differ from the compounds Ia1.1–Ia1.164 in that $R^1$ is methyl, $R^7$ is ethylaminocarbonylmethyl and $R^8$ is methyl:

Ia315

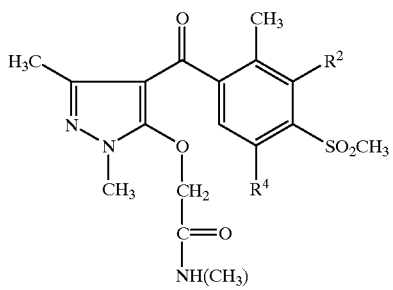

Ia318

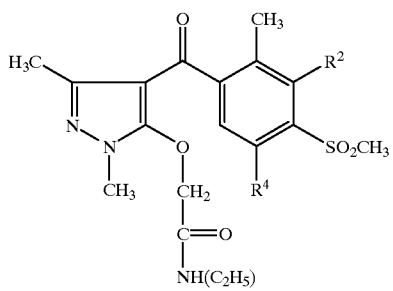

Likewise, most particular preference is given to the compounds Ia316; in particular to the compounds Ia316.1–Ia316.164, which differ from the compounds Ia1.1–Ia1.164 in that $R^1$ is methyl and $R^7$ is ethylaminocarbonylmethyl:

Likewise, most particular preference is given to the compounds Ia319; in particular to the compounds Ia319.1–Ia319.164, which differ from the compounds Ia1.1–Ia1.164 in that $R^1$ is methyl and $R^7$ is dimethylaminocarbonylmethyl:

Ia316

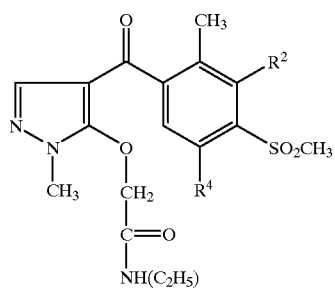

Ia319

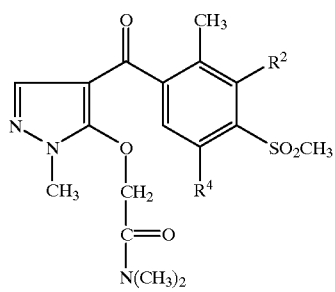

Likewise, most particular preference is given to the compounds Ia317; in particular to the compounds Ia317.1–Ia317.164, which differ from the compounds Ia1.1–Ia1.164 in that $R^1$ is methyl, $R^6$ is ethyl and $R^7$ is ethylaminocarbonylmethyl:

Likewise, most particular preference is given to the compounds Ia320; in particular to the compounds Ia320.1–Ia320.164, which differ from the compounds Ia1.1–Ia1.164 in that $R^1$ is methyl, $R^6$ is ethyl and $R^7$ is dimethylaminocarbonylmethyl:

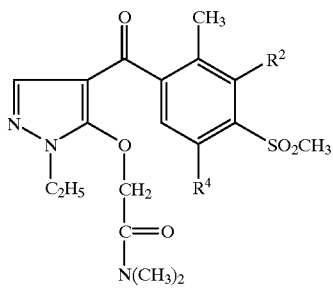

Ia320

Likewise, most particular preference is given to the compounds Ia321; in particular to the compounds Ia321.1–Ia321.164, which differ from the compounds Ia1.1–Ia1.164 in that $R^1$ is methyl, $R^7$ is dimethylaminocarbonylmethyl and $R^8$ is methyl:

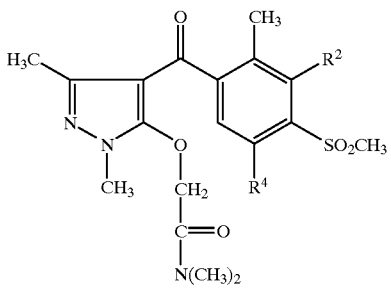

Ia321

Likewise, most particular preference is given to the compounds Ia322; in particular to the compounds Ia322.1–Ia322.164, which differ from the compounds Ia1.1–Ia1.164 in that $R^1$ is methyl and $R^7$ is diethylaminocarbonylmethyl:

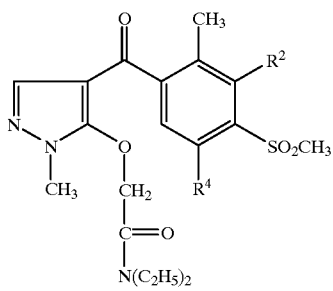

Ia322

Likewise, most particular preference is given to the compounds Ia323; in particular to the compounds Ia323.1–Ia323.164, which differ from the compounds Ia1.1–Ia1.164 in that $R^1$ is methyl, $R^6$ is ethyl and $R^7$ is diethylaminocarbonylmethyl:

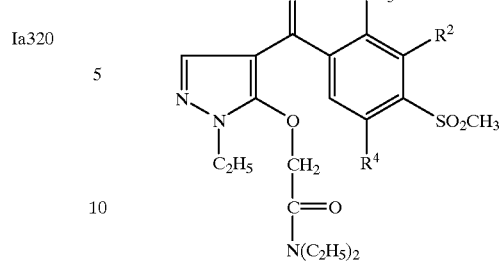

Ia323

Likewise, most particular preference is given to the compounds Ia324; in particular to the compounds Ia324.1–Ia324.164, which differ from the compounds Ia1.1–Ia1.164 in that $R^1$ is methyl, $R^7$ is diethylaminocarbonylmethyl and $R^8$ is methyl:

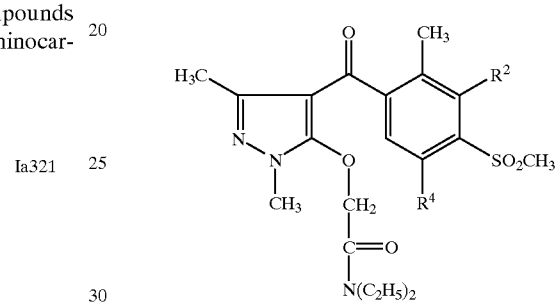

Ia324

Likewise, most particular preference is given to the compounds Ia325; in particular to the compounds Ia325.1–Ia325.164, which differ from the compounds Ia1.1–Ia1.164 in that $R^1$ is methyl and $R^7$ is allyl:

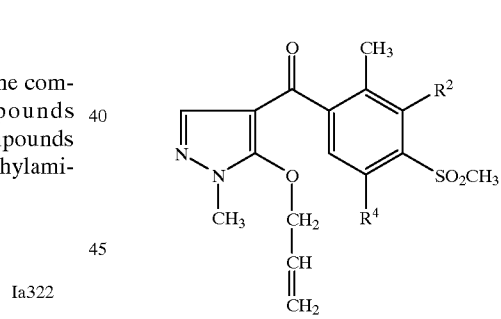

Ia325

Likewise, most particular preference is given to the compounds Ia326; in particular to the compounds Ia326.1–Ia326.164, which differ from the compounds Ia1.1–Ia1.164 in that $R^1$ is methyl, $R^6$ is ethyl and $R^7$ is allyl:

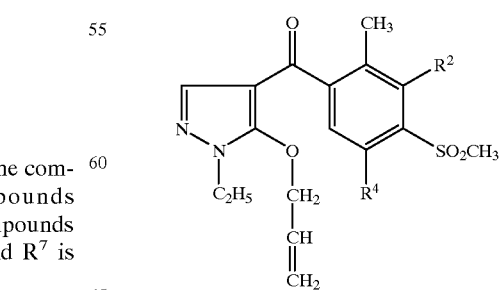

Ia326

Likewise, most particular preference is given to the compounds Ia327; in particular to the compounds Ia327.1–Ia327.164, which differ from the compounds Ia1.1–Ia1.164 in that $R^1$ is methyl, $R^7$ is allyl and $R^8$ is methyl:

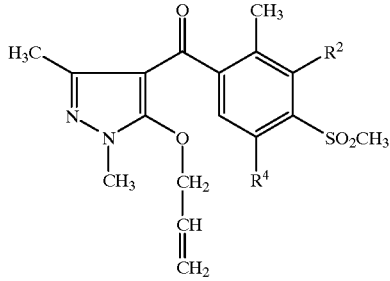

Ia327

Likewise, most particular preference is given to the compounds Ia328; in particular to the compounds Ia328.1–Ia328.164, which differ from the compounds Ia1.1–Ia1.164 in that $R^1$ is methyl and $R^7$ is propargyl:

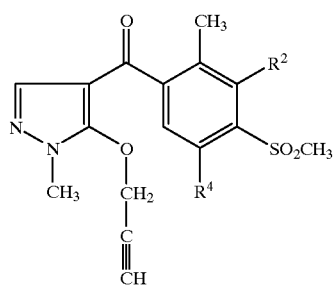

Ia328

Likewise, most particular preference is given to the compounds Ia329; in particular to the compounds Ia329.1–Ia329.164, which differ from the compounds Ia1.1–Ia1.164 in that $R^1$ is methyl, $R^6$ is ethyl and $R^7$ is propargyl:

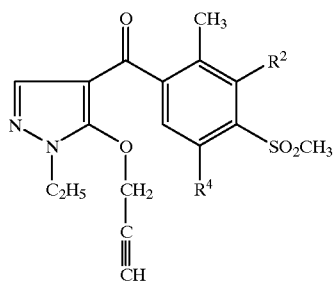

Ia329

Likewise, most particular preference is given to the compounds Ia330; in particular to the compounds Ia330.1–Ia330.164, which differ from the compounds Ia1.1–Ia1.164 in that $R^1$ is methyl, $R^7$ is propargyl and $R^8$ is methyl:

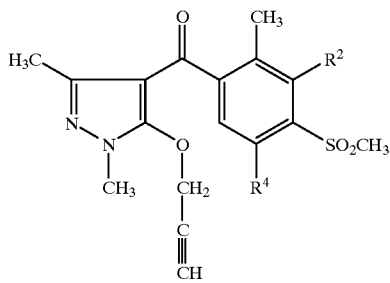

Ia330

Likewise, most particular preference is given to the compounds Ia331; in particular to the compounds Ia331.1–Ia331.164, which differ from the compounds Ia1.1–Ia1.164 in that $R^1$ is methyl and $R^7$ is methylcarbonyl:

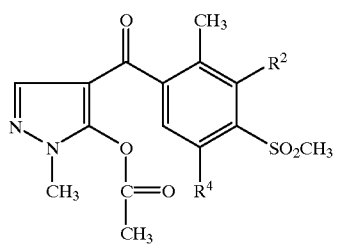

Ia331

Likewise, most particular preference is given to the compounds Ia332; in particular to the compounds Ia332.1–Ia332.164, which differ from the compounds Ia1.1–Ia1.164 in that $R^1$ is methyl, $R^6$ is ethyl and $R^7$ is methylcarbonyl:

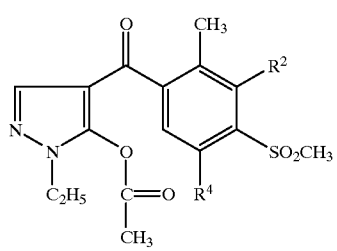

Ia332

Likewise, most particular preference is given to the compounds Ia333; in particular to the compounds Ia333.1–Ia333.164, which differ from the compounds Ia1.1–Ia1.164 in that $R^1$ is methyl, $R^6$ is n-propyl and $R^7$ is methylcarbonyl:

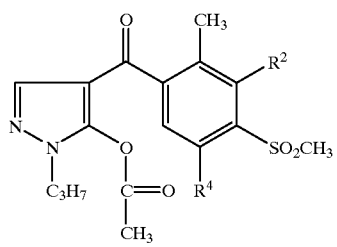

Ia333

Likewise, most particular preference is given to the compounds Ia334; in particular to the compounds Ia334.1–Ia334.164, which differ from the compounds Ia1.1–Ia1.164 in that $R^1$ is methyl, $R^6$ is isobutyl and $R^7$ is methylcarbonyl:

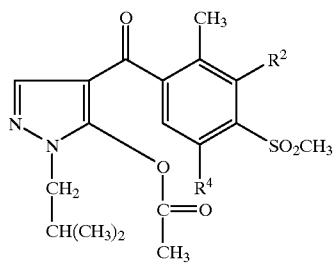

Ia334

Likewise, most particular preference is given to the compounds Ia335; in particular to the compounds Ia335.1–Ia335.164, which differ from the compounds Ia1.1–Ia1.164 in that $R^1$ is methyl, $R^7$ is methylcarbonyl and $R^8$ is methyl:

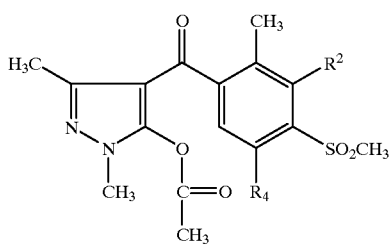

Ia335

Likewise, most particular preference is given to the compounds Ia336; in particular to the compounds Ia336.1–Ia336.164, which differ from the compounds Ia1.1–Ia1.164 in that $R^1$ is methyl and $R^7$ is ethylcarbonyl:

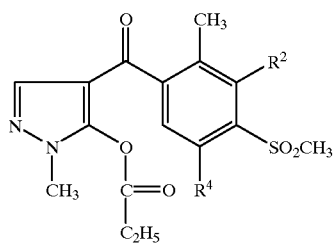

Ia336

Likewise, most particular preference is given to the compounds Ia337; in particular to the compounds Ia337.1–Ia337.164, which differ from the compounds Ia1.1–Ia1.164 in that $R^1$ is methyl, $R^6$ is ethyl and $R^7$ is ethylcarbonyl:

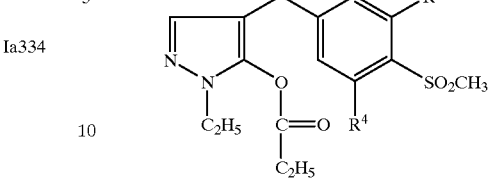

Ia337

Likewise, most particular preference is given to the compounds Ia338; in particular to the compounds Ia338.1–Ia338.164, which differ from the compounds Ia1.1–Ia1.164 in that $R^1$ is methyl, $R^6$ is n-propyl and $R^7$ is ethylcarbonyl:

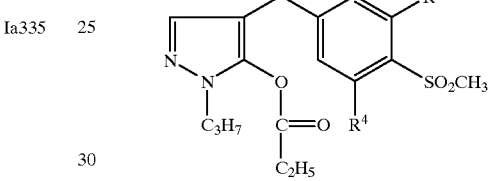

Ia338

Likewise, most particular preference is given to the compounds Ia339; in particular to the compounds Ia339.1–Ia339.164, which differ from the compounds Ia1.1–Ia1.164 in that $R^1$ is methyl, $R^6$ is isobutyl and $R^7$ is ethylcarbonyl:

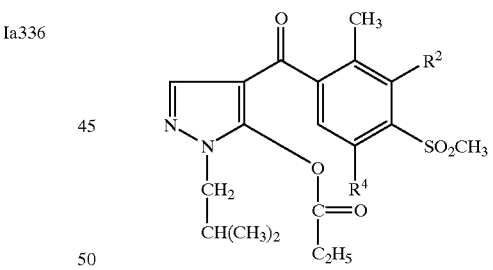

Ia339

Likewise, most particular preference is given to the compounds Ia340; in particular to the compounds Ia340.1–Ia340.164, which differ from the compounds Ia1.1–Ia1.164 in that $R^1$ is methyl, $R^7$ is ethylcarbonyl and $R^8$ is methyl:

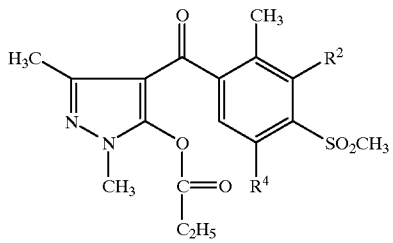

Ia340

Likewise, most particular preference is given to the compounds Ia341; in particular to the compounds Ia341.1–Ia341.164, which differ from the compounds Ia1.1–Ia1.164 in that $R^1$ is methyl and $R^7$ is methoxycarbonyl:

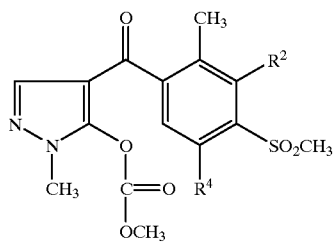

Ia341

Likewise, most particular preference is given to the compounds Ia342; in particular to the compounds Ia342.1–Ia342.164, which differ from the compounds Ia1.1–Ia1.164 in that $R^1$ is methyl, $R^6$ is ethyl and $R^7$ is methoxycarbonyl:

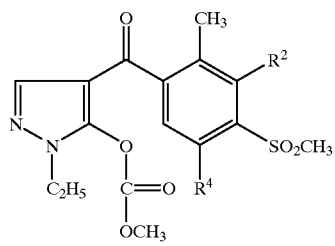

Ia342

Likewise, most particular preference is given to the compounds Ia343; in particular to the compounds Ia343.1–Ia343.164, which differ from the compounds Ia1.1–Ia1.164 in that $R^1$ is methyl, $R^7$ is methoxycarbonyl and $R^8$ is methyl:

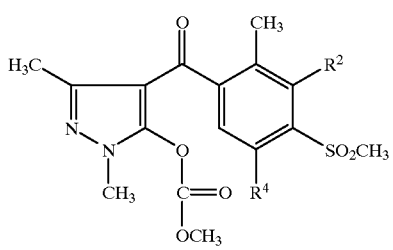

Ia343

Likewise, most particular preference is given to the compounds Ia344; in particular to the compounds Ia344.1–Ia344.164, which differ from the compounds Ia1.1–Ia1.164 in that $R^1$ is methyl and $R^7$ is ethoxycarbonyl:

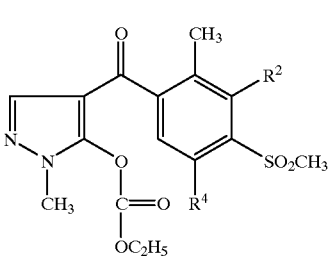

Ia344

Likewise, most particular preference is given to the compounds Ia345; in particular to the compounds Ia345.1–Ia345.164, which differ from the compounds Ia1.1–Ia1.164 in that $R^1$ is methyl, $R^6$ is ethyl and $R^7$ is ethoxycarbonyl:

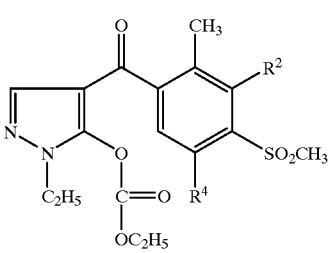

Ia345

Likewise, most particular preference is given to the compounds Ia346; in particular to the compounds Ia346.1–Ia346.164, which differ from the compounds Ia1.1–Ia1.164 in that $R^1$ is methyl, $R^7$ is ethoxycarbonyl and $R^8$ is methyl:

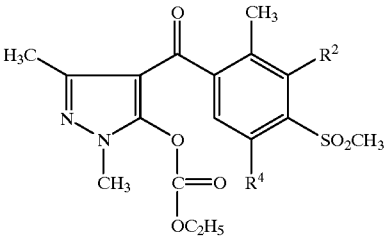

Ia346

Likewise, most particular preference is given to the compounds Ia347; in particular to the compounds Ia347.1–Ia347.164, which differ from the compounds Ia1.1–Ia1.164 in that $R^1$ is methyl and $R^7$ is dimethylaminocarbonyl:

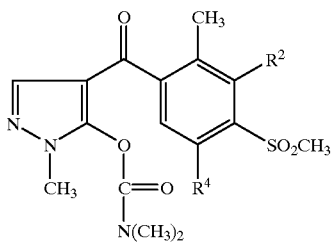

Ia347

Likewise, most particular preference is given to the compounds Ia348; in particular to the compounds Ia348.1–Ia348.164, which differ from the compounds Ia1.1–Ia1.164 in that $R^1$ is methyl, $R^6$ is ethyl and $R^7$ is dimethylaminocarbonyl:

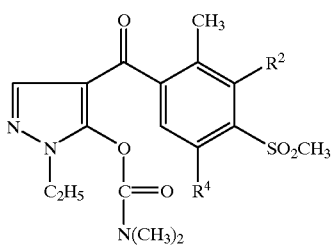

Ia348

Likewise, most particular preference is given to the compounds Ia349; in particular to the compounds Ia349.1–Ia349.164, which differ from the compounds Ia1.1–Ia1.164 in that $R^1$ is methyl, $R^7$ is dimethylaminocarbonyl and $R^8$ is methyl:

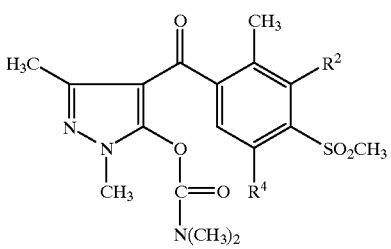

Ia349

Likewise, most particular preference is given to the compounds Ia350; in particular to the compounds Ia350.1–Ia350.164, which differ from the compounds Ia1.1–Ia1.164 in that $R^1$ is methyl and $R^7$ is diethylaminocarbonyl:

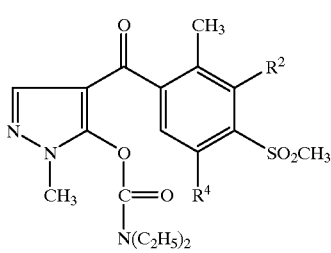

Ia350

Likewise, most particular preference is given to the compounds Ia351; in particular to the compounds Ia351.1–Ia351.164, which differ from the compounds Ia1.1–Ia1.164 in that $R^1$ is methyl, $R^6$ is ethyl and $R^7$ is diethylaminocarbonyl:

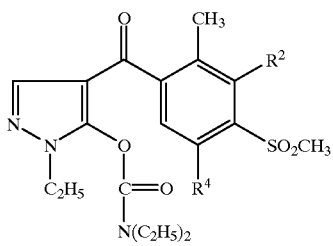

Ia351

Likewise, most particular preference is given to the compounds Ia352; in particular to the compounds Ia352.1–Ia352.164, which differ from the compounds Ia1.1–Ia1.164 in that $R^1$ is methyl, $R^7$ is diethylaminocarbonyl and $R^8$ is methyl:

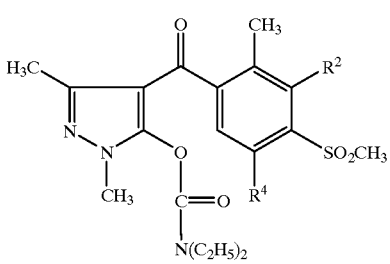

Ia352

Likewise, most particular preference is given to the compounds Ia353; in particular to the compounds Ia353.1–Ia353.164, which differ from the compounds Ia1.1–Ia1.164 in that $R^1$ is methyl and $R^7$ is N-methoxy-N-methylaminocarbonyl:

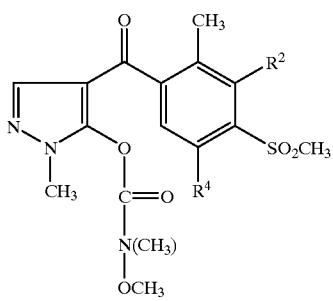

Ia353

Likewise, most particular preference is given to the compounds Ia354; in particular to the compounds Ia354.1–Ia354.164, which differ from the compounds Ia1.1–Ia1.164 in that $R^1$ is methyl, $R^6$ is ethyl and $R^7$ is N-methoxy-N-methylaminocarbonyl:

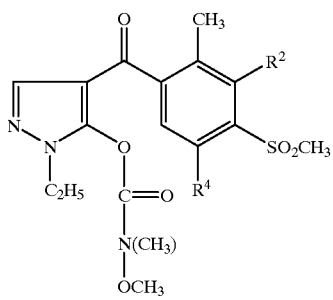

Ia354

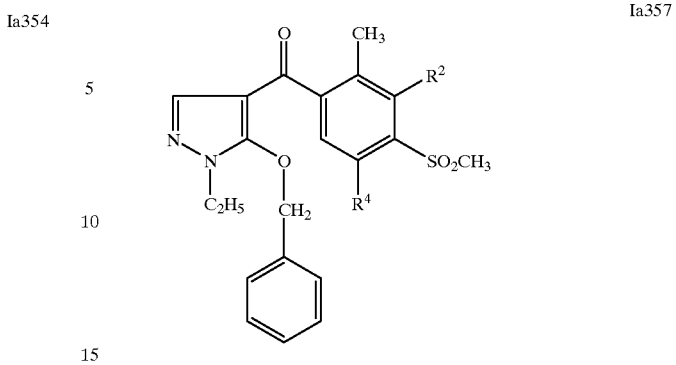

Ia357

Likewise, most particular preference is given to the compounds Ia355; in particular to the compounds Ia355.1–Ia355.164, which differ from the compounds Ia1.1–Ia1.164 in that $R^1$ is methyl, $R^7$ is N-methoxy-N-methylaminocarbonyl and $R^8$ is methyl:

Likewise, most particular preference is given to the compounds Ia358; in particular to the compounds Ia358.1–Ia358.164, which differ from the compounds Ia1.1–Ia1.164 in that $R^1$ is methyl, $R^6$ is n-propyl and $R^7$ is benzyl:

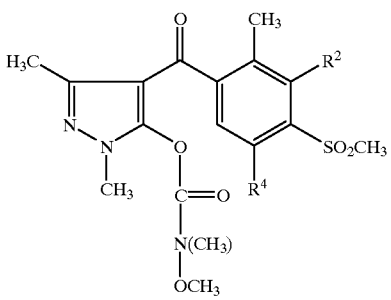

Ia355

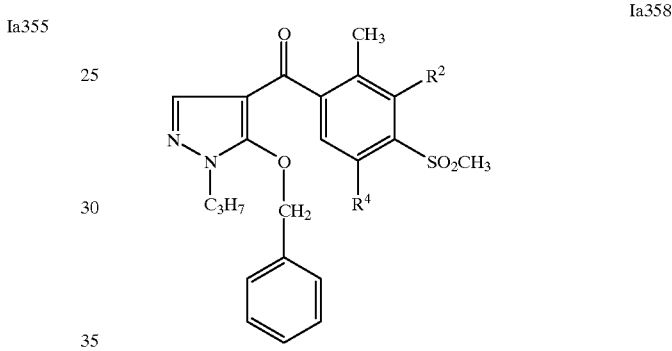

Ia358

Likewise, most particular preference is given to the compounds Ia356; in particular to the compounds Ia356.1–Ia356.164, which differ from the compounds Ia1.1–Ia1.164 in that $R^1$ is methyl and $R^7$ is benzyl:

Likewise, most particular preference is given to the compounds Ia359; in particular to the compounds Ia359.1–Ia359.164, which differ from the compounds Ia1.1–Ia1.164 in that $R^1$ is methyl, $R^6$ is isobutyl and $R^7$ is benzyl:

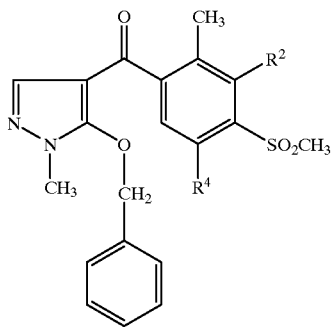

Ia356

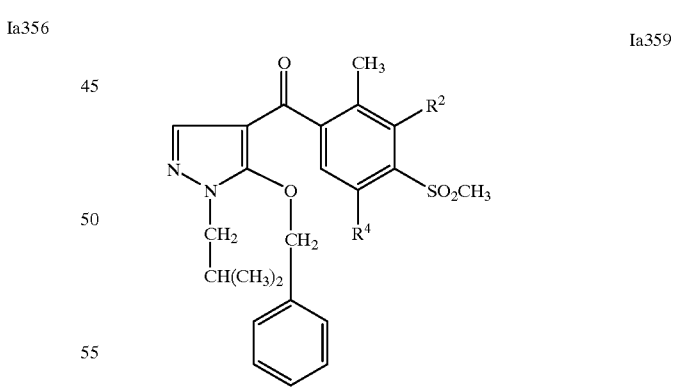

Ia359

Likewise, most particular preference is given to the compounds Ia357; in particular to the compounds Ia357.1–Ia357.164, which differ from the compounds Ia1.1–Ia1.164 in that $R^1$ is methyl, $R^6$ is ethyl and $R^7$ is benzyl:

Likewise, most particular preference is given to the compounds Ia360; in particular to the compounds Ia360.1–Ia360.164, which differ from the compounds Ia1.1–Ia1.164 in that $R^1$ is methyl, $R^7$ is benzyl and $R^8$ is methyl:

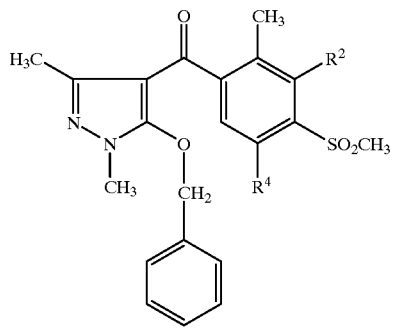

Ia360

Likewise, most particular preference is given to the compounds Ia361; in particular to the compounds Ia361.1–Ia361.164, which differ from the compounds Ia1.1–Ia1.164 in that $R^1$ is methyl and $R^7$ is 4-methylphenylmethyl:

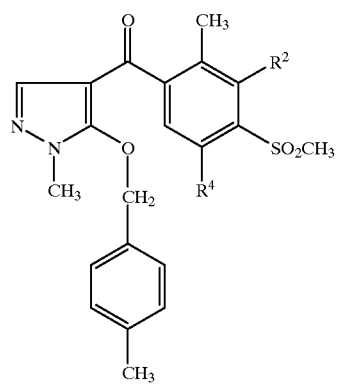

Ia361

Likewise, most particular preference is given to the compounds Ia362; in particular to the compounds Ia362.1–Ia362.164, which differ from the compounds Ia1.1–Ia1.164 in that $R^1$ is methyl, $R^6$ is ethyl and $R^7$ is 4-methylphenylmethyl:

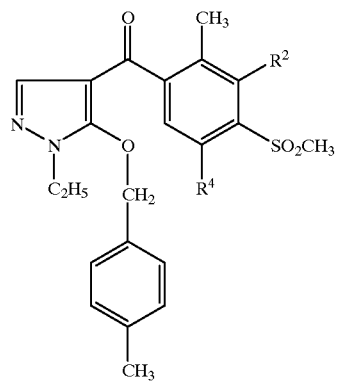

Ia362

Likewise, most particular preference is given to the compounds Ia363; in particular to the compounds Ia363.1–Ia363.164, which differ from the compounds Ia1.1–Ia1.164 in that $R^1$ is methyl, $R^6$ is n-propyl und $R^7$ is 4-methylphenylmethyl:

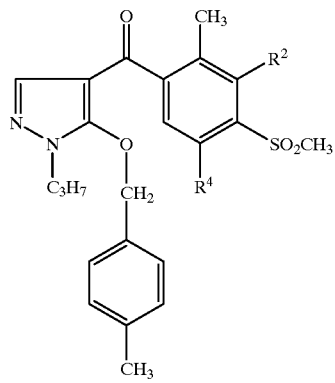

Ia363

Likewise, most particular preference is given to the compounds Ia364; in particular to the compounds Ia364.1–Ia364.164, which differ from the compounds Ia1.1–Ia1.164 in that $R^1$ is methyl, $R^6$ is isobutyl und $R^7$ is 4-methylphenylmethyl:

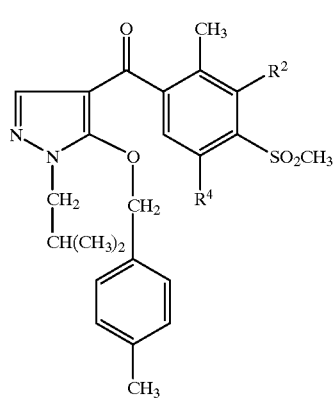

Ia364

Likewise, most particular preference is given to the compounds Ia365; in particular to the compounds Ia365.1–Ia365.164, which differ from the compounds Ia1.1–Ia1.164 in that $R^1$ is methyl, $R^7$ is 4-methylphenylmethyl and $R^8$ is methyl:

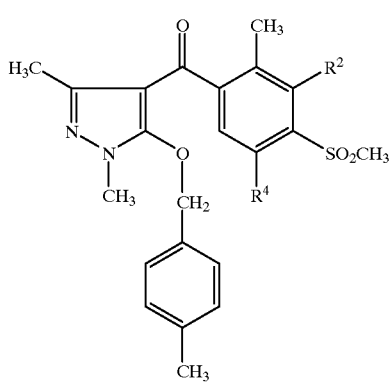

Ia365

Likewise, most particular preference is given to the compounds Ia366; in particular to the compounds Ia366.1–Ia366.164, which differ from the compounds Ia1.1–Ia1.164 in that R¹ is methyl and R⁷ is 4-chlorophenylmethyl:

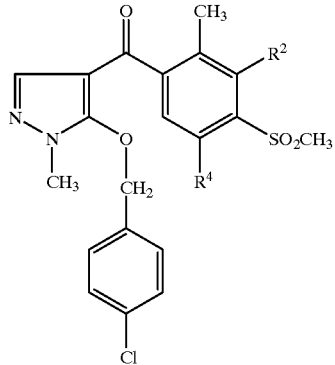

Ia366

Likewise, most particular preference is given to the compounds Ia367; in particular to the compounds Ia367.1–Ia367.164, which differ from the compounds Ia1.1–Ia1.164 in that R¹ is methyl, R⁶ is ethyl and R⁷ is 4-chlorophenylmethyl:

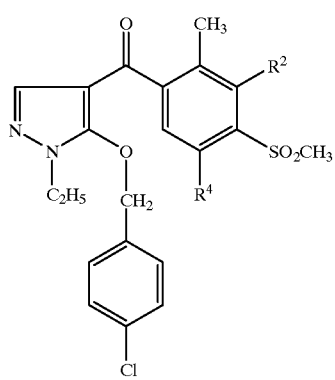

Ia367

Likewise, most particular preference is given to the compounds Ia368; in particular to the compounds Ia368.1–Ia368.164, which differ from the compounds Ia1.1–Ia1.164 in that R¹ is methyl, R⁶ is n-propyl und R⁷ is 4-chlorophenylmethyl:

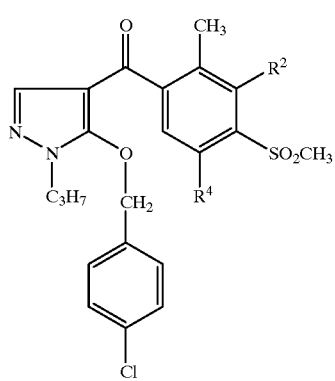

Ia368

Likewise, most particular preference is given to the compounds Ia369; in particular to the compounds Ia369.1–Ia369.164, which differ from the compounds Ia1.1–Ia1.164 in that R¹ is methyl, R⁶ is isobutyl und R⁷ is 4-chlorophenylmethyl:

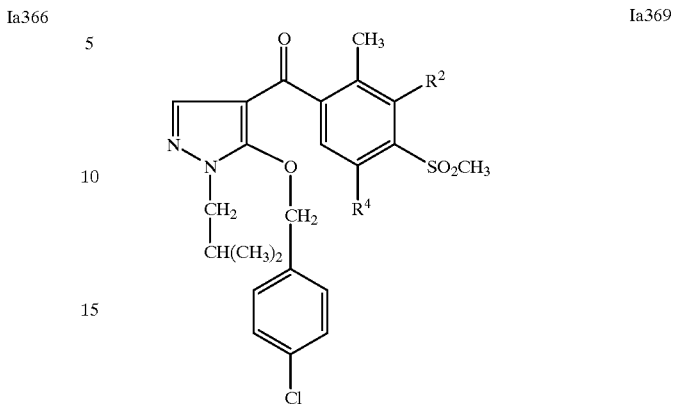

Ia369

Likewise, most particular preference is given to the compounds Ia370; in particular to the compounds Ia370.1–Ia370.164, which differ from the compounds Ia1.1–Ia1.164 in that R¹ is methyl, R⁷ is 4-chlorophenylmethyl and R⁸ is methyl:

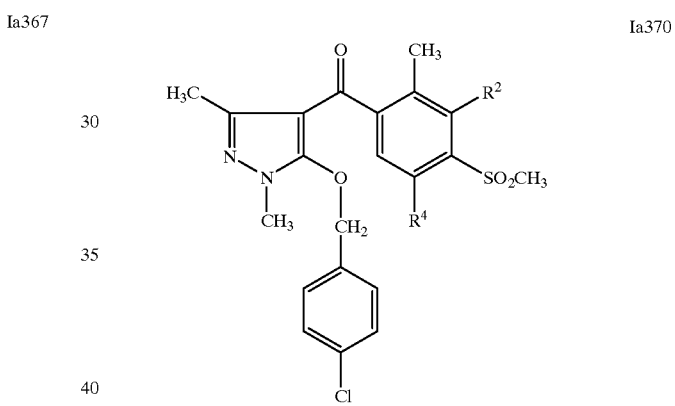

Ia370

Likewise, most particular preference is given to the compounds Ia371; in particular to the compounds Ia371.1–Ia371.164, which differ from the compounds Ia1.1–Ia1.164 in that R¹ is methyl and R⁷ is 4-methoxyphenylmethyl:

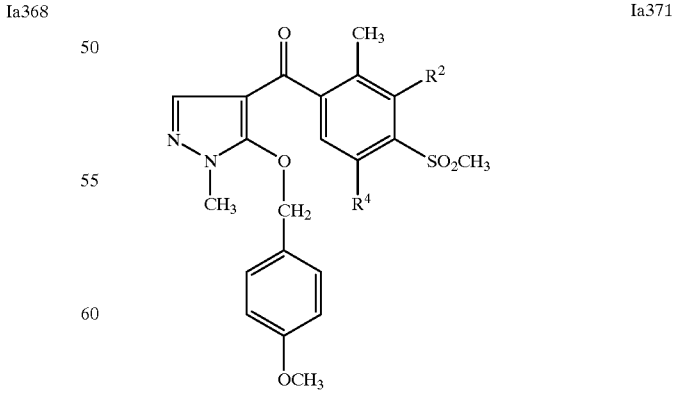

Ia371

Likewise, most particular preference is given to the compounds Ia372; in particular to the compounds Ia372.1–Ia372.164, which differ from the compounds Ia1.1–Ia1.164 in that $R^1$ is methyl, $R^6$ is ethyl and $R^7$ is 4-methoxyphenylmethyl:

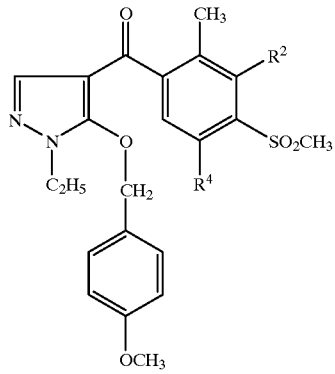

Ia372

Likewise, most particular preference is given to the compounds Ia373; in particular to the compounds Ia373.1–Ia373.164, which differ from the compounds Ia1.1–Ia1.164 in that $R^1$ is methyl, $R^7$ is 4-methoxyphenylmethyl and $R^8$ is methyl:

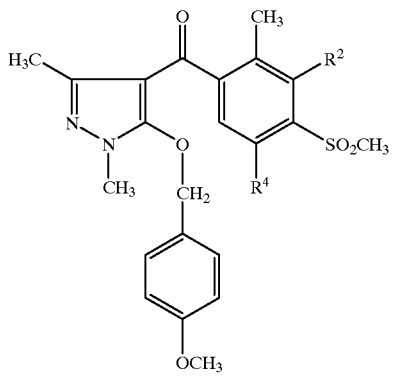

Ia373

Likewise, most particular preference is given to the compounds Ia374; in particular to the compounds Ia374.1–Ia374.164, which differ from the compounds Ia1.1–Ia1.164 in that $R^1$ is methyl and $R^7$ is 3-trifluoromethylphenylmethyl:

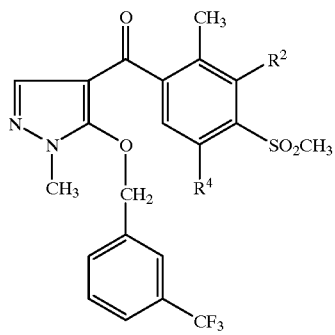

Ia374

Likewise, most particular preference is given to the compounds Ia375; in particular to the compounds Ia375.1–Ia375.164, which differ from the compounds Ia1.1–Ia1.164 in that $R^1$ is methyl, $R^6$ is ethyl and $R^7$ is 3-trifluoromethylphenylmethyl:

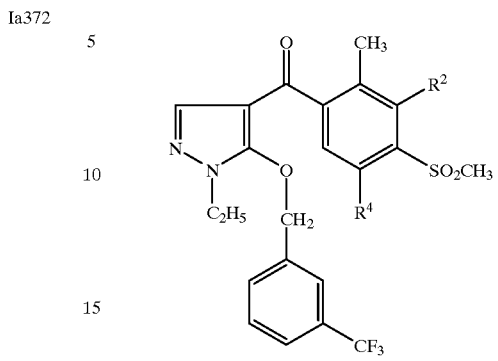

Ia375

Likewise, most particular preference is given to the compounds Ia376; in particular to the compounds Ia376.1–Ia376.164, which differ from the compounds Ia1.1–Ia1.164 in that $R^1$ is methyl, $R^7$ is 3-trifluoromethylphenylmethyl and $R^8$ is methyl:

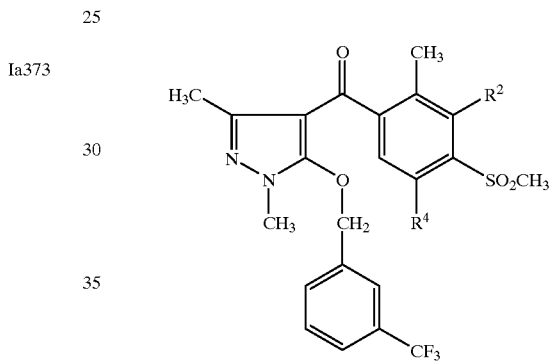

Ia376

Likewise, most particular preference is given to the compounds Ia377; in particular to the compounds Ia377.1–Ia377.164, which differ from the compounds Ia1.1–Ia1.164 in that $R^1$ is methyl and $R^7$ is 2,4-dichlorophenylmethyl:

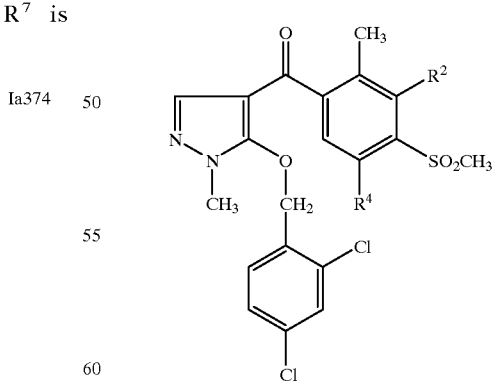

Ia377

Likewise, most particular preference is given to the compounds Ia378; in particular to the compounds Ia378.1–Ia378.164, which differ from the compounds Ia1.1–Ia1.164 in that $R^1$ is methyl, $R^6$ is ethyl and $R^7$ is 2,4-dichlorophenylmethyl:

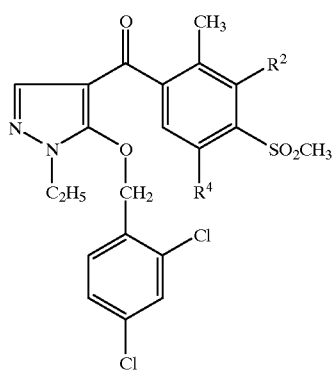

Ia378

Likewise, most particular preference is given to the compounds Ia379; in particular to the compounds Ia379.1–Ia379.164, which differ from the compounds Ia1.1–Ia1.164 in that $R^1$ is methyl, $R^7$ is 2,4-dichlorophenylmethyl and $R^8$ is methyl:

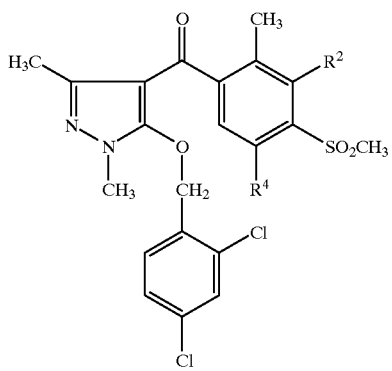

Ia379

Likewise, most particular preference is given to the compounds Ia380; in particular to the compounds Ia380.1–Ia380.164, which differ from the compounds Ia1.1–Ia1.164 in that $R^1$ is methyl and $R^7$ is phenylcarbonylmethyl:

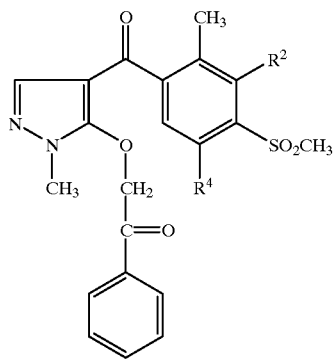

Ia380

Likewise, most particular preference is given to the compounds Ia381; in particular to the compounds Ia381.1–Ia381.164, which differ from the compounds Ia1.1–Ia1.164 in that $R^1$ is methyl, $R^6$ is ethyl and $R^7$ is phenylcarbonylmethyl:

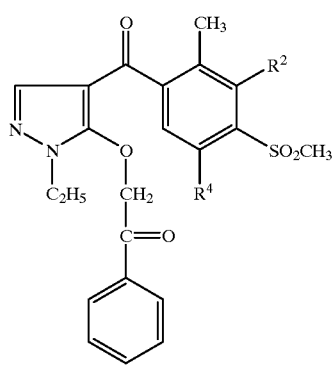

Ia381

Likewise, most particular preference is given to the compounds Ia382; in particular to the compounds Ia382.1–Ia382.164, which differ from the compounds Ia1.1–Ia1.164 in that $R^1$ is methyl, $R^6$ is n-propyl and $R^7$ is phenylcarbonylmethyl:

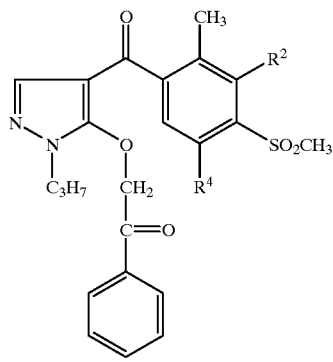

Ia382

Likewise, most particular preference is given to the compounds Ia383; in particular to the compounds Ia383.1–Ia383.164, which differ from the compounds Ia1.1–Ia1.164 in that $R^1$ is methyl, $R^6$ is isobutyl and $R^7$ is phenylcarbonylmethyl:

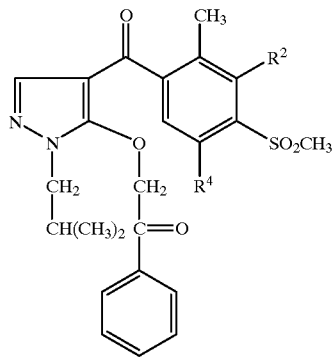

Ia383

Likewise, most particular preference is given to the compounds Ia384; in particular to the compounds Ia384.1–Ia384.164, which differ from the compounds Ia1.1–Ia1.164 in that $R^1$ is methyl, $R^7$ is phenylcarbonylmethyl and $R^8$ is methyl:

Ia384

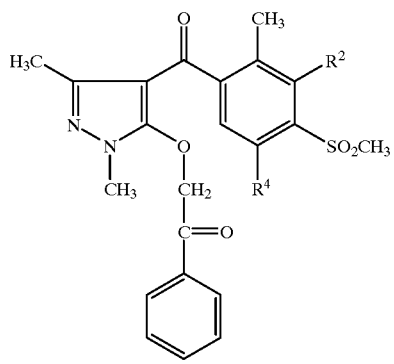

Likewise, most particular preference is given to the compounds Ia385; in particular to the compounds Ia385.1–Ia385.164, which differ from the compounds Ia1.1–Ia1.164 in that $R^1$ is methyl and $R^7$ is 4-methylphenylcarbonylmethyl:

Ia385

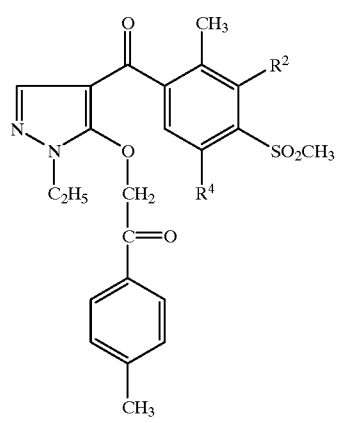

Likewise, most particular preference is given to the compounds Ia386; in particular to the compounds Ia386.1–Ia386.164, which differ from the compounds Ia1.1–Ia1.164 in that $R^1$ is methyl, $R^6$ is ethyl and $R^7$ is 4-methylphenylcarbonylmethyl:

Ia386

Likewise, most particular preference is given to the compounds Ia387; in particular to the compounds Ia387.1–Ia387.164, which differ from the compounds Ia1.1–Ia1.164 in that $R^1$ is methyl, $R^7$ is 4-methylphenylcarbonylmethyl and $R^8$ is methyl:

Ia387

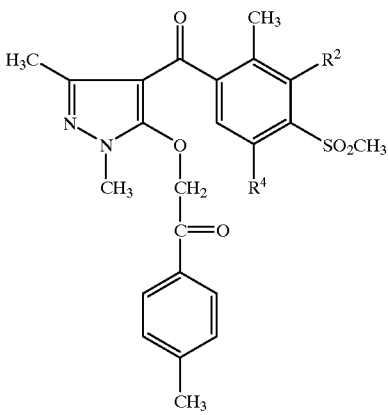

Likewise, most particular preference is given to the compounds Ia388; in particular to the compounds Ia388.1–Ia388.164, which differ from the compounds Ia1.1–Ia1.164 in that $R^1$ is methyl and $R^7$ is 1-(phenylcarbonyl)eth-1-yl:

Ia388

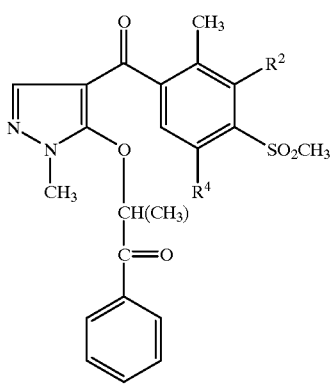

Likewise, most particular preference is given to the compounds Ia389; in particular to the compounds Ia389.1–Ia389.164, which differ from the compounds Ia1.1–Ia1.164 in that $R^1$ is methyl, $R^6$ is ethyl and $R^7$ is 1-(phenylcarbonyl)eth-1-yl:

Ia389

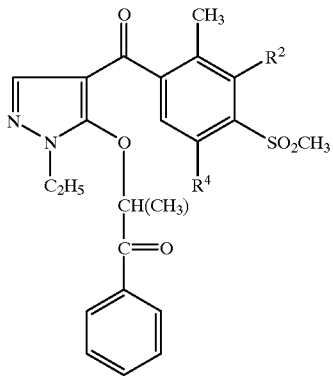

Likewise, most particular preference is given to the compounds Ia390; in particular to the compounds Ia390.1–Ia390.164, which differ from the compounds Ia1.1–Ia1.164 in that $R^1$ is methyl, $R^7$ is 1-(phenylcarbonyl)eth-1-yl and $R^8$ is methyl:

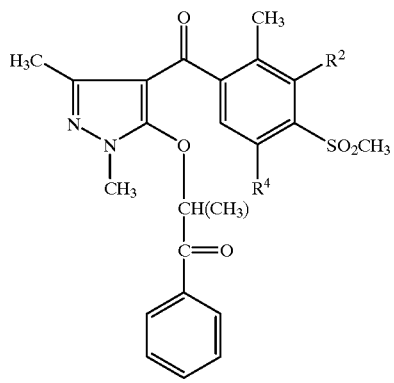
Ia390

Likewise, most particular preference is given to the compounds Ia391; in particular to the compounds Ia391.1–Ia391.164, which differ from the compounds Ia1.1–Ia1.164 in that $R^1$ is methyl and $R^7$ is phenylcarbonyl:

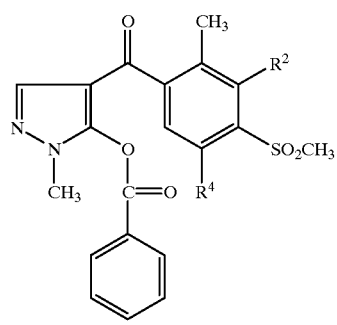
Ia391

Likewise, most particular preference is given to the compounds Ia392; in particular to the compounds Ia392.1–Ia392.164, which differ from the compounds Ia1.1–Ia1.164 in that $R^1$ is methyl, $R^6$ is ethyl and $R^7$ is phenylcarbonyl:

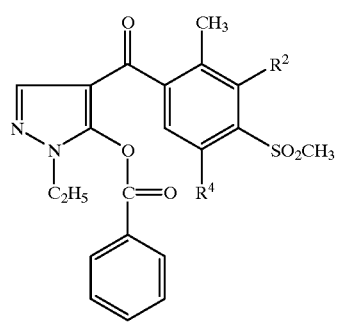
Ia392

Likewise, most particular preference is given to the compounds Ia393; in particular to the compounds Ia393.1–Ia393.164, which differ from the compounds Ia1.1–Ia1.164 in that $R^1$ is methyl, $R^7$ is phenylcarbonyl and $R^8$ is methyl:

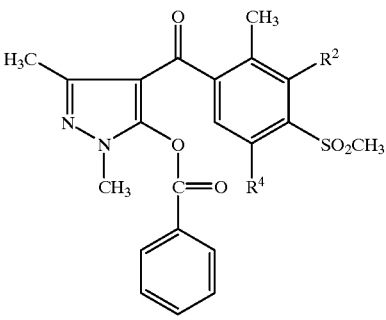
Ia393

Likewise, most particular preference is given to the compounds Ia394; in particular to the compounds Ia394.1–Ia394.164, which differ from the compounds Ia1.1–Ia1.164 in that $R^1$ is methyl and $R^7$ is 4-methylphenylcarbonyl:

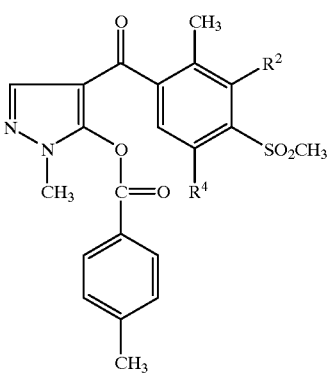
Ia394

Likewise, most particular preference is given to the compounds Ia395; in particular to the compounds Ia395.1–Ia395.164, which differ from the compounds Ia1.1–Ia1.164 in that $R^1$ is methyl, $R^6$ is ethyl and $R^7$ is 4-methylphenylcarbonyl:

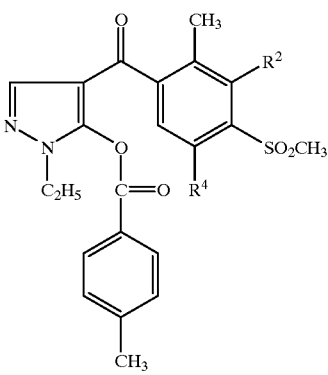
Ia395

Likewise, most particular preference is given to the compounds Ia396; in particular to the compounds Ia396.1–Ia396.164, which differ from the compounds Ia1.1–Ia1.164 in that $R^1$ is methyl, $R^7$ is 4-methylphenylcarbonyl and $R^8$ is methyl:

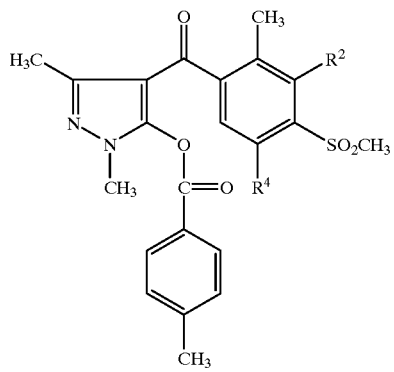

Likewise, most particular preference is given to the compounds Ia397; in particular to the compounds Ia397.1–Ia397.164, which differ from the compounds Ia1.1–Ia1.164 in that $R^1$ is methyl and $R^7$ is 4-chlorophenylcarbonyl:

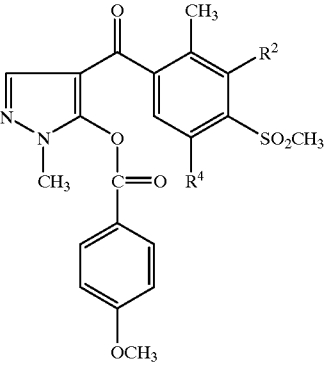

Likewise, most particular preference is given to the compounds Ia398; in particular to the compounds Ia398.1–Ia398.164, which differ from the compounds Ia1.1–Ia1.164 in that $R^1$ is methyl, $R^6$ is ethyl and $R^7$ is 4-chlorophenylcarbonyl:

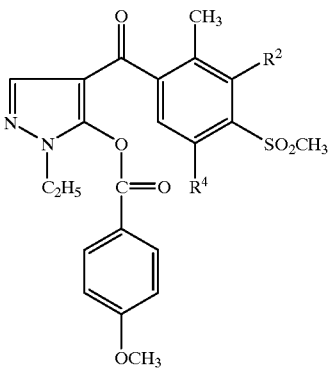

Likewise, most particular preference is given to the compounds Ia399; in particular to the compounds Ia399.1–Ia399.164, which differ from the compounds Ia1.1–Ia1.164 in that $R^1$ is methyl, $R^7$ is 4-chlorophenylcarbonyl and $R^8$ is methyl:

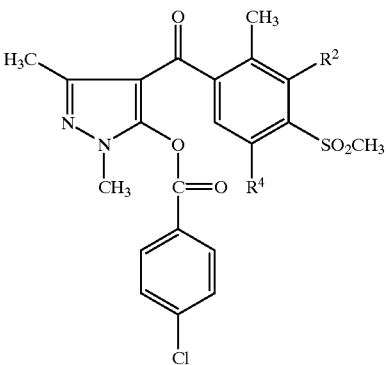

Likewise, most particular preference is given to the compounds Ia400; in particular to the compounds Ia400.1–Ia400.164, which differ from the compounds Ia1.1–Ia1.164 in that $R^1$ is methyl and $R^7$ is 4-methoxyphenylcarbonyl:

Likewise, most particular preference is given to the compounds Ia401; in particular to the compounds Ia401.1–Ia401.164, which differ from the compounds Ia1.1–Ia1.164 in that $R^1$ is methyl, $R^6$ is ethyl and $R^7$ is 4-methoxyphenylcarbonyl:

Likewise, most particular preference is given to the compounds Ia402; in particular to the compounds Ia402.1–Ia402.164, which differ from the compounds Ia1.1–Ia1.164 in that $R^1$ is methyl, $R^7$ is 4-methoxyphenylcarbonyl and $R^8$ is methyl:

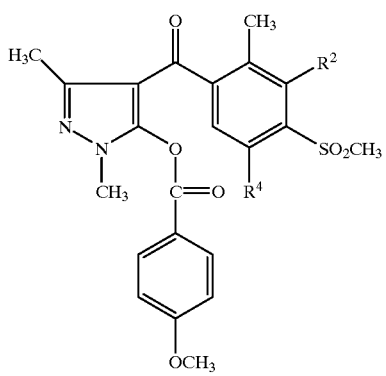

Ia402

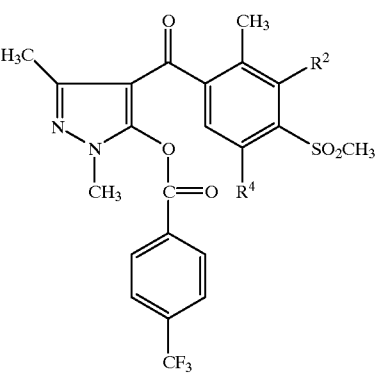

Ia405

Likewise, most particular preference is given to the compounds Ia403; in particular to the compounds Ia403.1–Ia403.164, which differ from the compounds Ia1.1–Ia1.164 in that $R^1$ is methyl and $R^7$ is 4-trifluoromethylphenylcarbonyl:

Likewise, most particular preference is given to the compounds Ia406; in particular to the compounds Ia406.1–Ia406.164, which differ from the compounds Ia1.1–Ia1.164 in that $R^1$ is methyl and $R^7$ is 2,4-dichlorophenylcarbonyl:

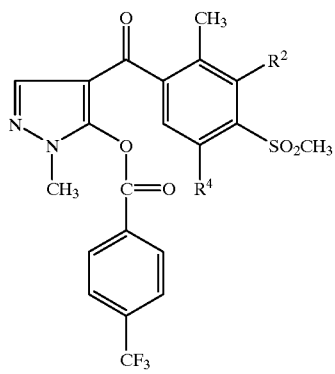

Ia403

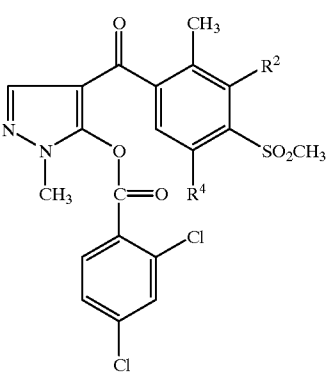

Ia406

Likewise, most particular preference is given to the compounds Ia404; in particular to the compounds Ia404.1–Ia404.164, which differ from the compounds Ia1.1–Ia1.164 in that $R^1$ is methyl, $R^6$ is ethyl and $R^7$ is 4-trifluoromethylphenylcarbonyl:

Likewise, most particular preference is given to the compounds Ia407; in particular to the compounds Ia407.1–Ia407.164, which differ from the compounds Ia1.1–Ia1.164 in that $R^1$ is methyl, $R^6$ is ethyl and $R^7$ is 2,4-dichlorophenylcarbonyl:

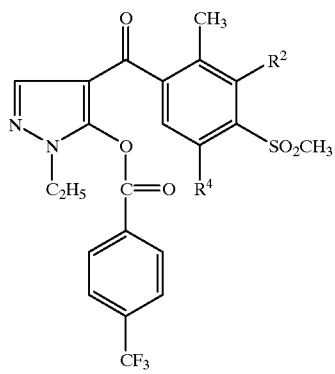

Ia404

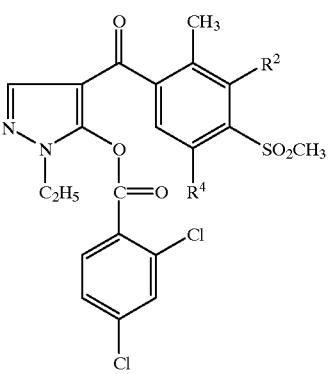

Ia407

Likewise, most particular preference is given to the compounds Ia405; in particular to the compounds Ia405.1–Ia405.164, which differ from the compounds Ia1.1–Ia1.164 in that $R^1$ is methyl, $R^7$ is 4-trifluoromethylphenylcarbonyl and $R^8$ is methyl:

Likewise, most particular preference is given to the compounds Ia408; in particular to the compounds Ia408.1–Ia408.164, which differ from the compounds Ia1.1–Ia1.164 in that $R^1$ is methyl, $R^7$ is 2,4-dichlorophenylcarbonyl and $R^8$ is methyl:

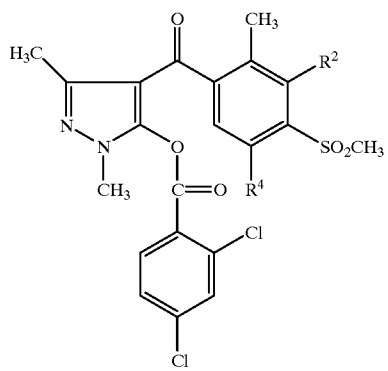
Ia408

Likewise, most particular preference is given to the compounds Ia409; in particular to the compounds Ia409.1–Ia409.164, which differ from the compounds Ia1.1–Ia1.164 in that $R^1$ is methoxy:

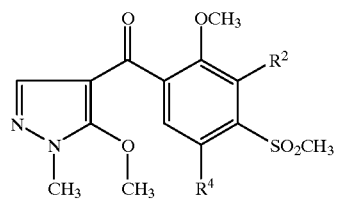
Ia409

Likewise, most particular preference is given to the compounds Ia410; in particular to the compounds Ia410.1–Ia410.164, which differ from the compounds Ia1.1–Ia1.164 in that $R^1$ is methoxy and $R^6$ is ethyl:

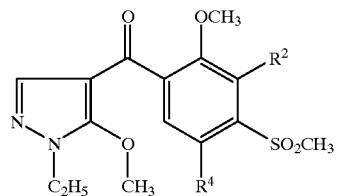
Ia410

Likewise, most particular preference is given to the compounds Ia411; in particular to the compounds Ia411.1–Ia411.164, which differ from the compounds Ia1.1–Ia1.164 in that $R^1$ is methoxy and $R^8$ is methyl:

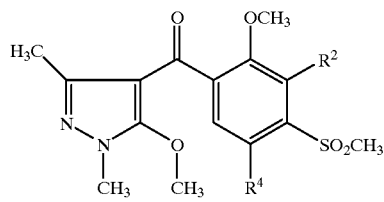
Ia411

Likewise, most particular preference is given to the compounds Ia412; in particular to the compounds Ia412.1–Ia412.164, which differ from the compounds Ia1.1–Ia1.164 in that $R^1$ is methoxy and $R^7$ is ethyl:

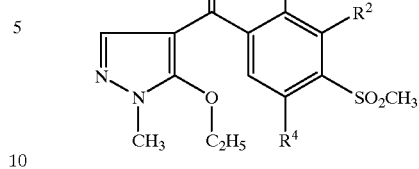
Ia412

Likewise, most particular preference is given to the compounds Ia413; in particular to the compounds Ia413.1–Ia413.164, which differ from the compounds Ia1.1–Ia1.164 in that $R^1$ is methoxy and $R^6$ and $R^7$ are each ethyl:

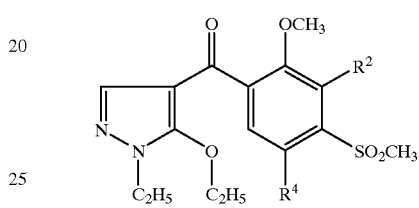
Ia413

Likewise, most particular preference is given to the compounds Ia414; in particular to the compounds Ia414.1–Ia414.164, which differ from the compounds Ia1.1–Ia1.164 in that $R^1$ is methoxy, $R^7$ is ethyl and $R^8$ is methyl:

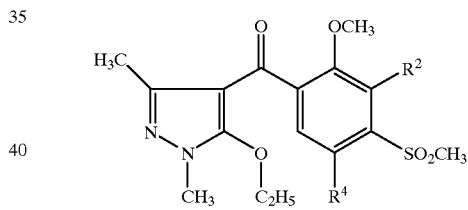
Ia414

Likewise, most particular preference is given to the compounds Ia415; in particular to the compounds Ia415.1–Ia415.164, which differ from the compounds Ia1.1–Ia1.164 in that $R^1$ is methoxy and $R^7$ is allyl:

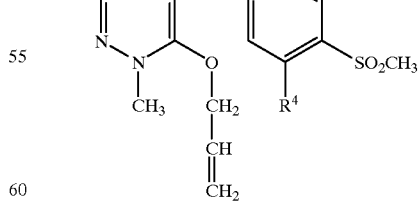
Ia415

Likewise, most particular preference is given to the compounds Ia416; in particular to the compounds Ia416.1–Ia416.164, which differ from the compounds Ia1.1–Ia1.164 in that $R^1$ is methoxy, $R^6$ is ethyl and $R^7$ is allyl:

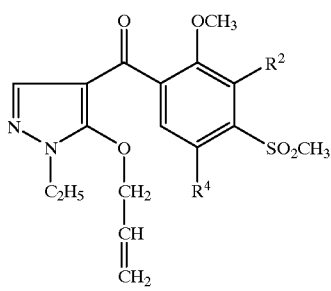

Ia416

Likewise, most particular preference is given to the compounds Ia417; in particular to the compounds Ia417.1–Ia417.164, which differ from the compounds Ia1.1–Ia1.164 in that $R^1$ is methoxy, $R^7$ is allyl and $R^8$ is methyl:

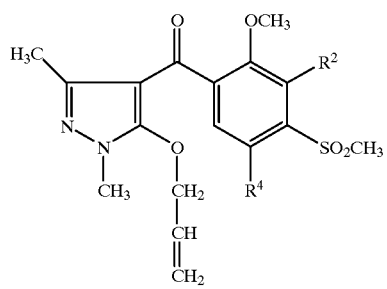

Ia417

Likewise, most particular preference is given to the compounds Ia418; in particular to the compounds Ia418.1–Ia418.164, which differ from the compounds Ia1.1–Ia1.164 in that $R^1$ is methoxy and $R^7$ is methylcarbonyl:

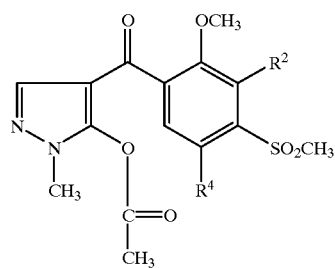

Ia418

Likewise, most particular preference is given to the compounds Ia419; in particular to the compounds Ia419.1–Ia419.164, which differ from the compounds Ia1.1–Ia1.164 in that $R^1$ is methoxy, $R^6$ is ethyl and $R^7$ is methylcarbonyl:

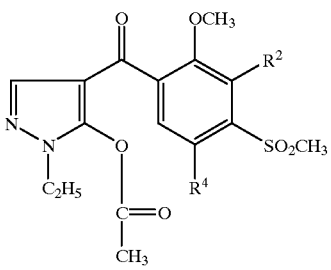

Ia419

Likewise, most particular preference is given to the compounds Ia420; in particular to the compounds Ia420.1–Ia420.164, which differ from the compounds Ia1.1–Ia1.164 in that $R^1$ is methoxy, $R^7$ is methylcarbonyl and $R^8$ is methyl:

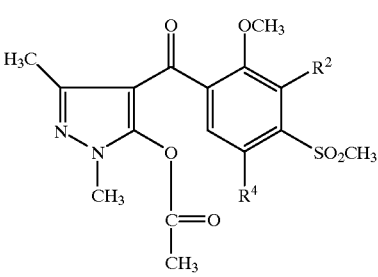

Ia420

Likewise, most particular preference is given to the compounds Ia421; in particular to the compounds Ia421.1–Ia421.164, which differ from the compounds Ia1.1–Ia1.164 in that $R^1$ is methoxy and $R^7$ is methoxycarbonyl:

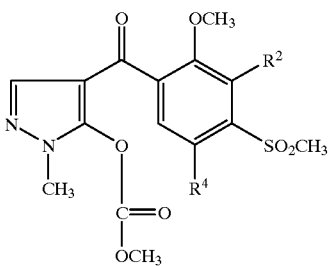

Ia421

Likewise, most particular preference is given to the compounds Ia422; in particular to the compounds Ia422.1–Ia422.164, which differ from the compounds Ia1.1–Ia1.164 in that $R^1$ is methoxy, $R^6$ is ethyl and $R^7$ is methoxycarbonyl:

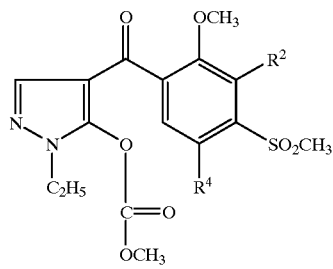
Ia422

Likewise, most particular preference is given to the compounds Ia423; in particular to the compounds Ia423.1–Ia423.164, which differ from the compounds Ia1.1–Ia1.164 in that $R^1$ is methoxy, $R^7$ is methoxycarbonyl and $R^8$ is methyl:

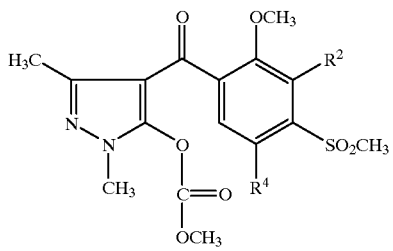
Ia423

Likewise, most particular preference is given to the compounds Ia424; in particular to the compounds Ia424.1–Ia424.164, which differ from the compounds Ia1.1–Ia1.164 in that $R^1$ is methoxy and $R^7$ is dimethylaminocarbonyl:

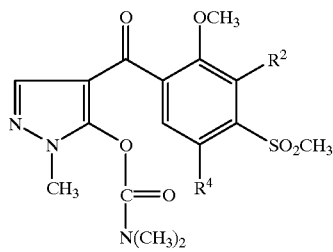
Ia424

Likewise, most particular preference is given to the compounds Ia425; in particular to the compounds Ia425.1–Ia425.164, which differ from the compounds Ia1.1–Ia1.164 in that $R^1$ is methoxy, $R^6$ is ethyl and $R^7$ is dimethylaminocarbonyl:

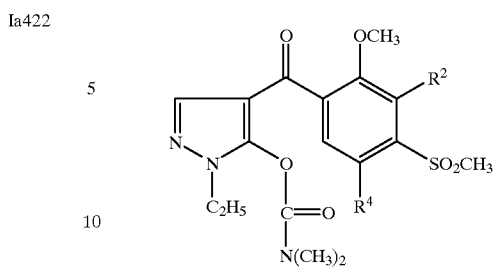
Ia425

Likewise, most particular preference is given to the compounds Ia426; in particular to the compounds Ia426.1–Ia426.164, which differ from the compounds Ia1.1–Ia1.164 in that $R^1$ is methoxy, $R^7$ is dimethylaminocarbonyl and $R^8$ is methyl:

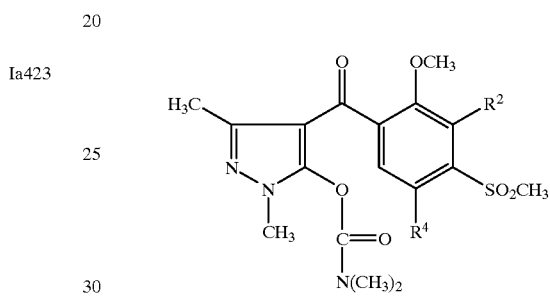
Ia426

Likewise, most particular preference is given to the compounds Ia427; in particular to the compounds Ia427.1–Ia427.164, which differ from the compounds Ia1.1–Ia1.164 in that $R^1$ is methoxy and $R^7$ is methoxycarbonylmethyl:

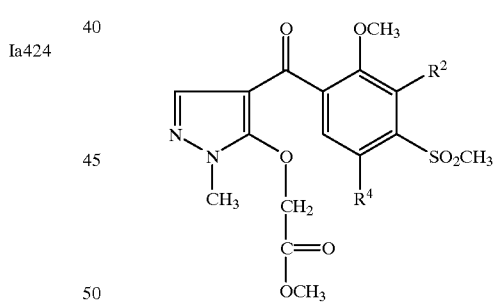
Ia427

Likewise, most particular preference is given to the compounds Ia428; in particular to the compounds Ia428.1–Ia428.164, which differ from the compounds Ia1.1–Ia1.164 in that $R^1$ is methoxy, $R^6$ is ethyl and $R^7$ is methoxycarbonylmethyl:

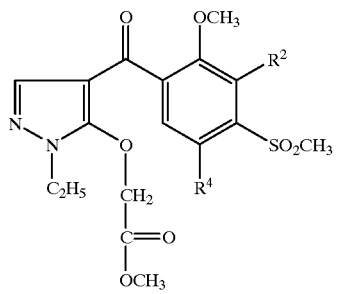
Ia428

Likewise, most particular preference is given to the compounds Ia429; in particular to the compounds Ia429.1–Ia429.164, which differ from the compounds Ia1.1–Ia1.164 in that $R^1$ is methoxy, $R^7$ is methoxycarbonylmethyl and $R^8$ is methyl:

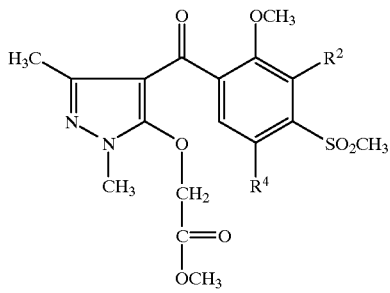
Ia429

Likewise, most particular preference is given to the compounds Ia430; in particular to the compounds Ia430.1–Ia430.164, which differ from the compounds Ia1.1–Ia1.164 in that $R^1$ is methoxy and $R^7$ is dimethylaminocarbonylmethyl:

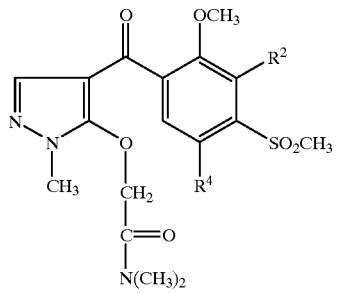
Ia430

Likewise, most particular preference is given to the compounds Ia431; in particular to the compounds Ia431.1–Ia431.164, which differ from the compounds Ia1.1–Ia1.164 in that $R^1$ is methoxy, $R^6$ is ethyl and $R^7$ is dimethylaminocarbonylmethyl:

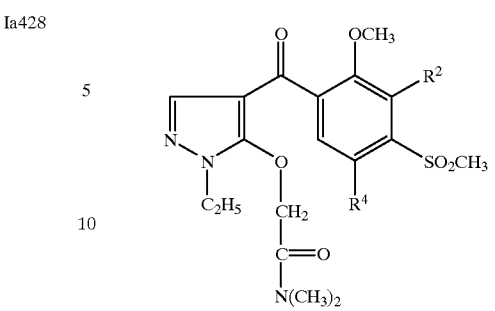
Ia431

Likewise, most particular preference is given to the compounds Ia432; in particular to the compounds Ia432.1–Ia432.164, which differ from the compounds Ia1.1–Ia1.164 in that $R^1$ is methoxy, $R^7$ is dimethylaminocarbonylmethyl and $R^8$ is methyl:

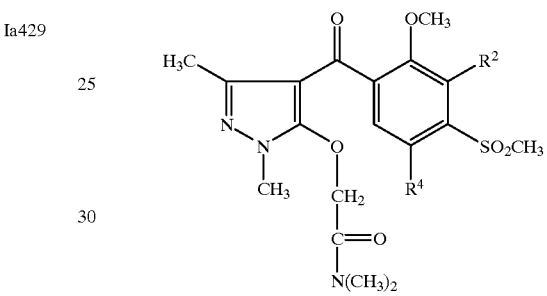
Ia432

Likewise, most particular preference is given to the compounds Ia433; in particular to the compounds Ia433.1–Ia433.164, which differ from the compounds Ia1.1–Ia1.164 in that $R^1$ is methoxy and $R^7$ is phenylcarbonylmethyl:

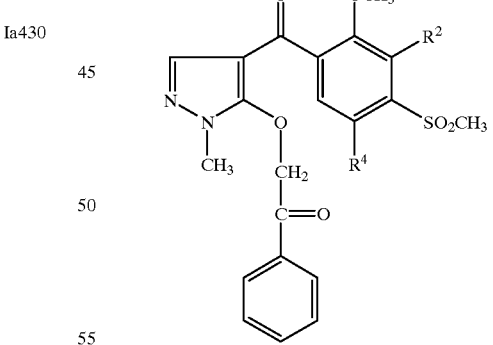
Ia433

Likewise, most particular preference is given to the compounds Ia434; in particular to the compounds Ia434.1–Ia434.164, which differ from the compounds Ia1.1–Ia1.164 in that $R^1$ is methoxy, $R^6$ is ethyl and $R^7$ is phenylcarbonylmethyl:

Ia434

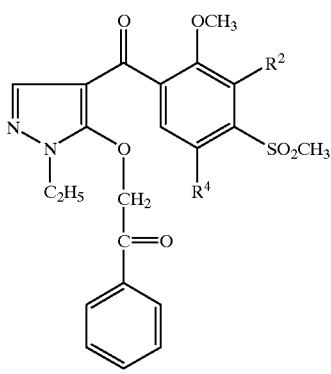

Likewise, most particular preference is given to the compounds Ia435; in particular to the compounds Ia435.1–Ia435.164, which differ from the compounds Ia1.1–Ia1.164 in that $R^1$ is methoxy, $R^7$ is phenylcarbonylmethyl and $R^8$ is methyl:

Ia435

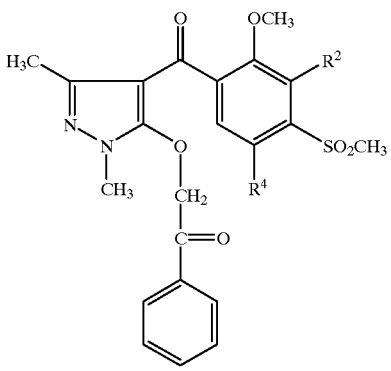

Likewise, most particular preference is given to the compounds Ia436; in particular to the compounds Ia436.1–Ia436.164, which differ from the compounds Ia1.1–Ia1.164 in that $R^1$ is methoxy and $R^7$ is 4-methylphenylcarbonylmethyl:

Ia436

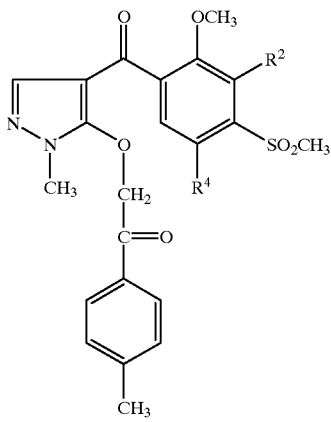

Likewise, most particular preference is given to the compounds Ia437; in particular to the compounds Ia437.1–Ia437.164, which differ from the compounds Ia1.1–Ia1.164 in that $R^1$ is methoxy, $R^6$ is ethyl and $R^7$ is 4-methylphenylcarbonylmethyl:

Ia437

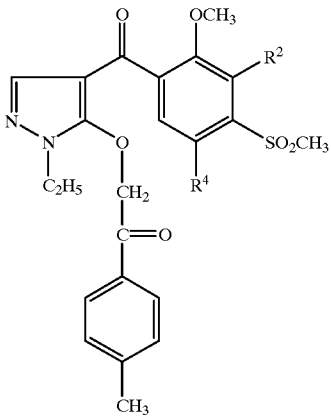

Likewise, most particular preference is given to the compounds Ia438; in particular to the compounds Ia438.1–Ia438.164, which differ from the compounds Ia1.1–Ia1.164 in that $R^1$ is methoxy, $R^7$ is 4-methylphenylcarbonylmethyl and $R^8$ is methyl:

Ia438

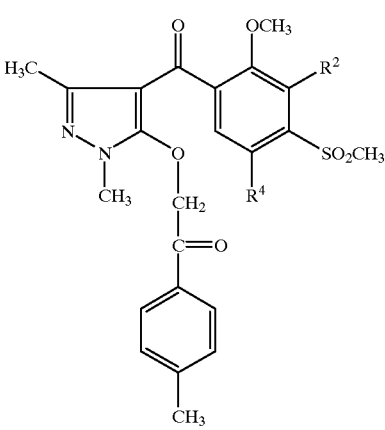

Likewise, most particular preference is given to the compounds Ia439; in particular to the compounds Ia439.1–Ia439.164, which differ from the compounds Ia1.1–Ia1.164 in that $R^1$ is methoxy and $R^7$ is phenylcarbonyl:

Ia439

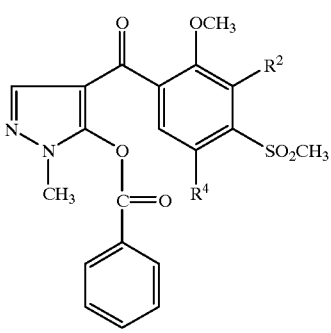

Likewise, most particular preference is given to the compounds Ia440; in particular to the compounds Ia440.1–Ia440.164, which differ from the compounds Ia1.1–Ia1.164 in that $R^1$ is methoxy, $R^6$ is ethyl and $R^7$ is phenylcarbonyl:

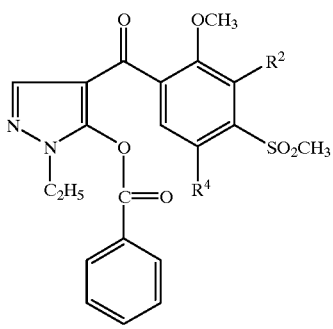
Ia440

Likewise, most particular preference is given to the compounds Ia441; in particular to the compounds Ia441.1–Ia441.164, which differ from the compounds Ia1.1–Ia1.164 in that $R^1$ is methoxy, $R^7$ is phenylcarbonyl and $R^8$ is methyl:

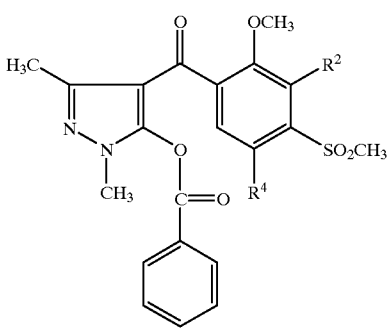
Ia441

Likewise, most particular preference is given to the compounds Ia442; in particular to the compounds Ia442.1–Ia442.164, which differ from the compounds Ia1.1–Ia1.164 in that $R^1$ is methoxy and $R^7$ is 4-methylphenylcarbonyl:

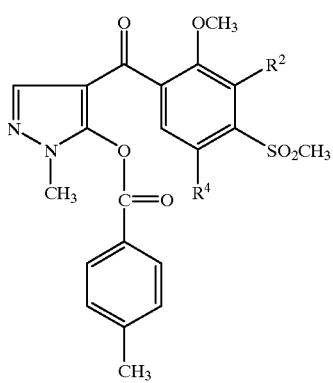
Ia442

Likewise, most particular preference is given to the compounds Ia443; in particular to the compounds Ia443.1–Ia443.164, which differ from the compounds Ia1.1–Ia1.164 in that $R^1$ is methoxy, $R^6$ is ethyl and $R^7$ is 4-methylphenylcarbonyl:

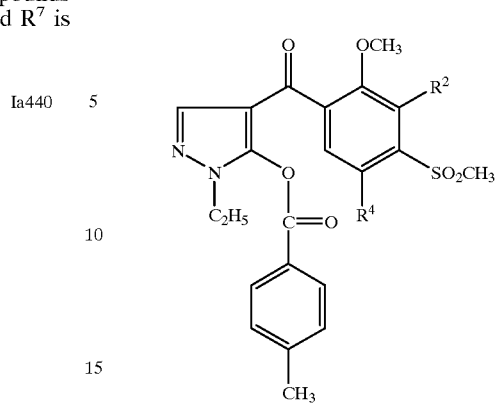
Ia443

Likewise, most particular preference is given to the compounds Ia444; in particular to the compounds Ia444.1–Ia444.164, which differ from the compounds Ia1.1–Ia1.164 in that $R^1$ is methoxy, $R^7$ is 4-methylphenylcarbonyl and $R^8$ is methyl:

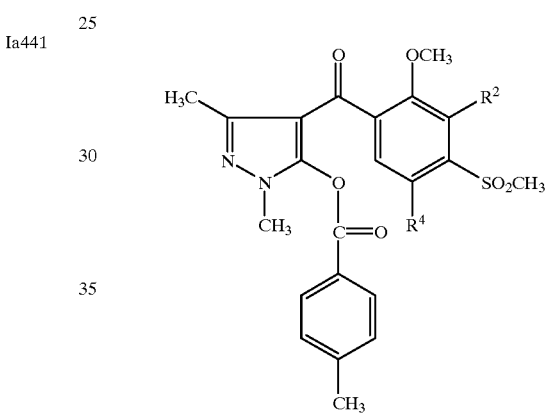
Ia444

Likewise, most particular preference is given to the compounds Ia445; in particular to the compounds Ia445.1–Ia445.164, which differ from the compounds Ia1.1–Ia1.164 in that $R^1$ is methoxy and $R^7$ is benzyl:

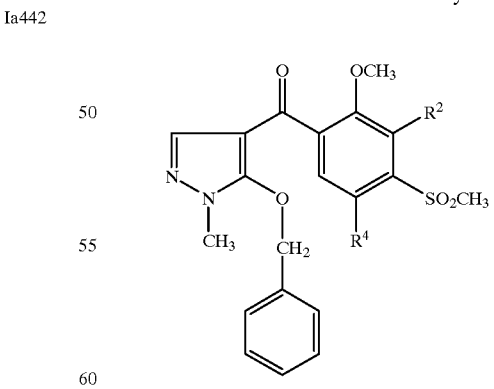
Ia445

Likewise, most particular preference is given to the compounds Ia446; in particular to the compounds Ia446.1–Ia446.164, which differ from the compounds Ia1.1–Ia1.164 in that $R^1$ is methoxy, $R^6$ is ethyl and $R^7$ is benzyl:

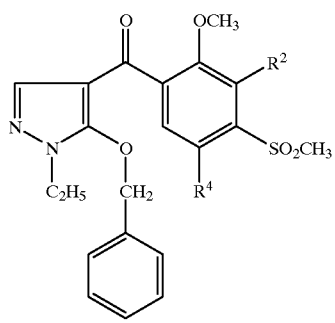
Ia446

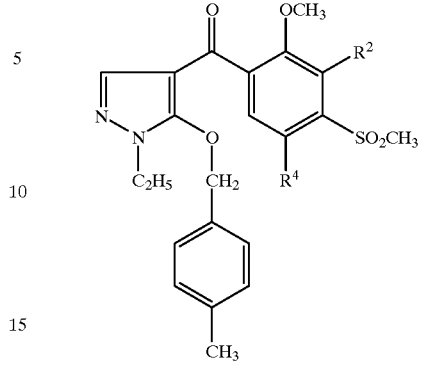
Ia449

Likewise, most particular preference is given to the compounds Ia447; in particular to the compounds Ia447.1–Ia447.164, which differ from the compounds Ia1.1–Ia1.164 in that $R^1$ is methoxy, $R^7$ is benzyl and $R^8$ is methyl:

Likewise, most particular preference is given to the compounds Ia450; in particular to the compounds Ia450.1–Ia450.164, which differ from the compounds Ia1.1–Ia1.164 in that $R^1$ is methoxy, $R^7$ is 4-methylphenylmethyl and $R^8$ is methyl:

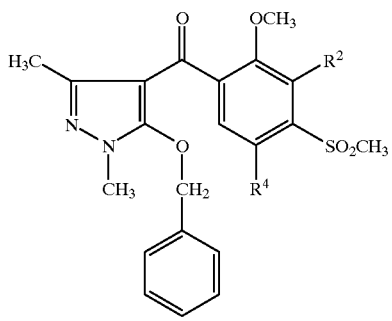
Ia447

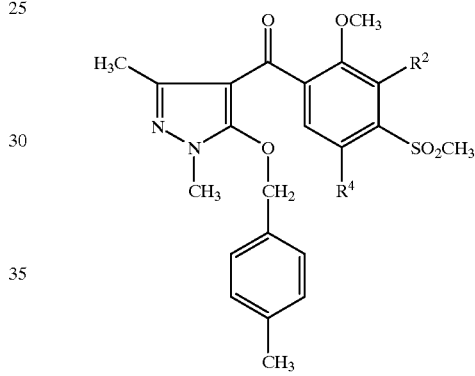
Ia450

Likewise, most particular preference is given to the compounds Ia448; in particular to the compounds Ia448.1–Ia448.164, which differ from the compounds Ia1.1–Ia1.164 in that $R^1$ is methoxy and $R^7$ is 4-methylphenylmethyl:

Likewise, most particular preference is given to the compounds Ia451; in particular to the compounds Ia451.1–Ia451.164, which differ from the compounds Ia1.1–Ia1.164 in that $R^1$ is methoxy and $R^7$ is 4-chlorophenylmethyl:

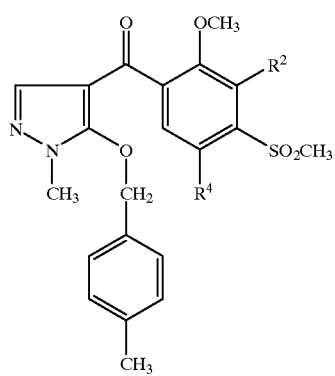
Ia448

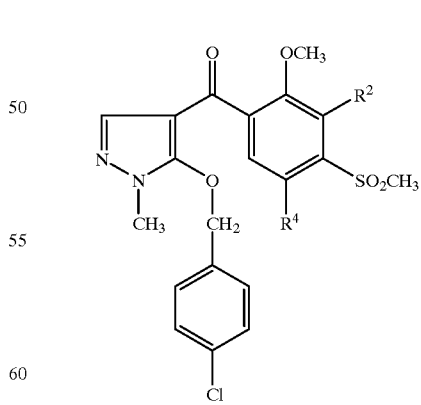
Ia451

Likewise, most particular preference is given to the compounds Ia449; in particular to the compounds Ia449.1–Ia449.164, which differ from the compounds Ia1.1–Ia1.164 in that $R^1$ is methoxy, $R^6$ is ethyl and $R^7$ is 4-methylphenylmethyl:

Likewise, most particular preference is given to the compounds Ia452; in particular to the compounds Ia452.1–Ia452.164, which differ from the compounds Ia1.1–Ia1.164 in that $R^1$ is methoxy, $R^6$ is ethyl and $R^7$ is 4-chlorophenylmethyl:

Ia452

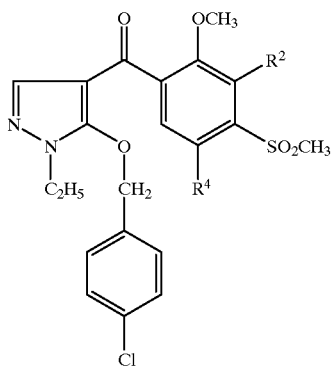

Likewise, most particular preference is given to the compounds Ia453; in particular to the compounds Ia453.1–Ia453.164, which differ from the compounds Ia1.1–Ia1.164 in that $R^1$ is methoxy, $R^7$ is 4-chlorophenylmethyl and $R^8$ is methyl:

Ia453

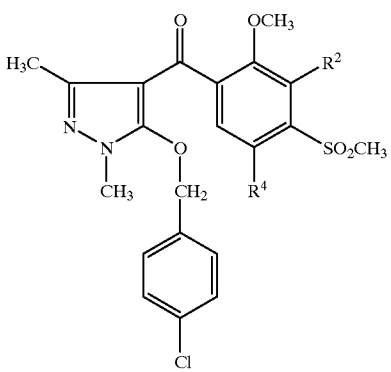

Likewise, most particular preference is given to the compounds Ia454; in particular to the compounds Ia454.1–Ia454.164, which differ from the compounds Ia1.1–Ia1.164 in that $R^3$ is ethylsulfonyl:

Ia454

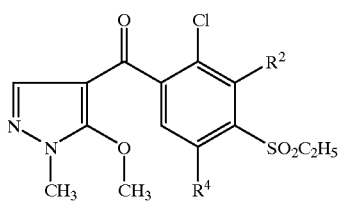

Likewise, most particular preference is given to the compounds Ia455; in particular to the compounds Ia455.1–Ia455.164, which differ from the compounds Ia1.1–Ia1.164 in that $R^3$ is ethylsulfonyl and $R^6$ is ethyl:

Ia455

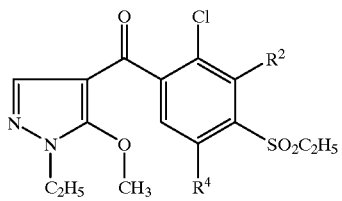

Likewise, most particular preference is given to the compounds Ia456; in particular to the compounds Ia456.1–Ia456.164, which differ from the compounds Ia1.1–Ia1.164 in that $R^3$ is ethylsulfonyl and $R^8$ is methyl:

Ia456

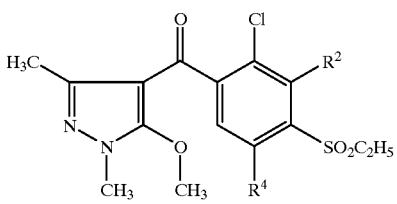

Likewise, most particular preference is given to the compounds Ia457; in particular to the compounds Ia457.1–Ia457.164, which differ from the compounds Ia1.1–Ia1.164 in that $R^3$ is ethylsulfonyl and $R^7$ is ethyl:

Ia457

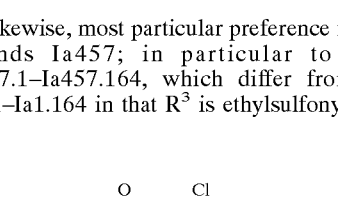

Likewise, most particular preference is given to the compounds Ia458; in particular to the compounds Ia458.1–Ia458.164, which differ from the compounds Ia1.1–Ia1.164 in that $R^3$ is ethylsulfonyl, $R^6$ and $R^7$ are each ethyl:

Ia458

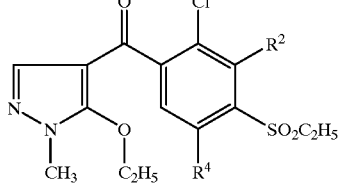

Likewise, most particular preference is given to the compounds Ia459; in particular to the compounds Ia459.1–Ia459.164, which differ from the compounds Ia1.1–Ia1.164 in that $R^3$ is ethylsulfonyl, $R^7$ is ethyl and $R^8$ is methyl:

Ia459

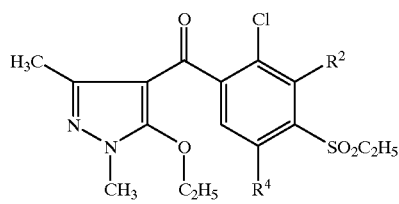

Likewise, most particular preference is given to the compounds Ia460; in particular to the compounds Ia460.1–Ia460.164, which differ from the compounds Ia1.1–Ia1.164 in that $R^3$ is ethylsulfonyl and $R^7$ is allyl:

Ia460

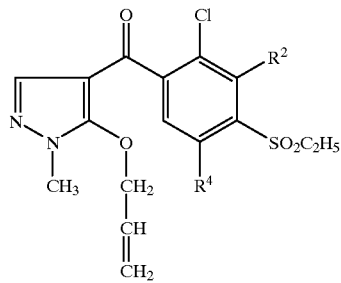

Likewise, most particular preference is given to the compounds Ia461; in particular to the compounds Ia461.1–Ia461.164, which differ from the compounds Ia1.1–Ia1.164 in that $R^3$ is ethylsulfonyl, $R^6$ and $R^7$ are each allyl:

Ia461

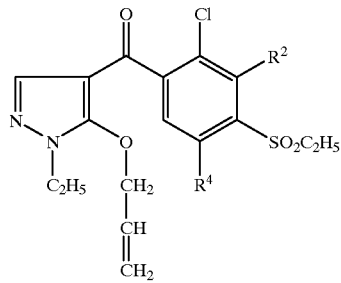

Likewise, most particular preference is given to the compounds Ia462; in particular to the compounds Ia462.1–Ia462.164, which differ from the compounds Ia1.1–Ia1.164 in that $R^3$ is ethylsulfonyl, $R^7$ is allyl and $R^8$ is methyl:

Ia462

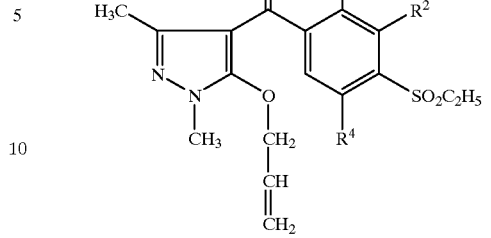

Likewise, most particular preference is given to the compounds Ia463; in particular to the compounds Ia463.1–Ia463.164, which differ from the compounds Ia1.1–Ia1.164 in that $R^3$ is ethylsulfonyl and $R^7$ is methylcarbonyl:

Ia463

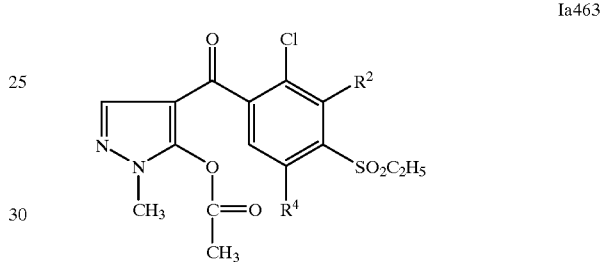

Likewise, most particular preference is given to the compounds Ia464; in particular to the compounds Ia464.1–Ia464.164, which differ from the compounds Ia1.1–Ia1.164 in that $R^3$ is ethylsulfonyl, $R^6$ is ethyl and $R^7$ is methylcarbonyl:

Ia464

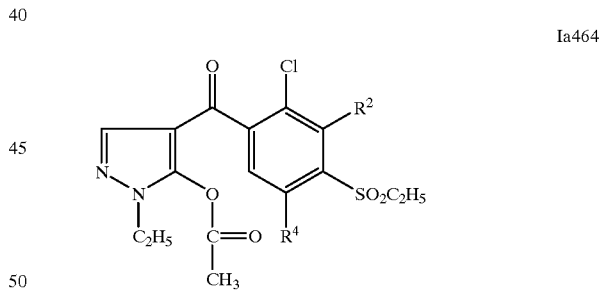

Likewise, most particular preference is given to the compounds Ia465; in particular to the compounds Ia465.1–Ia465.164, which differ from the compounds Ia1.1–Ia1.164 in that $R^3$ is ethylsulfonyl, $R^7$ is methylcarbonyl and $R^8$ is methyl:

Ia465

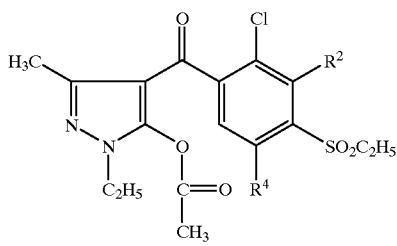

Likewise, most particular preference is given to the compounds Ia466; in particular to the compounds Ia466.1–Ia466.164, which differ from the compounds Ia1.1–Ia1.164 in that $R^3$ is ethylsulfonyl and $R^7$ is methoxycarbonyl:

Ia466

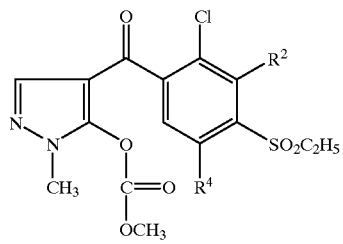

Likewise, most particular preference is given to the compounds Ia467; in particular to the compounds Ia467.1–Ia467.164, which differ from the compounds Ia1.1–Ia1.164 in that $R^3$ is ethylsulfonyl, $R^6$ is ethyl and $R^7$ is methoxycarbonyl:

Ia467

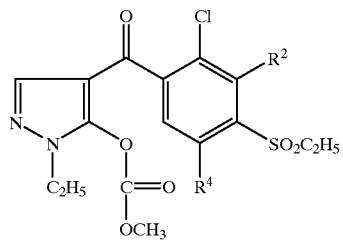

Likewise, most particular preference is given to the compounds Ia468; in particular to the compounds Ia468.1–Ia468.164, which differ from the compounds Ia1.1–Ia1.164 in that $R^3$ is ethylsulfonyl, $R^7$ is methoxycarbonyl and $R^8$ is methyl:

Ia468

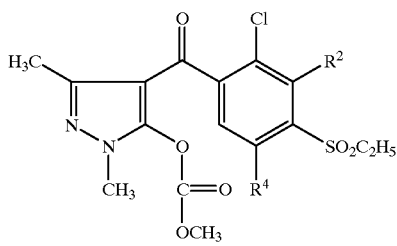

Likewise, most particular preference is given to the compounds Ia469; in particular to the compounds Ia469.1–Ia469.164, which differ from the compounds Ia1.1–Ia1.164 in that $R^3$ is ethylsulfonyl and $R^7$ is dimethylaminocarbonyl:

Ia469

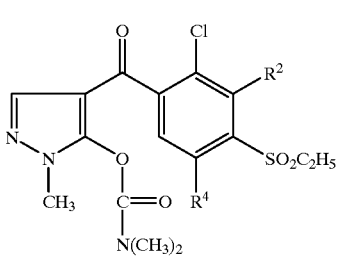

Likewise, most particular preference is given to the compounds Ia470; in particular to the compounds Ia470.1–Ia470.164, which differ from the compounds Ia1.1–Ia1.164 in that $R^3$ is ethylsulfonyl, $R^6$ is ethyl and $R^7$ is dimethylaminocarbonyl:

Ia470

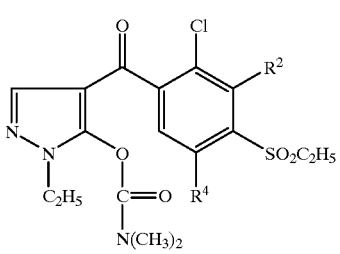

Likewise, most particular preference is given to the compounds Ia471; in particular to the compounds Ia471.1–Ia471.164, which differ from the compounds Ia1.1–Ia1.164 in that $R^3$ is ethylsulfonyl, $R^7$ is dimethylaminocarbonyl and $R^8$ is methyl:

Ia471

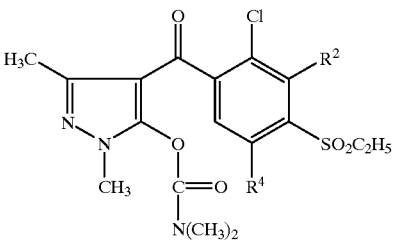

Likewise, most particular preference is given to the compounds Ia472; in particular to the compounds Ia472.1–Ia472.164, which differ from the compounds Ia1.1–Ia1.164 in that $R^3$ is ethylsulfonyl and $R^7$ is methoxycarbonylmethyl:

Ia472

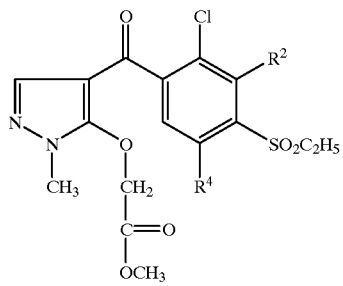

Likewise, most particular preference is given to the compounds Ia473; in particular to the compounds Ia473.1–Ia473.164, which differ from the compounds Ia1.1–Ia1.164 in that $R^3$ is ethylsulfonyl, $R^6$ is ethyl and $R^7$ is methoxycarbonylmethyl:

Ia473

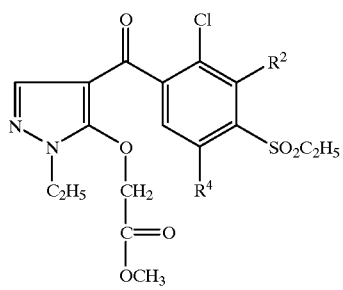

Likewise, most particular preference is given to the compounds Ia474; in particular to the compounds Ia474.1–Ia474.164, which differ from the compounds Ia1.1–Ia1.164 in that $R^3$ is ethylsulfonyl, $R^7$ is methoxycarbonylmethyl and $R^8$ is methyl:

Ia474

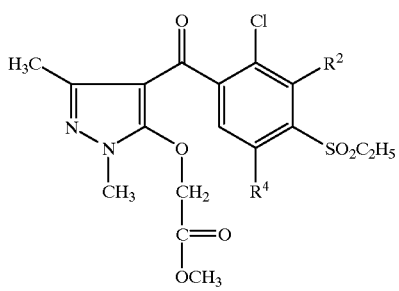

Likewise, most particular preference is given to the compounds Ia475; in particular to the compounds Ia475.1–Ia475.164, which differ from the compounds Ia1.1–Ia1.164 in that $R^3$ is ethylsulfonyl and $R^7$ is dimethylaminocarbonylmethyl:

Ia475

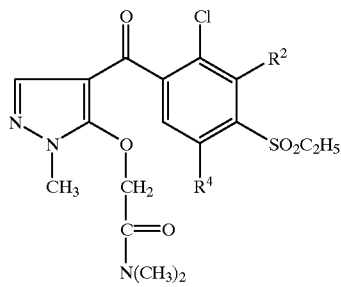

Likewise, most particular preference is given to the compounds Ia476; in particular to the compounds Ia476.1–Ia476.164, which differ from the compounds Ia1.1–Ia1.164 in that $R^3$ is ethylsulfonyl, $R^6$ is ethyl and $R^7$ is dimethylaminocarbonylmethyl:

Ia476

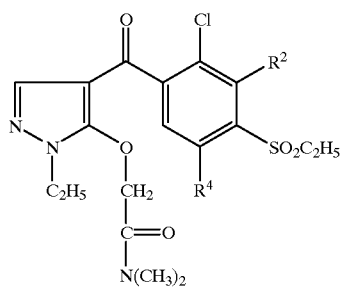

Likewise, most particular preference is given to the compounds Ia477; in particular to the compounds Ia477.1–Ia477.164, which differ from the compounds Ia1.1–Ia1.164 in that $R^3$ is ethylsulfonyl, $R^7$ is dimethylaminocarbonylmethyl and $R^8$ is methyl:

Ia477

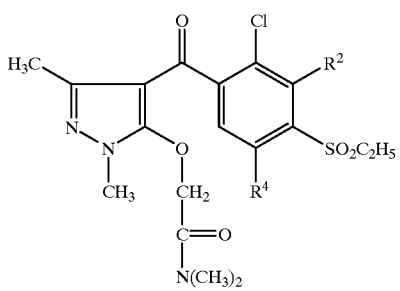

Likewise, most particular preference is given to the compounds Ia478; in particular to the compounds Ia478.1–Ia478.164, which differ from the compounds Ia1.1–Ia1.164 in that $R^3$ is ethylsulfonyl and $R^7$ is phenylcarbonylmethyl:

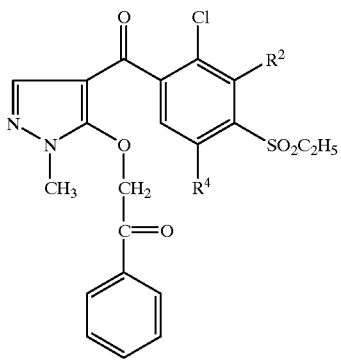

Ia478

Likewise, most particular preference is given to the compounds Ia479; in particular to the compounds Ia479.1–Ia479.164, which differ from the compounds Ia1.1–Ia1.164 in that $R^3$ is ethylsulfonyl, $R^6$ is ethyl and $R^7$ is phenylcarbonylmethyl:

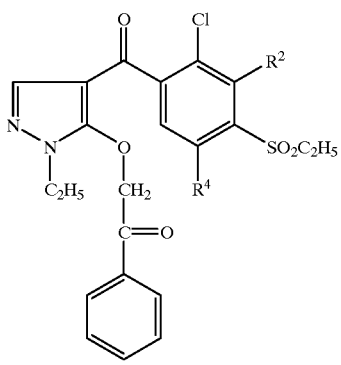

Ia479

Likewise, most particular preference is given to the compounds Ia480; in particular to the compounds Ia480.1–Ia480.164, which differ from the compounds Ia1.1–Ia1.164 in that $R^3$ is ethylsulfonyl, $R^7$ is phenylcarbonylmethyl and $R^8$ is methyl:

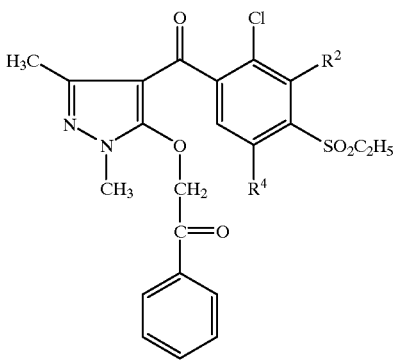

Ia480

Likewise, most particular preference is given to the compounds Ia481; in particular to the compounds Ia481.1–Ia481.164, which differ from the compounds Ia1.1–Ia1.164 in that $R^3$ is ethylsulfonyl and $R^7$ is 4-methylphenylcarbonylmethyl:

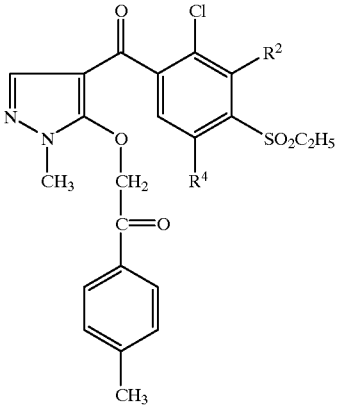

Ia481

Likewise, most particular preference is given to the compounds Ia482; in particular to the compounds Ia482.1–Ia482.164, which differ from the compounds Ia1.1–Ia1.164 in that $R^3$ is ethylsulfonyl, $R^6$ s ethyl and $R^7$ is 4-methylphenylcarbonylmethyl:

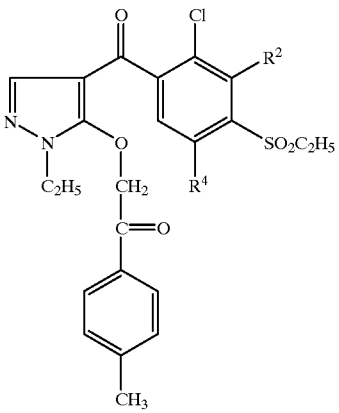

Ia482

Likewise, most particular preference is given to the compounds Ia483; in particular to the compounds Ia483.1–Ia483.164, which differ from the compounds Ia1.1–Ia1.164 in that $R^3$ is ethylsulfonyl, $R^7$ 4-methylphenylcarbonylmethyl and $R^8$ is methyl:

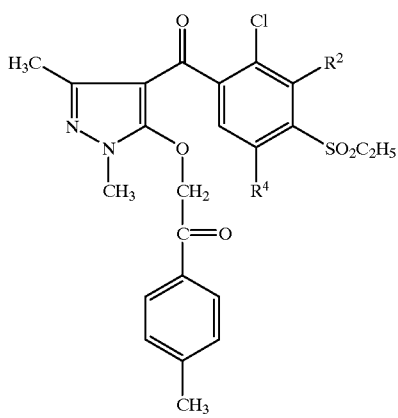

Ia483

Likewise, most particular preference is given to the compounds Ia484; in particular to the compounds Ia484.1–Ia484.164, which differ from the compounds Ia1.1–Ia1.164 in that $R^3$ is ethylsulfonyl and is phenylcarbonyl:

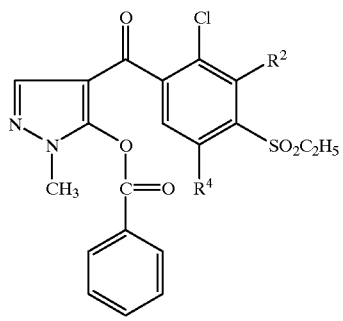

Ia484

Likewise, most particular preference is given to the compounds Ia485; in particular to the compounds Ia485.1–Ia485.164, which differ from the compounds Ia1.1–Ia1.164 in that $R^3$ is ethylsulfonyl, $R^6$ is ethyl and $R^7$ is phenylcarbonyl:

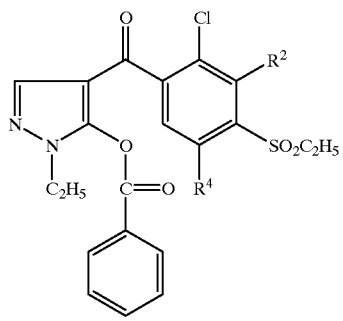

Ia485

Likewise, most particular preference is given to the compounds Ia486; in particular to the compounds Ia486.1–Ia486.164, which differ from the compounds Ia1.1–Ia1.164 in that $R^3$ is ethylsulfonyl, $R^7$ is phenylcarbonyl and $R^8$ is methyl:

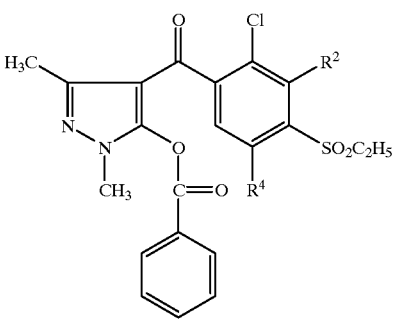

Ia486

Likewise, most particular preference is given to the compounds Ia487; in particular to the compounds Ia487.1–Ia487.164, which differ from the compounds Ia1.1–Ia1.164 in that $R^3$ is ethylsulfonyl and $R^7$ is 4-methylphenylcarbonyl:

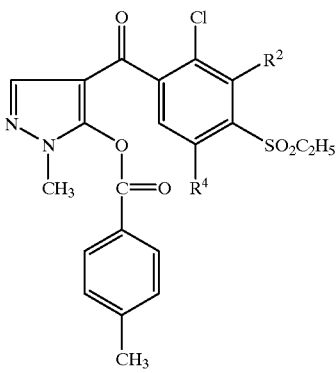

Ia487

Likewise, most particular preference is given to the compounds Ia488; in particular to the compounds Ia488.1–Ia488.164, which differ from the compounds Ia1.1–Ia1.164 in that $R^3$ is ethylsulfonyl, $R^6$ is ethyl and $R^7$ is 4-methylphenylcarbonyl:

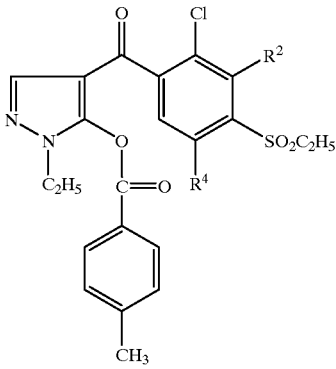

Ia488

Likewise, most particular preference is given to the compounds Ia489; in particular to the compounds Ia489.1–Ia489.164, which differ from the compounds Ia1.1–Ia1.164 in that $R^3$ is ethylsulfonyl, $R^7$ is 4-methylphenylcarbonyl and $R^8$ is methyl:

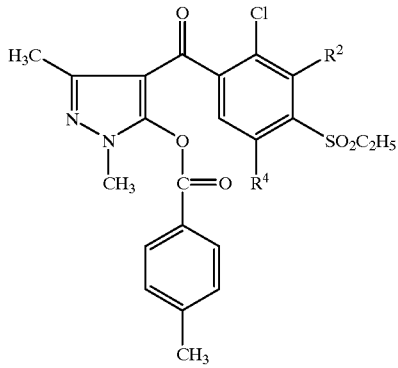
Ia489

Likewise, most particular preference is given to the compounds Ia490; in particular to the compounds Ia490.1–Ia490.164, which differ from the compounds Ia1.1–Ia1.164 in that $R^3$ is ethylsulfonyl and $R^7$ is benzyl:

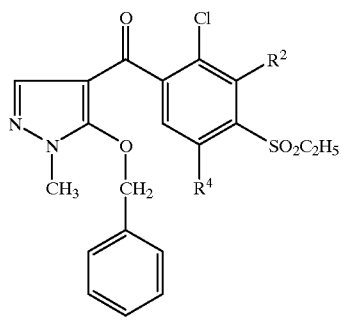
Ia490

Likewise, most particular preference is given to the compounds Ia491; in particular to the compounds Ia491.1–Ia491.164, which differ from the compounds Ia1.1–Ia1.164 in that $R^3$ is ethylsulfonyl, $R^6$ is ethyl and $R^7$ is benzyl:

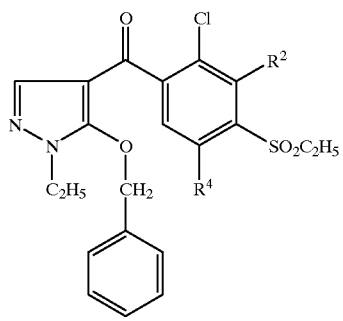
Ia491

Likewise, most particular preference is given to the compounds Ia492; in particular to the compounds Ia492.1–Ia492.164, which differ from the compounds Ia1.1–Ia1.164 in that $R^3$ is ethylsulfonyl, $R^7$ is benzyl and $R^8$ is methyl:

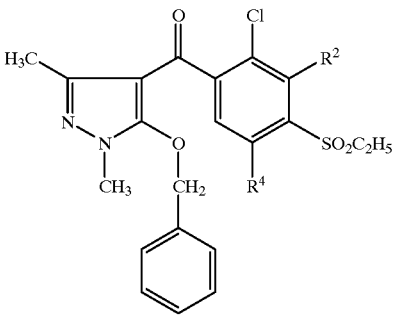
Ia492

Likewise, most particular preference is given to the compounds Ia493; in particular to the compounds Ia493.1–Ia493.164, which differ from the compounds Ia1.1–Ia1.164 in that $R^3$ is ethylsulfonyl and $R^7$ is 4-methylphenylmethyl:

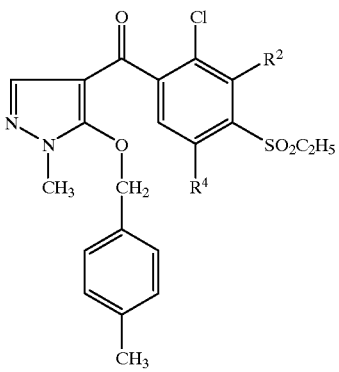
Ia493

Likewise, most particular preference is given to the compounds Ia494; in particular to the compounds Ia494.1–Ia494.164, which differ from the compounds Ia1.1–Ia1.164 in that $R^3$ is ethylsulfonyl, $R^6$ is ethyl and $R^7$ is 4-methylphenylmethyl:

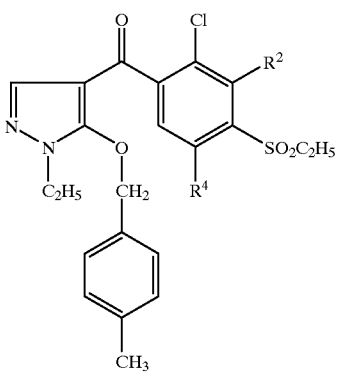
Ia494

Likewise, most particular preference is given to the compounds Ia495; in particular to the compounds Ia495.1–Ia495.164, which differ from the compounds Ia1.1–Ia1.164 in that $R^3$ is ethylsulfonyl, $R^7$ is 4-methylphenylmethyl and $R^8$ is methyl:

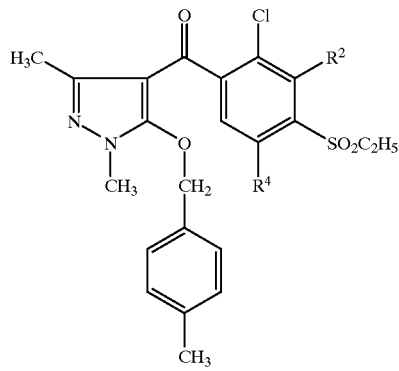

Ia495

Likewise, most particular preference is given to the compounds Ia496; in particular to the compounds Ia496.1–Ia496.164, which differ from the compounds Ia1.1–Ia1.164 in that $R^3$ is ethylsulfonyl and $R^7$ is 4-chlorophenylmethyl:

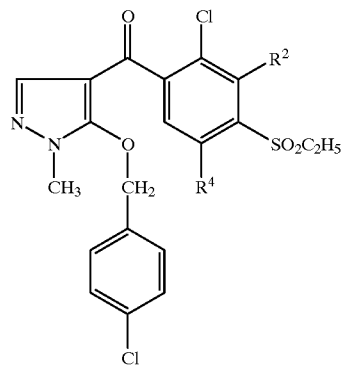

Ia496

Likewise, most particular preference is given to the compounds Ia497; in particular to the compounds Ia497.1–Ia497.164, which differ from the compounds Ia1.1–Ia1.164 in that $R^3$ is ethylsulfonyl, $R^6$ is ethyl and $R^7$ is 4-chlorophenylmethyl:

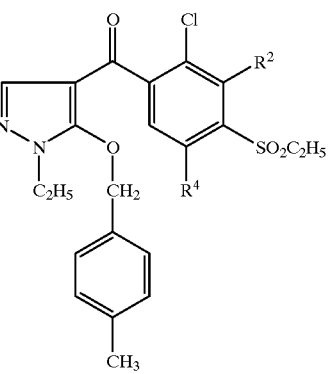

Ia497

Likewise, most particular preference is given to the compounds Ia498; in particular to the compounds Ia498.1–Ia498.164, which differ from the compounds Ia1.1–Ia1.164 in that $R^3$ is ethylsulfonyl, $R^7$ is 4-chlorophenylmethyl and $R^8$ is methyl:

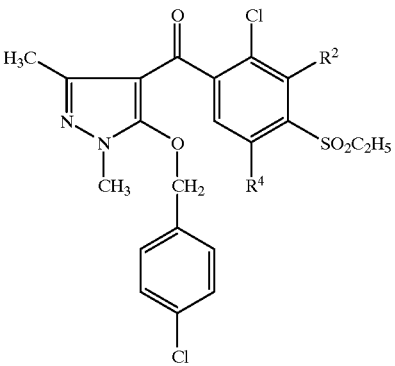

Ia498

Likewise, most particular preference is given to the compounds Ia499; in particular to the compounds Ia499.1–Ia499.164, which differ from the compounds Ia1.1–Ia1.164 in that $R^1$ is trifluoromethyl:

Ia499

Likewise, most particular preference is given to the compounds Ia500; in particular to the compounds Ia500.1–Ia500.164, which differ from the compounds Ia1.1–Ia1.164 in that $R^1$ is trifluoromethyl and $R^6$ is ethyl:

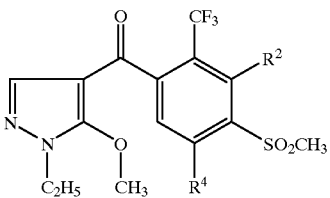

Ia500

Likewise, most particular preference is given to the compounds Ia501; in particular to the compounds Ia501.1–Ia501.164, which differ from the compounds Ia1.1–Ia1.164 in that $R^1$ is trifluoromethyl and $R^7$ is ethyl:

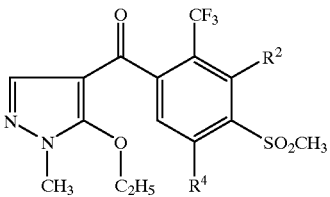

Ia501

Likewise, most particular preference is given to the compounds Ia502; in particular to the compounds Ia502.1–Ia502.164, which differ from the compounds Ia1.1–Ia1.164 in that $R^1$ is trifluoromethyl and $R^6$ and $R^7$ are each ethyl:

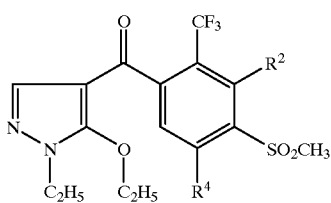

Ia502

Likewise, most particular preference is given to the compounds Ia503; in particular to the compounds Ia503.1–Ia503.164, which differ from the compounds Ia1.1–Ia1.164 in that $R^1$ is trifluoromethyl and $R^7$ is methylcarbonyl:

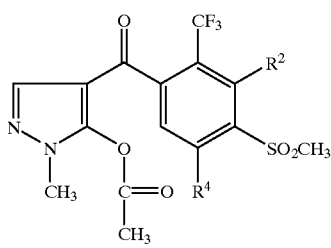

Ia503

Likewise, most particular preference is given to the compounds Ia504; in particular to the compounds Ia504.1–Ia504.164, which differ from the compounds Ia1.1–Ia1.164 in that $R^1$ is trifluoromethyl, $R^6$ is ethyl and $R^7$ is methylcarbonyl:

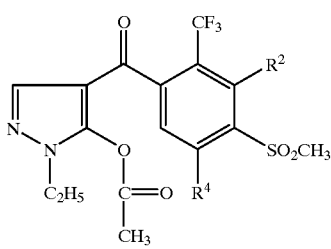

Ia504

Likewise, most particular preference is given to the compounds Ia505; in particular to the compounds Ia505.1–Ia505.164, which differ from the compounds Ia1.1–Ia1.164 in that $R^1$ is trifluoromethyl and $R^7$ is methoxycarbonyl:

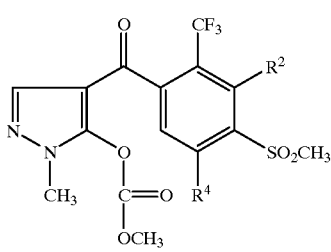

Ia505

Likewise, most particular preference is given to the compounds Ia506; in particular to the compounds Ia506.1–Ia506.164, which differ from the compounds Ia1.1–Ia1.164 in that $R^1$ is trifluoromethyl, $R^6$ is ethyl and $R^7$ is methoxycarbonyl:

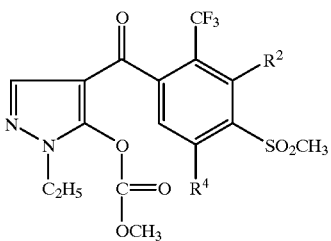

Ia506

Likewise, most particular preference is given to the compounds Ia507; in particular to the compounds Ia507.1–Ia507.164, which differ from the compounds Ia1.1–Ia1.164 in that $R^1$ is trifluoromethyl and $R^7$ is dimethylaminocarbonyl:

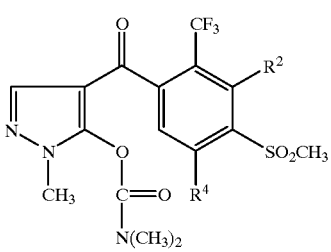

Ia507

Likewise, most particular preference is given to the compounds Ia508; in particular to the compounds Ia508.1–Ia508.164, which differ from the compounds Ia1.1–Ia1.164 in that $R^1$ is trifluoromethyl, $R^6$ is ethyl and $R^7$ is dimethylaminocarbonyl:

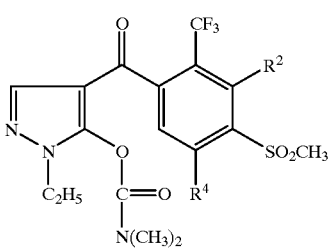

Ia508

Likewise, most particular preference is given to the compounds Ia509; in particular to the compounds Ia509.1–Ia509.164, which differ from the compounds Ia1.1–Ia1.164 in that $R^1$ is trifluoromethyl and $R^7$ is methoxycarbonylmethyl:

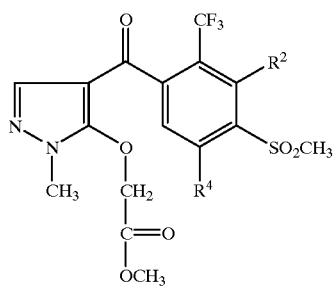
Ia509

Likewise, most particular preference is given to the compounds Ia510; in particular to the compounds Ia510.1–Ia510.164, which differ from the compounds Ia1.1–Ia1.164 in that $R^1$ is trifluoromethyl, $R^6$ is ethyl and $R^7$ is methoxycarbonylmethyl:

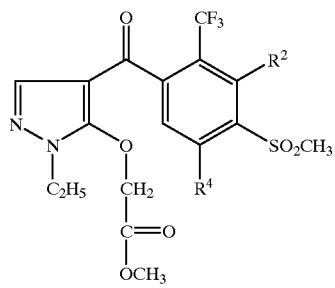
Ia510

Likewise, most particular preference is given to the compounds Ia511; in particular to the compounds Ia511.1–Ia511.164, which differ from the compounds Ia1.1–Ia1.164 in that $R^1$ is trifluoromethyl and $R^7$ is phenylcarbonylmethyl:

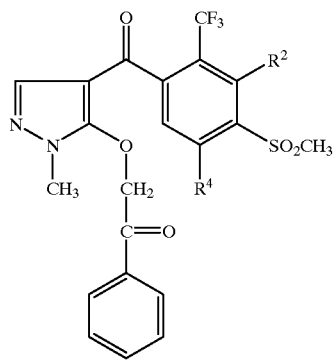
Ia511

Likewise, most particular preference is given to the compounds Ia512; in particular to the compounds Ia512.1–Ia512.164, which differ from the compounds Ia1.1–Ia1.164 in that $R^1$ is trifluoromethyl, $R^6$ is ethyl and $R^7$ is phenylcarbonylmethyl:

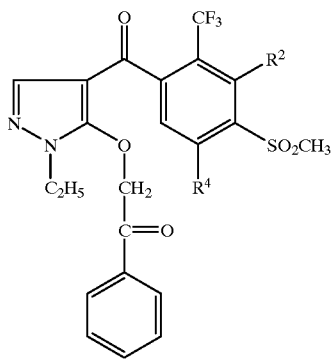
Ia512

Likewise, most particular preference is given to the compounds Ia513; in particular to the compounds Ia513.1–Ia513.164, which differ from the compounds Ia1.1–Ia1.164 in that $R^1$ is trifluoromethyl and $R^7$ is phenylcarbonyl:

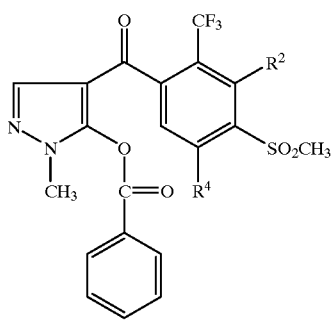
Ia513

Likewise, most particular preference is given to the compounds Ia514; in particular to the compounds Ia514.1–Ia514.164, which differ from the compounds Ia1.1–Ia1.164 in that $R^1$ is trifluoromethyl, $R^6$ is ethyl and $R^7$ is phenylcarbonyl:

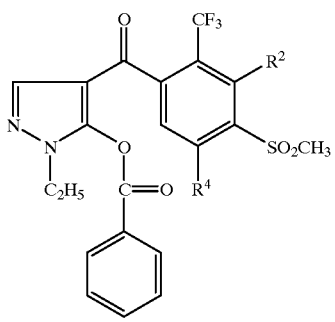
Ia514

Likewise, most particular preference is given to the compounds Ia515; in particular to the compounds Ia515.1–Ia515.164, which differ from the compounds Ia1.1–Ia1.164 in that $R^1$ is trifluoromethyl and $R^7$ is benzyl:

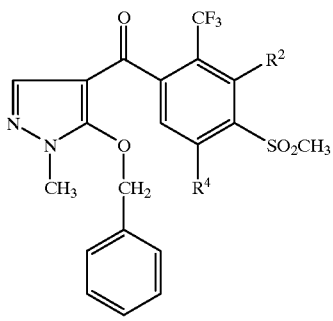
Ia515

Likewise, most particular preference is given to the compounds Ia516; in particular to the compounds Ia516.1–Ia516.164, which differ from the compounds Ia1.1–Ia1.164 in that $R^1$ is trifluoromethyl, $R^6$ is ethyl and $R^7$ is benzyl:

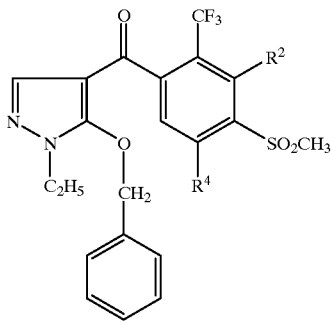
Ia516

Likewise, most particular preference is given to the compounds Ia517; in particular to the compounds Ia517.1–Ia517.164, which differ from the compounds Ia1.1–Ia1.164 in that $R^1$ is hydrogen:

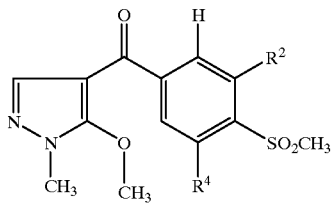
Ia517

Likewise, most particular preference is given to the compounds Ia518; in particular to the compounds Ia518.1–Ia518.164, which differ from the compounds Ia1.1–Ia1.164 in that $R^1$ is hydrogen and $R^6$ is ethyl:

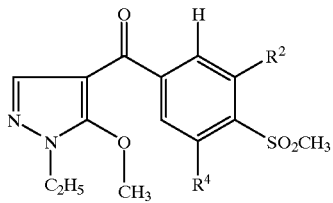
Ia518

Likewise, most particular preference is given to the compounds Ia519; in particular to the compounds Ia519.1–Ia519.164, which differ from the compounds Ia1.1–Ia1.164 in that $R^1$ is hydrogen and $R^7$ is ethyl:

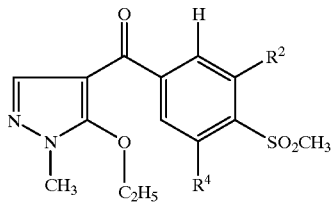
Ia519

Likewise, most particular preference is given to the compounds Ia520; in particular to the compounds Ia520.1–Ia520.164, which differ from the compounds Ia1.1–Ia1.164 in that $R^1$ is hydrogen and $R^6$ and $R^7$ are each ethyl:

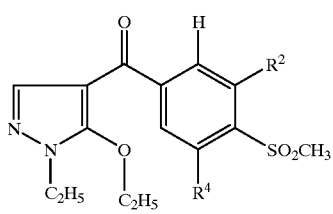
Ia520

Likewise, most particular preference is given to the compounds Ia521; in particular to the compounds Ia521.1–Ia521.164, which differ from the compounds Ia1.1–Ia1.164 in that $R^1$ is hydrogen and $R^7$ is methylcarbonyl:

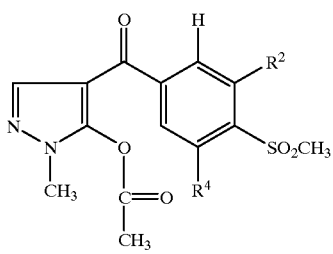
Ia521

Likewise, most particular preference is given to the compounds Ia522; in particular to the compounds Ia522.1–Ia522.164, which differ from the compounds Ia1.1–Ia1.164 in that $R^1$ is hydrogen, $R^6$ is ethyl and $R^7$ is methylcarbonyl:

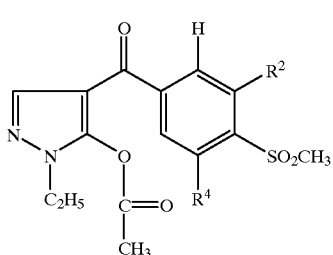
Ia522

Likewise, most particular preference is given to the compounds Ia523; in particular to the compounds Ia523.1–Ia523.164, which differ from the compounds Ia1.1–Ia1.164 in that $R^1$ is hydrogen and $R^7$ is methoxycarbonyl:

Ia523

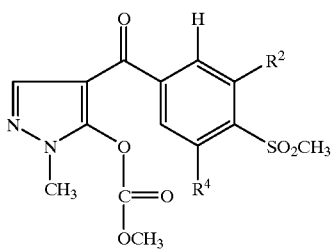

Likewise, most particular preference is given to the compounds Ia524; in particular to the compounds Ia524.1–Ia524.164, which differ from the compounds Ia1.1–Ia1.164 in that $R^1$ is hydrogen, $R^6$ is ethyl and $R^7$ is methoxycarbonyl:

Ia524

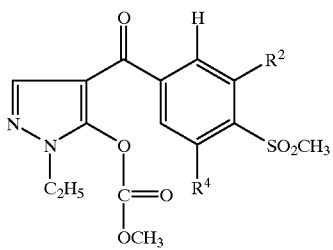

Likewise, most particular preference is given to the compounds Ia525; in particular to the compounds Ia525.1–Ia525.164, which differ from the compounds Ia1.1–Ia1.164 in that $R^1$ is hydrogen and $R^7$ is dimethylaminocarbonyl:

Ia525

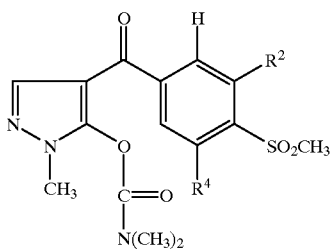

Likewise, most particular preference is given to the compounds Ia526; in particular to the compounds Ia526.1–Ia526.164, which differ from the compounds Ia1.1–Ia1.164 in that $R^1$ is hydrogen, $R^6$ is ethyl and $R^7$ is dimethylaminocarbonyl:

Ia526

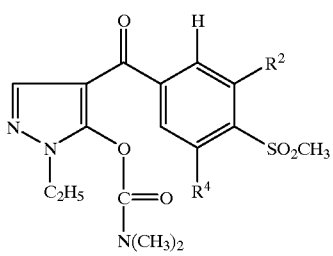

Likewise, most particular preference is given to the compounds Ia527; in particular to the compounds Ia527.1–Ia527.164, which differ from the compounds Ia1.1–Ia1.164 in that $R^1$ is hydrogen and $R^7$ is methoxycarbonylmethyl:

Ia527

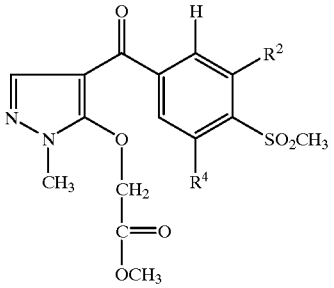

Likewise, most particular preference is given to the compounds Ia528; in particular to the compounds Ia528.1–Ia528.164, which differ from the compounds Ia1.1–Ia1.164 in that $R^1$ is hydrogen, $R^6$ is ethyl and $R^7$ is methoxycarbonylmethyl:

Ia528

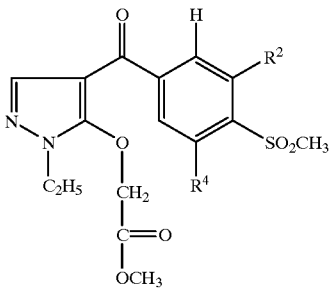

Likewise, most particular preference is given to the compounds Ia529; in particular to the compounds Ia529.1–Ia529.164, which differ from the compounds Ia1.1–Ia1.164 in that $R^1$ is hydrogen and $R^7$ is phenylcarbonylmethyl:

Ia529

Likewise, most particular preference is given to the compounds Ia530; in particular to the compounds Ia530.1–Ia530.164, which differ from the compounds Ia1.1–Ia1.164 in that $R^1$ is hydrogen, $R^6$ is ethyl and $R^7$ is phenylcarbonylmethyl:

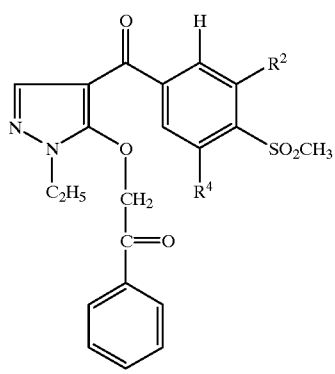

Ia530

Likewise, most particular preference is given to the compounds Ia531; in particular to the compounds Ia531.1–Ia531.164, which differ from the compounds Ia1.1–Ia1.164 in that $R^1$ is hydrogen and $R^7$ is phenylcarbonyl:

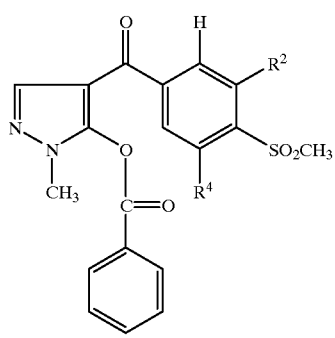

Ia531

Likewise, most particular preference is given to the compounds Ia532; in particular to the compounds Ia532.1–Ia532.164, which differ from the compounds Ia1.1–Ia1.164 in that $R^1$ is hydrogen, $R^6$ is ethyl and $R^7$ is phenylcarbonyl:

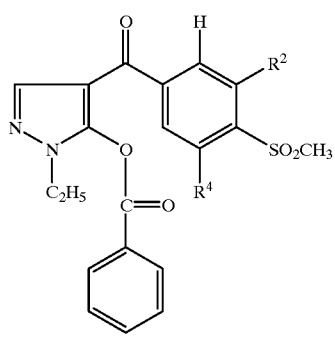

Ia532

Likewise, most particular preference is given to the compounds Ia533; in particular to the compounds Ia533.1–Ia533.164, which differ from the compounds Ia1.1–Ia1.164 in that $R^1$ is hydrogen and $R^7$ is benzyl:

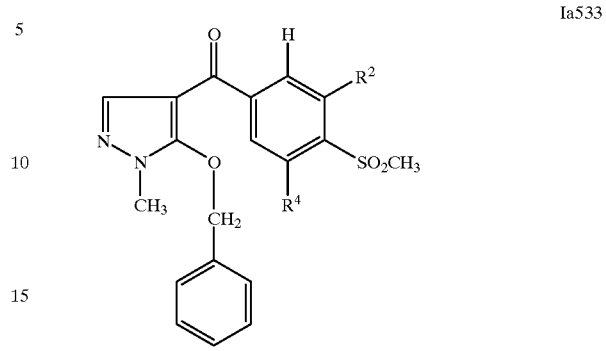

Ia533

Likewise, most particular preference is given to the compounds Ia534; in particular to the compounds Ia534.1–Ia534.164, which differ from the compounds Ia1.1–Ia1.164 in that $R^1$ is hydrogen, $R^6$ is ethyl and $R^7$ is benzyl:

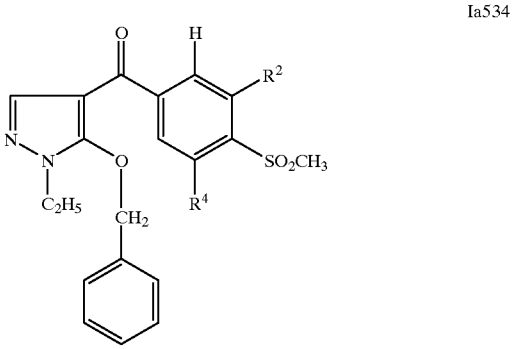

Ia534

Likewise, most particular preference is given to the compounds Ia535; in particular to the compounds Ia535.1–Ia535.164, which differ from the compounds Ia1.1–Ia1.164 in that $R^1$ is methyl and $R^3$ is hydrogen:

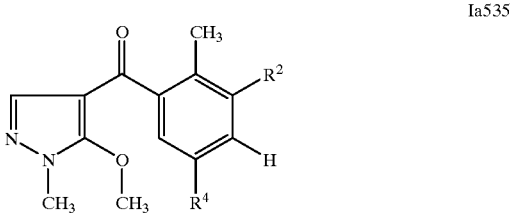

Ia535

Likewise, most particular preference is given to the compounds Ia536; in particular to the compounds Ia536.1–Ia536.164, which differ from the compounds Ia1.1–Ia1.164 in that $R^1$ is methyl, $R^3$ is hydrogen and $R^6$ is ethyl:

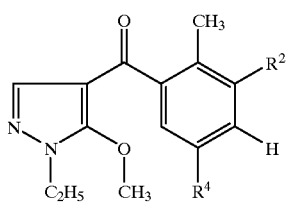

Ia536

Likewise, most particular preference is given to the compounds Ia537; in particular to the compounds Ia537.1–Ia537.164, which differ from the compounds Ia1.1–Ia1.164 in that $R^1$ is methyl, $R^3$ is hydrogen and $R^7$ is ethyl:

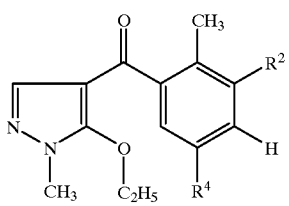

Ia537

Likewise, most particular preference is given to the compounds Ia538; in particular to the compounds Ia538.1–Ia538.164, which differ from the compounds Ia1.1–Ia1.164 in that $R^1$ is methyl, $R^3$ is hydrogen and $R^6$ and $R^7$ are each ethyl:

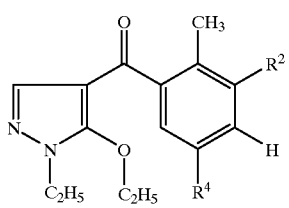

Ia538

Likewise, most particular preference is given to the compounds Ia539; in particular to the compounds Ia539.1–Ia539.164, which differ from the compounds Ia1.1–Ia1.164 in that $R^1$ is methyl, $R^3$ is hydrogen and $R^7$ is methylcarbonyl:

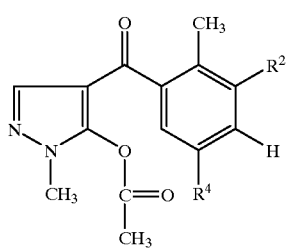

Ia539

Likewise, most particular preference is given to the compounds Ia540; in particular to the compounds Ia540.1–Ia540.164, which differ from the compounds Ia1.1–Ia1.164 in that $R^1$ is methyl, $R^3$ is hydrogen, $R^6$ is ethyl and $R^7$ is methylcarbonyl:

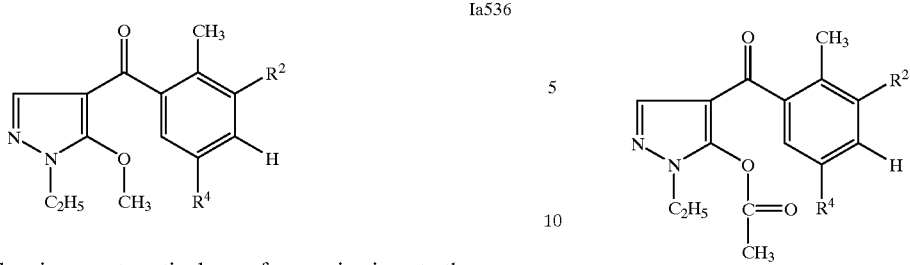

Ia540

Likewise, most particular preference is given to the compounds Ia541; in particular to the compounds Ia541.1–Ia541.164, which differ from the compounds Ia1.1–Ia1.164 in that $R^1$ is methyl, $R^3$ is hydrogen and $R^7$ is methoxycarbonyl:

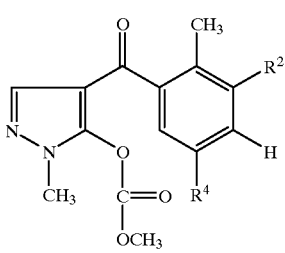

Ia541

Likewise, most particular preference is given to the compounds Ia542; in particular to the compounds Ia542.1–Ia542.164, which differ from the compounds Ia1.1–Ia1.164 in that $R^1$ is methyl, $R^3$ is hydrogen, $R^6$ is ethyl and $R^7$ is methoxycarbonyl:

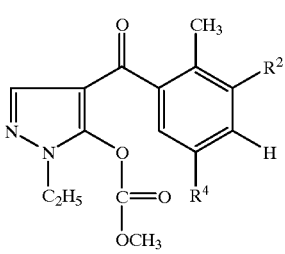

Ia542

Likewise, most particular preference is given to the compounds Ia543; in particular to the compounds Ia543.1–Ia543.164, which differ from the compounds Ia1.1–Ia1.164 in that $R^1$ is methyl, $R^3$ is hydrogen and $R^7$ is dimethylaminocarbonyl:

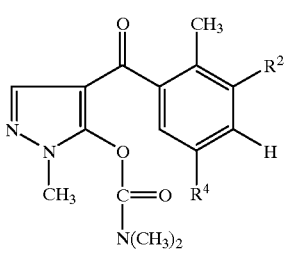

Ia543

Likewise, most particular preference is given to the compounds Ia544; in particular to the compounds Ia544.1–Ia544.164, which differ from the compounds Ia1.1–Ia1.164 in that $R^1$ is methyl, $R^3$ is hydrogen, $R^6$ is ethyl and $R^7$ is dimethylaminocarbonyl:

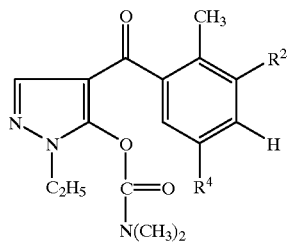

Ia544

Likewise, most particular preference is given to the compounds Ia545; in particular to the compounds Ia545.1–Ia545.164, which differ from the compounds Ia1.1–Ia1.164 in that $R^1$ is methyl, $R^3$ is hydrogen and $R^7$ is methoxycarbonylmethyl:

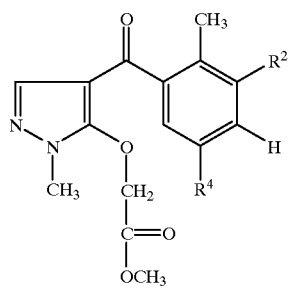

Ia545

Likewise, most particular preference is given to the compounds Ia546; in particular to the compounds Ia546.1–Ia546.164, which differ from the compounds Ia1.1–Ia1.164 in that $R^1$ is methyl, $R^3$ is hydrogen, $R^6$ is ethyl and $R^7$ is methoxycarbonylmethyl:

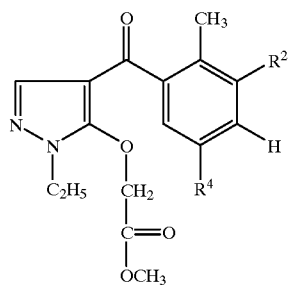

Ia546

Likewise, most particular preference is given to the compounds Ia547; in particular to the compounds Ia547.1–Ia547.164, which differ from the compounds Ia1.1–Ia1.164 in that $R^1$ is methyl, $R^3$ is hydrogen and $R^7$ is phenylcarbonylmethyl:

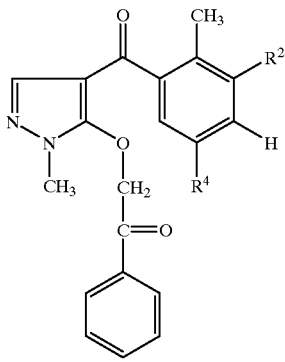

Ia547

Likewise, most particular preference is given to the compounds Ia548; in particular to the compounds Ia548.1–Ia548.164, which differ from the compounds Ia1.1–Ia1.164 in that $R^1$ is methyl, $R^3$ is hydrogen, $R^6$ is ethyl and $R^7$ is phenylcarbonylmethyl:

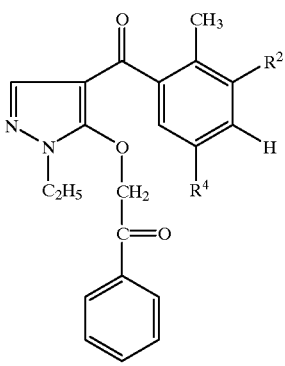

Ia548

Likewise, most particular preference is given to the compounds Ia549; in particular to the compounds Ia549.1–Ia549.164, which differ from the compounds Ia1.1–Ia1.164 in that $R^1$ is methyl, $R^3$ is hydrogen and $R^7$ is phenylcarbonyl:

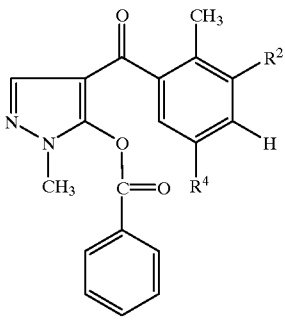

Ia549

Likewise, most particular preference is given to the compounds Ia550; in particular to the compounds Ia550.1–Ia550.164, which differ from the compounds Ia1.1–Ia1.164 in that $R^1$ is methyl, $R^3$ is hydrogen, $R^6$ is ethyl and $R^7$ is phenylcarbonyl:

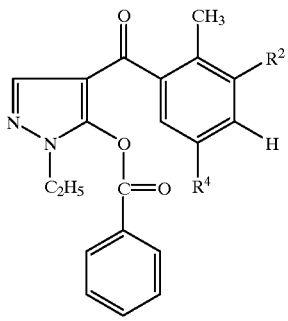

Ia550

Likewise, most particular preference is given to the compounds Ia551; in particular to the compounds Ia551.1–Ia551.164, which differ from the compounds Ia1.1–Ia1.164 in that $R^1$ is methyl, $R^3$ is hydrogen and $R^7$ is benzyl:

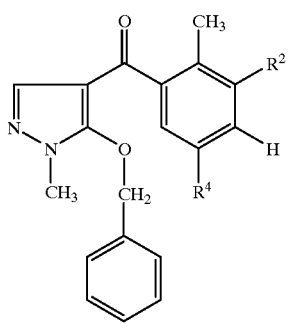

Ia551

Likewise, most particular preference is given to the compounds Ia552; in particular to the compounds Ia552.1–Ia552.164, which differ from the compounds Ia1.1–Ia1.164 in that $R^1$ is methyl, $R^3$ is hydrogen, $R^6$ is ethyl and $R^7$ is benzyl:

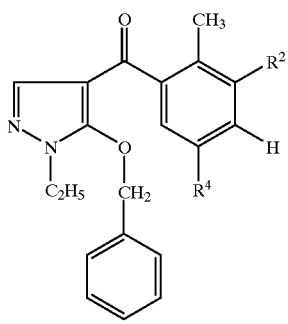

Ia552

Likewise, most particular preference is given to the compounds Ia553; in particular to the compounds Ia553.1–Ia553.164, which differ from the compounds Ia1.1–Ia1.164 in that $R^1$ is methyl and $R^3$ is chlorine:

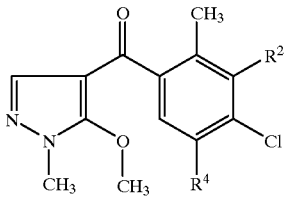

Ia553

Likewise, most particular preference is given to the compounds Ia554; in particular to the compounds Ia554.1–Ia554.164, which differ from the compounds Ia1.1–Ia1.164 in that $R^1$ is methyl, $R^3$ is chlorine and $R^6$ is ethyl:

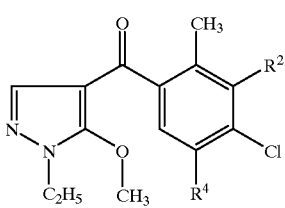

Ia554

Likewise, most particular preference is given to the compounds Ia555; in particular to the compounds Ia555.1–Ia555.164, which differ from the compounds Ia1.1–Ia1.164 in that $R^1$ is methyl, $R^3$ is chlorine and $R^7$ is ethyl:

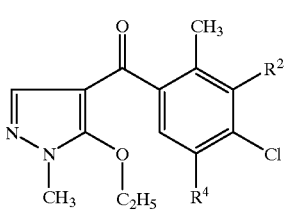

Ia555

Likewise, most particular preference is given to the compounds Ia556; in particular to the compounds Ia556.1–Ia556.164, which differ from the compounds Ia1.1–Ia1.164 in that $R^1$ is methyl, $R^3$ is chlorine, $R^6$ and $R^7$ are each ethyl:

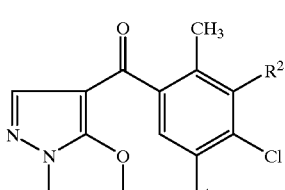

Ia556

Likewise, most particular preference is given to the compounds Ia557; in particular to the compounds Ia557.1–Ia557.164, which differ from the compounds Ia1.1–Ia1.164 in that $R^1$ is methyl, $R^3$ is chlorine and $R^7$ is methylcarbonyl:

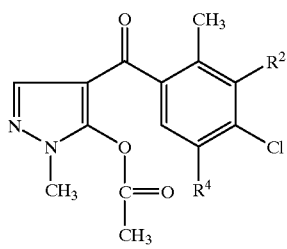
Ia557

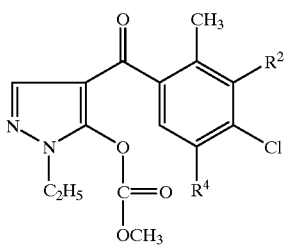
Ia560

Likewise, most particular preference is given to the compounds Ia558; in particular to the compounds Ia558.1–Ia558.164, which differ from the compounds Ia1.1–Ia1.164 in that $R^1$ is methyl, $R^3$ is chlorine, $R^6$ is ethyl and $R^7$ is methylcarbonyl:

Likewise, most particular preference is given to the compounds Ia561; in particular to the compounds Ia561.1–Ia561.164, which differ from the compounds Ia1.1–Ia1.164 in that $R^1$ is methyl, $R^3$ is chlorine and $R^7$ is dimethylaminocarbonyl:

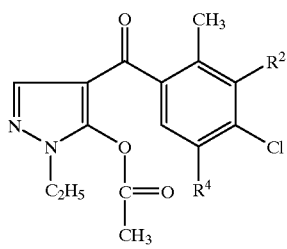
Ia558

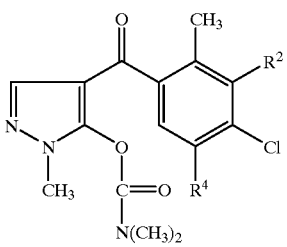
Ia561

Likewise, most particular preference is given to the compounds Ia559; in particular to the compounds Ia559.1–Ia559.164, which differ from the compounds Ia1.1–Ia1.164 in that $R^1$ is methyl, $R^3$ is chlorine and $R^7$ is methoxycarbonyl:

Likewise, most particular preference is given to the compounds Ia562; in particular to the compounds Ia562.1–Ia562.164, which differ from the compounds Ia1.1–Ia1.164 in that $R^1$ is methyl, $R^3$ is chlorine, $R^6$ is ethyl and $R^7$ is dimethylaminocarbonyl:

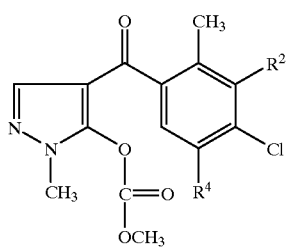
Ia559

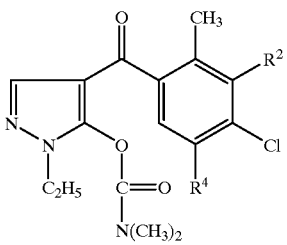
Ia562

Likewise, most particular preference is given to the compounds Ia560; in particular to the compounds Ia560.1–Ia560.164, which differ from the compounds Ia1.1–Ia1.164 in that $R^1$ is methyl, $R^3$ is chlorine, $R^6$ is ethyl and $R^7$ is methoxycarbonyl:

Likewise, most particular preference is given to the compounds Ia563; in particular to the compounds Ia563.1–Ia563.164, which differ from the compounds Ia1.1–Ia1.164 in that $R^1$ is methyl, $R^3$ is chlorine and $R^7$ is methoxycarbonylmethyl:

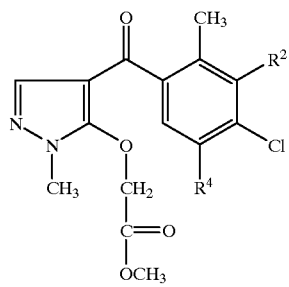
Ia563

Likewise, most particular preference is given to the compounds Ia564; in particular to the compounds Ia564.1–Ia564.164, which differ from the compounds Ia1.1–Ia1.164 in that $R^1$ is methyl, $R^3$ is chlorine, $R^6$ is ethyl and $R^7$ is methoxycarbonylmethyl:

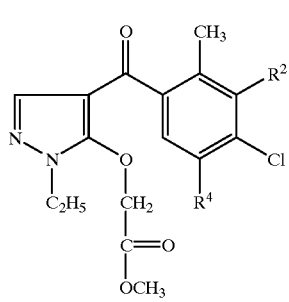
Ia564

Likewise, most particular preference is given to the compounds Ia565; in particular to the compounds Ia565.1–Ia565.164, which differ from the compounds Ia1.1–Ia1.164 in that $R^1$ is methyl, $R^3$ is chlorine and $R^7$ is phenylcarbonylmethyl:

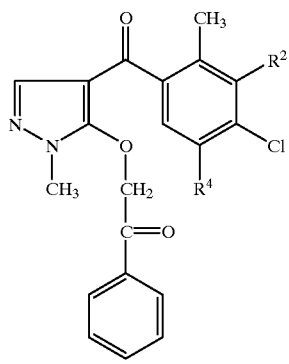
Ia565

Likewise, most particular preference is given to the compounds Ia566; in particular to the compounds Ia566.1–Ia566.164, which differ from the compounds Ia1.1–Ia1.164 in that $R^1$ is methyl, $R^3$ is chlorine, $R^6$ is ethyl and $R^7$ is phenylcarbonylmethyl:

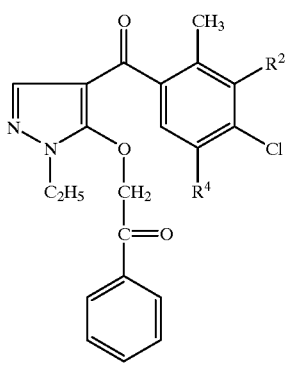
Ia566

Likewise, most particular preference is given to the compounds Ia567; in particular to the compounds Ia567.1–Ia567.164, which differ from the compounds Ia1.1–Ia1.164 in that $R^1$ is methyl, $R^3$ is chlorine and $R^7$ is phenylcarbonyl:

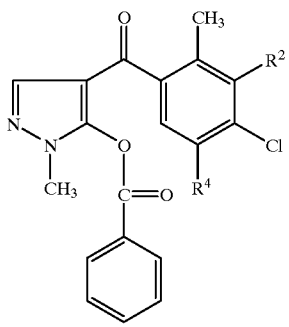
Ia567

Likewise, most particular preference is given to the compounds Ia568; in particular to the compounds Ia568.1–Ia568.164, which differ from the compounds Ia1.1–Ia1.164 in that $R^1$ is methyl, $R^3$ is chlorine, $R^6$ is ethyl and $R^7$ is phenylcarbonyl:

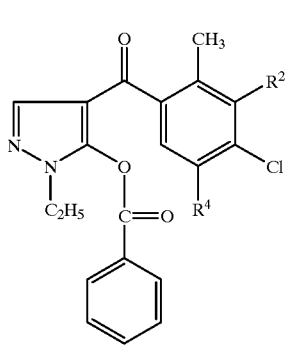
Ia568

Likewise, most particular preference is given to the compounds Ia569; in particular to the compounds Ia569.1–Ia569.164, which differ from the compounds Ia1.1–Ia1.164 in that $R^1$ is methyl, $R^3$ is chlorine and $R^7$ is benzyl:

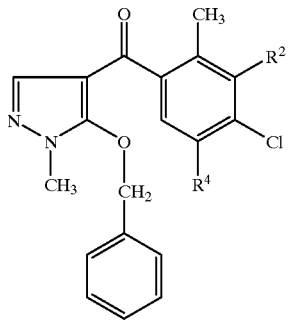

Ia569

Likewise, most particular preference is given to the compounds Ia570; in particular to the compounds Ia570.1–Ia570.164, which differ from the compounds Ia1.1–Ia1.164 in that $R^1$ is methyl, $R^3$ is chlorine, $R^6$ is ethyl and $R^7$ is benzyl:

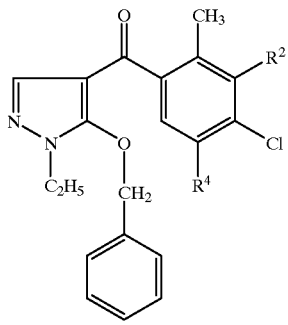

Ia570

Likewise, most particular preference is given to the compounds Ia571; in particular to the compounds Ia571.1–Ia571.164, which differ from the compounds Ia1.1–Ia1.164 in that $R^3$ is methyl and $R^7$ is ethyl:

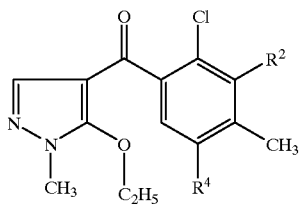

Ia571

Likewise, most particular preference is given to the compounds Ia572; in particular to the compounds Ia572.1–Ia572.164, which differ from the compounds Ia1.1–Ia1.164 in that $R^3$ is methyl, $R^6$ and $R^7$ are each ethyl:

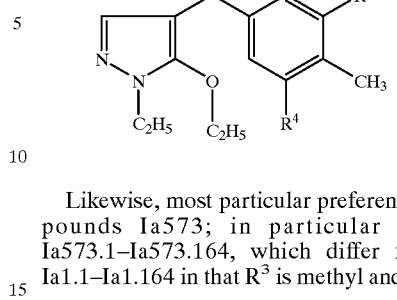

Ia572

Likewise, most particular preference is given to the compounds Ia573; in particular to the compounds Ia573.1–Ia573.164, which differ from the compounds Ia1.1–Ia1.164 in that $R^3$ is methyl and $R^7$ is methylcarbonyl:

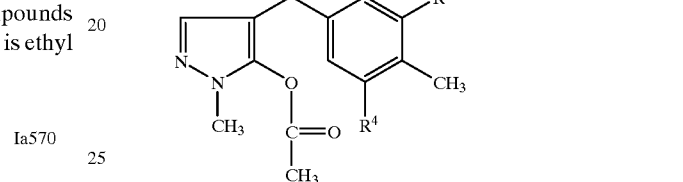

Ia573

Likewise, most particular preference is given to the compounds Ia574; in particular to the compounds Ia574.1–Ia574.164, which differ from the compounds Ia1.1–Ia1.164 in that $R^3$ is methyl, $R^6$ ethyl and $R^7$ is methylcarbonyl:

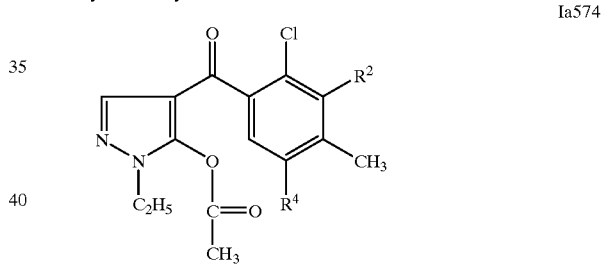

Ia574

Likewise, most particular preference is given to the compounds Ia575; in particular to the compounds Ia575.1–Ia575.164, which differ from the compounds Ia1.1–Ia1.164 in that $R^3$ is methyl and $R^7$ is dimethylaminocarbonyl:

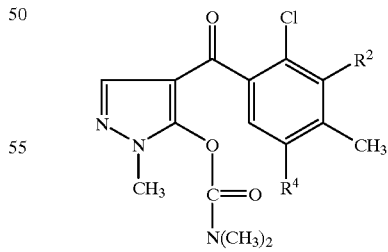

Ia575

Likewise, most particular preference is given to the compounds Ia576; in particular to the compounds Ia576.1–Ia576.164, which differ from the compounds Ia1.1–Ia1.164 in that $R^3$ is methyl, $R^6$ is ethyl and $R^7$ is dimethylaminocarbonyl:

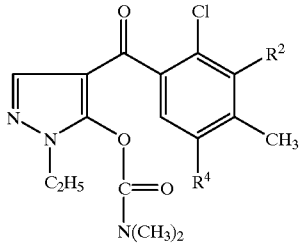

Ia576

Likewise, most particular preference is given to the compounds Ia577; in particular to the compounds Ia577.1–Ia577.164, which differ from the compounds Ia1.1–Ia1.164 in that $R^3$ is methyl and $R^7$ is phenylcarbonylmethyl:

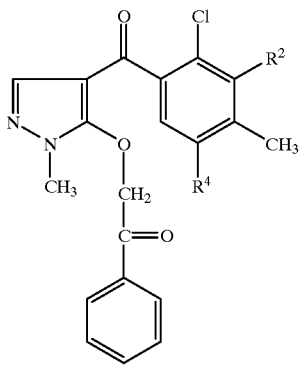

Ia577

Likewise, most particular preference is given to the compounds Ia578; in particular to the compounds Ia578.1–Ia578.164, which differ from the compounds Ia1.1–Ia1.164 in that $R^3$ is methyl, $R^6$ is ethyl and $R^7$ is phenylcarbonylmethyl:

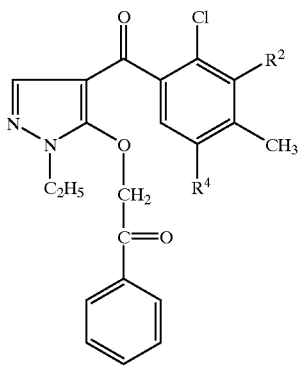

Ia578

Likewise, most particular preference is given to the compounds Ia579; in particular to the compounds Ia579.1–Ia579.164, which differ from the compounds Ia1.1–Ia1.164 in that $R^3$ is methyl and $R^7$ is benzyl:

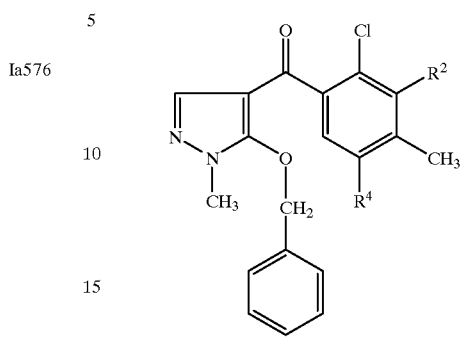

Ia579

Likewise, most particular preference is given to the compounds Ia580; in particular to the compounds Ia580.1–Ia580.164, which differ from the compounds Ia1.1–Ia1.164 in that $R^3$ is methyl, $R^6$ is ethyl and $R^7$ is benzyl:

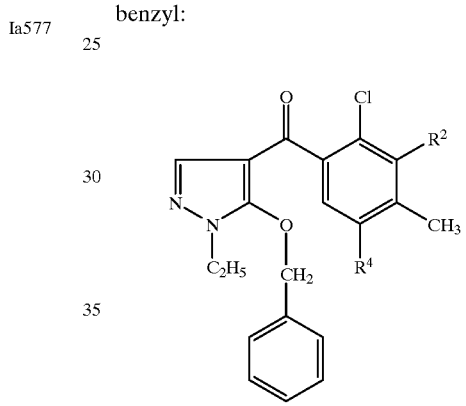

Ia580

Likewise, most particular preference is given to the compounds Ia581; in particular to the compounds Ia581.1–Ia581.164, which differ from the compounds Ia1.1–Ia1.164 in that $R^1$ and $R^4$ are each methyl and $R^7$ is ethyl:

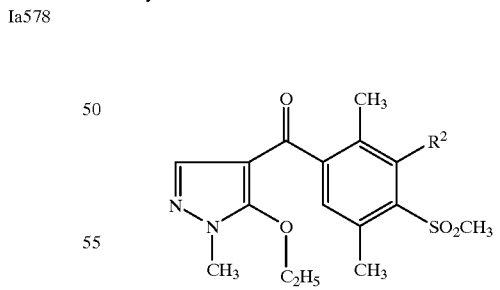

Ia581

Likewise, most particular preference is given to the compounds Ia582; in particular to the compounds Ia582.1–Ia582.164, which differ from the compounds Ia1.1–Ia1.164 in that $R^1$ and $R^4$ are each methyl and $R^6$ and $R^7$ are each ethyl:

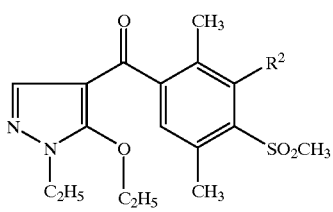

Ia582

Likewise, most particular preference is given to the compounds Ia583; in particular to the compounds Ia583.1–Ia583.164, which differ from the compounds Ia1.1–Ia1.164 in that $R^1$ and $R^4$ are each methyl and $R^7$ is methylcarbonyl:

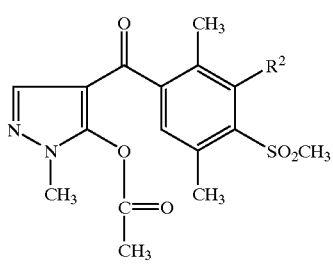

Ia583

Likewise, most particular preference is given to the compounds Ia584; in particular to the compounds Ia584.1–Ia584.164, which differ from the compounds Ia1.1–Ia1.164 in that $R^1$ and $R^4$ are each methyl, $R^6$ is ethyl and $R^7$ is methylcarbonyl:

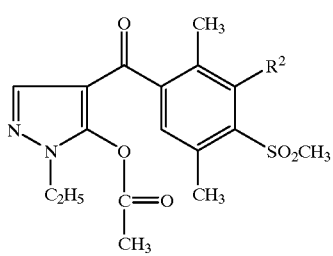

Ia584

Likewise, most particular preference is given to the compounds Ia585; in particular to the compounds Ia585.1–Ia585.164, which differ from the compounds Ia1.1–Ia1.164 in that $R^1$ and $R^4$ are each methyl and $R^7$ is dimethylaminocarbonyl:

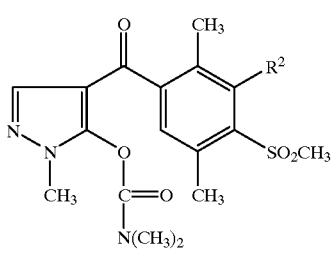

Ia585

Likewise, most particular preference is given to the compounds Ia586; in particular to the compounds Ia586.1–Ia586.164, which differ from the compounds Ia1.1–Ia1.164 in that $R^1$ and $R^4$ are each methyl, $R^6$ is ethyl and $R^7$ is dimethylaminocarbonyl:

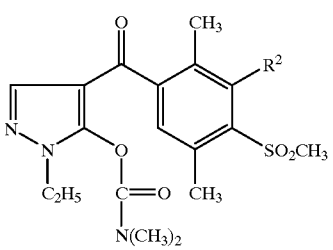

Ia586

Likewise, most particular preference is given to the compounds Ia587; in particular to the compounds Ia587.1–Ia587.164, which differ from the compounds Ia1.1–Ia1.164 in that $R^1$ and $R^4$ are each methyl and $R^7$ is phenylcarbonylmethyl:

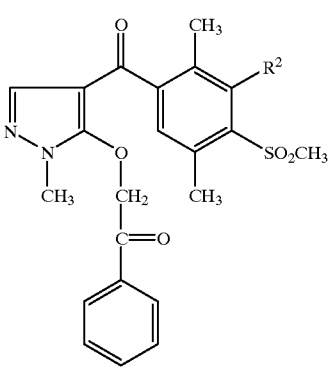

Ia587

Likewise, most particular preference is given to the compounds Ia588; in particular to the compounds Ia588.1–Ia588.164, which differ from the compounds Ia1.1–Ia1.164 in that $R^1$ and $R^4$ are each methyl, $R^6$ is ethyl and $R^7$ is phenylcarbonylmethyl:

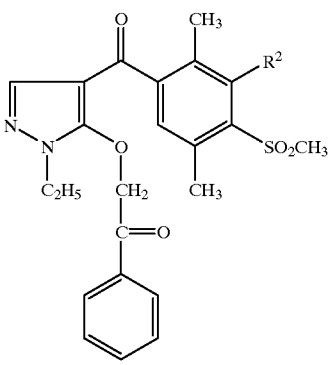

Ia588

Likewise, most particular preference is given to the compounds Ia589; in particular to the compounds Ia589.1–Ia589.164, which differ from the compounds Ia1.1–Ia1.164 in that $R^1$ and $R^4$ are each methyl and $R^7$ is benzyl:

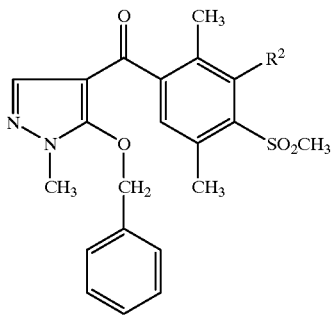

Ia589

Likewise, most particular preference is given to the compounds Ia590; in particular to the compounds Ia590.1–Ia590.164, which differ from the compounds Ia1.1–Ia1.164 in that $R^1$ and $R^4$ are each methyl, $R^6$ is ethyl and $R^7$ is benzyl:

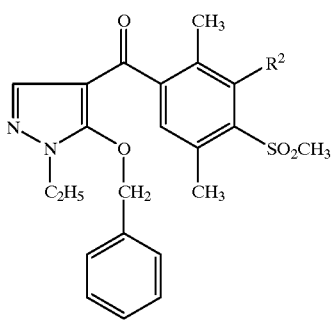

Ia590

Likewise, most particular preference is given to the compounds Ia591; in particular to the compounds Ia591.1–Ia591.164, which differ from the compounds Ia1.1–Ia1.164 in that $R^3$ is trifluoromethyl and $R^7$ is ethyl:

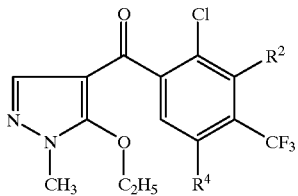

Ia591

Likewise, most particular preference is given to the compounds Ia592; in particular to the compounds Ia592.1–Ia592.164, which differ from the compounds Ia1.1–Ia1.164 in that $R^3$ is trifluoromethyl and $R^6$ and $R^7$ are each ethyl:

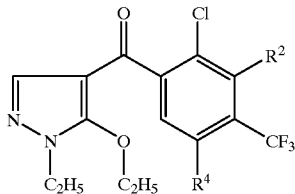

Ia592

Likewise, most particular preference is given to the compounds Ia593; in particular to the compounds Ia593.1–Ia593.164, which differ from the compounds Ia1.1–Ia1.164 in that $R^3$ is trifluoromethyl and $R^7$ is methylcarbonyl:

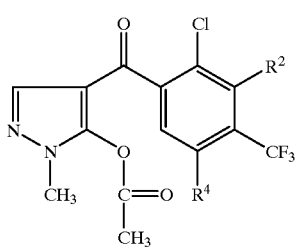

Ia593

Likewise, most particular preference is given to the compounds Ia594; in particular to the compounds Ia594.1–Ia594.164, which differ from the compounds Ia1.1–Ia1.164 in that $R^3$ is trifluoromethyl, $R^6$ is ethyl and $R^7$ is methylcarbonyl:

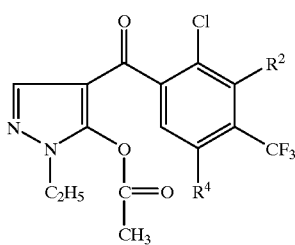

Ia594

Likewise, most particular preference is given to the compounds Ia595; in particular to the compounds Ia595.1–Ia595.164, which differ from the compounds Ia1.1–Ia1.164 in that $R^3$ is trifluoromethyl and $R^7$ is dimethylaminocarbonyl:

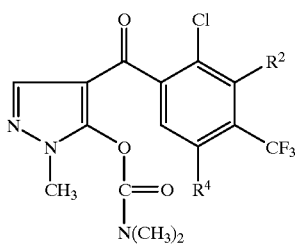

Ia595

Likewise, most particular preference is given to the compounds Ia596; in particular to the compounds Ia596.1–Ia596.164, which differ from the compounds Ia1.1–Ia1.164 in that $R^3$ is trifluoromethyl, $R^6$ is ethyl and $R^7$ is dimethylaminocarbonyl:

Ia596

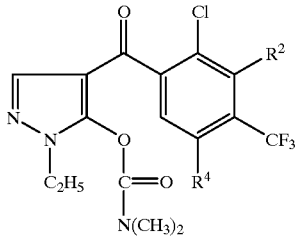

Likewise, most particular preference is given to the compounds Ia597; in particular to the compounds Ia597.1–Ia597.164, which differ from the compounds Ia1.1–Ia1.164 in that $R^3$ is trifluoromethyl and $R^7$ is phenylcarbonylmethyl:

Ia597

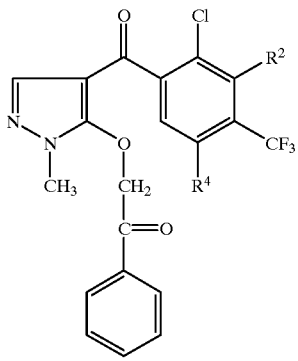

Likewise, most particular preference is given to the compounds Ia598; in particular to the compounds Ia598.1–Ia598.164, which differ from the compounds Ia1.1–Ia1.164 in that $R^3$ is trifluoromethyl, $R^6$ is ethyl and $R^7$ is phenylcarbonylmethyl:

Ia598

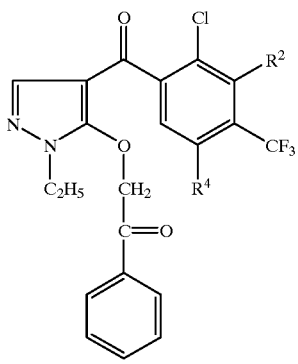

Likewise, most particular preference is given to the compounds Ia599; in particular to the compounds Ia599.1–Ia599.164, which differ from the compounds Ia1.1–Ia1.164 in that $R^3$ is trifluoromethyl and $R^7$ is benzyl:

Ia599

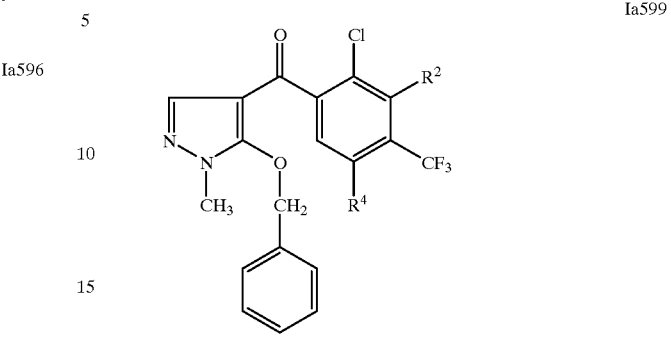

Likewise, most particular preference is given to the compounds Ia600; in particular to the compounds Ia600.1–Ia600.164, which differ from the compounds Ia1.1–Ia1.164 in that $R^3$ is trifluoromethyl, $R^6$ is ethyl and $R^7$ is benzyl:

Ia600

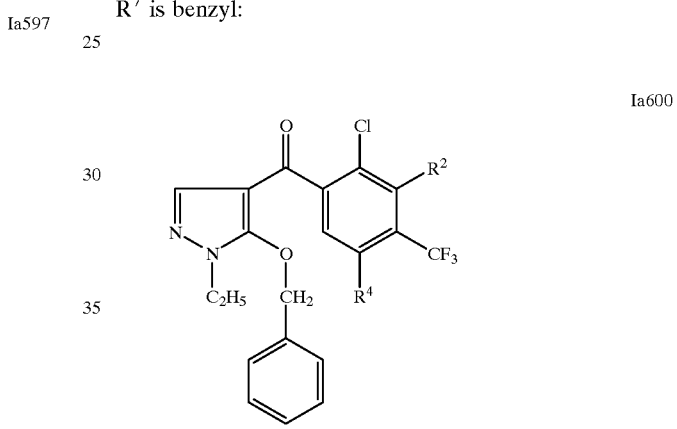

Likewise, most particular preference is given to the compounds Ia601; in particular to the compounds Ia601.1–Ia601.164, which differ from the compounds Ia1.1–Ia1.164 in that $R^1$ is nitro and $R^7$ is ethyl:

Ia601

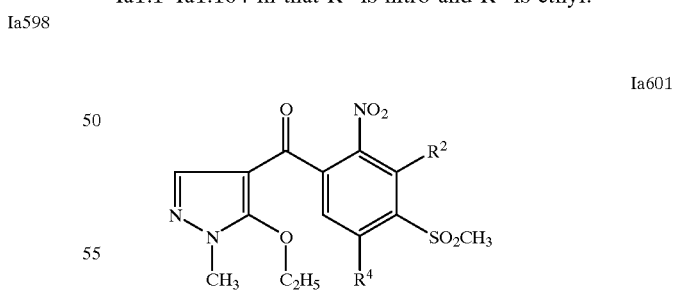

Likewise, most particular preference is given to the compounds Ia602; in particular to the compounds Ia602.1–Ia602.164, which differ from the compounds Ia1.1–Ia1.164 in that $R^1$ is nitro and $R^6$ and $R^7$ are each ethyl:

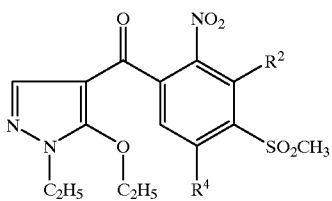

Ia602

Likewise, most particular preference is given to the compounds Ia603; in particular to the compounds Ia603.1–Ia603.164, which differ from the compounds Ia1.1–Ia1.164 in that $R^1$ is nitro and $R^7$ is methylcarbonyl:

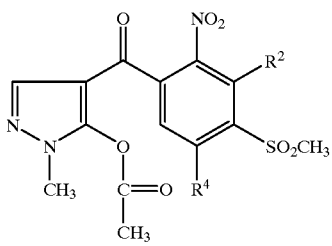

Ia603

Likewise, most particular preference is given to the compounds Ia604; in particular to the compounds Ia604.1–Ia604.164, which differ from the compounds Ia1.1–Ia1.164 in that $R^1$ is nitro, $R^6$ is ethyl and $R^7$ is methylcarbonyl:

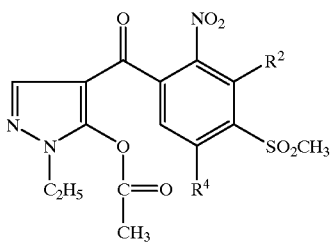

Ia604

Likewise, most particular preference is given to the compounds Ia605; in particular to the compounds Ia605.1–Ia605.164, which differ from the compounds Ia1.1–Ia1.164 in that $R^1$ is nitro and $R^7$ is dimethylaminocarbonyl:

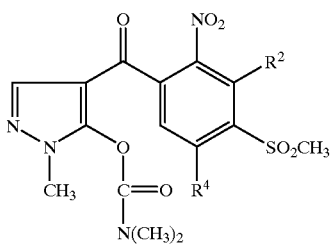

Ia605

Likewise, most particular preference is given to the compounds Ia606; in particular to the compounds Ia606.1–Ia606.164, which differ from the compounds Ia1.1–Ia1.164 in that $R^1$ is nitro, $R^6$ is ethyl and $R^7$ is dimethylaminocarbonyl:

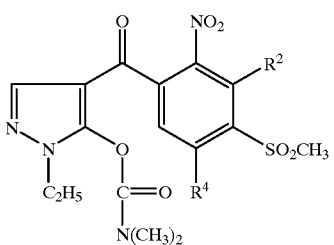

Ia606

Likewise, most particular preference is given to the compounds Ia607; in particular to the compounds Ia607.1–Ia607.164, which differ from the compounds Ia1.1–Ia1.164 in that $R^1$ is nitro and $R^7$ is phenylcarbonylmethyl:

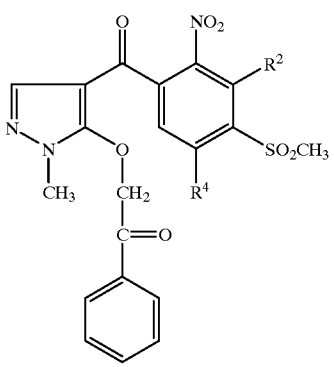

Ia607

Likewise, most particular preference is given to the compounds Ia608; in particular to the compounds Ia608.1–Ia608.164, which differ from the compounds Ia1.1–Ia1.164 in that $R^1$ is nitro, $R^6$ is ethyl and $R^7$ is phenylcarbonylmethyl:

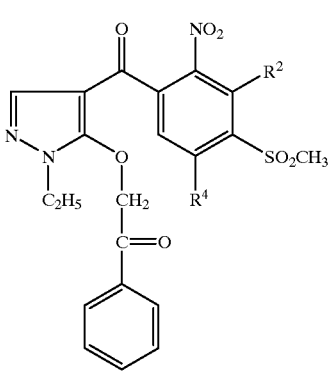

Ia608

Likewise, most particular preference is given to the compounds Ia609; in particular to the compounds Ia609.1–Ia609.164, which differ from the compounds Ia1.1–Ia1.164 in that $R^1$ is nitro and $R^7$ is benzyl:

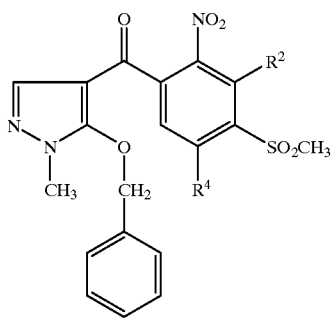
Ia609

Likewise, most particular preference is given to the compounds Ia610; in particular to the compounds Ia610.1–Ia610.164, which differ from the compounds Ia1.1–Ia1.164 in that $R^1$ is nitro, $R^6$ is ethyl and $R^7$ is benzyl:

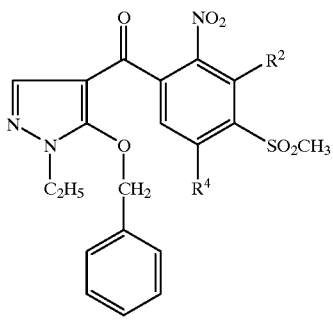
Ia610

Likewise, most particular preference is given to the compounds Ia611; in particular to the compounds Ia611.1–Ia611.164, which differ from the compounds Ia1.1–Ia1.164 in that $R^1$ is nitro, $R^3$ is chlorine and $R^7$ is ethyl:

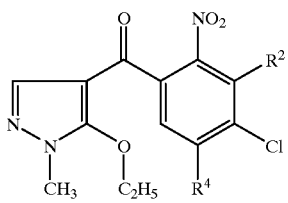
Ia611

Likewise, most particular preference is given to the compounds Ia612; in particular to the compounds Ia612.1–Ia612.164, which differ from the compounds Ia1.1–Ia1.164 in that $R^1$ is nitro, $R^3$ is chlorine and $R^6$ and $R^7$ are each ethyl:

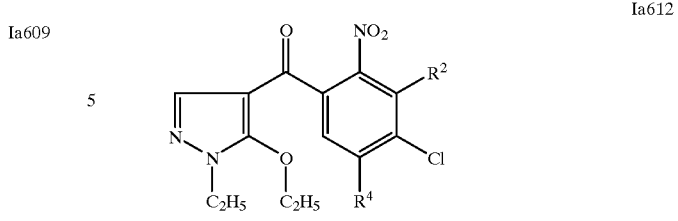
Ia612

Likewise, most particular preference is given to the compounds Ia613; in particular to the compounds Ia613.1–Ia613.164, which differ from the compounds Ia1.1–Ia1.164 in that $R^1$ is nitro, $R^3$ is chlorine and $R^7$ is methylcarbonyl:

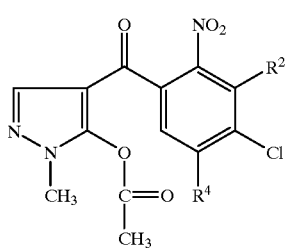
Ia613

Likewise, most particular preference is given to the compounds Ia614; in particular to the compounds Ia614.1–Ia614.164, which differ from the compounds Ia1.1–Ia1.164 in that $R^1$ is nitro, $R^3$ is chlorine, $R^6$ is ethyl and $R^7$ is methylcarbonyl:

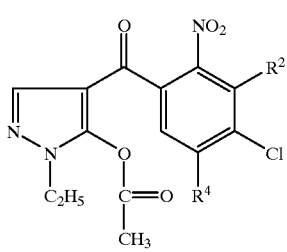
Ia614

Likewise, most particular preference is given to the compounds Ia615; in particular to the compounds Ia615.1–Ia615.164, which differ from the compounds Ia1.1–Ia1.164 in that $R^1$ is nitro, $R^3$ is chlorine and $R^7$ is dimethylaminocarbonyl:

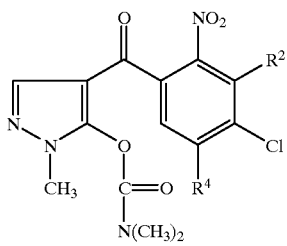
Ia615

Likewise, most particular preference is given to the compounds Ia616; in particular to the compounds Ia616.1–Ia616.164, which differ from the compounds Ia1.1–Ia1.164 in that $R^1$ is nitro, $R^3$ is chlorine, $R^6$ is ethyl and $R^7$ is dimethylaminocarbonyl:

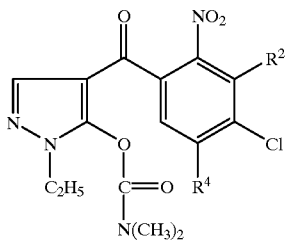

Ia616

Likewise, most particular preference is given to the compounds Ia617; in particular to the compounds Ia617.1–Ia617.164, which differ from the compounds Ia1.1–Ia1.164 in that $R^1$ is nitro, $R^3$ chlorine and $R^7$ is phenylcarbonylmethyl:

Ia617

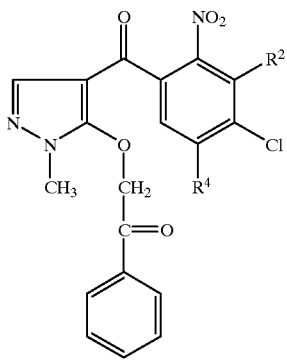

Likewise, most particular preference is given to the compounds Ia618; in particular to the compounds Ia618.1–Ia618.164, which differ from the compounds Ia1.1–Ia1.164 in that $R^1$ is nitro, $R^3$ is chlorine, $R^6$ is ethyl and $R^7$ is phenylcarbonylmethyl:

Ia618

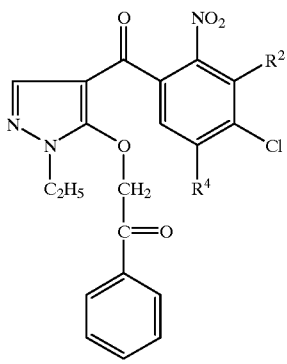

Likewise, most particular preference is given to the compounds Ia619; in particular to the compounds Ia619.1–Ia619.164, which differ from the compounds Ia1.1–Ia1.164 in that $R^1$ is nitro, $R^3$ is chlorine and $R^7$ is benzyl:

Ia619

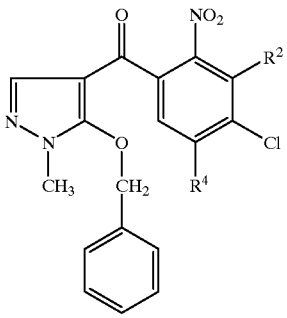

Likewise, most particular preference is given to the compounds Ia620; in particular to the compounds Ia620.1–Ia620.164, which differ from the compounds Ia1.1–Ia1.164 in that $R^1$ is nitro, $R^3$ is chlorine, $R^6$ is ethyl and $R^7$ is benzyl:

Ia620

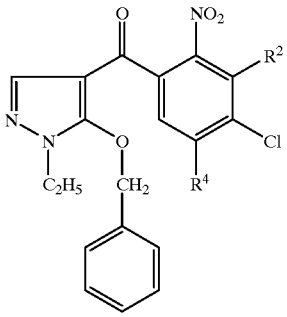

Furthermore, very particular preference is given to the 4-(3-heterocyclyl-1-benzoyl)pyrazoles of the formula I where:

$R^1$ is halogen or $C_1$–$C_6$-alkyl; in particular chlorine or methyl;

$R^2$ is 4,5-dihydroisoxazol-3-yl, 4,5-dihydrothiazol-2-yl, 1,3-dithiolan-2-yl, 1,3-dioxan-2-yl, thiazol-2-yl, isoxazol-3-yl, isoxazol-4-yl, isoxazol-5-yl or 1,2,4-oxadiazol-5-yl with or without substitution; in particular 4,5-dihydroisoxazol-3-yl, 4,5-dihydrothiazol-2-yl, 1,3-dithiolan-2-yl or 1,3-dioxan-2-yl with or without substitution;

$R^3$ is hydrogen, nitro, halogen or $C_1$–$C_6$-alkylsulfonyl; in particular hydrogen, chlorine or $C_1$–$C_4$-alkylsulfonyl;

$R^4$ is hydrogen;

$R^6$ is $C_1$–$C_6$-alkyl; in particular methyl, ethyl, propyl, 2-methylpropyl or butyl;

$R^7$ is $C_1$–$C_6$-alkyl, $C_3$–$C_6$-alkenyl, $C_3$–$C_6$-alkynyl, $C_1$–$C_6$-alkylcarbonyl, $C_2$–$C_6$-alkenylcarbonyl, $C_1$–$C_6$-alkoxycarbonyl, N-($C_1$–$C_6$-alkoxy)-N-($C_1$–$C_6$-alkyl)aminocarbonyl, $C_1$–$C_6$-alkoxyimino-$C_1$–$C_6$-alkyl, where the alkyl and alkoxy radicals mentioned may be partially or fully halogenated and/or may carry one to three of the following groups: cyano, hydroxyl, $C_1$–$C_4$-alkylcarbonyl, $C_1$–$C_4$-alkoxycarbonyl, hydroxycarbonyl or $C_3$–$C_6$-cycloalkyl; phenyl-$C_1$–$C_6$-alkyl, phenylcarbonyl-$C_1$–$C_6$-alkyl, phenyl-$C_2$–$C_6$-alkenylcarbonyl or phenylcarbonyl, where the phenyl radical of the last 4 substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^8$ is hydrogen;
and their agriculturally useful salts.

The 4-(3-heterocyclyl-1-benzoyl)pyrazoles of the formula I can be obtained in a variety of ways, for example by the process below.

Reaction of 4-(3-heterocyclyl-1-benzoyl)pyrazoles of the formula III with a compound of the formula IV (Scheme 1):

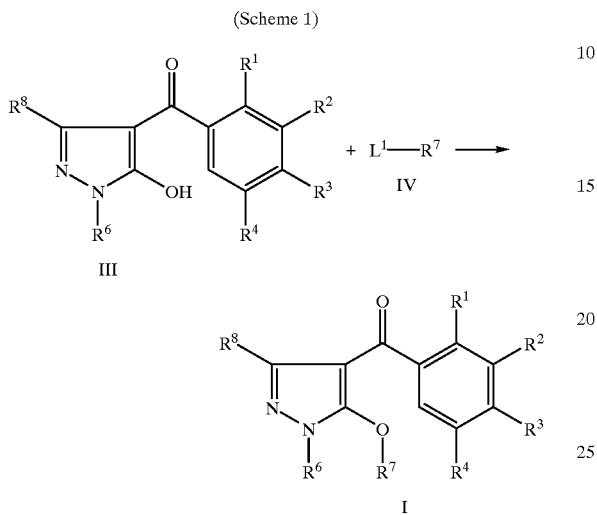

$L^1$ is a nucleophilically displaceable leaving group such as halogen, for example bromine or chlorine, hetaryl, for example imidazolyl or pyridyl, carboxylate, for example acetate or trifluoroacetate, or sulfonate, for example mesylate or triflate, etc.

The compounds of the formula IV can be employed directly, for example in the case of the alkyl halides, acyl halides, sulfonyl halides, carboxylic anhydrides and sulfonic anhydrides, or be prepared in situ, for example activated carboxylic acids (using carboxylic acid and dicyclohexylcarbodiimide, carbonyldiimidazole, etc.).

In general, the starting materials are employed in an equimolar ratio. However, it may be advantageous to employ an excess of one or the other component.

If appropriate, it may be advantageous to carry out the reaction in the presence of a base. The reactants and the base are advantageously employed in equimolar amounts. An excess of base, for example 1.5 to 3 molar equivalents, based on III, may be advantageous in certain cases.

Suitable bases are tertiary alkylamines such as triethylamine, aromatic amines such as pyridine, alkali metal carbonates, for example sodium carbonate or potassium carbonate, or alkali metal hydrides, for example sodium hydride. Preference is given to using triethylamine or pyridine.

Suitable solvents are, for example, chlorinated hydrocarbons such as methylene chloride or 1,2-dichloroethane, aromatic hydrocarbons, for example toluene, xylene or chlorobenzene, ethers such as diethyl ether, methyl tert-butyl ether, tetrahydrofuran or dioxane, polar aprotic solvents such as acetonitrile, dimethylformamide or dimethyl sulfoxide, or esters such as ethyl acetate, or mixtures thereof.

The reaction temperature is generally in the range from 0° C. to the boiling point of the reaction mixture.

Work-up can be carried out in a manner known per se to give the product.

The benzoylpyrazoles of the formula III are known or can be prepared by processes known per se (for example WO 96/26206 or the earlier German Patent Application DE-A 1970 1446), for example by reacting pyrazoles of the formula V with an activated benzoic acid VIa or a benzoic acid VIβ which is preferably activated in situ, to give the acylation product VII, and subsequent rearrangement.

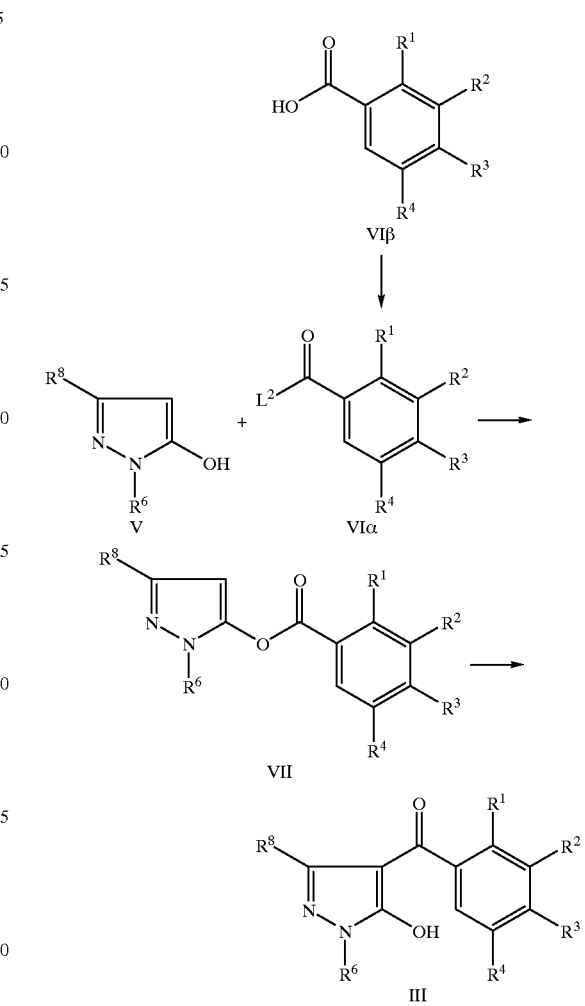

$L^2$ is a nucleophilically displaceable leaving group such as halogen, for example bromine or chlorine, hetaryl, for example imidazolyl or pyridyl, carboxylate, for example acetate or trifluoroacetate, etc.

The activated benzoic acid VIa can be employed directly, as in the case of the benzoyl halides, or be prepared in situ, for example using dicyclohexylcarbodiimide, triphenylphosphine/azodicarboxylic esters, 2-pyridine disulfide/triphenylphosphine, carbonyldiimidazole, etc.

If appropriate, it may be advantageous to carry out the acylation reaction in the presence of a base. For this purpose, the reactants and the auxiliary base are advantageously employed in equimolar amounts. A slight excess of auxiliary base, for example 1.2 to 1.5 molar equivalents, based on V, may be advantageous in certain cases.

Suitable auxiliary bases are tertiary alkylamines, pyridine or alkali metal carbonates. Suitable solvents are, for example, chlorinated hydrocarbons such as methylene chloride or 1,2-dichloroethane, aromatic hydrocarbons such as toluene, xylene or chlorobenzene, ethers such as diethyl ether, methyl tert-butyl ether, tetrahydrofuran or dioxane, polar aprotic solvents such as acetonitrile, dimethylformamide or dimethyl sulfoxide, or esters such as ethyl acetate, or mixtures of these.

If the activated carboxylic acid component used is a benzoyl halide, it may be advantageous to cool the reaction mixture to 0–10° C. when adding this reaction partner. Subsequently, the mixture is stirred at 20–100° C., preferably at 25–50° C., until the reaction has ended. Work-up is carried out in a conventional manner, for example by pouring the reaction mixture into water and extracting the product of value. Suitable solvents for this purpose are in particular methylene chloride, diethyl ether and ethyl acetate. After drying of the organic phase and removal of the solvent, the crude ester can be employed without any further purification in the rearrangement.

The rearrangement of the esters to the compounds of the formula I is advantageously carried out at 20–100° C. in a solvent and in the presence of a base and, if appropriate, using a cyano compound as catalyst.

Suitable solvents are, for example, acetonitrile, methylene chloride, 1,2-dichloroethane, dioxane, ethyl acetate, toluene or mixtures of these. Preferred solvents are acetonitrile and dioxane.

Suitable bases are tertiary amines such as triethylamine, aromatic amines such as pyridine or alkali metal carbonates such as sodium carbonate or potassium carbonate, preferably employed in equimolar amounts or up to four-fold excess, based on the ester. Preference is given to using triethylamine or alkali metal carbonate, preferably in twice the equimolar amount, based on the ester.

Suitable cyano compounds are inorganic cyanides such as sodium cyanide or potassium cyanide and organic cyano compounds such as acetone cyanohydrin or trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent, based on the ester.

Work-up can be carried out in a manner known per se. For example, the reaction mixture is acidified with dilute mineral acid such as 5% strength hydrochloric acid or sulfuric acid, and extracted with an organic solvent, for example methylene chloride or ethyl acetate. The organic extract may be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, dried and concentrated. (Examples of the preparation of esters of hydroxypyrazoles and of the rearrangement of the esters are given, for example, in EP-A 282 944 and U.S. Pat. No. 4,643,757).

The benzoyl halides of the formula VIα' (where $L^{2'}$=Cl, Br) can be prepared in a manner known per se by reacting the benzoic acids of the formula VIβ with halogenating agents such as thionyl chloride, thionyl bromide, phosgene, diphosgene, triphosgene, oxalyl chloride, oxalyl bromide.

The benzoic acids of the formula VIβ can be prepared in a manner known per se by acidic or basic hydrolysis from the corresponding esters of the formula VIγ ($L^3$=$C_1$–$C_6$-alkoxy).

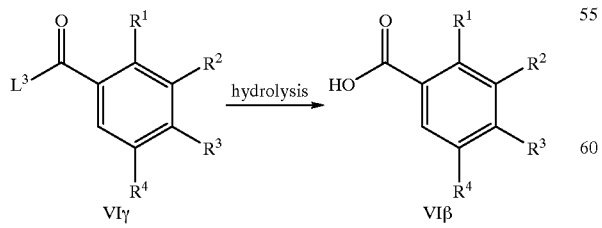

Likewise, the benzoic acids of the formula VIβ can be obtained by reacting the corresponding bromine- or iodine-substituted compounds of the formula VIII in the presence of a palladium, nickel, cobalt or rhodium transition metal catalyst and a base with carbon monoxide and water under elevated pressure.

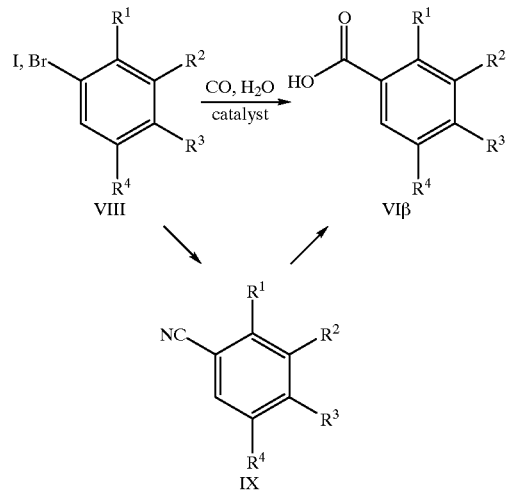

Furthermore, it is possible to convert compounds of the formula VIII into the corresponding nitriles of the formula IX by the Rosenmund-von Braun reaction (cf. for example Org. Synth. Vol. III, 212 (1955)), and to convert these into the compounds of the formula VIβ by subsequent hydrolysis.

The esters of the formula VIγ can be obtained by reacting haloaryl compounds or aryl sulfonates of the formula X, where $L^4$ is a leaving group such as bromine, iodine, triflate, fluorosulfonyloxy, etc., with heterocyclyl stannates (Stille coupling), heterocyclyl boron compounds (Suzuki coupling) or heterocyclyl zinc compounds (Negishi reaction) XI, where M is $Sn(C_1$–$C_4$-alkyl$)_3$, $B(OH)_2$, ZnHal (where Hal= chlorine, bromine), etc., respectively, in a manner known per se (cf. for example Tetrahedron Lett. 27 (1986), 5269) in the presence of a palladium or nickel transition metal catalyst and, if appropriate, a base.

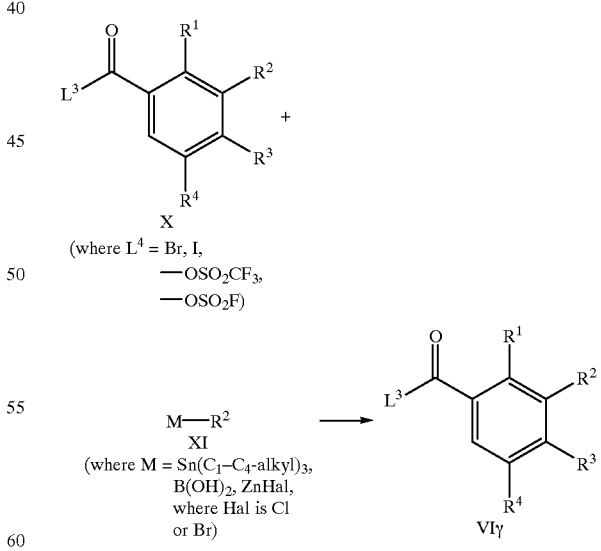

Likewise, it is possible to obtain esters of the formula VIγ by synthesizing the heterocycle attached in position 3.

For example, 1,2,4-oxadiazolin-3-yl derivatives can be prepared from amidoximes of the formula XII by condensation with aldehydes or ketones (cf. for example Arch. Phar. 326 (1993), 383–389).

The thioamides of the formula XIII are suitable precursors for 2-thiazolinyl derivatives (cf. for example Tetrahedron 42 (1986), 1449–1460). However, it is also possible to employ them for the synthesis of 2-thiazolyl- or 5,6-dihydro-4H-1,3-thiazin-2-yl derivatives (cf. for example Houben-Weyl, Methoden der organischen Chemie, 4th Edition, Vol. E5, p. 1268 ff (1985)). Likewise, they can be employed in the preparation of 1,2,4-thiadiazol-5-yl derivatives (cf. for example J. Org. Chem. 45 (1980), 3750–3753) or 1,3,4-thiadiazol-2-yl derivatives (J. Chem. Soc. Perkin Trans. I (1992), 1987–1991).

2-Oxazolinyl, 2-thiazolinyl and 2-imidazolinyl derivatives are accessible from the carboxylic acids of the formula XIV (cf. for example Tetrahedron Let. 22 (1981), 4471–4474).

1,3-Thiazol-5(4H)-thion-2-yl (cf. for example Helv. Chim. Acta 69 (1986), 374–388) and 5-oxo-2-imidazolin-2-yl derivatives (cf. for example Heterocycles 29 (1989), 1185–1189) can be prepared by rocesses known from the literature from acyl halides of the formula XV where Hal is halogen, in particular from acyl hlorides.

2-Oxazolyl, 1,2,4-oxadiazol-5-yl and 1,3,4-oxadiazol-2-yl derivatives (cf. for example J. Heterocyclic Chem. 28 (1991), 17–28) or 2-pyrrolyl derivatives (cf. for example Heterocycles 26 (1987), 3141–3151) can be prepared in a manner known per se from the carboxylic acids of the formula XIV or the acyl halides of the formula XV.

Oximes of the formula XVI can be converted into 4,5-dihydroisoxazol-3-yl or into isoxazol-3-yl derivatives in a manner known per se via hydroxamic acid chloride intermediates. The latter are employed to generate nitrile oxides in situ which are reacted with alkenes or alkynes to give the desired products (cf. for example Chem. Ber. 106 (1973), 3258–3274). 1,3-Dipolar cyclo-additions of chlorosulfonyl isocyanate to nitrile oxides afford 1,2,4-oxadiazolin-5-on-3-yl derivatives (cf. for example Heterocycles 27 (1988), 683–685).

The aldehydes of the formula XVIII can be converted into 2,4-dihydro-1,2,4-triazol-3-on-5-yl derivatives via semicarbazone intermediates (cf. for example J. Heterocyclic Chem. 23 (1986), 881–883).

2-Imidazolinyl derivatives are preparable from benzonitriles of the formula XIX by known methods (cf. for example J. Org. Chem. 52 (1987), 1017–1021).

The benzonitriles of the formula XIX can also be used to prepare 1,2,4-triazol-3-yl derivatives by known methods (cf. for example J. Chem. Soc. (1954), 3461–3464). 3-Pyrazolinyl or 4-pyrazolinyl derivatives or 4,5-dihydroisoxazol-4-yl or 4,5-dihydroisoxazol-5-yl derivatives can be prepared by 1,3-dipolar cycloaddition of diazoalkanes, nitrilimines or nitrile oxides with arylalkenes of the formula XX (where R* is one of the possible subsubstituents entioned under $R^2$).

The arylalkynes XXI (where R* is one of the possible subsubstituents under $R^2$) can be reacted in a 1,3-dipolar ycloaddition, for example with the abovementioned 1,3-dipoles, to give pyrazol-3-yl or pyrazol-4-yl, or isoxazol-4-yl or isoxazol-5-yl derivatives.

The aldehydes XVIII can be converted by Wittig reaction using phosphonium salts (Ph)$_3$P+CH$_2$COR*X- (R* has the meaning of one of the substituents mentioned under $R^2$) in a manner known per se (J. March, "Advanced Organic Chemistry", 3rd edition, p. 864 ff., Wiley-Interscience Publication, 1985) to give α,β-unsatuated ketones XXII. By reaction with hydroxylamine, these yield the corresponding oximes which can be converted into the 5-isoxazolyl derivatives by oxidative cyclization (J. Am. Chem. Soc. 94 (1972) 9128).

The aldehydes XVIII can also be converted into the corresponding enol ethers using alkoxymethylphosphonium salts, in a manner known per se (J. March, "Advanced Organic Chemistry", 3rd edition, p. 864 ff., Wiley-Interscience Publication, 1985). Cleavage of these enol ethers similar to processes known from literature affords the acetaldehyde derivatives XXIII. By bromination in the a position, these can be converted into the α-bromoacetaldehyde derivatives (Tetrahydron Lett. 29 (1988) 5893), which, by cyclization with amides, thioamides and amidines, yield oxazoles, thiazoles and imidazoles. Furthermore, using dimethylformamide dimethyl acetal, the acetaldehyde derivatives XXIII can be converted into the corresponding enamines which can then be converted into isoxazoles and pyrazoles using hydroxylamines or hydrazines, respectively.

Furthermore, the aldehydes XVIII can be converted into hydroxyketone derivatives by aldol reaction with ketones. Subsequent oxidation leads to 1,3-diketones which can be converted into isoxazoles, pyrazoles and pyrimidines using hydroxylamine, hydrazines and amidines, respectively.

The aldehydes XVIII can also be converted into the corresponding diazo compounds XXIV using methods known from the literature (Houben-Weyl, "Methoden der organischen Chemie", 4th edition, Vol. E14b). 1,3-Dipolar cycloaddition to alkenes and alkynes and subsequent isomerization leads to pyrazolines and pyrazoles, respectively.

Similar to methods known from the literature, for example by the Sandmeyer reaction, the bromine- or iodine-substituted compounds of the formula VIII used as starting materials can be obtained from the corresponding anilines, which are synthesized in turn by reducing suitable nitro compounds. The bromine-substituted compounds of the formula VIII can also be obtained by direct bromination of suitable starting materials (cf. Monatsh. Chem. 99 (1968), 815–822).

The nitriles of the formula IX can be obtained as described above. Likewise, it is possible to prepare them from the corresponding anilines using the Sandmeyer reaction.

The starting materials of the formula X are known (cf. for example Coll. Czech. Chem. Commun. 40 (1975), 3009–3019), or they can be prepared in a simple manner by a suitable combination of known syntheses.

The sulfonates X ($L^4$=—OSO$_2$CF$_3$, —OSO$_2$F), for example, can be obtained from the corresponding phenols, which in turn are known (cf. for example EP-A 195 247) or can be prepared by known methods (cf. for example Synthesis 1993, 735–762).

The halogen compounds X ($L^4$=Cl, Br or I) can be obtained for example from the corresponding anilines of the formula XXV by Sandmeyer reaction.

The amidoximes of the formula XII, the thioamides of the formula XIII and the carboxylic acids of the formula XIV can be prepared from the nitrites of the formula XIX in a manner known per se.

Furthermore, it is possible to prepare the carboxylic acids of the formula XIV from the aldehydes of the formula XVIII by known methods (cf. for example J. March, Advanced Organic Chemistry, 3rd Edition, p. 629 ff, Wiley-Interscience Publication (1985)).

The acyl halides of the formula XV can be obtained from the corresponding carboxylic acids of the formula XIV by standard methods.

The oximes of the formula XVI are advantageously obtained by reacting aldehydes of the formula XVIII with hydroxylamine in a manner known per se (cf. for example J. March, Advanced Organic Chemistry, 3rd Edition, p. 805–806, Wiley-Interscience Publication (1985)).

The aldehydes of the formula XVIII are known or preparable by known methods. Thus, they can be prepared from methyl compounds of the formula XXVI by bromination, for example with N-bromosuccinimide or 1,3-dibromo-5,5-dimethylhydantoin, and subsequent oxidation (cf. Synth. Commun. 22 (1992), 1967–1971).

e;.5qThe conversion of the oximes of the formula XVI into nitriles of the formula XIX can likewise be carried out by methods known per se (cf. for example J. March, Advanced Organic Chemistry, 3rd Edition, p. 931–932, Wiley-Interscience Publication (1985)).

Arylalkenes of the formula XX can be prepared starting from the halogen compounds or sulfonates of the formula X ($L^4$=Br, Cl, $OSO_2CF_3$, $OSO_2F$), inter alia by Heck reaction with olefins in the presence of a palladium catalyst (cf. for example Heck, Palladium Reagents in Organic Synthesis, Academic Press, London 1985; Synthesis 1993, 735–762).

The arylalkynes of the formula XXI can be prepared in a manner known per se by reaction of haloaryl compounds or aryl sulfonates of the formula X with substituted alkynes in the presence of a palladium or nickel transition metal catalyst (for example Heterocycles 24 (1986), 31–32). Alkynes having terminal hydrogen functions are advantageously obtained from the corresponding silyl compounds (cf. for example J. Org. Chem. 46 (1981) 2280–2286).

The compounds of the formula IV used as starting materials are known or can be prepared by methods known from the literature.

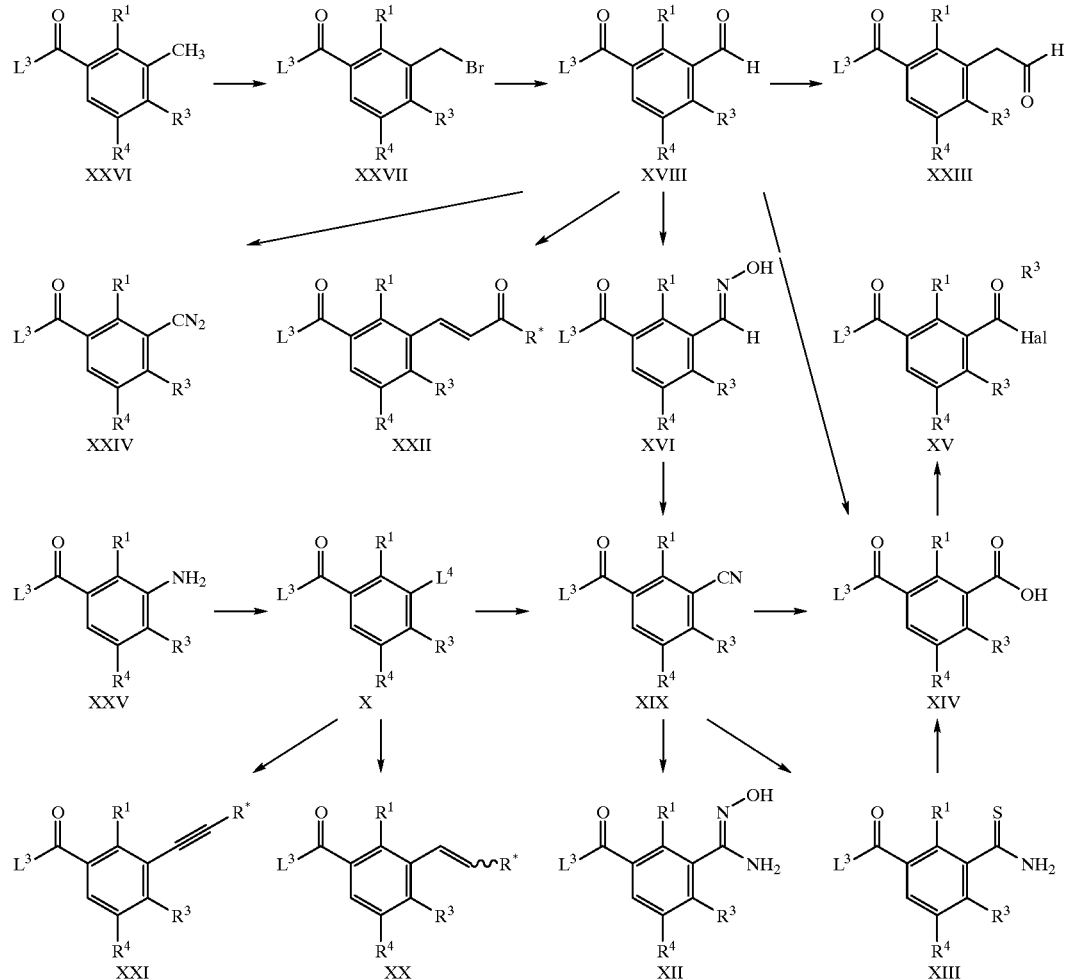

PREPARATION EXAMPLES

5-Benzyloxy-4-[2-chloro-3-(4,5-dihydroisoxazol-3-yl)-4-methylsulfonylbenzoyl]-1-ethyl-1H-pyrazole (compound 2.45)

1.44 g (60 mmol) of sodium hydride and 10.40 g (60 mmol) of benzyl bromide were added a little at a time to a solution of 6.00 g (15 mmol) of 4-[2-chloro-3-(4,5-dihydroisoxazol-3-yl)-4-methylsulfonylbenzoyl]-1-ethyl-5-hydroxy-1H-pyrazole in 300 ml of dry dioxane. The mixture was stirred under reflux for 24 hours, the solvent was removed under reduced pressure and the residue was taken up in dichloromethane and washed three times with water. The organic phase was dried and concentrated and the residue was chromatographed over silica gel (eluent: N-pentane/ethyl acetate). 1.5 g (20% of theory) of 5-benzyloxy-4-[2-chloro-3-(4,5-dihydroisoxazol-3-yl)-4-methylsulfonylbenzoyl]-1-ethyl-1H-pyrazole were obtained (mp.: 70–75° C.).

In addition to the abovementioned compound, other 4-(3-heterocyclyl-1-benzoyl)pyrazoles of the formula I which were prepared or are preparable in a similar manner are listed in Table 2:

TABLE 2

[Structure: pyrazole-benzoyl compound with substituents $R^1$, $R^2$, $R^3$, $R^4$, $R^6$, $R^7$, $R^8$]

| No. | $R^1$ | $R^2$ | $R^3$ | $R^4$ | $R^6$ | $R^7$ | $R^8$ | Physical data Mp. [° C.]; $^1$H NMR [δ in ppm] |
|---|---|---|---|---|---|---|---|---|
| 2.1 | Cl | 5,5-dimethyl-4,5-dihydroisoxazol-3-yl | SO$_2$CH$_3$ | H | n-C$_3$H$_7$ | C$_6$H$_5$CH$_2$ | H | 0.78(t); 1.50(s); 1.62(sext); 3.18(s); 3.36(s); 3.85(t); 5.51(s); 7.41(m); 7.54(s); 7.90(d); 8.14(d). |
| 2.2 | Cl | 5,5-dimethyl-4,5-dihydroisoxazol-3-yl | SO$_2$CH$_3$ | H | n-C$_4$H$_9$ | C$_6$H$_5$CH$_2$ | H | 0.80(t); 1.15(m); 1.48(s); 1.50(m); 3.15(s); 3.34(s); 3.84(t); 5.49(s); 7.42(m); 7.52(s); 7.88(d); 8.13(d). |
| 2.3 | Cl | 4,5-dihydroisoxazol-3-yl | SO$_2$CH$_3$ | H | C$_2$H$_5$ | CH$_3$OCO | H | 68–75 |
| 2.4 | Cl | 4,5-dihydroisoxazol-3-yl | SO$_2$CH$_3$ | H | CH$_3$ | C$_2$H$_5$CO | H | 65–70 |
| 2.5 | Cl | 4,5-dihydroisoxazo-3-yl | SO$_2$CH$_3$ | H | C$_2$H$_5$ | C$_2$H$_5$CO | H | 1.28(t); 1.45(t); 2.69(q); 3.28(s); 3.43(s); 4.03(q); 4.61(t); 7.56(s); 7.62(d); 8.14(d). |
| 2.6 | Cl | 4,5-dihydroisoxazol-3-yl | SO$_2$CH$_3$ | H | C$_2$H$_5$ | 4-Cl—C$_6$H$_4$CO | H | 105–108 |
| 2.7 | Cl | 4,5-dihydroisoxazdl-3-yl | SO$_2$CH$_3$ | H | C$_2$H$_5$ | C$_6$H$_5$CO | H | 207–209 |
| 2.8 | Cl | 4,5-dihydroisoxazol-3-yl | SO$_2$CH$_3$ | H | C$_2$H$_5$ | CH$_3$CO | H | 67–73 |
| 2.9 | Cl | 5,5-dimethyl-4,5-dihydroisoxazol-3-yl | SO$_2$CH$_3$ | H | CH$_3$ | C$_6$H$_5$CH$_2$ | H | 1.36(s); 3.02(s); 3.19(s); 3.43(s); 5.31(s); 7.28(m); 7.42(s); 7.76(d); 8.00(d). |
| 2.10 | Cl | 5,5-dimethyl-4,5-dihydroisoxazol-3-yl | SO$_2$CH$_3$ | H | C$_2$H$_5$ | C$_6$H$_5$CH$_2$ | H | 1.12(t); 1.48(s); 3.15(s); 3.33(s); 3.89(q); 5.59(s); 7.41(m); 7.54(s); 7.89(d); 8.13(d). |
| 2.11 | Cl | 5,5-dimethyl-4,5-dihydroisoxazol-3-yl | SO$_2$CH$_3$ | H | i-C$_4$H$_9$ | C$_6$H$_5$CH$_2$ | H | 0.78(d); 1.49(s); 2.01(m); 3.15(s); 3.35(s); 3.68(d); 5.49(s); 7.39(m); 7.52(s); 7.89(d); 8.13(d). |
| 2.12 | Cl | 4,5-dihydroisoxazol-3-yl | SO$_2$CH$_3$ | H | CH$_3$ | i-C$_3$H$_7$ | H | 1.28(d); 3.33(s); 3.36(m); 3.69(s); 4.52(t); 4.98(m); 7.55(s); 7.86(d); 8.12(d). |
| 2.13 | Cl | 4,5-dihydroisoxazol-3-yl | SO$_2$CH$_3$ | H | C$_2$H$_5$ | i-C$_3$H$_7$ | H | 1.30(d); 1.32(t); 3.35(s); 3.38(m); 4.15(q); 4.52(t); 5.08(m); 7.55(s); 7.90(d); 8.12(d). |
| 2.14 | Cl | 4,5-dihydroisoxazol-3-yl | SO$_2$CH$_3$ | H | CH$_3$ | C$_2$H$_5$ | H | 83–88 |
| 2.15 | Cl | 4,5-dihydroisoxazol-3-yl | SO$_2$CH$_3$ | H | C$_2$H$_5$ | C$_2$H$_5$ | H | 1.26(t); 1.32(t); 3.34(s); 3.37(t); 4.03(q); 4.41(q); 4.50(t); 7.56(s); 7.88(d); 8.11(d). |
| 2.16 | Cl | 4,5-dihydroisoxazol-3-yl | SO$_2$CH$_3$ | H | C$_2$H$_5$ | C$_6$H$_5$COCH$_2$ | H | 168–173 |
| 2.17 | Cl | 5-ethyl-4,5-dihydroisoxazol-3-yl | SO$_2$CH$_3$ | H | C$_2$H$_5$ | C$_2$H$_5$ | H | 0.96(t); 1.28(t); 1.32(t); 1.72(m); 3.01(dd); 3.31(s); 3.38(dd); 4.05(q); 4.41(q); 4.75(m), 7.54(s); 7.86(d); 8.10(d). |
| 2.18 | Cl | 5-ethyl-4,5-dihydroisoxazol-3-yl | SO$_2$CH$_3$ | H | C$_2$H$_5$ | i-C$_3$H$_7$ | H | 0.95(t); 1.30(d); 1.32(t); 1.75(m); 3.03(dd); 3.34(s); 3.45(dd); 4.00(q); 4.75(m); 5.07(m); 7.50(s); 7.88(d); 8.09(d). |
| 2.19 | Cl | 5-ethyl-4,5-dihydroisoxazol-3-yl | SO$_2$CH$_3$ | H | CH$_3$ | C$_2$H$_5$ | H | 0.96(t); 1.22(t); 1.74(m); 3.00(dd); 3.32(s); 3.44(dd); 3.67(s); 4.40(q); 4.75(m); 7.56(s); 7.87(d); 8.10(d). |
| 2.20 | Cl | 5-ethyl-4,5-dihydroisoxazol-3-yl | SO$_2$CH$_3$ | H | CH$_3$ | i-C$_3$H$_7$ | H | 0.96(t); 1.25(d); 1.73(m); 3.02(dd); 3.31(s); 3.41(dd); 3.67(s); 4.74(m); 4.98(m); 7.53(s); 7.88(d); 8.10(d). |
| 2.21 | Cl | 5,5-diethyl-4,5-dihydroisoxazol-3-yl | SO$_2$CH$_3$ | H | CH$_3$ | C$_2$H$_5$ | H | 0.91(t); 1.24(t); 1.35(t); 3.11(s); 3.35(s); 3.67(s); 4.36(q); 7.54(s); 7.86(d); 8.10(d). |
| 2.22 | Cl | 5,5-diethyl-4,5-dihydroisoxazol-3-yl | SO$_2$CH$_3$ | H | CH$_3$ | i-C$_3$H$_7$ | H | 1.91(t); 1.29(d); 1.35(d); 1.75(m); 3.12(s); 3.35(s); 3.65(s); 4.98(m); 7.50(s); 7.86(d); 8.10(d). |
| 2.23 | Cl | 5,5-diethyl-4,5-dihydroisoxazol-3-yl | SO$_2$CH$_3$ | H | C$_2$H$_5$ | C$_2$H$_5$ | H | 0.94(t); 1.31(m); 1.76(m); 3.10(s); 3.32(s); 4.03(q); 4.40(q); 7.53(s); 7.85(d); 8.10(d). |
| 2.24 | Cl | 5,5-diethyl-4,5-dihydroisoxazol-3-yl | SO$_2$CH$_3$ | H | C$_2$H$_5$ | i-C$_3$H$_7$ | H | 0.90(t); 1.32(m); 1.75(m); 3.12(s); 3.34(s); 4.00(q); 5.05(m); 5.20(m); 7.50(s); 7.86(d); 8.08(d). |
| 2.25 | Cl | (4,5-dihydroisoxazol-5-spirocycl-pentan)-3-yl | SO$_2$CH$_3$ | H | CH$_3$ | C$_2$H$_5$ | H | 148–153 |
| 2.26 | Cl | (4,5-dihydroisoxazol-5-spirocycl-pentan)-3-yl | SO$_2$CH$_3$ | H | C$_2$H$_5$ | C$_2$H$_5$ | H | 1.25(t); 1.32(t); 1.74(m): 2.02(m); 3.05(s); 3.37(s); 4.04(q); 4.39(q); |

TABLE 2-continued

[Structure: A pyrazole ring bearing R8 at the 3-position, R6 on N1, OR7 at position 5, connected at position 4 via C=O to a benzene ring substituted with R1 (ortho), R2 (meta), R3 (para), R4 (other meta)]

| No. | R¹ | R² | R³ | R⁴ | R⁶ | R⁷ | R⁸ | Physical data Mp. [° C.]; ¹H NMR [δ in ppm] |
|---|---|---|---|---|---|---|---|---|
| | | | | | | | | 7.54(s); 7.86(d); 8.09(d). |
| 2.27 | Cl | 2-thiazolyl | SO₂CH₃ | H | C₂H₅ | CH₃CO | H | 173–174 |
| 2.28 | Cl | 2-thiazolyl | SO₂CH₃ | H | C₂H₅ | C₆H₅CO | H | 158 |
| 2.29 | Cl | 2-thiazolyl | SO₂CH₃ | H | C₂H₅ | C₆H₅CH=CHCO | H | 98 |
| 2.30 | Cl | 2-thiazolyl | SO₂CH₃ | H | C₂H₅ | (3-Cl—C₆H₄)CO | H | 165 |
| 2.31 | Cl | 2-thiazolyl | SO₂CH₃ | H | C₂H₅ | (CH₃)₂C=CHCO | H | 158–160 |
| 2.32 | Cl | 2-thiazolyl | SO₂CH₃ | H | C₂H₅ | C₂H₅OCO | H | 151 |
| 2.33 | Cl | 2-thiazolyl | SO₂CH₃ | H | C₂H₅ | C₂H₅CO | H | 141–144 |
| 2.34 | Cl | 2-thiazolyl | SO₂CH₃ | H | C₂H₅ | n-C₃H₇CO | H | 1.09(t); 1.46(t); 1.81(q); 2.63(t); 3.27(s); 4.05(q); 7.62(s); 7.66(d); 7.71(d); 7.98(d); 8.25(d). |
| 2.35 | Cl | 2-thiazolyl | SO₂CH₃ | H | C₂H₅ | CH₃OCO | H | 91 |
| 2.36 | Cl | 2-thiazolyl | SO₂CH₃ | H | C₂H₅ | (4-Cl—C₆H₄)CO | H | 148–149 |
| 2.37 | Cl | 2-thiazolyl | SO₂CH₃ | H | C₂H₅ | C₆H₅CH₂ | H | 56 |
| 2.38 | Cl | 2-thiazolyl | SO₂CH₃ | H | C₂H₅ | [(CH₃O)CH₃N]CO | H | 62 |
| 2.39 | Cl | 2-thiazolyl | SO₂CH₃ | H | C₂H₅ | C₂H₅ | H | 145–147 |
| 2.40 | Cl | 1,3-dithiolan-2-yl | Cl | H | C₂H₅ | C₂H₅CO | H | 52–54 |
| 2.41 | Cl | 5,5-dimethyl-1,3-dioxan-2-yl | Cl | H | C₂H₅ | n-C₃H₇ | H | 0.82(s); 1.06(t); 1.41(m); 1.81(m); 3.68(d); 3.83(d); 4.07(q); 4.49(t); 6.15(s); 7.28(m); 7.43(d) |
| 2.42 | Cl | 5,5-dimethyl-1,3-dioxan-2-yl | Cl | H | C₂H₅ | C₂H₅CO | H | 0.82(s); 1.22(t); 1.42(q); 2.60(q); 3.69(d); 3.84(d); 4.02(q); 6.15(s); 7.22(d); 7.41(d); 7.61(s) |
| 2.43 | Cl | 5,5-dimethyl-1,3-dioxan-2-yl | Cl | H | C₂H₅ | C₆H₅CH₂ | H | 0.82(s); 1.21(t); 1.42(s); 3.68(d); 3.89(m); 5.59(s); 6.18(s); 7.24(m); 7.41(m) |
| 2.44 | Cl | 4,5-dihydroisoxazol-3-yl | SO₂CH₃ | H | CH₃ | C₆H₅CH₂ | H | 195–200 |
| 2.45 | Cl | 4,5-dihydroisoxazol-3-yl | SO₂CH₃ | H | CH₃ | C₆H₅CH₂ | H | 70–75 |
| 2.46 | Cl | 4,5-dihydroisoxazol-3-yl | SO₂CH₃ | H | CH₃ | (CH₃)₂NCS | H | 85–95 |
| 2.47 | CH₃ | 4,5-dihydrothiazol-2-yl | H | H | C₂H₅ | C₆H₅CH₂ | H | 1.29(t); 2.46(s); 3.49(t); 3.91(q); 4.53(t); 5.57(s); 7.31(m); 7.59(d). |
| 2.48 | Cl | 5-methyl-4,5-dihydroisoxazol-3-yl | n-SO₂C₃H₇ | H | C₂H₅ | C₆H₅CH₂ | H | 0.94(t); 1.12(t); 1.39(d); 1.61(m); 2.98(m); 3.42(m); 3.87(m); 4.98(m); 5.49(s); 7.41(m); 7.59(s); 7.90(d); 8.10(d) |
| 2.49 | Cl | 4,5-dihydroisoxazol-3-yl | SO₂CH₃ | H | CH₃ | i-C₄H₉ | H | 94–96 |
| 2.50 | Cl | 4,5-dihydroisoxazol-3-yl | SO₂CH₃ | H | C₂H₅ | i-C₄H₉ | H | 55–60 |
| 2.51 | Cl | 4,5-dihydroisoxazol-3-yl | SO₂CH₃ | H | C₂H₅ | CH₃COCH₂ | H | |
| 2.52 | Cl | 4,5-dihydroisoxazol-3-yl | SO₂CH₃ | H | CH₃ | (C₂H₅)₂CH | H | 64–68 |
| 2.53 | Cl | 4,5-dihydroisoxazol-3-yl | SO₂CH₃ | H | CH₃ | (C₂H₅)₂CH | H | 58–62 |
| 2.54 | Cl | 4,5-dihydroisoxazol-3-yl | SO₂CH₃ | H | CH₃ | (CH₃)₂NCS | H | 85–90 |
| 2.55 | Cl | 4,5-dihydroisoxazol-3-yl | SO₂CH₃ | H | CH₃ | C₆H₅CH₂ | H | 195–200 |
| 2.56 | Cl | 4,5-dihydroisoxazol-3-yl | SO₂CH₃ | H | C₂H₅ | C₆H₅CH₂ | H | 70–75 |
| 2.57 | Cl | 4,5-dihydroisoxazol-3-yl | SO₂CH₃ | H | CH₃ | CH₃ | H | 78–92 |
| 2.58 | Cl | 4,5-dihydroisoxazol-3-yl | SO₂CH₃ | H | C₂H₅ | CH₃ | H | 70–75 |
| 2.59 | Cl | 4,5-dihydroisoxazol-3-yl | SO₂CH₃ | H | CH₃ | CH₃OCOCH₂ | H | 88–93 |
| 2.60 | Cl | 4,5-dihydroisoxazol-3-yl | SO₂CH₃ | H | C₂H₅ | CH₃OCOCH₂ | H | 120–123 |
| 2.61 | Cl | 4,5-dihydroisoxazol-3-yl | SO₂CH₃ | H | CH₃ | C₂H₅OCO—C(=NOCH₃)CH₂ | H | 57–62 |
| 2.62 | Cl | 4,5-dihydroisoxazol-3-yl | SO₂CH₃ | H | C₂H₅ | C₂H₅OCO—C(=NOCH₃)CH₂ | H | 1.38(m); 3.29(s); 3.46(t); 4.02(q); 4.13(s); 4.35(m); 4.62(t); 5.48(s); 7.29(d); 7.65(d); 8.16(d) |
| 2.63 | Cl | 4,5-dihydroisoxazol-3-yl | SO₂CH₃ | H | CH₃ | CH₃C(=NOCH₃)CH₂ | H | 183–186 |
| 2.64 | Cl | 4,5-dihydroisoxazol-3-yl | SO₂CH₃ | H | CH₃ | CH₃COCH₂ | H | |
| 2.65 | Cl | 5-methyl-4,5-dihydroisoxazol-3-yl | SO₂-n-C₃H₇ | H | CH₃ | C₆H₅CH₂ | H | 0.94(3H); 1.12(3H); 1.39(3H); 1.61(2H); 2.70(1H); 2.98(1H); 3.42(2H); 3.87(2H); 4.98(1H); 5.49(2H); 7.41(5H); 7.59(1H); 7.90(1H); 8.10(1H) |
| 2.66 | Cl | 5-chloromethyl-4,5-dihydro-isoxazol-3-yl | SO₂CH₃ | H | CH₃ | C₂H₅CO | H | 69–74 |
| 2.67 | Cl | 3-tert-butylisoxazol-4-yl | Cl | H | CH₃ | C₂H₅CO | H | 1.3(t); 1.4(s); 2.6(q); 3.7(s); 6.4(s); 7.4(d); 7.5(d); 7.7(s) |
| 2.68 | Cl | 5,5-dimethyl-1,3-dioxan-2-yl | SO₂CH₃ | H | C₂H₅ | n-C₄H₉ | H | 0.8(s); 1.0(t); 1.4(t); 1.8(m); 3.2(s); 3.7(d); 3.8(d); 4.0(m); 4.6(t); 6.6(s); |

TABLE 2-continued

Structure: Pyrazole-methanone with substituted phenyl; R1 at ortho, R2 at meta, R3 at para, R4 at other meta; R6 on pyrazole N; OR7 on pyrazole; R8 on pyrazole C3.

| No. | R¹ | R² | R³ | R⁴ | R⁶ | R⁷ | R⁸ | Physical data Mp. [° C.]; ¹H NMR [δ in ppm] |
|---|---|---|---|---|---|---|---|---|
| | | | | | | | | 7.5(d); 8.0(bs); 8.2(d) |
| 2.69 | CH₃ | 4,5-dihydroisoxazol-3-yl | SO₂CH₃ | H | C₂H₅ | i-C₃H₇ | H | 155–160 |
| 2.70 | Cl | 3-methylisoxazol-5-yl | Cl | H | CH₃ | C₂H₅CO | H | |
| 2.71 | Cl | 2-thiazolyl | SO₂CH₃ | H | C₂H₅ | C₆H₅CH(CH₃) | H | 1.26(t); 1.82(d); 3.26(s); 3.89(q); 6.20(q); 7.35(m); 7.58(d); 7.71(d); 7.99(d); 8.23(d) |
| 2.72 | Cl | 2-thiazolyl | SO₂CH₃ | H | C₂H₅ | (4-CH₃—C₆H₄)CH₂ | H | 131–136 |
| 2.73 | Cl | 2-thiazolyl | SO₂CH₃ | H | C₂H₅ | CH₂—CHCH₂ | H | 1.44(t); 3.29(s); 4.11(q); 5.10(d); 5.31(d); 5.42(d); 6.04(m); 7.37(s); 7.69(d); 7.72(d); 7.99(d); 8.27(d) |
| 2.74 | Cl | 2-thiazolyl | SO₂CH₃ | H | C₂H₅ | CH≡CCH₂ | H | 1.46(t); 2.57(m); 3.29(s); 4.15(q); 5.32(d); 7.39(s); 7.70(m); 7.99(d); 8.29(d) |
| 2.75 | Cl | 2-thiazolyl | SO₂CH₃ | H | C₂H₅ | (4-CH₃—C₆H₄)COCH₂ | H | 1.52(t); 2.41(s); 3.23(s); 4.32(q); 6.16 (s); 7.27(m); 7.60(d); 7.70(d); 7.82(d); 7.98(d); 8.21(d) |
| 2.76 | Cl | 2-thiazolyl | SO₂CH₃ | H | C₂H₅ | C₆H₅COCH₂ | H | 199–202 |
| 2.77 | Cl | 4,5-dihydroisoxazol-3-yl | SO₂CH₃ | H | CH₃ | (cyclo-C₃H₅)—CH₂ | H | 135–140 |
| 2.78 | Cl | 4,5-dihydroisoxazol-3-yl | SO₂CH₃ | H | C₂H₅ | (cyclo-C₃H₅)—CH₂ | H | 135–140 |
| 2.79 | Cl | 4,5-dihydroisoxazol-3-yl | SO₂CH₃ | H | CH₃ | CF₃ | H | |
| 2.80 | Cl | 4,5-dihydroisoxazol-3-yl | SO₂CH₃ | H | CH₃ | CF₃ | H | |
| 2.81 | Cl | 4,5-dihydroisoxazol-3-yl | SO₂CH₃ | H | CH₃ | CHF₂ | H | |
| 2.82 | Cl | 4,5-dihydroisoxazol-3-yl | SO₂CH₃ | H | C₂H₅ | HOCOCH₂ | H | 50–53 |
| 2.83 | Cl | 4,5-dihydroisoxazol-3-yl | SO₂CH₃ | H | CH₃ | CH₃C(=NOCH₃)CH₂ | H | 183–186 |
| 2.84 | Cl | 4,5-dihydroisoxazol-3-yl | SO₂CH₃ | H | CH₃ | CH₃ | H | 78–84 |
| 2.85 | Cl | 4,5-dihydroisoxazol-3-yl | SO₂CH₃ | H | C₂H₅ | CH₃ | H | 112–116 |
| 2.86 | Cl | 4,5-dihydroisoxazol-3-yl | SO₂CH₃ | H | C₂H₅ | CH₃CH(OH)CH₂ | H | 1.02(d); 1.18(t); 3.26(s); 3.33(m); 3.53(m); 3.75(q); 4.50(t); 7.06(s); 7.70(d); 8.10(d) |
| 2.87 | Cl | 5-methylisoxazol-3-yl | SO₂CH₃ | H | CH₃ | i-C₃H₇ | H | 101–102 |
| 2.88 | Cl | 5-methylisoxazol-3-yl | SO₂CH₃ | H | CH₃ | H₃COCOCH₂ | H | 92–96 |
| 2.89 | Cl | 4,5-dimethyl-4,5-dihydroisoxazol-3-yl | SO₂CH₃ | H | CH₃ | H₃COCOCH₂ | H | 68–70 |
| 2.90 | Cl | 3-isopropyl-1,2,4-oxadiazol-5-yl | Cl | H | C₂H₅ | i-C₃H₇ | H | 1.38–1.43(m); 3.22(m); 4.08(q); 5.30(sept); 7.32(s); 7.48(d); 7.51(d) |
| 2.91 | Cl | 3-isopropyl-1,2,4-oxadiazol-5-yl | Cl | H | CH₃ | i-C₃H₇ | H | 1.38(d); 1.45(d); 3.24(s); 3.70(s); 5.24(m); 7.33(s); 7.47(d); 7.52(d) |
| 2.92 | Cl | 4,5-dimethyl-4,5-dihydroisoxazol-3-yl | SO₂CH₃ | H | CH₃ | i-C₃H₇ | H | 141–144 |
| 2.93 | Cl | 4,5-dihydroisoxazol-3-yl | SO₂CH₃ | H | C₂H₅ | HOCH₂CH₂ | H | 68–72 |
| 2.94 | Cl | 4,5-dihydroisoxazol-3-yl | SO₂CH₃ | H | CH₃ | NCCH₂ | H | 96–99 |
| 2.95 | Cl | 4,5-dihydroisoxazol-3-yl | SO₂CH₃ | H | C₂H₅ | NCCH₂ | H | 135–138 |
| 2.96 | Cl | 4,5-dihydroisoxazol-3-yl | SO₂CH₃ | H | CH₃ | CH₂=CHCH₂ | H | 105–108 |
| 2.97 | Cl | 4,5-dihydroisoxazol-3-yl | SO₂CH₃ | H | C₂H₅ | CH₂=CHCH₂ | H | 128–131 |
| 2.98 | Cl | 4,5-dihydroisoxazol-3-yl | SO₂CH₃ | H | CH₃ | HOCH₂CH₂ | H | 120–123 |
| 2.99 | Cl | 4,5-dihydroisoxazol-3-yl | SO₂CH₃ | H | C₂H₅ | n-C₃H₇ | H | 114–118 |
| 2.100 | Cl | 4,5-dihydroisoxazol-3-yl | SO₂CH₃ | H | CH₃ | FCH₂CH₂CH₂ | H | 115–117 |
| 2.101 | Cl | 4,5-dihydroisoxazol-3-yl | SO₂CH₃ | H | C₂H₅ | FCH₂CH₂CH₂ | H | 1.43(t); 2.25(m); 3.30(s); 3.45(t); 4.06(q); 4.66(m); 4.75(t); 7.30(s); 7.63(d); 8.16(d) |
| 2.102 | Cl | 4,5-dihydroisoxazol-3-yl | SO₂CH₃ | H | CH₃ | s-C₄H₉ | H | 168–173 |
| 2.103 | Cl | 4,5-dihydroisoxazol-3-yl | SO₂CH₃ | H | C₂H₅ | s-C₄H₉ | H | 165–170 |
| 2.104 | Cl | 4,5-dihydroisoxazol-3-yl | SO₂CH₃ | H | CH₃ | HC≡CCH₂ | H | 164–168 |
| 2.105 | Cl | 4,5-dihydroisoxazol-3-yl | SO₂CH₃ | H | C₂H₅ | HC≡CCH₂ | H | 122–125 |
| 2.106 | Cl | 4,5-dihydroisoxazol-3-yl | SO₂CH₃ | H | CH₃ | H₃CCH=CHCH₂ | H | 145–147 |
| 2.107 | Cl | 4,5-dihydroisoxazol-3-yl | SO₂CH₃ | H | C₂H₅ | CH₃CH=CHCH₂ | H | 123–126 |
| 2.108 | Cl | 4,5-dihydroisoxazol-3-yl | SO₂CH₃ | H | CH₃ | n-C₃H₇ | H | 55–60 |
| 2.109 | Cl | 5-methylisoxazol-3-yl | SO₂CH₃ | H | C₂H₅ | CH₃ | H | 1.30(t); 2.50(s); 3.30(s); 4.05(q); 4.13 (s); 6.53(s); 7.52(s); 7.93(d); 8.16(d) |
| 2.110 | Cl | 5-methylisoxazol-3-yl | SO₂CH₃ | H | C₂H₅ | i-C₃H₇ | H | 70–73 |
| 2.111 | Cl | 4,5-diethylisoxazol-3-yl | SO₂CH₃ | H | CH₃ | i-C₃H₇ | H | 0.93(t); 1.25(m; 2.23(m); 2.83(q); 3.65(s); 4.95(sept); 7.48(s); 7.93(d); 8.20(d) |
| 2.112 | Cl | 5-t-butylisoxazol-3-yl | SO₂CH₃ | H | C₂H₅ | i-C₃H₇ | H | 1.31–1.35(m); 3.31(s); 4.02(q); 5.08(sept); 6.52(s); 7.49(s); 7.90(d); 8.16(d) |

TABLE 2-continued

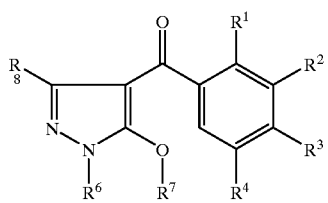

I

| No. | R¹ | R² | R³ | R⁴ | R⁶ | R⁷ | R⁸ | Physical data Mp. [° C.]; ¹H NMR [δ in ppm] |
|---|---|---|---|---|---|---|---|---|
| 2.113 | Cl | 5-n-propylisoxazol-3-yl | SO₂CH₃ | H | CH₃ | i-C₃H₇ | H | 0.93(t); 1.30(d); 1.74(sept); 2.85(t); 3.37(s); 3.68(s); 5.02(sept); 6.56(s); 7.53(s); 7.90(d); 8.18(d) |

The syntheses of some starting materials are listed below:

4-[2-Chloro-3-(4,5-dihydroisoxazol-3-yl)-4-methylsulfonylbenzoyl]-5-hydroxy-1-methyl-1H-pyrazole (compound 3.21)

Step a) 2-Chloro-3-methyl-4-methylthioacetophenone

At 15–20° C., a solution of 157 g (2 mol) of acetyl chloride in 420 ml of 1,2-dichloroethane was added dropwise to a suspension of 286 g (2.14 mol) of aluminum trichloride in 420 ml of 1,2-dichloroethane. A solution of 346 g (2 mol) of 2-chloro-6-methylthiotoluene in 1 l of 1,2-dichloroethane was subsequently added dropwise. The reaction mixture was stirred for 12 hours and then poured into a mixture of 3 l of ice and 1 l of conc. hydrochloric acid. The mixture was extracted with methylene chloride and the organic phase was washed with water, dried with sodium sulfate and concentrated. The residue was distilled under reduced pressure. 256 g (60% of theory) of 2-chloro-3-methyl-4-methylthioacetophenone were obtained.

(Mp.: 46° C.)

Step b) 2-Chloro-3-methyl-4-methylsulfonylacetophenone 163.0 g (0.76 mol) of 2-chloro-3-methyl-4-methylthioacetophenone were dissolved in 1.5 l of glacial acetic acid and admixed with 18.6 g of sodium tungstate. With cooling, 173.3 g of a 30% strength hydrogen peroxide solution were added dropwise. The mixture was stirred for 2 days and subsequently diluted with water. The precipitated solid was filtered off with suction, washed with water and dried. 164.0 g (88% of theory) of 2-chloro-3-methyl-4-methylsulfonylacetophenone were obtained.

(Mp.: 110–111° C.)

Step c) 2-Chloro-3-methyl-4-methylsulfonylbenzoic acid 82 g (0.33 mol) of 2-chloro-3-methyl-4-methylsulfonylacetophenone were dissolved in 700 ml of dioxane and, at room temperature, admixed with 1 l of a 12.5% strength solution of sodium hypochlorite. The mixture was subsequently stirred at 80° C. for 1 hour. After cooling, two phases formed, the heavier one of which was diluted with water and acidified slightly. The precipitated solid was filtered off with suction, washed with water and dried. 60 g (73% of theory) of 2-chloro-3-methyl-4-methylsulfonylbenzoic acid were obtained.

(Mp.: 230–231° C.)

Step d) Methyl 2-chloro-3-methyl-4-methylsulfonylbenzoate 100 g (0.4 mol) of 2-chloro-3-methyl-4-methylsulfonylbenzoic acid were dissolved in 1 l of methanol, and hydrogen chloride gas was introduced at reflux temperature for 5 hours. The mixture was subsequently concentrated. 88.5 g (84% of theory) of methyl 2-chloro-3-methyl-4-methylsulfonylbenzoate were obtained.

(Mp.: 107–108° C.)

Step e) Methyl 3-bromomethyl-2-chloro-4-methylsulfonylbenzoate 82 g (0.31 mol) of methyl 2-chloro-3-methyl-4-methylsulfonylbenzoate were dissolved in 2 l of carbon tetrachloride, and 56 g (0.31 mol) of N-bromosuccinimide were added a little at a time while the mixture was exposed to light. The reaction mixture was filtered, the filtrate was concentrated and the residue was taken up in 200 ml of methyl tert-butyl ether. The solution was admixed with petroleum ether and the precipitated solid was filtered off with suction and dried. 74.5 g (70% of theory) of methyl 3-bromomethyl-2-chloro-4-methylsulfonylbenzoate were obtained.

(Mp.: 74–75° C.)

Step f) Methyl 2-chloro-3-formyl-4-methylsulfonylbenzoate

A solution of 41.0 g (0.12 mol) of methyl 3-bromomethyl-2-chloro-4-methylsulfonylbenzoate in 250 ml of acetonitrile was admixed with 42.1 g (0.36 mol) of N-methylmorpholine N-oxide. The reaction was stirred at room temperature for 12 hours and then concentrated and the residue was taken up in ethyl acetate. The solution was washed with water, dried and concentrated. 31.2 g (94% of theory) of methyl 2-chloro-3-formyl-4-methylsulfonylbenzoate were obtained.

(Mp.: 98–105° C.)

Step g) Methyl 2-chloro-3-hydroxyiminomethyl-4-methylsulfonylbenzoate 15.00 g (54 mmol) of methyl 2-chloro-3-formyl-4-methylsulfonylbenzoate and 4.20 g (60 mmol) of hydroxylamine hydrochloride were taken up in 300 ml of methanol, and a solution of 3.18 g (30 mmol) of sodium carbonate in 80 ml of water was added dropwise. After the mixture had been stirred at room temperature for 12 hours, the methanol was distilled off and the residue was diluted with water and extracted with diethyl ether. The organic phase was dried and the solvent was removed. 14.40 g (91% of theory) of methyl 2-chloro-3-hydroxyiminomethyl-4-methylsulfonylbenzoate were obtained.

(Mp.: 126–128° C.)

Step h) Methyl 2-chloro-3-(4,5-dihydroisoxazol-3-yl)-4-methylsulfonylbenzoate (compound 4.3)

At 15–20° C., ethylene is introduced into a solution of 158.0 g (0.54 mol) of methyl 2-chloro-3-hydroxyiminomethyl-4-methylsulfonylbenzoate and 1 l of dichloromethane for 30 minutes. After the addition of 1.6 g of sodium acetate, 454 ml of sodium hypochlorite solution were added dropwise at 10° C., while simultaneously introducing ethylene. Subsequently, ethylene was introduced at 10° C. for a further 15 minutes. The mixture was stirred for 12 hours, the phases were separated and the organic phase was washed with water, dried and concentrated. 156.5 g (90% of theory) of methyl 2-chloro-(4,5-dihydroisoxazol-3-yl)-4-methylsulfonylbenzoate were obtained.

($^1$H NMR (δ in ppm): 3.24 (s); 3.42 (t); 3.99 (s); 4.60 (t); 7.96 (d); 8.10 (d)).

Step i) 2-Chloro-3-(4,5-dihydroisoxazol-3-yl)-4-methylsulfonylbenzoic acid (compound 4.4)

At 40–45° C., a solution of 32.8 g of sodium hydroxide in 330 ml of methanol was slowly added dropwise to a mixture of 170.0 g (0.54 mol) of methyl 2-chloro-3-(4,5-dihydroisoxazol-3-yl)-4-methylsulfonylbenzoate and 1 l of methanol. The suspension was stirred at 50° C. for 5 hours. The solvent was distilled off, the residue was taken up in 1.5 l of water and the aqueous phase was extracted three times with ethyl acetate. The aqueous phase was acidified with hydrochloric acid and extracted three times with ethyl acetate. The combined organic phases were subsequently washed neutral with water, dried and concentrated. 148.8 g (91% of theory) of 2-chloro-3-(4,5-dihydroisoxazol-3-yl)-4-methylsulfonylbenzoic acid were obtained.

($^1$H NMR (δ in ppm): 3.26 (s); 3.45 (t); 4.63 (t); 8.15 (s); 8.53 (s, br)).

Step j) 2-Chloro-3-(4,5-dihydroisoxazol-3-yl)-4-methylsulfonylbenzoyl chloride (compound 4.5)

At 50° C., 74.8 g (0.63 mol) of thionyl chloride in 50 ml of dry toluene were added dropwise to a solution of 139.0 g of 2-chloro-3-(4,5-dihydroisoxazol-3-yl)-4-methylsulfonylbenzoic acid, 1 ml of dimethylformamide and 1 l of dry toluene. The mixture was heated to 110° C. for 6 hours, after which the solvent was distilled off. 2-Chloro-3-(4,5-dihydroisoxazol-3-yl)-4-methylsulfonylbenzoyl chloride was obtained in quantitative yield.

($^1$H NMR (δ in ppm): 3.25 (s); 3.46 (t); 4.62 (t); 8.21 (dd)).

Step k) 4-[2-Chloro-3-(4,5-dihydroisoxazol-3-yl)-4-methylsulfonylbenzoyl]-5-hydroxy-1-methyl-1H-pyrazole (compound 3.21)

At room temperature and under an atmosphere of protective gas, 43.60 g (0.13 mol) of 2-chloro-3-(4,5-dihydroisoxazol-3-yl)-4-methylsulfonylbenzoyl chloride in 375 ml of anhydrous dioxane and 13.56 g (0.134 mol) of triethylamine in 375 ml of anhydrous dioxane were simultaneously added dropwise to a solution of 12.74 g (0.13 mol) of 5-hydroxy-1-methylpyrazole and 300 ml of anhydrous dioxane. The reaction mixture was stirred at room temperature for 2 hours and then filtered off through silica gel, which was rinsed with dioxane. The eluate was concentrated under reduced pressure to about 500 ml and admixed with 17.94 g (0.13 mol) of dried, finely powdered potassium carbonate. After 6 hours under reflux, the solvent was distilled off under reduced pressure and the residue was taken up in about 700 ml of water. Insoluble components were filtered off and the pH of the filtrate was adjusted to 2–3 by slowly adding 10% strength hydrochloric acid. The precipitate that formed was filtered off with suction. 46.16 g (92% of theory) of 4-[2-chloro-3-(4,5-dihydroisoxazol-3-yl)-4-methylsulfonylbenzoyl]-5-hydroxy-1-methyl-1H-pyrazole were obtained.

(Mp. >250° C.)

4-[2-Chloro-3-(5-methyl-4,5-dihydroisoxazol-3-yl)-4-methylsulfonylbenzoyl]-5-hydroxy-1-methyl-1H-pyrazole (compound 3.5)

Step a) Methyl 2-chloro-3-(5-methyl-4,5-dihydroisoxazol-3-yl)-4-methylsulfonylbenzoate (compound 4.25)

At room temperature, propene was introduced into a solution of 15.0 g (52 mmol) of methyl 2-chloro-3-hydroxyiminomethyl-4-methylsulfonylbenzoate and 200 ml of dichloromethane for 30 minutes. After the addition of 1.6 g of sodium acetate, 42.8 ml of sodium hypochlorite solution were added dropwise, with the simultaneous introduction of propene. At room temperature, propene was subsequently introduced into the mixture for a further 15 minutes. The mixture was heated for 3 hours under reflux and then stirred for 12 hours at room temperature, propene was introduced once more under reflux for 5 hours and the mixture was stirred at room temperature for another 12 hours. The phases were separated and the organic phase was washed with water, dried and concentrated. 15.5 g (89% of theory) of methyl 2-chloro-(5-methyl-4,5-dihydroisoxazol-3-yl)-4-methylsulfonylbenzoate were obtained.

(Mp.: 130–135° C.)

Step b) 2-Chloro-3-(5-methyl-4,5-dihydroisoxazol-3-yl)-4-methylsulfonylbenzoate (compound 4.26)

A solution of 3.52 g (88 mmol) of sodium hydroxide in 100 ml of methanol was slowly added dropwise to a mixture of 15.00 g (45 mmol) of methyl 2-chloro-3-(5-methyl-4,5-dihydroisoxazol-3-yl)-4-methylsulfonylbenzoate and 200 ml of methanol. The suspension was stirred at room temperature for 48 hours. The solvent was distilled off, the residue was taken up in water and the aqueous phase was washed three times with ethyl acetate. The aqueous phase was acidified with hydrochloric acid and extracted three times with ethyl acetate. The combined organic phases were subsequently washed neutral with water, dried and concentrated. 13.20 g (92% of theory) of 2-chloro-3-(5-methyl-4,5-dihydroisoxazol-3-yl)-4-methylsulfonylbenzoic acid were obtained.

(Mp.: 173–178° C.)

Step c) 2-Chloro-3-(5-methyl-4,5-dihydroisoxazol-3-yl)-4-methylsulfonylbenzoyl chloride (compound 4.39)

At room temperature, 5.7 g (51 mmol) of thionyl chloride were added dropwise to a solution of 13.0 g (41 mmol) of 2-chloro-3-(5-methyl-4,5-dihydroisoxazol-3-yl)-4-methylsulfonylbenzoic acid, 1 ml of dimethylformamide and 250 ml of dry toluene. The mixture was subsequently heated under reflux until the reaction had gone to completion. After cooling, the solvent was distilled off. 14.2 g of 2-chloro-3-(5-methyl-4,5-dihydroisoxazol-3-yl)-4-methylbenzoyl chloride were obtained in quantitative yield.

Step d) 4-(2-Chloro-3-(5-methyl-4,5-dihydroisoxazol-3-yl)-4-methylsulfonylbenzoyl]-5-hydroxy-1-methyl-1H-pyrazole (compound 3.5)

At room temperature, initially 4.00 g (12 mmol) of 2-chloro-3-(5-methyl-4,5-dihydroisoxazol-3-yl)-4-methylsulfonylbenzoyl chloride in 50 ml of dioxane and then 1.20 g (12.2 mmol) of triethylamine in 30 ml of dioxane were added dropwise to a solution of 1.20 g (12 mmol) of 5-hydroxy-1-methylpyrazole in 30 ml of dioxane. The reaction mixture was stirred for 12 hours and then filtered through silica gel and the filtrate was admixed with 0.50 g (3.6 mmol) of potassium carbonate and heated under reflux for 12 hours. After a further 12 hours of stirring at room temperature, a spatula tipful of potassium carbonate was added, and the mixture was once again heated under reflux. After cooling, the solvent was distilled off under reduced pressure, the residue was taken up in water and washed with ethyl acetate, the pH was adjusted to 1–2 using 10% strength hydrochloric acid and the mixture was extracted repeatedly with ethyl acetate. The combined organic phases were washed with water and dried and the solvent was removed. The residue was digested in cold ethyl acetate. 1.60 g (34% of theory) of 4-[2-chloro-3-(5-methyl-4,5-dihydroisoxazol-3-yl)-4-methylsulfonylbenzoyl]-5-hydroxy-1-methyl-1H-pyrazole were obtained.

(Mp.: 230–235° C.)

4-[2-Chloro-3-(4,4-dimethyl-4,5-dihydrooxazol-2-yl)-4-methylsulfonylbenzoyl]-5-hydroxy-1-methyl-1H-pyrazole (compound 3.29)

Step a) Methyl 2-chloro-3-hydroxycarbonyl-4-methylsulfonylbenzoate

At 5° C., 13.8 g (0.11 mol) of sodium hydrogen phosphate monohydrate in 170 ml of water, 49.3 g (0.43 mol) of a 30% strength solution of hydrogen peroxide and 66.2 g (0.59 mol) of an 80% strength aqueous sodium chloride solution were added successively to a solution of 115.3 g (0.42 mol) of methyl 2-chloro-3-formyl-4-methylsulfonylbenzoate and 2000 ml of acetonitrile. The reaction solution was subsequently stirred at 5° C. for 1 hour and then at room temperature for 12 hours. The pH was then adjusted to 1 using 10% strength hydrochloric acid, and 1500 ml of aqueous 40% strength sodium hydrogen sulfite solution were added. The mixture was stirred at room temperature for 1 hour and the aqueous phase was extracted three times with ethyl acetate. The combined organic phases were washed with sodium hydrogen sulfite solution and dried. The solvent was distilled off, yielding 102.0 g of methyl 2-chloro-3-hydroxycarbonyl-4-methylsulfonylbenzoate.

($^1$H NMR ($\delta$ in ppm): 3.34 (s); 3.93 (s); 8.08 (s); 14.50 (s, br.)).

Step b) Methyl 2-chloro-3-chlorocarbonyl-4-methylsulfonylbenzoate 2 drops of dimethylformamide and 11.9 g (0.1 mol) of thionyl chloride were added to a solution of 6.0 g (0.021 mol) of methyl 2-chloro-3-hydroxycarbonyl-4-methylsulfonylbenzoate and 50 ml of dry toluene. The solution was heated under reflux for 4 hours. Removal of the solvent under reduced pressure gave 6.2 g of methyl 2-chloro-3-chlorocarbonyl-4-methylsulfonylbenzoate.

($^1$H NMR ($\delta$ in ppm): 3.21 (s); 4.02 (s); 8.02 (d); 8.07 (d)).

Step c) Methyl 2-chloro-3-(1-hydroxy-2,2-dimethyleth-2-ylaminocarbonyl)-4-methylsulfonylbenzoate At 0–5° C., a solution of 7.80 g (25 mmol) of methyl 2-chloro-3-chlorocarbonyl-4-methylsulfonylbenzoate was added dropwise to a solution of 4.54 g (50 mmol) of 2,2-dimethylethanolamine in 40 ml of dichloromethane. The reaction solution was stirred at room temperature for 6 hours and then extracted three times with water, dried and concentrated. 8.20 g (80% of theory) of methyl 2-chloro-3-(1-hydroxy-2,2-dimethyleth-2-ylaminocarbonyl)-4-methylsulfonylbenzoate were obtained.

(Mp.: 70–72° C.).

Step d) Methyl 2-chloro-3-(1-chloro-2,2-dimethyleth-2-ylaminocarbonyl)-4-methylsulfonylbenzoate A mixture of 6.9 g (20 mmol) of methyl 2-chloro-3-(1-hydroxy-2,2-dimethyleth-2-ylaminocarbonyl)-4-methylsulfonylbenzoate and 5 ml of thionyl chloride was stirred at room temperature for 6 hours. The solution was diluted with 50 ml of dichloromethane and subsequently concentrated. The residue was dissolved in 20 ml of dichloromethane. Addition of cyclohexane resulted in the formation of a crystalline precipitate which was filtered off with suction and dried. 6.4 g (88% of theory) of methyl 2-chloro-3-(1-chloro-2,2-dimethyleth-2-ylaminocarbonyl)-4-methylsulfonylbenzoate were obtained.

Step e) 2-Chloro-3-(4,4-dimethyl-4,5-dihydrooxazol-2-yl)-4-methylsulfonylbenzoic acid (compound 4.38)

A solution of 5.82 g (15 mmol) of methyl 2-chloro-3-(1-chloro-2,2-dimethyleth-2-ylaminocarbonyl)-4-methylsulfonylbenzoate and 0.81 g (20 mmol) of sodium hydroxide in 80 ml of methanol was stirred at room temperature for 8 hours. The solvent was distilled off and the residue was taken up in water and washed three times with ethyl acetate. The aqueous phase was acidified with hydrochloric acid and extracted three times with ethyl acetate. The organic phase was dried and the solvent was removed under reduced pressure. 3.10 g (56% of theory) of 2-chloro-3-(4,4-dimethyl-4,5-dihydrooxazol-2-yl)-4-methylsulfonylbenzoic acid were obtained.

($^1$H NMR ($\delta$ in ppm): 1.34 (s); 3.40 (s); 4.13 (s); 8.07 (s); 13.95 (s, br)).

Step f) 2-Chloro-3-(1-chloro-2,2-dimethyleth-2-ylaminocarbonyl)-4-methylsulfonylbenzoyl chloride A solution of 3.00 g (9 mmol) of 2-chloro-3-(4,4-dimethyl-4,5-dihydrooxazol-2-yl)-4-methylsulfonylbenzoic acid, 1.43 g of thionyl chloride and 1 drop of dimethylformamide in 80 ml of dry toluene was heated under reflux for 3 hours. After cooling, the solvent was distilled off under reduced pressure. 3.43 g (86% of theory) of 2-chloro-3-(1-chloro-2,2-dimethyleth-2-ylaminocarbonyl)-4-methylsulfonylbenzoyl chloride were obtained.

Step g) 4-[2-Chloro-3-(4,4-dimethyl-4,5-dihydrooxazol-2-yl)-4-methylsulfonylbenzoyl]-5-hydroxy-1-methyl-1H-pyrazole (compound 3.29)

At 15° C., 1.65 g (4.3 mmol) of 2-chloro-3-(1-chloro-2,2-dimethyleth-2-ylaminocarbonyl)-4-methylsulfonylbenzoyl chloride in 25 ml of dioxane and 0.45 g (4.5 mmol) of triethylamine in 10 ml of dioxane were added dropwise to a mixture of 0.42 g (4.3 mmol) of 5-hydroxy-1-methylpyrazole in 10 ml of dioxane. The mixture was stirred at room temperature for 4 hours and then filtered off through silica gel, which was rinsed with dioxane. The combined filtrates were concentrated to 60 ml and admixed with 1.24 g (9 mmol) of finely powdered potassium carbonate. The mixture was heated under reflux for 5 hours and cooled, the solvent was removed under reduced pressure, the residue was taken up in water, insoluble components were filtered off and the solution was acidified using 10% strength hydrochloric acid and extracted repeatedly with ethyl acetate. The combined organic phases were subsequently washed with water, dried and concentrated. 1.2 g (68% of theory) of 4-[2-chloro-3-(4,4-dimethyl-4,5-dihydrooxazol-2-yl)-4-methylsulfonylbenzoyl]-5-hydroxy-1-methyl-1H-pyrazole were obtained.

(Mp.: 132–135° C.)

Methyl 2-chloro-3-(1,3,4-oxathiazolin-2-on-5-yl)-4-methylsulfonylbenzoate (compound 4.22)

Step a) Methyl 3-aminocarbonyl-2-chloro-4-methylsulfonylbenzoate

Ammonia was introduced into a solution of 15.0 g (48 mmol) of methyl 2-chloro-3-chlorocarbonyl-4-methylsulfonylbenzoate and 300 ml of dry dioxane for 2 hours. The resulting precipitate was filtered off with suction and the filtrate was concentrated. This gave 15.2 g of methyl 3-aminocarbonyl-2-chloro-4-methylsulfonylbenzoate in quantitative yield.

Step b) Methyl 2-chloro-3-(1,3,4-oxathiazolin-2-on-5-yl)-4-methylsulfonylbenzoate 9.80 g (75 mmol) of chlorocarbonylsulfenyl chloride were added dropwise to a solution of 4.37 g (15 mmol) of methyl 3-aminocarbonyl-2-chloro-4-methylsulfonylbenzoate in 150 ml of dry toluene. The mixture was stirred under reflux for 48 hours, and the solvent was then removed under reduced pressure and the residue was chromatographed over silica gel (eluent: ethyl acetate/cyclohexane=1/1). 3.70 g (70% of theory) of methyl 2-chloro-3-(1,3,4-oxathiazolin-2-on-5-yl)-4-methylsulfonylbenzoate were obtained.

4-[2,4-Dichloro-3-(1-methyl-3-methylcarbonyl-1H-pyrazol-5-yl)benzoyl]-1-ethyl-5-hydroxy-1H-pyrazole (compound 3.60)

Step a) Methyl 2,4-dichloro-3-[N-(4-methylphenylsulfonylamino)iminomethyl]benzoate At room temperature, 39.2 g (0.21 mol) of 4-methylphenylsulfonohydrazide were added to 49.0 g (0.21 mol) of methyl 2,4-dichloro-3-formylbenzoate in 600 ml of methanol, and the mixture was stirred for 48 hours. The precipitate that had formed was filtered off with suction and the filtrate was concentrated. The combined precipitates were chromatographed over silica gel (eluent: cyclohexane/ethyl acetate=7/3). 76.8 g (91% of theory) of methyl 2,4-dichloro-3-[N-(4-methylphenylsulfonylamino)iminomethyl]benzoate were obtained.

Step b) 2-Hydroxyethyl 2,4-dichloro-3-(3-methylcarbonyl-1H-pyrazol-5-yl)benzoate At −10° C. and under an atmosphere of protective gas, 250 ml of ethylene glycol were added to 1.5 g (62.3 mmol) of sodium hydride. The mixture was warmed to room temperature, 12.5 g (31.2 mmol) of methyl 2,4-dichloro-3-[N-(4-methylphenylsulfonylamino)iminomethyl]benzoate were added and the mixture was heated at 85° C. for 15 minutes. After cooling, the diazo compound was extracted with diethyl ether or ethyl acetate, the combined organic phases were washed with 10% strength aqueous sodium hydroxide solution and water and dried and a large part of the solvent was removed. 4.7 g (68.6 mmol) of 3-butyn-2-one were subsequently added and the mixture was heated at 80° C. for 2.5 hours. The mixture was stirred at room temperature for 48 hours and then washed with water, dried and concentrated. The residue was chromatographed over silica gel (eluent: cyclohexane/ethyl acetate=1/1). 5.75 g (54% of theory) of 2-hydroxyethyl 2,4-dichloro-3-(3-methylcarbonyl-1H-pyrazol-5-yl)benzoate were obtained.

Step c) 2,4-Dichloro-3-(3-methylcarbonyl-1H-pyrazol-5-yl)benzoic acid 1.11 g (27.7 mmol) of sodium hydroxide in 20 ml of water were added to 3.80 g (11.1 mmol) of 2-hydroxyethyl 2,4-dichloro-3-(3-methylcarbonyl-1H-pyrazol-5-yl)benzoate in 40 ml of methanol, and the mixture was stirred under reflux for 3 hours. The organic solvent was subsequently removed and the residue was taken up in water and washed with methyl tert-butyl ether. The aqueous phase was then acidified (pH=1) using 10% strength hydrochloric acid and extracted with ethyl acetate. The organic phase was then dried and concentrated. 2.10 g (62% of theory) of 2,4-dichloro-3-(3-methylcarbonyl-1H-pyrazol-5-yl)benzoate were obtained.

(Mp.: 196–198°)

Step d) 2,4-Dichloro-3-(1-methyl-3-methylcarbonyl-1H-pyrazol-5-yl)benzoic acid

At room temperature and under protective gas, 2.0 g (6.7 mmol) of 2,4-dichloro-3-(5-methylcarbonyl-1H-pyrazol-3-yl)benzoic acid in 50 ml of tetrahydrofuran were added dropwise to 0.40 g (16.7 mmol) of sodium hydride. The mixture was stirred for 1 hour, 4.8 g (33.4 mmol) of methyl iodide were added, the mixture was stirred for 10 hours and another 4.8 g (33.4 mmol) of methyl iodide were added, the mixture was stirred at 50° C. for 5 hours and 0.16 g (6.7 mmol) of sodium hydride and another 4.8 g (33.4 mmol) of methyl iodide were then added and the mixture was heated at 50° C. for 1 hour. After cooling, the reaction mixture was stirred into 100 ml of a sodium chloride solution and a pH of 1 was adjusted using hydrochloric acid. The product was then extracted with methyl tert-butyl ether and the combined organic phases were washed with water, dried and concentrated. The residue was then chromatographed over silica gel (eluent: toluene/tetrahydrofuran/acetic acid=8/1/1). 1.25 g (60% of theory) of 2,4-dichloro-3-(1-methyl-3-methylcarbonyl-1H-pyrazol-5-yl)benzoic acid were obtained.

(Mp.: 200–203°)

Step e) (1-Ethylpyrazol-5-yl) 2,4-dichloro-3-(1-methyl-3-methylcarbonyl-1H-pyrazol-5-yl)benzoate 0.21 g (1.9 mmol) of 1-ethyl-5-hydroxy-1H-pyrazole and 0.39 g (1.9 mmol) of N,N-dicyclohexylcarbodiimide were added to 0.59 g (1.9 mmol) of 2,4-dichloro-3-(1-methyl-3-methylcarbonyl-1H-pyrazol-5-yl)benzoic acid in 8 ml of acetonitrile. The mixture was stirred at room temperature for 12 hours and 25 ml of 5% strength sodium carbonate solution and 50 ml of ethyl acetate were added, insoluble components were filtered off and the organic phase was separated off, dried and concentrated. The residue was subsequently chromatographed over silica gel (eluent: ethyl acetate:cyclohexane=1:1). 0.21 g (27% of theory) of (1-ethylpyrazol-5-yl) 2,4-dichloro-3-(1-methyl-3-methylcarbonyl-1H-pyrazol-5-yl)benzoate was obtained.

Step f) 4-(2,4-Dichloro-3-(1-methyl-3-methylcarbonyl-1H-pyrazol-5-yl)benzoyl]-1-ethyl-5-hydroxy-1H-pyrazole 0.076 g (0.6 mmol) of potassium carbonate was added to 0.16 g (0.4 mmol) of (1-ethylpyrazol-5-yl) 2,4-dichloro-3-(1-methyl-3-methylcarbonyl-1H-pyrazol-5-yl)benzoate in 3 ml of dioxane and the mixture was heated under reflux for 3 hours and then stirred at room temperature for 12 hours. 50 ml of water were added, the solution was washed with methylene chloride and methyl t-butyl ether, nitrogen was passed through and the pH was adjusted to 1 using 10% strength hydrochloric acid. The precipitate that had formed was filtered off with suction, washed with water and taken up in ethyl acetate. After drying, this organic phase was concentrated. 0.11 g (69% of theory) of 4-[2,4-dichloro-3-(1-methyl-3-methylcarbonyl-1H-pyrazol-5-yl)benzoyl]-1-ethyl-5-hydroxy-1H-pyrazole was obtained.

4-[2,4-Dichloro-3-(3-i-propyl-1,2,4-oxadiazol-5-yl)benzoyl]-5-hydroxy-1-methyl-1H-pyrazole (compound 3.48)

Step a) Methyl 3-[(1-amino-2-methylprop-1-yl)iminooxycarbonyl]-2,4-dichlorobenzoate At room temperature, 9.10 g (90 mmol) of triethylamine in 200 ml of toluene and 7.65 g (75 mmol) of 2-methylpropanecarbohydroximamide in 200 ml of toluene were added successively, dropwise and with stirring, to 20.00 g (75 mmol) of methyl 2,4-dichloro-3-chloroformylbenzoate in 400 ml of toluene. After 48 hours of stirring at room temperature, the mixture was concentrated and the residue was taken up in 400 ml of 2.5% strength potassium carbonate solution and extracted five times with 400 ml of ethyl acetate each time. The combined organic phases were dried and concentrated. 21.70 g (89% of theory) of methyl 3-[(1-amino-2-methylprop-1-yl)iminooxycarbonyl]-2,4-dichlorobenzoate were obtained.

(Mp.: 154–157° C.)

Step b) Methyl 2,4-dichloro-3-(3-i-propyl-1,2,4-oxadiazol-5-yl)benzoate 19.4 g (58 mmol) of methyl 3-[(1-amino-2-methylprop-1-yl)iminooxycarbonyl]-2,4-dichlorobenzoate were heated under reflux in 500 ml of acetic acid until the reaction had gone to completion. The mixture was subsequently concentrated and the residue was taken up in 300 ml of 5% strength potassium carbonate solution and extracted repeatedly with methylene chloride. The combined organic phases were dried and concentrated. 13.5 g (74% of theory) of methyl 2,4-dichloro-3-(3-i-propyl-1,2,4-oxadiazol-5-yl)benzoate were obtained in the form of a brown oil.

Step c) 2,4-Dichloro-3-(3-i-propyl-1,2,4-oxadiazol-5-yl) benzoic acid 2.06 g (51.5 mmol) of sodium hydroxide in 150 ml of methanol were added dropwise to 13.50 g (42.9 mmol) of methyl 2,4-dichloro-3-(3-i-propyl-1,2,4-oxadiazol-5-yl) benzoate in 330 ml of methanol. The mixture was stirred at room temperature for 12 hours and a further 0.52 g (12.9 mmol) of sodium hydroxide were added. The mixture was subsequently stirred at room temperature for a further 48 hours and the solvent was then removed. The residue was taken up in 200 ml of 5% strength potassium carbonate solution and washed once with ethyl acetate and twice with methylene chloride. The aqueous phase that remained was then acidified (pH=2) using hydrochloric acid and extracted repeatedly with methylene chloride. The combined organic phases were dried and concentrated. 7.20 g (56% of theory) of 2,4-dichloro-3-(3-i-propyl-1,2,4-oxadiazol-5-yl)benzoic acid were obtained.

(Mp.: 104–107° C.)

Step d) 2,4-Dichloro-3-(3-i-propyl-1,2,4-oxadiazol-5-yl) benzoyl chloride

At room temperature, 1.18 g (9.9 mmol) of thionyl chloride were added dropwise to 2.00 g (6.6 mmol) of 2,4-dichloro-3-(3-i-propyl-1,2,4-oxadiazol-5-yl)benzoic acid in 35 ml of toluene. The mixture was subsequently slowly heated to reflux temperature, and this temperature was maintained for 8 hours. The mixture was then stirred at room temperature for 12 hours, the insoluble components were filtered off and the mixture was concentrated. The residue that remained was taken up in toluene and the solvent was once more removed. 2.00 g (95% of theory) of 2,4-dichloro-3-(3-i-propyl-1,2,4-oxadizol-5-yl)benzoyl chloride were obtained.

Step e) 4-[2,4-Dichloro-3-(3-i-propyl-1,2,4-oxadiazol-5-yl) benzoyl]-5-hydroxy-1-methyl-1H-pyrazole At 5–10° C., 2.00 g (6.3 mmol) of 2,4-dichloro-3-(3-i-propyl-1,2,4-oxadiazol-5-yl)benzoyl chloride in 10 ml of dimethoxyethane were added dropwise to 0.62 g (6.3 mmol) of 5-hydroxy-1-methyl-1H-pyrazole and 1.74 g (12.6 mmol) of potassium carbonate in 20 ml of dimethoxyethane. After 2.5 hours of stirring at room temperature, the mixture was heated under reflux for 2 hours and then once more stirred at room temperature for 12 hours. The reaction mixture was then taken up in water and washed with methylene chloride or toluene; the aqueous phase that remained was adjusted to pH=3 using hydrochloric acid and the precipitate that had formed was filtered off with suction and dried. 1.90 g (79% of theory) of 4-[2,4-dichloro-3-(3-i-propyl-1,2,4-oxadiazol-5-yl)benzoyl]-5-hydroxy-1-methyl-1H-pyrazole were obtained.

(Mp.: 138–144° C.)

2-Chloro-4-methylsulfonyl-3-(1,3,4-oxadiazol-2-yl) benzoic acid (compound 4.53)

Step a) Methyl 2-chloro-3-hydrazinocarbonyl-4-methylsulfonylbenzoate

At room temperature, 3.11 g (10 mmol) of methyl 2-chloro-3-chloroformyl-4-methylsulfonylbenzoate in 50 ml of methylene chloride were added dropwise to 1.0 g (20 mmol) of hydrazine hydrate in 30 ml of methylene chloride. The reaction mixture was stirred at room temperature for 1 hour and then washed with water, dried and concentrated. 1.2 g (39% of theory) of methyl 2-chloro-3-hydrazinocarbonyl-4-methylsulfonylbenzoate were obtained.

(Mp.: 85–95° C.)

Step b) Methyl 2-chloro-4-methylsulfonyl-3-(1,3,4-oxadiazol-2-yl)benzoate 1.16 g (3.8 mmol) of methyl 2-chloro-3-hydrazinocarbonyl-4-methylsulfonylbenzoate and 10 ml of triethyl orthoformate were heated under reflux for 6 hours. The precipitate that had formed was filtered off with suction, washed with n-hexane and subsequently taken up in 20 ml of toluene. After the addition of p-toluenesulfonic acid, the mixture was heated at reflux for 3 hours and then cooled, washed with water, dried and concentrated. 0.62 g (52% of thoery) of methyl 2-chloro-4-methylsulfonyl-3-(1,3,4-oxadiazol-2-yl)benzoate was obtained.

Step c) 2-Chloro-4-methylsulfonyl-3-(1,3,4-oxadiazol-2-yl) benzoic acid

At reflux temperature, 1.5 g (4.7 mmol) of methyl 2-chloro-4-methylsulfonyl-3-(1,3,4-oxadiazol-2-yl) benzoate in 50 ml of pyridine were added dropwise to 2.5 g (18.9 mmol) of lithium iodide in 50 ml of pyridine, and the mixture was heated under reflux until the reaction had gone to completion. The mixture was cooled, the solvent was removed, the residue was taken up in water, insoluble components were filtered off and the mixture was acidified using hydrochloric acid and extracted with methylene chloride or ethyl acetate. The combined organic phases were dried and concentrated. 1.2 g (86% of theory) of 2-chloro-4-methylsulfonyl-3-(1,3,4-oxadiazol-2-yl)benzoic acid were obtained.

Methyl 2,4-dichloro-3-(2-oxoeth-1-yl)benzoate

Step a) Methyl 2,4-dichloro-3-(2-methoxyethen-1-yl) benzoate

At 0–5° C., 10.1 g (90 mmol) of potassium t-butoxide in 100 ml of tetrahydrofuran were added dropwise to 14.0 g (60 mmol) of methyl 2,4-dichloro-3-formylbenzoate and 39.2 g (114 mmol) of (methoxymethyl)triphenylphosphonium chloride in 500 ml of tetrahydrofuran. The reaction mixture was stirred for 1 hour and then diluted with water, extracted with methyl t-butyl ether and stirred with diethyl ether. The insoluble components were subsequently separated off, the filtrate was concentrated and the residue was chromatographed over silica gel (eluent: cyclohexane:ethyl acetate= 9:1). 12.2 g (78% of theory) of methyl 2,4-dichloro-3-(2-methoxyethen-1-yl)benzoate.

Step b) Methyl 2,4-dichloro-3-(2-oxoeth-1-yl)benzoate 6 ml of 85% strength phosphoric acid and 6 ml of $H_2O$ were added dropwise to 2.6 g (10 mmol) of methyl 2,4-dichloro-3-(2-methoxyethen-1-yl)benzoate in 80 ml of dioxane. The mixture was heated under reflux for 12 hours and then stirred at room temperature for 12 hours. The solvent was removed and the residue was taken up in ethyl acetate, washed with 10% strength sodium bicarbonate solution, dried and concentrated. The residue was chromatographed over silica gel (eluent: cyclohexane:ethyl acetate=9:1). 1.4 g (57% of theory) of methyl 2,4-dichloro-3-(2-oxoeth-1-yl) benzoate were obtained.

4-[2,4-Dichloro-3-(3-methylisoxazol-5-yl)benzoyl]-5-hydroxy-1-methyl-1H-pyrazole (compound 3.52)

Step a) Methyl 2,4-dichloro-3-(2-oxobut-3-en-4-yl) benzoate

At room temperature, first 14.0 g (125 mmol) of potassium t-butoxide and then, after 30 minutes, 23.3 g (100 mmol) of methyl 2,4-dichloro-3-formylbenzoate in 200 ml of tetrahydrofuran were added to 53.2 g (150 mmol) of (2-oxopropyl)triphenylphosphonium chloride in 300 ml of tetrahydrofuran. The mixture was stirred at room temperature for 4.5 hours and 400 ml of water were then added, the organic phase was separated off and the aqueous phase was extracted with methyl t-butyl ether. The combined organic phases were dried and concentrated and the resulting residue was chromatographed over silica gel (eluent: cyclohexane::ethyl acetate=9:1). 24.0 g (88% of theory) of methyl 2,4-dichloro-3-(2-oxobut-3-en-4-yl)benzoate were obtained.

Step b) Methyl 2,4-dichloro-(2-hydroxyiminobut-3-en-4-yl)benzoate 1.8 g (25.9 mmol) of hydroxylamine hydrochloride and 1.5 g (11.0 mmol) of potassium carbonate were added to 5.0 g (18.3 mmol) of methyl 2,4-dichloro-3-(2-oxobut- 3-en-4-yl)benzoate in 160 ml of ethanol, and the reaction mixture was admixed with water until a clear solution was obtained. The mixture was heated under reflux for 3 hours and then cooled and the reaction mixture was taken up in 400 ml of water and extracted with ethyl acetate. The combined organic phases were dried and the solvent was removed. Methyl 2,4-dichloro-(2-hydroxyiminobut-3-en-4-yl) benzoate was obtained in quantitative yield.

Step c) Methyl 2,4-dichloro-3-(3-methylisoxazol-5-yl)benzoate 4.7 g (55.6 mmol) of sodium bicarbonate in 50 ml of water were added to 4.0 g (13.9 mmol) of methyl 2,4-dichloro-(2-hydroxyiminobut-3-en-4-yl)benzoate in 100 ml of tetrahydrofuran. Under the exclusion of light, 7.9 g (47.8 mmol) of potassium iodide and 3.7 g (14.6 mmol) of iodine in 50 ml of water were then added and the mixture was heated under reflux for 4 hours. The mixture was then cooled and 100 ml of a 24% strength sodium pyrosulfite solution were added a little at a time and the solution was extracted with diethyl ether and concentrated. The residue was subsequently chromatographed over silica gel (eluent: cyclohexane:ethyl acetate=9:1). 2.4 g (60% of theory) of methyl 2,4-dichloro-3-(3-methylisoxazol-5-yl)benzoate were obtained.

Step d) 2,4-Dichloro-3-(3-methylisoxazol-5-yl)benzoic acid 0.35 g (8.8 mmol) of sodium hydroxide in 35 ml of water was added to 2.3 g (8.0 mmol) of methyl 2,4-dichloro-3-(3-methylisoxazol-5-yl)benzoate in a mixture of 50 ml of methanol and 50 ml of tetrahydrofuran. The mixture was stirred at room temperature for 12 hours, the solvent was removed and the residue was taken up in ethyl acetate/water. After phase separation, the organic phase was separated off and the aqueous phase was washed with ethyl acetate. The remaining aqueous phase was acidified and then extracted with ethyl acetate; the resulting organic phase was dried and concentrated. 2.1 g (96% of theory) of 2,4-dichloro-3-(3-methylisoxazol-5-yl)benzoic acid were obtained.

Step e) 2,4-Dichloro-3-(3-methylisoxazol-5-yl)benzoyl chloride 1 drop of dimethylformamide and 1.1 g (9.5 mmol) of thionyl chloride were added to 2.0 g (7.35 mmol) of 2,4-dichloro-3-(3-methylisoxazol-5-yl)benzoic acid in 50 ml of toluene. The mixture was heated under reflux for 2 hours and then cooled, and the solvent was removed.

Step f) 4-[2,4-Dichloro-3-(3-methylisoxazol-5-yl)benzoyl]-5-hydroxy-1-methyl-1H-pyrazole At 0 to 5° C., the 2,4-dichloro-3-(3-methylisoxazol-5-yl)benzoyl chloride obtained above (step e) in 40 ml of dimethoxyethane was added to 0.7 g (7.35 mmol) of 5-hydroxy-1-methyl-1H-pyrazole in 30 ml of dimethoxyethane and 2.0 g (14.7 mmol) of potassium carbonate. The mixture was stirred at room temperature for 3.5 hours, heated under reflux for 1 hour and stirred at room temperature for 12 hours. The precipitate that had formed was filtered off with suction and introduced into 50 ml of water. The mixture is acidified to pH=1 and the solid is filtered off with suction and dried. Likewise, the first-mentioned filtrate was taken up in 400 ml of water, washed with methyl t-butyl ether, adjusted to pH 3 and extracted with methylene chloride. The combined organic phases were dried and concentrated. 1.9 g (73% of theory) of 4-[2,4-dichloro-3-(3-methylisoxazol-5-yl)benzoyl]-5-hydroxy-1-methyl-1H-pyrazole were obtained.

(Mp.: 143–144° C.)

In addition to the compounds described above, other compounds of the formula III or benzoic acid derivatives of the formula VI which have been prepared or are preparable in a similar manner are listed in Tables 3 and 4, respectively, below:

TABLE 3

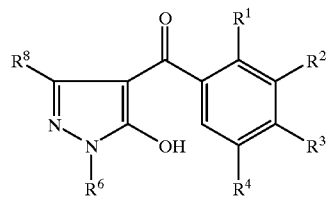

III

| No. | $R^1$ | $R^2$ | $R^3$ | $R^4$ | $R^6$ | $R^8$ | Physical data Mp. [° C.]; $^1$H NMR [δ in ppm] |
|---|---|---|---|---|---|---|---|
| 3.1 | Cl | 4,5-dihydroisoxazol-3-yl | Cl | H | n-$C_4H_9$ | H | 116–117 |
| 3.2 | Cl | 4,5-dihydroisoxazol-3-yl | Cl | H | i-$C_4H_9$ | H | 148–151 |
| 3.3 | Cl | 5-ethoxycarbonyl-4,5-dihydroisoxazol-3-yl | $SO_2CH_3$ | H | $CH_3$ | H | 70–75 |
| 3.4 | Cl | 5-ethoxycarbonyl-4,5-dihydroisoxazol-3-yl | $SO_2CH_3$ | H | $C_2H_5$ | H | 65–70 |
| 3.5 | Cl | 5-methyl-4,5-dihydroisoxazol-3-yl | $SO_2CH_3$ | H | $CH_3$ | H | 230–235 |
| 3.6 | Cl | 5-methyl-4,5-dihydroisoxazol-3-yl | $SO_2CH_3$ | H | $C_2H_5$ | H | 210–215 |
| 3.7 | Cl | 5-methyl-4,5-dihydroisoxazol-3-yl | $SO_2CH_3$ | H | n-$C_3H_7$ | H | 95–100 |
| 3.8 | Cl | 5,5-dimethyl-4,5-dihydroisoxazol-3-yl | $SO_2CH_3$ | H | $CH_3$ | H | 220–225 |
| 3.9 | Cl | 5,5-dimethyl-4,5-dihydroisoxazol-3-yl | $SO_2CH_3$ | H | $C_2H_5$ | H | 82–86 |
| 3.10 | Cl | 5,5-dimethyl-4,5-dihydroisoxazol-3-yl | $SO_2CH_3$ | H | n-$C_3H_7$ | H | 70–75 |

TABLE 3-continued

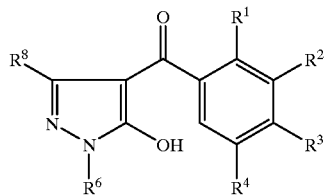

| No. | $R^1$ | $R^2$ | $R^3$ | $R^4$ | $R^6$ | $R^8$ | Physical data Mp. [° C.]; $^1$H NMR [δ in ppm] |
|---|---|---|---|---|---|---|---|
| 3.11 | Cl | 5,5-dimethyl-4,5-dihydroisoxazol-3-yl | $SO_2CH_3$ | H | n-$C_4H_9$ | H | 68–73 |
| 3.12 | Cl | 5,5-dimethyl-4,5-dihydroisoxazol-3-yl | $SO_2CH_3$ | H | i-$C_4H_9$ | H | 45–50 |
| 3.13 | Cl | 5-ethyl-4,5-dihydroisoxazol-3-yl | $SO_2CH_3$ | H | $CH_3$ | H | 220–225 |
| 3.14 | Cl | 5-ethyl-4,5-dihydroisoxazol-3-yl | $SO_2CH_3$ | H | $C_2H_5$ | H | 170–175 |
| 3.15 | Cl | 4,5-dihydroisoxazol-3-yl | $SO_2CH_3$ | H | n-$C_3H_7$ | H | 65–70 |
| 3.16 | Cl | 4,5-dihydroisoxazol-3-yl | $SO_2CH_3$ | H | n-$C_4H_9$ | H | 55–60 |
| 3.17 | Cl | 4,5-dihydroisoxazol-3-yl | $SO_2CH_3$ | H | i-$C_4H_9$ | H | 58–63 |
| 3.18 | Cl | 4,5-dihydroisoxazol-3-yl | Cl | H | n-$C_3H_7$ | H | 119–121 |
| 3.19 | Cl | 4,5-dihydroisoxazol-3-yl | Cl | H | $CH_3$ | $CH_3$ | 115–117 |
| 3.20 | Cl | 4,5-dihydroisoxazol-3-yl | $NO_2$ | H | $C_2H_5$ | H | 217–218 |
| 3.21 | Cl | 4,5-dihydroisoxazol-3-yl | $SO_2CH_3$ | H | $CH_3$ | H | >250 |
| 3.22 | Cl | 4,5-dihydroisoxazol-3-yl | Cl | H | $C_2H_5$ | H | 125–128 |
| 3.23 | Cl | 5,5-dimethyl-4,5-dihydroisoxazol-3-yl | $SO_2C_2H_5$ | H | $CH_3$ | H | >200 |
| 3.24 | Cl | 5-methyl-4,5-dihydroisoxazol-3-yl | $SO_2C_2H_5$ | H | $CH_3$ | H | 220–223 |
| 3.25 | Cl | 5-methyl-4,5-dihydroisoxazol-3-yl | $SO_2C_2H_5$ | H | $C_2H_5$ | H | >230 |
| 3.26 | Cl | 5-methyl-4,5-dihydroisoxazol-3-yl | $SO_2$-n-$C_3H_7$ | H | $CH_3$ | H | 1.12(t); 1.53(d); 1.76(quin); 3.18(dd); 3.38(t); 3.55(dd); 3.73(s); 5.04(m); 5.55(s, br.); 7.37(s); 7.68(d); 8.13(d). |
| 3.27 | Cl | 5-methyl-4,5-dihydroisoxazol-3-yl | $SO_2$-n-$C_3H_7$ | H | $C_2H_5$ | H | 1.07(t); 1.50(m); 1.78(quin); 3.07(dd); 3.39(t); 3.55(dd); 4.12(t); 5.08(m); 7.38(s); 7.69(d); 8.11(d). |
| 3.28 | Cl | 4,5-dihydrooxazol-2-yl | $SO_2CH_3$ | H | $CH_3$ | H | |
| 3.29 a) | Cl | 4,4-dimethyl-4,5-dihydrooxazol-2-yl | $SO_2CH_3$ | H | $CH_3$ | H | 1.33(s); 3.40(s); 4.17(s); 7.43(s); 7.79(d); 8.04(d). |
| 3.30 a) | Cl | 4,4-dimethyl-4,5-dihydrooxazol-2-yl | $SO_2CH_3$ | H | $C_2H_5$ | H | 1.27(t); 1.36(s); 3.4l(q); 4.01(q); 4.18(s); 7.47(s); 7.83(s); 8.07(d). |
| 3.31 | Cl | 3a,5,6,6a-tetrahydro-4H-cyclopent[d]isoxazol-3-yl | $SO_2CH_3$ | H | $CH_3$ | H | 99–104 |
| 3.32 | Cl | 3a,5,6,6a-tetrahydro-4H-cyclopent[d]isoxazol-3-yl | $SO_2CH_3$ | H | $C_2H_5$ | H | 95–100 |
| 3.33 | Cl | 4,5-dihydroisoxazol-5-spirocyclopentan-3-yl | $SO_2CH_3$ | H | $CH_3$ | H | 230–235 |
| 3.34 | Cl | 4,5-dihydroisoxazol-5-spirocyclopentan-3-yl | $SO_2CH_3$ | H | $C_2H_5$ | H | 190–195 |
| 3.35 | Cl | 4,5-dihydroisoxazol-5-spiro-4-tetrahydropyran-3-yl | $SO_2CH_3$ | H | $C_2H_5$ | H | 95–100 |
| 3.36 | Cl | 5,5-dimethyl-4,5-dihydroisoxazol-3-yl | $SO_2C_2H_5$ | H | $CH_3$ | H | >230 |
| 3.37 | Cl | 5,5-dimethyl-4,5-dihydroisoxazol-3-yl | $SO_2C_2H_5$ | H | $C_2H_5$ | H | 198–200 |
| 3.38 | Cl | 4,5-dihydroisoxazol-3-yl | $SO_2C_2H_5$ | H | $CH_3$ | H | 215–218 |
| 3.39 | Cl | 4,5-dihydroisoxazol-3-yl | $SO_2C_2H_5$ | H | $C_2H_5$ | H | 213–215 |
| 3.40 | Cl | 4,5-dihydroisoxazol-3-yl | $SO_2$-n-$C_3H_7$ | H | $CH_3$ | H | 186–190 |
| 3.41 | Cl | 4,5-dihydroisoxazol-3-yl | $SO_2$-n-$C_3H_7$ | H | $C_2H_5$ | H | 84–86 |
| 3.42 | Cl | 4,5-dihydroisoxazol-5-spiro-4-tetrahydropyran-3-yl | $SO_2CH_3$ | H | $CH_3$ | H | 90–95 |
| 3.43 | Cl | 5,5-diethyl-4,5-dihydroisoxazol-3-yl | $SO_2CH_3$ | H | $CH_3$ | H | 70–75 |
| 3.44 | Cl | 5,5-diethyl-4,5-dihydroisoxazol-3-yl | $SO_2CH_3$ | H | $C_2H_5$ | H | 50–55 |
| 3.45 | $CH_3$ | 4,5-dihydrothiazol-2-yl | H | H | $C_2H_5$ | H | 1.44(t); 2.50(s); 3.49(t); 4.09(q); 4.53(t); 7.35(m); 7.48(d); 7.62(d). |
| 3.46 | Cl | 1,3-dithiolan-2-yl | Cl | H | $C_2H_5$ | H | 1.46(t); 3.28(m); 3.67(m); 4.10(q); 6.80(s); 7.24(d); 7.36(s); 7.36(d) |
| 3.47 | Cl | 5,5-dimethyl-1,3-dioxan-2-yl | Cl | H | $C_2H_5$ | H | 147–152 |
| 3.48 | Cl | 3-isopropyl-1,2,4-oxadiazol-5-yl | Cl | H | $CH_3$ | H | 138–144 |
| 3.49 | Cl | 3-isopropyl-1,2,4-oxadiazol-5-yl | Cl | H | $C_2H_5$ | H | 106–109 |
| 3.50 | $CH_3$ | 4-phenylthiazol-2-yl | H | H | $C_2H_5$ | H | 93–97 |
| 3.51 | $CH_3$ | 4-methylthiazol-2-yl | H | H | $C_2H_5$ | H | 1.48(t); 2.53(5); 4.09(q); 7.00(s); 7.40(m); 7.50(d); 7.75(d) |
| 3.52 | Cl | 3-methylisoxazol-5-yl | Cl | H | $CH_3$ | H | 143–144 |
| 3.53 | Cl | 3-methylisoxazol-5-yl | $SO_2CH_3$ | H | $CH_3$ | H | 102–108 |
| 3.54 | $CH_3$ | 5,6-dihydro-4H-1,3-thiazin-2-yl | H | H | $C_2H_5$ | H | 156–157 |
| 3.55 | Cl | 1,3-dithiolan-2-yl | Cl | H | $CH_3$ | H | 64–67 |
| 3.56 | Cl | 4-tert-butylthiazol-2-yl | $SO_2CH_3$ | H | $C_2H_5$ | H | 1.40(s); 1.48(t); 3.28(s); 4.09(q); 7.27(s); 7.40(s); 7.71(d); 8.28(d) |
| 3.57 | Cl | 2-thiazolyl | Cl | H | $C_2H_5$ | H | 1.39(t); 3.96(q); 7.39(m); 7.60(d); 8.01(d) |

TABLE 3-continued

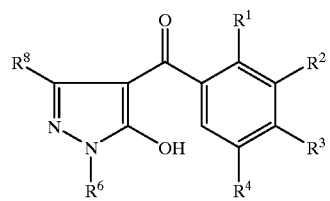

III

| No. | R¹ | R² | R³ | R⁴ | R⁶ | R⁸ | Physical data Mp. [° C.]; ¹H NMR [δ in ppm] |
|---|---|---|---|---|---|---|---|
| 3.58 | Cl | 3-tert-butylisoxazol-4-yl | Cl | H | CH₃ | H | 1.4(s); 3.7(s); 6.4(s); 7.4(s); 7.5(d); 7.6(d) |
| 3.59 | Cl | 5,5-dimethyl-1,3-dioxan-2-yl | SO₂CH₃ | H | C₂H₅ | H | 225–229 |
| 3.60 | Cl | 3-acetyl-1-methylpyrazol-5-yl | Cl | H | C₂H₅ | H | 1.26(t); 2.52(s); 3.17(s); 3.93(q); 6.87(s); 7.50 (s); 7.63(d); 7.80(d) |
| 3.61 | Cl | 5-methoxyethylisoxazol-3-yl | SO₂CH₃ | H | CH₃ | H | 80–85 |
| 3.62 | Cl | 5-methoxyethylisoxazol-3-yl | SO₂CH₃ | H | C₂H₅ | H | 170–175 |
| 3.63 | Cl | 4,5-dimethylisoxazol-3-yl | SO₂CH₃ | H | CH₃ | H | 95–100 |
| 3.64 | Cl | 5-(n-propyl)isoxazol-3-yl | SO₂CH₃ | H | CH₃ | H | 65–70 |
| 3.65 | Cl | 5-(t-butyl)isoxazol-3-yl | SO₂CH₃ | H | CH₃ | H | 225–230 |
| 3.66 | Cl | 5-(t-butyl)isoxazol-3-yl | SO₂CH₃ | H | C₂H₅ | H | 70–75 |
| 3.67 | Cl | 4,5-diethylisoxazol-3-yl | SO₂CH₃ | H | CH₃ | H | 125–130 |
| 3.68 | Cl | 4,5-diethylisoxazol-3-yl | SO₂CH₃ | H | C₂H₅ | H | 70–75 |
| 3.69 | Cl | 5-(n-propyl)isoxazol-3-yl | SO₂CH₃ | H | C₂H₅ | H | 60–65 |
| 3.70 | Cl | 4,5-dimethylisoxazol-3-yl | SO₂CH₃ | H | C₂H₅ | H | 75–80 |
| 3.71 | Cl | 5-chloromethylisoxazol-3-yl | SO₂CH₃ | H | C₂H₅ | H | 55–60 |
| 3.72 | Cl | 5-ethoxyisoxazol-3-yl | SO₂CH₃ | H | CH₃ | H | 80–85 |
| 3.73 | Cl | 5-ethoxyisoxazol-3-yl | SO₂CH₃ | H | CH₃ | H | 70–75 |
| 3.74 | Cl | 5-methylisoxazol-3-yl | SO₂CH₃ | H | C₂H₅ | H | 232–234 |
| 3.75 | Cl | 5-(2-methylpropyl)isoxazol-3-yl | SO₂CH₃ | H | C₂H₅ | H | 0.95(d); 1.28(t); 2.04(m); 2.73(d); 3.31(s); 3.91(q); 6.54(s); 7.50(s); 7.82(d); 8.14(d) |
| 3.76 | Cl | 5-(2-methylpropyl)isoxazol-3-yl | SO₂CH₃ | H | CH₃ | H | 0.94(d); 2.03(m); 2.73(d); 3.30(s); 3.52(s); 6.52(s); 7.47(s); 7.81(d); 8.13(d) |
| 3.77 | Cl | 5-methylisoxazol-3-yl | SO₂CH₃ | H | CH₃ | H | 190–194 | a)Prepared from 2-chloro-3-(1'-chloro-2',2'-dimethylethylaminocarbonyl)-4-methylsulfonylbenzoyl chloride using two equivalents of potassium carbonate

TABLE 4

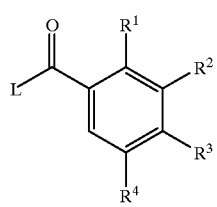

VI

| No. | R¹ | R² | R³ | R⁴ | L | Physical data Mp. [° C.]; ¹H NMR [δ in ppm] |
|---|---|---|---|---|---|---|
| 4.1 | Cl | 4,5-dihydroisoxazol-3-yl | Cl | H | OCH₃ | 3.29(t); 3.91(s); 4.58(t); 7.46(d); 7.83(d). |
| 4.2 | Cl | 4,5-dihydroisoxazol-3-yl | Cl | H | OH | 3.28(t); 4.60(t); 7.02(s, br); 7.46(d); 7.98(d). |
| 4.3 | Cl | 4,5-dihydroisoxazol-3-yl | SO₂CH₃ | H | OCH₃ | 3.24(s); 3.42(t); 3.99(s); 4.60(t); 7.96(d); 8.10(d). |
| 4.4 | Cl | 4,5-dihydroisoxazol-3-yl | SO₂CH₃ | H | OH | 3.26(s); 3.45(t); 4.63(t); 8.15(s); 8.53(s, br). |
| 4.5 | Cl | 4,5-dihydroisoxazol-3-yl | SO₂CH₃ | H | Cl | 3.25(s); 3.46(t); 4.62(t); 8.21(dd). |
| 4.6 | Cl | 4,4-dimethyl-4,5-dihydrooxazol-2-yl | Cl | H | OH | 1.31(s); 4.16(s); 7.69(d); 7.90(d); 13.8(s, br). |
| 4.7 | Cl | 5,5-dimethyl-4,5-dihydroisoxazol-3-yl | SO₂C₂H₅ | H | OCH₃ | 1.25(t); 1.57(s); 3.21(s); 3.42(q); 3.99(s); 7.94(d); 8.07(d). |
| 4.8 | Cl | 5,5-dimethyl-4,5-dihydroisoxazol-3-yl | SO₂C₂H₅ | H | OH | 1.13(t); 1.47(s); 3.15(s); 3.43(q); 8.06(s); 13.8(s, br). |
| 4.9 | Cl | 4,5-dihydroisoxazol-3-yl | SO₂C₂H₅ | H | OCH₃ | 1.28(t); 3.41(m); 4.02(s); 4.62(t); 7.95(d); 8.06(d). |
| 4.10 | Cl | 4,5-dihydroisoxazol-3-yl | SO₂C₂H₅ | H | OH | 137–140 |
| 4.11 | Cl | 5-methyl-4,5-dihydroisoxazol-3-yl | SO₂C₂H₅ | H | OCH₃ | 1.26(t); 1.53(s); 3.06(dd); 3.42(q); 3.49(dd); 5.05(m); 7.95(d); 8.07(d). |
| 4.12 | Cl | 5-methyl-4,5-dihydroisoxazol-3-yl | SO₂C₂H₅ | H | OH | 140–143 |
| 4.13 | Cl | 4,5-dihydrooxazol-2-yl | SO₂CH₃ | H | OCH₃ | 3.30(s); 3.98(s); 4.11(t); 4.55(t); 7.97(d); |

TABLE 4-continued

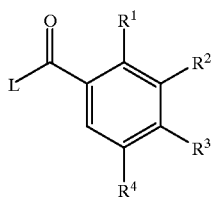

VI

| No. | R¹ | R² | R³ | R⁴ | L | Physical data Mp. [° C.]; ¹H NMR [δ in ppm] |
|---|---|---|---|---|---|---|
| | | | | | | 8.08(d). |
| 4.14 | Cl | 4,5-dihydrooxazol-2-yl | $SO_2CH_3$ | H | OH | 3.38(s); 4.00(t); 4.46(t); 8.08(s). |
| 4.15 | Cl | 4,5-dihydroisoxazol-3-yl | $SO_2CH_3$ | H | OH | 3.30(s); 3.35(t); 4.15(s, br); 4.50(t); 8.05(s). |
| 4.16 | Cl | 5,5-dimethyl-4,5-dihydroisoxazol-3-yl | $SO_2$-n-$C_3H_7$ | H | $OCH_3$ | 0.95(t); 1.47(s); 1.58(quin); 3.12(s); 3.31(s); 3.43(t); 3.93(s); 8.09(dd). |
| 4.17 | Cl | 5,5-dimethyl-4,5-dihydroisoxazol-3-yl | $SO_2$-n-$C_3H_7$ | H | OH | 0.93(t); 1.47(s); 1.58(quin); 3.15(s); 3.42(t); 8.05(s). |
| 4.18 | Cl | 4,5-dihydroisoxazol-3-yl | $SO_2$-n-$C_3H_7$ | H | $OCH_3$ | 0.92(t); 1.55(quin); 3.39(m); 3.93(s); 4.50(t); 8.08(dd). |
| 4.19 | Cl | 4,5-dihydroisoxazol-3-yl | $SO_2$-n-$C_3H_7$ | H | OH | 148–150 |
| 4.20 | Cl | 5-methyl-4,5-dihydroisoxazol-3-yl | $SO_2$-n-$C_3H_7$ | H | $OCH_3$ | 0.93(t); 1.49(d); 1.58(quin); 2.94(dd); 3.42(m); 3.93(s); 4.97(m); 8.10(dd). |
| 4.21 | Cl | 5-methyl-4,5-dihydroisoxazol-3-yl | $SO_2$-n-$C_3H_7$ | H | OH | 0.94(t); 1.39(d); 1.58(quin); 2.96(dd); 3.50(m); 4.95(m); 8.05(s). |
| 4.22 | Cl | 1,3,4-oxathiazolin-2-on-5-yl | $SO_2CH_3$ | H | $OCH_3$ | 3.24(s); 4.02(s); 8.14(dd). |
| 4.23 | Cl | 5-ethoxycarbonyl-4,5-dihydroisoxazol-3-yl | $SO_2CH_3$ | H | $OCH_3$ | 118–121 |
| 4.24 | Cl | 5-ethoxycarbonyl-4,5-dihydroisoxazol-3-yl | $SO_2CH_3$ | H | OH | |
| 4.25 | Cl | 5-methyl-4,5-dihydroisoxazol-3-yl | $SO_2CH_3$ | H | $OCH_3$ | 130–135 |
| 4.26 | Cl | 5-methyl-4,5-dihydroisoxazol-3-yl | $SO_2CH_3$ | H | OH | 173–178 |
| 4.27 | Cl | 5,5-dimethyl-4,5-dihydroisoxazol-3-yl | $SO_2CH_3$ | H | $OCH_3$ | 1.57(s); 3.18(s); 3.27(s); 4.01(s); 7.97(d); 8.12(d). |
| 4.28 | Cl | 5,5-dimethyl-4,5-dihydroisoxazol-3-yl | $SO_2CH_3$ | H | OH | 1.48(s); 3.15(s); 3.34(s); 8.08(dd). |
| 4.29 | Cl | 5-ethyl-4,5-dihydroisoxazol-3-yl | $SO_2CH_3$ | H | $OCH_3$ | 0.97(t); 1.72(m); 3.10(dd); 3.32(s); 3.37(dd); 4.72(m); 8.08(dd). |
| 4.30 | Cl | 3a,5,6,6a-tetrahydro-4H-cyclopent[d]isoxazol-3-yl | $SO_2CH_3$ | H | $OCH_3$ | 1.57(m); 1.81(m); 2.21(m); 3.20(s); 4.02(s); 4.32(t); 5.35(dd); 7.92(d); 8.18(d). |
| 4.31 | Cl | 3a,5,6,6a-tetrahydro-4H-cyclopent[d]isoxazol-3-yl | $SO_2CH_3$ | H | OH | 1.72(m); 2.01(m); 3.27(s); 4.24(t); 5.23(dd); 8.05(d); 8.15(d); 13.8(s, br). |
| 4.32 | Cl | 4,5-dihydroisoxazol-5-spiro-4-tetrahydropyran-3-yl | $SO_2CH_3$ | H | $OCH_3$ | 2.00(m); 3.23(s); 3.27(s); 3.72(m); 4.00(s); 7.96(d);8.04(d). |
| 4.33 | Cl | 4,5-dihydroisoxazol-5-spiro-4-tetrahydropyran-3-yl | $SO_2CH_3$ | H | OH | 78–83 |
| 4.34 | Cl | 4,5-dihydroisoxazol-5-spiro-cyclopentan-3-yl | $SO_2CH_3$ | H | $OCH_3$ | 1.78(m); 2.24(m); 3.27(s); 3.36(s); 3.98(s); 7.94(d); 8.12(d). |
| 4.35 | Cl | 4,5-dihydroisoxazol-5-spiro-cyclopentan-3-yl | $SO_2CH_3$ | H | OH | 1.76(m); 2.05(m); 3.30(s); 3.33(s); 8.09(dd). |
| 4.36 | Cl | 5,5-diethyl-4,5-dihydroisoxazol-3-yl | $SO_2CH_3$ | H | $OCH_3$ | 1.00(t); 1.85(m); 3.13(s); 3.27(s); 3.98(s); 7.94(d); 8.11(d). |
| 4.37 | Cl | 5,5-diethyl-4,5-dihydroisoxazol-3-yl | $SO_2CH_3$ | H | OH | 0.91(t); 1.76(m); 3.12(s); 3.33(s); 8.07(dd); 13.75(s, br). |
| 4.38 | Cl | 4,4-dimethyl-4,5-dihydrooxazol-2-yl | $SO_2CH_3$ | H | OH | 1.34(s); 3.40(s); 4.13(s); 8.07.(s); 13.95(s, br). |
| 4.39 | Cl | 5-methyl-4;5-dihydroisoxazol-3-yl | $SO_2CH_3$ | H | Cl | |
| 4.40 | $CH_3$ | 4,5-dihydrothiazol-2-yl | H | H | $OCH_3$ | 2.62(s); 3.48(t); 3.90(s); 4.51(t); 7.28(t); 7.57(d); 7.96(d) |
| 4.41 | $CH_3$ | 4,5-dihydrothiazol-2-yl | H | H | OH | 2.50(s); 3.50(t); 4.44(t); 7.27(t); 7.54(d); 7.79(d) |
| 4.42 | Cl | 1,3-dithiolan-2-yl | Cl | H | $OCH_3$ | 3.44(m); 3.68(m); 3.93(s); 6.80(s); 7.38(d); 7.52(d) |
| 4.43 | Cl | 1,3-dithiolan-2-yl | Cl | H | OH | 195–198 |
| 4.44 | Cl | 5,5-dimethyl-1,3-dioxan-2-yl | Cl | H | $OCH_3$ | 0.83(s); 1.42(s); 3.68(d); 3.83(d); 3.91(s); 6.19(s); 7.38(d); 7.58(d) |
| 4.45 | Cl | 5,5-dimethyl-1,3-dioxan-2-yl | Cl | H | OH | 150–152 |
| 4.46 | Cl | 5-(cyclopropyl)isoxazol-3-yl | $SO_2CH_3$ | H | OH | 1.14(4H); 2.12(1;H); 3.19(3H); 6.12(1H); 8.07(1H); 8.16(1H) |
| 4.47 | Cl | 5-trifluoromethylisoxazol-3-yl | $SO_2CH_3$ | H | $OCH_3$ | 3.22(3H); 4.01(3H); 6.92(1H); 8.07(1H); 8.20(1H) |
| 4.48 | Cl | 1,2,4-oxadiazol-3-yl | $SO_2CH_3$ | H | $OCH_3$ | 122–127 |
| 4.49 | Cl | 5-(n-propyl)isoxazol-3-yl | $SO_2CH_3$ | H | $OCH_3$ | 1.05(3H); 1.83(2H); 2.86(2H); 3.23(3H); 3.96(3H); 6.20(1H); 7.96(1H); 8.20(1H) |
| 4.50 | Cl | 5-(n-propyl)isoxazol-3-yl | $SO_2CH_3$ | H | OH | 0.95(3H); 1.72(2H); 2.82(2H); 3.30(3H); 6.54(1H); 8.09(1H); 8.15(1H) |
| 4.51 | Cl | 5-(t-butyl)isoxazol-3-yl | $SO_2CH_3$ | H | $OCH_3$ | 115–120 |
| 4.52 | Cl | 5-(t-butyl)isoxazol-3-yl | $SO_2CH_3$ | H | OH | 160–165 |
| 4.53 | Cl | 1,3,4-oxadiazol-2-yl | $SO_2CH_3$ | H | OH | 3.37(s); 8.22(d); 8.30(d); 9.62(s) |

TABLE 4-continued

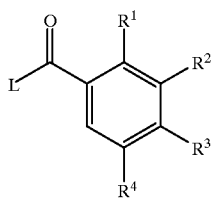

VI

| No. | R¹ | R² | R³ | R⁴ | L | Physical data Mp. [° C.]; ¹H NMR [δ in ppm] |
|---|---|---|---|---|---|---|
| 4.54 | Cl | 3-isopropyl-1,2,4-oxadiazol-5-yl | Cl | H | OCH₃ | 1.42(6H); 3.25(1H); 3.94(3H), 7.52(1H); 7.99(1H) |
| 4.55 | Cl | 3-isopropyl-1,2,4-oxadiazol-5-yl | Cl | H | OH | 104–107 |
| 4.56 | Cl | oxazol-2-yl | SO₂CH₃ | H | OCH₃ | 177 |
| 4.57 | Cl | 5-methoxymethylisoxazol-3-yl | SO₂CH₃ | H | OCH₃ | 3.21(3H); 3.47(3H); 3.98(3H); 4.69(2H); 6.49(1H); 7.99(1H); 8.20(1H) |
| 4.58 | Cl | 5-methoxymethylisoxazol-3-yl | SO₂CH₃ | H | OH | 3.30(3H); 3.37(3H); 4.66(2H); 6.83(1H); 8.13(1H); 8.18(1H) |
| 4.59 | Cl | 5-(2-hydroxyeth-1-yl)isoxazol-3-yl | SO₂CH₃ | H | OCH₃ | 2.36(1H); 3.10(2H); 3.24(3H); 3.99(5H); 6.32(1H); 7.98(1H); 8.16(1H) |
| 4.60 | Cl | 1,3,4-oxadiazol-2-yl | SO₂CH₃ | H | OCH₃ | 3.29(3H); 4.01(3H); 8.20(2H); 8.69(1H) |
| 4.61 | Cl | 5-methyl-1,3,4-oxadiazol-2-yl | SO₂CH₃ | H | OCH₃ | 2.63(3H); 3.49(3H); 4.95(3H); 8.25(1H); 8.32(1H) |
| 4.62 | Cl | 5-methylisoxazol-3-yl | SO₂CH₃ | H | OCH₃ | 127 |
| 4.63 | Cl | 5-methylisoxazol-3-yl | SO₂CH₃ | H | OH | 148–150 |
| 4.64 | Cl | 4,5-dimethylisoxazol-3-yl | SO₂CH₃ | H | OCH₃ | 120–125 |
| 4.65 | Cl | 4,5-dimethylisoxazol-3-yl | SO₂CH₃ | H | OH | 85–90 |
| 4.66 | Cl | 4,5-diethylisoxazol-3-yl | SO₂CH₃ | H | OCH₃ | 90–95 |
| 4.67 | Cl | 4,5-diethylisoxazol-3-yl | SO₂CH₃ | H | OH | 0.90(3H); 1.26(3H); 2.20(2H); 2.83(2H); 3.30(3H); 8.12(1H); 8.18(1H) |
| 4.68 | Cl | 5-(cyclopropyl)isoxazol-3-yl | SO₂CH₃ | H | OCH₃ | 1.10(4H); 2.15(1H); 3.22(3H); 3.98(3H); 6.12(1H); 7.95(1H); 8.18(1H) |
| 4.69 | Cl | 5-methyl-1,2,4-oxadiazol-3-yl | SO₂CH₃ | H | OCH₃ | 102–107 |
| 4.70 | Cl | 5,6-dihydro-4-H-1,3-thiazin-2-yl | H | H | OCH₃ | 184–188 |
| 4.71 | Cl | 4,5-dihydrothiazol-2-yl | SO₂CH₃ | H | OH | 3.31(s); 3.60(t); 4.38(t); 8.04(d); 8.10(d) |
| 4.72 | Cl | 5-hydroxymethylisoxazol-3-yl | SO₂CH₃ | H | OCH₃ | 50–53 |
| 4.73 | Cl | 5-hydroxymethylisoxazol-3-yl | SO₂CH₃ | H | OH | 65–66 |
| 4.74 | Cl | 5-(2-methylpropyl)isoxazol-3-yl | SO₂CH₃ | H | OCH₃ | 1.01(d); 2.13(sept); 2.75(d); 3.24(s); 3.99(s); 6.19(d); 7.97(d); 8.20(d) |
| 4.75 | Cl | 5-(2-methylpropyl)isoxazol-3-yl | SO₂CH₃ | H | OH | 0.96(d); 2.03(sept); 2.74(d); 3.29(s); 6.53(s); 8.08(d); 8.13(d) |
| 4.76 | Cl | 5-(N,N-dimethylaminomethyl)isoxazol-3-yl | SO₂CH₃ | H | OCH₃ | 2.37(s); 3.23(s); 4.00(s); 6.40(s); 7.98(d); 8.18(d) |
| 4.77 | Cl | 5-chloromethylisoxazol-3-yl | SO₂CH₃ | H | OH | 3.30(s); 3.36(s); 4.66(s); 5.06(s); 6.82(s); 6.93(s); 8.10(d); 8.16(s) |
| 4.78 | Cl | 5-ethoxyisoxazol-3-yl | SO₂CH₃ | H | OH | 1.39(t); 3.33(s); 4.33(q); 5.95(s); 8.07(d); 8.16(d) |
| 4.79 | Cl | 5-methylcarbonylisoxazol-3-yl | SO₂CH₃ | H | OH | 2.65(s); 3.30(s); 7.71(s); 8.17(d); 8.20(d) |
| 4.80 | Cl | 5-methylcarbonylisoxazol-3-yl | SO₂CH₃ | H | OCH₃ | 145–150 |
| 4.81 | Cl | 5-ethoxyisoxazol-3-yl | SO₂CH₃ | H | OCH₃ | 1.50(t); 3.28(s); 3.98(s); 4.36(q); 5.43(s); 7.95(d); 8.16(d) |
| 4.82 | Cl | 5-chloromethylisoxazol-3-yl | SO₂CH₃ | H | OCH₃ | 115–120 |

The 4-(3-heterocyclyl-1-benzoyl)pyrazoles of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and grass weeds in crops such as wheat, rice, maize, soy and cotton without causing any significant damage to the crop plants. This effect is mainly observed at low rates of application.

Depending on the application method used, the compounds of the formula I, or the compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also ighly concentrated aqueous, oily or other suspensions or dispersions, emulsions, oil dispersions, pastes, dusts, materials for broadcasting, or granules, by means of spraying, atomizing, dusting, broadcasting or watering. The use forms depend on the intended aims; in any case, they should guarantee a very fine distribution of the active compounds according to the invention.

The herbicidal compositions comprise a herbicidally effective amount of at least one compound of the formula I or an agriculturally useful salt of I, and auxiliaries which are conventionally used in the formulation of crop protection agents.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohenanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the 4-(3-heterocyclyl-1-benzoyl)pyrazoles, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the active compounds together with a solid carrier.

Granules, eg. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground syntheticomaterials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to the NMR spectrum).

The following formulation examples illustrate the preparation of such preparations:

I. 20 parts by weight of the compound No. 2.1 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 2.6 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. 2.18 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. 2.27 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. 2.36 are mixed with 97 parts by weight of finely divided kaolin. This gives a dust which comprises 3% by weight of active compound.

VI. 20 parts by weight of the active compound No. 2.37 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

II. 1 part by weight of the compound No. 2.45 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

III. 1 part by weight of the compound No. 2.48 is dissolved in a mixture composed of 80 parts by weight of cyclohexanone and 20 parts by weight of Wettol® EM 31 (nonionic emulsifier based on ethoxylated castor oil). This gives a stable emulsion concentrate.

The compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The application rates of compound of the formula I are from 0.001 to 3.0, preferably 0.01 to 1.0 kg/ha of active substance (a.s.), depending on the control target, the season, the target plants and the growth stage.

To widen the activity spectrum and to achieve synergistic effects, the 4-(3-heterocyclyl-1-benzoyl)pyrazoles of the formula I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het) aryloxyalkanoic acids and their derivatives, benzoic acid and its derivatives, benzothiadiazinones, 2-(hetaroylaroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

USE EXAMPLES

The herbicidal activity of the 4-(3-heterocyclyl-1-benzoyl)pyrazoles of the Formula I was demonstrated by greenhouse experiments:

The culture containers used were plastic flower-pots containing loamy sand with approximately 3.0% of humus as the substrate. The seeds of the test plants were sown separately for each species.

For the pre-emergence treatment, the active compounds, which have been suspended or emulsified in water, were applied directly after sowing by means of finely distributing nozzles. The containers were irrigated gently to promote germination and growth and subsequently covered with translucent plastic hoods until the plants had rooted. This cover causes uniform germination of the test plants, unless this was adversely affected by the active compounds.

For the post-emergence treatment, the test plants were first grown to a height of 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 62.5 or 31.3 kg/ha of a.s. (active substance).

Depending on the species, the plants were kept at 10–25° C. or 20–35° C. . The test period extended over 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments belonged to the following species:

| Scientific name | Common name |
| --- | --- |
| Abutilon theophrasti | velvet leaf |
| Amaranthus retroflexus | redroot pigweed |
| Echinochloa crus-galli | barnyard grass |
| Setaria faberii | giant foxtail |

At application rates of 62.5 or 31.3 g/ha, the compound 2.37 (Table 2), applied by the post-emergence method, had a very good activity against the abovementioned mono- and dicotyledonous harmful plants.

We claim:

1. A 4-(3-heterocyclyl-1-benzoyl)pyrazole of the formula I

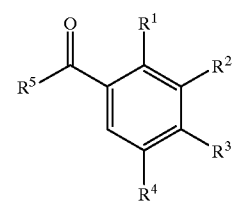

where:

$R^1$ and $R^3$ are each hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N-($C_1$–$C_6$-alkyl)aminosulfonyl, N,N-di($C_1$–$C_6$-alkyl)aminosulfonyl, N-($C_1$–$C_6$-alkylsulfonyl) amino, N-($C_1$–$C_6$-haloalkylsulfonyl)amino, N-($C_1$–$C_6$-alkyl)-N-($C_1$–$C_6$-alkylsulfonyl)amino or N-($C_1$–$C_6$-alkyl)-N-($C_1$–$C_6$-haloalkylsulfonyl)amino;

$R^2$ is an optionally substituted 5- or 6-membered heterocyclyl radical which comprises, in addition to carbon ring members, one to four identical or different hetero atoms selected from the group consisting of: oxygen, sulfur and nitrogen;

$R^4$ is hydrogen, halogen or $C_1$–$C_6$-alkyl;

$R^5$ is a pyrazole radical of the formula II

which is attached in position 4, where $R^6$ is $C_1$–$C_6$-alkyl;

$R^7$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, ($C_1$–$C_6$-alkyl)aminocarbonyl, ($C_3$–$C_6$-alkenyl)aminocarbonyl, ($C_3$–$C_6$-alkynyl)aminocarbonyl, di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)-aminocarbonyl, N-($C_3$–$C_6$-alkynyl)-N-($C_1$–$C_6$-alkoxy)aminocarbonyl, di($C_1$–$C_6$-alkyl)aminothiocarbonyl, $C_1$–$C_6$-alkylcarbonyl-$C_1$–$C_6$-alkyl, $C_1$–$C_6$-alkoxyimino-$C_1$–$C_6$-alkyl, N-($C_1$–$C_6$-alkylamino)imino-$C_1$–$C_6$-alkyl or N-(di-$C_1$–$C_6$-alkylamino)-imino-$C_1$–$C_6$-alkyl, where the alkyl, cycloalkyl and alkoxy radicals mentioned may be partially or fully halogenated and may be substituted by one to three of the following groups: cyano, hydroxyl, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, heterocyclyloxycarbonyl, phenylaminocarbonyl, N-($C_1$–$C_6$-alkyl)-N-(phenyl)-aminocarbonyl, heterocyclylaminocarbonyl, N-($C_1$–$C_6$-alkyl)-N-(heterocyclyl)-aminocarbonyl, phenyl-$C_2$–$C_6$-alkenylcarbonyl or heterocyclyl-$C_2$–$C_6$-alkenylcarbonyl, where the phenyl and the heterocyclyl radical of the last 16 substituents may be partially or fully halogenated and may be substituted by one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^8$ is hydrogen, $C_1$–$C_6$-alkyl or $C_1$–$C_6$-haloalkyl;

or an agriculturally useful salt thereof.

2. The 4-(3-heterocyclyl-1-benzoyl)pyrazole of the formula I defined in claim 1 where $R^7$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, ($C_1$–$C_6$-alkyl)aminocarbonyl, ($C_3$–$C_6$-alkenyl)aminocarbonyl, ($C_3$–$C_6$-alkynyl) aminocarbonyl, di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl, N-($C_3$–$C_6$-alkynyl)-N-($C_1$–$C_6$-alkoxy)aminocarbonyl, di($C_1$–$C_6$-alkyl)aminothiocarbonyl, $C_1$–$C_6$-alkylcarbonyl-$C_1$–$C_6$-alkyl, $C_1$–$C_6$-alkoxyimino-$C_1$–$C_6$-alkyl, N-($C_1$–$C_6$-alkylamino)imino-$C_1$–$C_6$-alkyl or N-(di-$C_1$–$C_6$-alkylamino)imino-$C_1$–$C_6$-alkyl, where the alkyl, cycloalkyl and alkoxy radicals mentioned may be partially or fully halogenated and may be substituted by one to three of the following groups: cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, heterocyclyloxycarbonyl, phenylaminocarbonyl, N-($C_1$–$C_6$-alkyl)-N-(phenyl)-aminocarbonyl, heterocyclylaminocarbonyl, N-($C_1$–$C_6$-alkyl)-N-(heterocyclyl)-aminocarbonyl, phenyl-$C_2$–$C_6$-alkenylcarbonyl or heterocyclyl-$C_2$–$C_6$-alkenylcarbonyl, where the phenyl and the heterocyclyl radical of the last 16 substituents may be partially or fully halogenated and may be substituted by one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

3. The 4-(3-heterocyclyl-1-benzoyl)pyrazole of the formula I defined in claim 1 where $R^7$ is $C_1$–$C_6$-alkyl, $C_3$–$C_6$-alkenyl, $C_3$–$C_6$-alkynyl, $C_1$–$C_6$-alkylcarbonyl, $C_2$–$C_6$-alkenylcarbonyl, $C_3$–$C_6$-cycloalkylcarbonyl, $C_1$–$C_6$-alkoxycarbonyl, $C_1$–$C_6$-alkylaminocarbonyl, di($C_1$–$C_6$-alkyl)aminocarbonyl, N-($C_1$–$C_6$-alkoxy)-N-($C_1$–$C_6$-alkyl)aminocarbonyl, di($C_1$–$C_6$-alkyl)aminothiocarbonyl, $C_1$–$C_6$-alkoxyimino-$C_1$–$C_6$-alkyl, where the alkyl, cycloalkyl and alkoxy radicals mentioned may be partially or fully halogenated and may be substituted by one to three of the following groups: cyano, hydroxyl, $C_1$–$C_4$-alkoxy, $C_1$–$C_4$-alkylthio, $C_1$–$C_4$-alkylcarbonyl, di($C_1$–$C_4$-alkyl)amino, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

phenyl, phenyl-$C_1$–$C_6$-alkyl, phenylcarbonyl-$C_1$–$C_6$-alkyl, phenyl-$C_2$–$C_6$-alkenylcarbonyl or phenylcarbonyl, where the phenyl radical of the last 5 substituents may be partially or fully halogenated and may be substituted by one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

4. The 4-(3-heterocyclyl-1-benzoyl)pyrazole of the formula I defined in claim 1 where $R^2$ is a 5- or 6-membered heterocyclic radical which contains, in addition to carbon ring members, one to four identical or different hetero atoms selected from the group consisting of: oxygen, sulfur and nitrogen, where the heterocyclic radical is unsubstituted or carries one to three substituents selected from the group consisting of:

halogen, cyano, nitro, $C_1$–$C_4$-alkyl, $C_1$–$C_4$-alkoxy-$C_1$–$C_4$-alkyl, di($C_1$–$C_4$-alkoxy)-$C_1$–$C_4$-alkyl, di($C_1$–$C_4$-alkyl)amino-$C_1$–$C_4$-alkyl, [2,2-di($C_1$–$C_4$-alkyl)-hydrazino-1]-$C_1$–$C_4$-alkyl, $C_1$–$C_6$-alkyliminooxy-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, di($C_1$–$C_4$-alkyl)aminocarbonyl-$C_1$–$C_4$-alkyl, $C_1$–$C_4$-haloalkyl, $C_1$–$C_4$-cyanoalkyl, $C_3$–$C_6$-cycloalkyl, $C_1$–$C_4$-alkoxy, $C_1$–$C_4$-alkoxy-$C_1$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $C_1$–$C_4$-alkylcarbonyl, $C_1$–$C_4$-haloalkylcarbonyl, $C_1$–$C_4$-alkoxycarbonyl, $C_1$–$C_4$-alkoxy-$C_1$–$C_4$-alkoxycarbonyl, $C_1$–$C_4$-haloalkoxycarbonyl, $C_3$–$C_6$-alkenyloxycarbonyl, $C_3$–$C_6$-alkynyloxycarbonyl, $C_1$–$C_4$-alkylaminocarbonyl, di($C_1$–$C_4$-alkyl) aminocarbonyl; phenyl or benzyl, where the last two substituents may in turn be partially or fully halogenated and may be substituted by one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;

hydroxyl, which may alternatively be present in the tautomeric form as an oxo group;

$C_3$–$C_6$-spirocycloalkane, where one carbon may be replaced by oxygen or by nitrogen with or without $C_1$–$C_4$-alkyl-substitution; and together with a fused phenyl ring, a $C_3$–$C_6$-carbocycle or a 5- to 6-membered heterocycle forms a bicyclic system, where the fused ring system may be substituted by one to three substituents selected from the group consisting of: halogen, nitro, cyano, $C_1$–$C_4$-alkyl, $C_1$–$C_4$-haloalkyl, $C_1$–$C_4$-alkoxy and $C_1$–$C_4$-haloalkoxy.

5. The 4-(3-heterocyclyl-1-benzoyl)pyrazole of the formula I defined in claim 1 where $R^4$ is hydrogen.

6. The 4-(3-heterocyclyl-1-benzoyl)pyrazole of the formula I defined in claim 1 where $R^1$ and $R^3$ are each nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl.

7. The 4-(3-heterocyclyl-1-benzoyl)pyrazole of the formula I defined in claim 1 where $R^2$ is an optionally substituted 5-membered carbon-linked heterocyclyl radical which contains, in addition to carbon ring members, one to three identical or different hetero atoms selected from the group consisting of: oxygen, sulfur and nitrogen.

8. The 4-(3-heterocyclyl-1-benzoyl)pyrazole of the formula I defined in claim 1 where $R^2$ is a 5-membered carbon-linked heterocyclyl radical which contains, in addition to carbon ring members, two identical or different hetero atoms selected from the group consisting of: oxygen, sulfur and nitrogen, and which is unsubstituted or which is substituted by one to two radicals selected from the group consisting of: $C_1$–$C_4$-alkyl, $C_3$–$C_6$-cycloalkyl, $C_1$–$C_4$-haloalkyl, $C_1$–$C_4$-alkoxy-$C_1$–$C_4$-alkyl, $C_1$–$C_4$-alkoxycarbonyl, $C_1$–$C_4$-alkoxy and $C_3$–$C_6$-spirocycloalkane.

9. The 4-(3-heterocyclyl-1-benzoyl)pyrazole of the formula I defined in claim 1 where $R^2$ is an optionally substituted 5-membered carbon-bonded saturated or partially saturated heterocyclyl radical which contains in addition to carbon ring members, one to three identical or different hetero atoms selected from the group consisting of: oxygen, sulfur and nitrogen.

10. The 4-(3-heterocyclyl-1-benzoyl)pyrazole of the formula I defined in claim 1 where $R^2$ is an optionally substituted 5-membered carbon-bonded unsaturated heterocyclyl radical which contains, in addition to carbon ring members, one to three identical or different hetero atoms selected from the group consisting of: oxygen, sulfur and nitrogen.

11. The 4-(3-heterocyclyl-1-benzoyl)pyrazole of the formula I defined in claim 1 where $R^2$ is an optionally substituted 6-membered carbon-bonded saturated, partially saturated or unsaturated heterocyclyl radical which contains, in addition to carbon ring members, one to three identical or different hetero atoms selected from the group consisting of: oxygen, sulfur and nitrogen.

12. A process for preparing a 4-(3-heterocyclyl-1-benzoyl)pyrazole of the formula I as defined in claim 1, which comprises reacting a benzoyl compound of the formula III

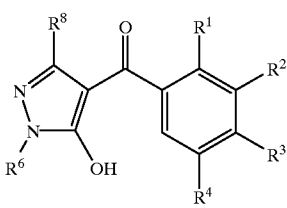

with a compound of the formula IV $L^1$—$R^7$     IV wherein $L^1$ is a nucleophilically displaceable leaving group.

13. A composition, which comprises a herbicidally effective amount of at least one 4-(3-heterocyclyl-1-benzoyl)pyrazole of the formula I or an agriculturally useful salt of I as defined in claim 1, and auxiliaries which are customarily used for formulating crop protection agents.

14. A process for preparing the composition defined in claim 13, which comprises mixing a herbicidally effective amount of at least one 4-(3-heterocyclyl-1-benzoyl)pyrazole of the formula I or an agriculturally useful salt of I and auxiliaries which are customarily used for formulating crop protection agents.

15. A method for controlling undesirable vegetation, which comprises treating a plant, its habitat or its seed with a herbicidally effective amount of at least one 4-(3-heterocyclyl-1-benzoyl)pyrazole of the formula I or an agriculturally useful salt of I as defined in claim 1.

16. The 4-(3-heterocyclyl-1-benzoyl)pyrazole of the formula I defined in claim 1 where $R^1$ and $R^3$ are each nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkythio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsufonyl, $R^2$ is an optional substituted 5-membered carbon-bonded saturated or partially saturated heterocyclyl radical which contains, in addition to carbon ring members, one to three identical or different hetero atoms selected from the group consisting of: oxygen, sulfur and nitrogen.

271

17. The 4-(3-heterocyclyl-1-benzoyl)pyrazole of the formula I defined in claim 16 where $R^1$ is nitro, halogen, $C_1$–$C_6$-alkyl, $C_1$–$C_6$-haloalkyl, $C_1$–$C_6$-alkoxy, $C_1$–$C_6$-alkysulfonyl or $C_1$–$C_6$-haloalkylsulfonyl, and $R^3$ nitro, halogen, $C_1$–$C_6$-haloakyl, $C_1$–$C_6$-alkylsulfonyl or $C_1$–$C_6$-haloalkylsulfonyl.

18. The 4-(3-heterocyclyl-1-benzoyl)pyrazole of the formula I defined in claim 17 where $R^2$ is optionally substituted tetrahydrooxazol-2-yl, tetrahydrothiazoly-2-yl, 1,3-dioxolan-2yl, 1,3oxathiolan-2-yl, 1,3-dithiolan-2-yl, 4,5-dihydroisoxazol-3-yl, 4,5-dihydro-1-H-imidazol-2-yl, 4,5-dihydrooxazol-2-yl, 4,5-dihydrothiazol-2-yl 3-H1, 2,4-dithiazol-5-yl, 2H1,3,4-dithiazol-5-yl or 2H-1,3,4-oxathiazol-5-yl.

19. The 4-(3-heterocyclyl-1-benzoyl)pyrazole of the formula I defined in claim 18 where $R^7$ is $C_1$–$C_6$-alkyl, $C_3$–$C_6$-alkenyl, $C_3$–$C_6$-alkynyl, $C_1$–$C_6$-alkycarbonyl, $C_2$–$C_6$-alkenylcarbonyl, $C_3$–$C_6$-cycloalkylcarbonyl, $C_1$–$C_6$-alkoxycarbonyl, $C_1$–$C_6$-alkylaminocarbonyl, di($C_1$–$C_6$-alkyl)aminocarbonyl, N-($C_1$–$C_6$-alkoxy)-N-($C_1$–$C_6$-alkyl)aminocarbonyl, di($C_1$–$C_6$-alkyl)aminothiocarbonyl, $C_1$–$C_6$-alkoxyimino- $C_1$–$C_6$-alkyl, alkyl, where the alkyl, cycloalkyl and alkoxy radicals mentioned may be partially or fully halogenated and may be substituted by one to three of the following groups: cyano, hydroxyl, $C_1$–$C_4$-alkoxy, $C_1$–$C_4$-alkylthio, $C_1$–$C_4$-alkylcarbonyl, di($C_1$–$C_4$-alkyl)amino, $C_1$–$C_4$-alkoxycarbonyl, $C_1$–$C_4$-alkoxy- $C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl; pehyl, phenyl-$C_1$–$C_6$-alkyl, phenylcarbonyl-$C_1$–$C_6$-alkyl, phenyl-$C_2$–$C_6$-alkenylcarbony or phenylcarbonyl, where the phenyl radical of the last 5 substituents may be partially or fully halogenated and may be substituted by one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

20. The 4-(3-heterocyclyl-1-benzoyl)pyrazole of the formula I defined in claim 19 where $R^2$ is optionally substituted 4,5-dihydroisoxazol-3-yl.

21. The 4-(3-heterocyclyl-1-benzoyl)pyrazole of the formula I defined in claim 20 where $R^4$ is hydrogen.

22. The 4-(3-heterocyclyl-1-benzoyl)pyrazole of the formula I defined in claim 16 where $R^7$ $C_1$–$C_6$- cyanoalkyl, $C_1$–$C_4$-alkoxy-$C_1$–$C_6$-alkyl, $C_1$–$C_4$-alkylcar bonyloxy-$C_1$–$C_6$-alkyl, $C_1$–$C_4$-alkoxycarbonyl-$C_1$–$C_6$-alkyl, $C_1$–$C_4$-alkoxy-$C_1$–$C_4$-alkoxycarbonyl-$C_1$–$C_6$-alkyl, di($C_1$–$C_4$-al kyl)amino-$C_1$–$C_4$-alkoxycarbonyl-$C_1$–$C_6$-alkyl, $C_1$–$C_4$-alkylamino carbonyl-$C_1$–$C_6$-alkyl, di-($C_1$–$C_4$-alkyl)aminocarbonyl-$C_1$–$C_6$-al- kyl, $C_3$–$C_6$-alkenyl, $C_3$–$C_6$alkynyl, $C_3$–$C_6$-alkenylcarbonyl, N-($C_1$–$C_6$-alkoxy)-N-($C_1$–$C_6$-alkyl)aminocarbonyl, or di($C_1$–$C_6$-alkyl)aminothiocarbonyl.

23. The 4-(3-heterocyclyl-1-benzoyl)pyrazole of the formula I defined in claim 16 where $R^1$ is methyl or ethyl, $R^3$ is methylsulfonyl or ethylsulfonyl, $R^7$ is $C_1$–$C_6$-alkyl, $C_1$–$C_4$-alkoxy-$C_1$–$C_6$-alkyl, $C_1$–$C_4$-alkylcarbonyloxy-$C_1$–$C_6$-alkyl, $C_1$–$C_4$-alkoxycarbonyl-$C_1$–$C_6$-alkyl, $C_1$–$C_4$-alkoxy-$C_1$–$C_4$-alkoxycarbonyl-$C_1$–$C_6$-alkl, di($C_1$–$C_4$-alkyl)amino-$C_1$–$C_4$-alkoxycarbonyl-$C_1$–$C_6$-alkyl $C_1$–$C_4$-alkylaminocarbonyl-$C_1$–$C_6$-alkyl, di($C_1$–$C_4$-alkyl)aminocarbonyl-$C_1$–$C_6$-alkyl, $C_3$–$C_6$-alkenyl, $C_3$–$C_6$-alkynyl, $C_1$–$C_6$-alkoxycarbonyl, $C_3$–$C_6$-alkenylcarbonyl, $C_1$–$C_6$-alkoxycarbonyl, di($C_1$–$C_6$-alkyl)aminocarbonyl, N-($C_1$–$C_6$-alkoxy)-N-($C_1$–$C_6$-alkyl)aminocarbonyl or di($C_1$–$C_6$-alkyl) aminothiocarbonyl, phenylcarbonyl-$C_1$–$C_6$-alkyl, phenylcarbonyl-$C_2$–$C_6$-alkenyl or phenylcarbonyl, where the phenyl radical of the last 3 substituents may be partially or fully halogenated and may be substituted by one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

24. The 4-(3-heterocyclyl-1-benzoyl)pyrazole of the formula I defined in claim 23 where $R^7$ is $C_1$–$C_6$-alkyl, $C_1$–$C_6$-cyanoalkyl, $C_1$–$C_4$-alkoxy-$C_1$–$C_6$-alkyl, $C_1$–$C_4$-alkylcarbonyloxy-$C_1$–$C_6$-alkyl, $C_1$–$C_4$-alkoxycarbonyl-$C_1$–$C_6$-alkyl, $C_1$–$C_4$-alkoxy-$C_1$–$C_4$-alkoxycarbonyl-$C_1$–$C_6$-alkl, di($C_1$–$C_4$-alkyl)amino-$C_1$–$C_4$-alkoxycarbonyl-$C_1$–$C_6$-alkyl, $C_1$–$C_4$-alkylaminocarbonyl-$C_1$–$C_6$-alkyl, di($C_1$–$C_4$-alkyl)aminocarbonyl-$C_1$–$C_6$-alkyl, $C_3$–$C_6$-alkenyl, $C_3$–$C_6$-alkynyl, $C_1$–$C_6$-alkoxycarbonyl, $C_3$–$C_6$-alkenylcarbonyl, $C_1$–$C_6$-alkoxycarbonyl, di($C_1$–$C_6$-alkyl)aminocarbonyl, N-($C_1$–$C_6$-alkoxy)-N-($C_1$–$C_6$-alkyl)aminocarbonyl or di($C_1$–$C_6$-alkyl) aminothiocarbonyl, phenylcarbonyl-$C_2$–$C_6$-alkenyl or phenylcarbonyl, where the phenyl radical of the last 2 substituents may be partially or fully halogenated and may be substituted by one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

25. The 4-(3-heterocyclyl-1-benzoyl)pyrazole of the formula I defined in claim 16 where $R^1$ is methyl or ethyl, $R^2$ is optionally substituted 2-furyl, 3-thienyl, pyrrol-1-yl, pyrrol-2-yl, pyrazol-3-yl, pyrazol-4-yl, isoxazol-3-yl, isoxazol-4-yl, isothiazol-3-yl, oxazol-2-yl, oxazol-5-yl, thiazol-2-yl, thiazol-4-yl, thiazol-5-yl, 1,2,4-oxadiazol-3yl, 1,2,4- thiadiazol-5yl, 1,3,4- thiadiazol-2yl, 1,2,4- triadiazol-1yl, 1,2,4- triadiazol-3yl, $R^3$ is methylsulfonyl or ethylsufonyl, and $R^7$ is $C_1$–$C_6$-alkyl, $C_3$–$C_6$-alkenyl, $C_3$–$C_6$-alkynyl, $C_1$–$C_6$-alkylcarbonyl, $C_2$–$C_6$-alkenylcarbonyl, $C_3$–$C_6$-cycloalkylcarbonyl, $C_1$–$C_6$-alkoxycarbonyl, $C_1$–$C_6$-alkylaminocarbonyl, di($C_1$–$C_6$-alkyl)aminocarbonyl, N-($C_1$–$C_6$-alkoxy)-N-($C_1$–$C_6$-alkyl)aminocarbonyl, di($C_1$–$C_6$-alkyl)aminothiocarbonyl, or $C_1$–$C_6$-alkoxyimino-$C_1$–$C_6$-alkyl, where the alkyl, cycloalkyl and alkoxy radicals may be partially or fully halogenated and may be substituted by one to three of the following groups: cyano, hydroxyl, $C_1$–$C_4$-alkoxy, $C_1$–$C_4$-alkylthio, $C_1$–$C_4$-alkylcarbonyl, di($C_1$–$C_4$-alkyl)amino, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl.

26. The 4-(3-heterocyclyl-1-benzoyl)pyrazole of the formula I defined in claim 1 where $R^2$ is an optionally substituted 6-membered carbon-bonded saturated or partially saturated heterocyclyl radical which contains, in addition to carbon ring members, one to three identical or different hetero atoms selected from the group consisting of: oxygen, sulfur and nitrogen, and is hydrogen.

27. The 4-(3-heterocyclyl-1-benzoyl)pyrazole of the formula I defined in claim 26 where $R^1$ and $R^3$ are each nitro, halogen, cyano, $C^1$–$C^6$-alkyl, $C^1$–$C^6$-haloalkyl, $C^1$–$C^6$-alkoxy, $C^1$–$C^6$-haloalkoxy, $C^1$–$C^6$-alkylthio, $C^1$–$C^6$-haloalkylthio, $C^1$–$C^6$-alkylsulfinyl, $C^1$–$C^6$-haloalkylsulfinyl, $C^1$–$C^6$-alkylsufonyl or $C^1$–$C^6$-haloalkylsufonyl 28. The 4-(3-heterocyclyl-1-benzoyl)pyrazole of the formula I defined in claim 26 where $R^1$ is nitro, halogen, $C^1$–$C^6$-alkyl, $C^1$–$C^6$-haloalkyl, $C^1$–$C^6$-alkoxy, $C^1$–$C^6$-alkylsulfonyl or $C^1$–$C^6$-haloalkylsulfony, and $R^3$ is nitro, halogen, $C^1$–$C^6$-haloalkyl, $C^1$–$C^6$-alkylsulfonyl or $C^1$–$C^6$-haloalkylsulfonyl.

* * * * *

UNITED STATES PATENT AND TRADEMARK OFFICE
CERTIFICATE OF CORRECTION

PATENT NO.: 6,165,944

DATED: December 26, 2000

INVENTOR(S): VON DEYN et al.

It is certified that error appears in the above-identified patent and that said Letters Patent is hereby corrected as shown below:

On the cover page, item [30], the foreign application priority data should read:
--Jan. 17, 1997 [DE] Germany ............... 197 01 446
Sep. 15, 1997 [DE] Germany ............... 197 40 494--.

Col. 270, claim 9, line 1, after "contains" insert a comma --,--.

Col. 271, claim 18, line 14, "3-H1" should be --3H-1,--.

Col. 271, claim 18, line 15, "2H1" should be --2H-1--.

Col. 271, claim 19, line 25, "alkoxyimino- $C_1$-$C_6$-alkyl, alkyl," should be --alkoxyimino-$C_1$-$C_6$-alkyl,--.

Col. 271, claim 19, line 36, "pehyl" should be --phenyl--.

Col. 271, claim 22, line 52, "$C_1$-$C_4$-alkylcar bonyloxy" should be --$C_1$-$C_4$-alkylcarbonyloxy--.

Col. 271, claim 22, line 54, "di($C_1$-$C_4$-al kyl)amino-" should be --di($C_1$-$C_4$-alkyl)amino- --.

Col. 271, claim 22, line 56, "alkylamino carbonyl" should be --alkylaminocarbonyl--.

UNITED STATES PATENT AND TRADEMARK OFFICE
CERTIFICATE OF CORRECTION

PATENT NO.: 6,165,944

DATED: December 26, 2000

INVENTOR(S): VON DEYN et al.

It is certified that error appears in the above-identified patent and that said Letters Patent is hereby corrected as shown below:

Col. 271, claim 22, line 56, "aminocarbonyl-$C_1$-$C_6$-al- kyl," should be --aminocarbonyl-$C_1$-$C_6$-alkyl,--.

Col. 271, claim 22, line 57, "al- kyl" should be --alkyl--.

Col. 271, claim 22, line 58, after "alkenylcarbonyl," add --$C_1$-$C_6$-alkoxycarbonyl, di($C_1$-$C_6$-alkyl)aminocarbonyl,--.

Col. 271, claim 23, line 65, "is $C_1$-$C_6$-alkyl, $C_1$-$C_4$-alkoxy-" should be --is $C_1$-$C_6$-alkyl, $C_1$-$C_6$-cyanoalkyl, $C_1$-$C_4$-alkoxy- --.

Col. 272, claim 23, line 1, "alkl" should be --alkyl--.

Col. 272, claim 23, line 5, "alkoxycarbonyl" should be --allkylcarbonyl--.

Col. 272, claim 24, line 18, "is $C_1$-$C_6$-alkyl" should be --is $C_1$-$C_6$-alky--.

Col. 272, claim 24, line 21, "alkl" should be --alkyl--.

Col. 272, claim 24, line 25, "$C_1$-$C_6$-alkoxycarbonyl" should be --$C_1$-$C_6$-alkylcarbonyl--.

Col. 272, claim 25, line 39, after "2-furyl," insert --3-furyl--.

Col. 272, claim 25, line 43, after "oxadiazol-3yl," insert --1,3,4-oxadiazol-2-yl,--.

Col. 273, claim 26, line 3, "and is hydrogen" should be --and $R^4$ is hydrogen--.

UNITED STATES PATENT AND TRADEMARK OFFICE
CERTIFICATE OF CORRECTION

PATENT NO.: 6,165,944

DATED: December 26, 2000

INVENTOR(S): VON DEYN et al.

It is certified that error appears in the above-identified patent and that said Letters Patent is hereby corrected as shown below:

Col. 273, claim 27, lines 6-10, after "cyano," the lines should read:
-- $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl or $C_1$-$C_6$-haloalkylsulfonyl.--

Col. 274, claim 28, lines 3-7, after "halogen," the lines should read:
-- $C_1$-$C_6$-alkyl, $C_1$-$C_6$-haloalkyl, $C_1$-$C_6$-alkoxy, $C_1$-$C_6$-alkylsulfonyl or $C_1$-$C_6$-haloalkylsulfonyl, and
$R^3$ is nitro, halogen, $C_1$-$C_6$-haloalkyl, $C_1$-$C_6$-alkylsulfonyl or $C_1$-$C_6$-haloalkylsulfonyl--.

Signed and Sealed this

First Day of May, 2001

Attest:

NICHOLAS P. GODICI

Attesting Officer

Acting Director of the United States Patent and Trademark Office